United States Patent
Kim et al.

(10) Patent No.: US 11,730,731 B2
(45) Date of Patent: Aug. 22, 2023

(54) SUSTAINED FORMULATION FOR PREVENTION OR TREATMENT OF AUTOIMMUNE DISEASE CONTAINING NALTREXONE AND METHOD USING THE SAME

(71) Applicant: INVENTAGE LAB INC., Seongnam-si (KR)

(72) Inventors: Ju Hee Kim, Seongnam-si (KR); Mase Lee, Paju-si (KR); Donghoon Kim, Seongnam-si (KR)

(73) Assignee: INVENTAGE LAB INC., Seongnam-si (KR)

( * ) Notice: Subject to any disclaimer, the term of this patent is extended or adjusted under 35 U.S.C. 154(b) by 0 days.

(21) Appl. No.: 17/871,428

(22) Filed: Jul. 22, 2022

(65) Prior Publication Data
US 2022/0370437 A1    Nov. 24, 2022

Related U.S. Application Data

(63) Continuation of application No. PCT/KR2022/003317, filed on Mar. 8, 2022.

(30) Foreign Application Priority Data

Mar. 9, 2021  (KR) .................. 10-2021-0030791
Mar. 7, 2022  (KR) .................. 10-2022-0028995

(51) Int. Cl.
*A61K 31/485*  (2006.01)
*A61P 21/00*   (2006.01)
*A61P 19/02*   (2006.01)
*A61K 9/00*    (2006.01)
*A61K 9/16*    (2006.01)

(52) U.S. Cl.
CPC .......... *A61K 31/485* (2013.01); *A61K 9/0021* (2013.01); *A61K 9/1647* (2013.01); *A61P 19/02* (2018.01); *A61P 21/00* (2018.01)

(58) Field of Classification Search
CPC .. A61K 31/485; A61K 9/0021; A61K 9/1647; A61P 19/02
See application file for complete search history.

(56) References Cited

FOREIGN PATENT DOCUMENTS

KR    20200044977    4/2020

OTHER PUBLICATIONS

Beneitez et al., Opioid Addiction: Social Problems Associated and Implications of Both Current and Possible Future Treatments, including Polymeric Therapeutics for Giving Up the Habit of Opioid Consumption, BioMed Research International, Article ID 7120815 (Year: 2017).*
Li et al, "Low-dose naltrexone (LDN): A promising treatment in Immune-related diseases and cancer therapy", International Immunopharmacology 61 , 178-184 (Year: 2018).*
Vivitrol(R) trade paper (Year: 2022).*

* cited by examiner

*Primary Examiner* — Carlos A Azpuru
(74) *Attorney, Agent, or Firm* — STIP Law Group, LLC

(57) ABSTRACT

The present disclosure provides a sustained formulation for prevention or treatment of autoimmune disease, comprising microparticles comprising naltrexone or pharmaceutically acceptable salts thereof, and biodegradable polymers, and a method using the same. Accordingly, it may be used to prevent or treat autoimmune diseases for a prolonged period of time with a single administration.

26 Claims, 78 Drawing Sheets

[FIG. 1A]
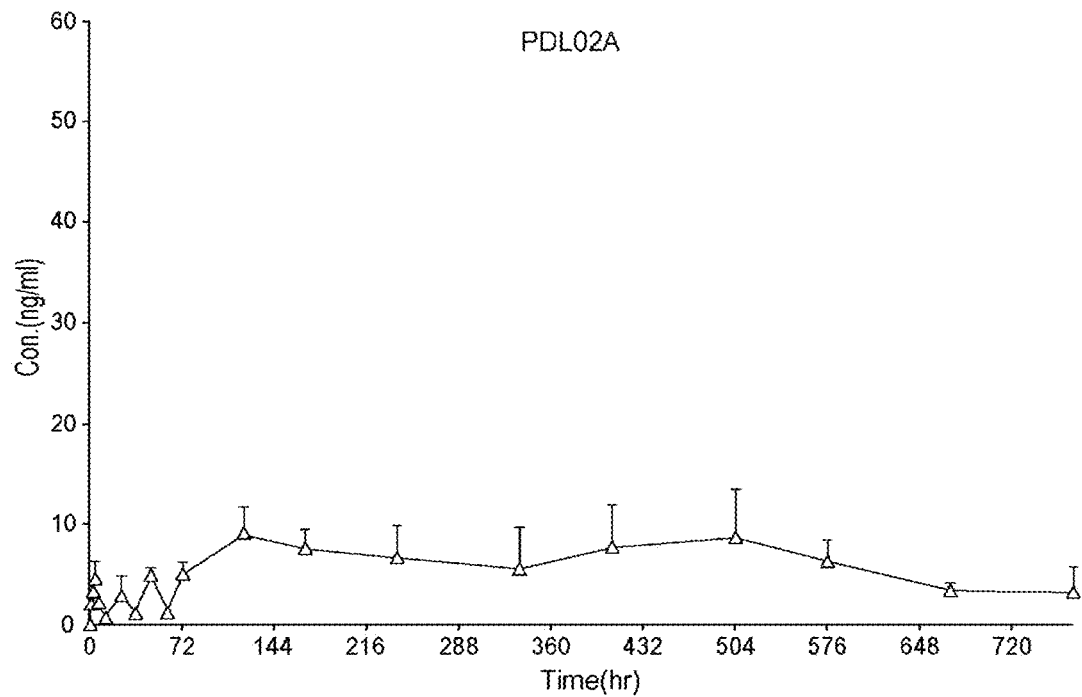
[FIG. 1B]
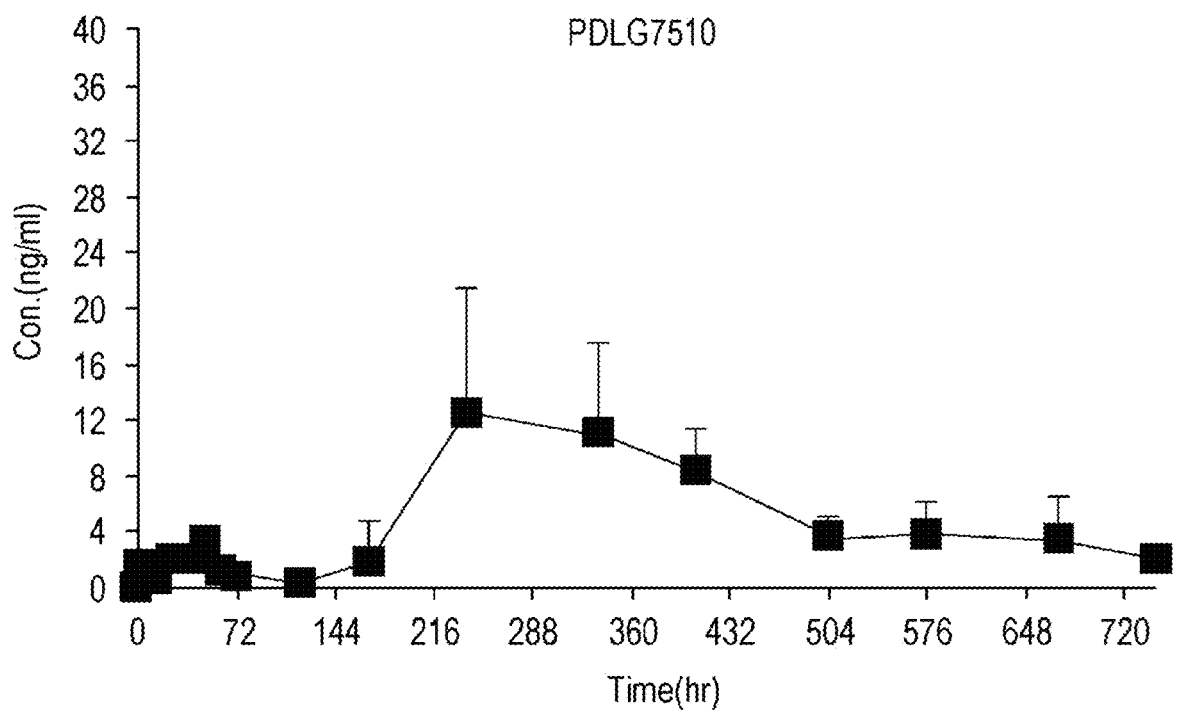

[FIG. 1C]
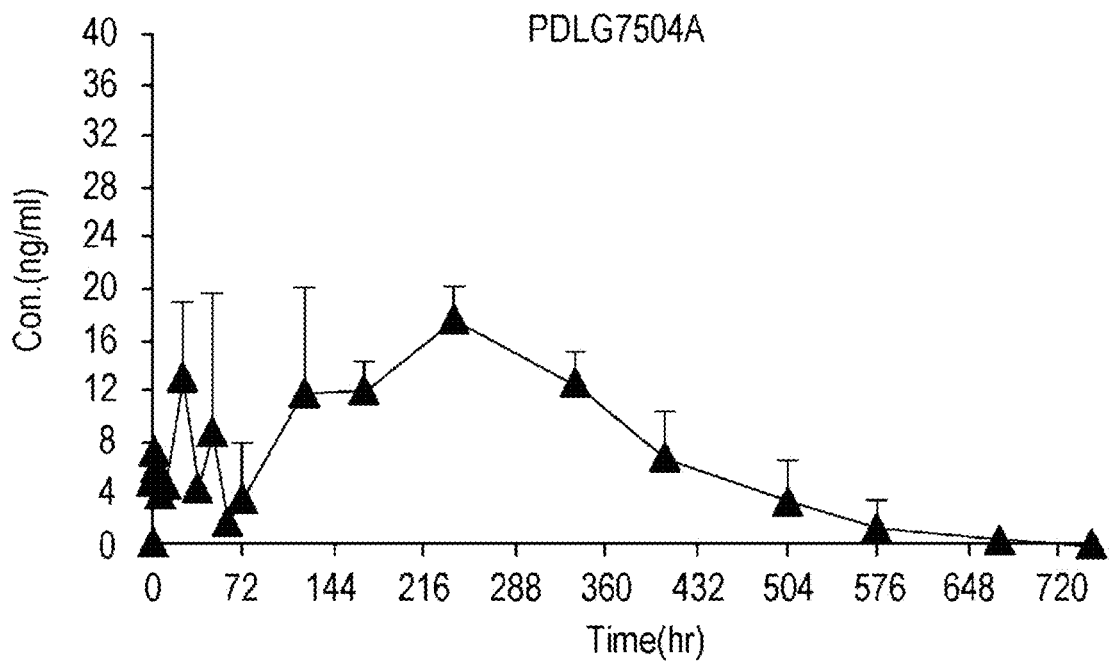
[FIG. 1D]
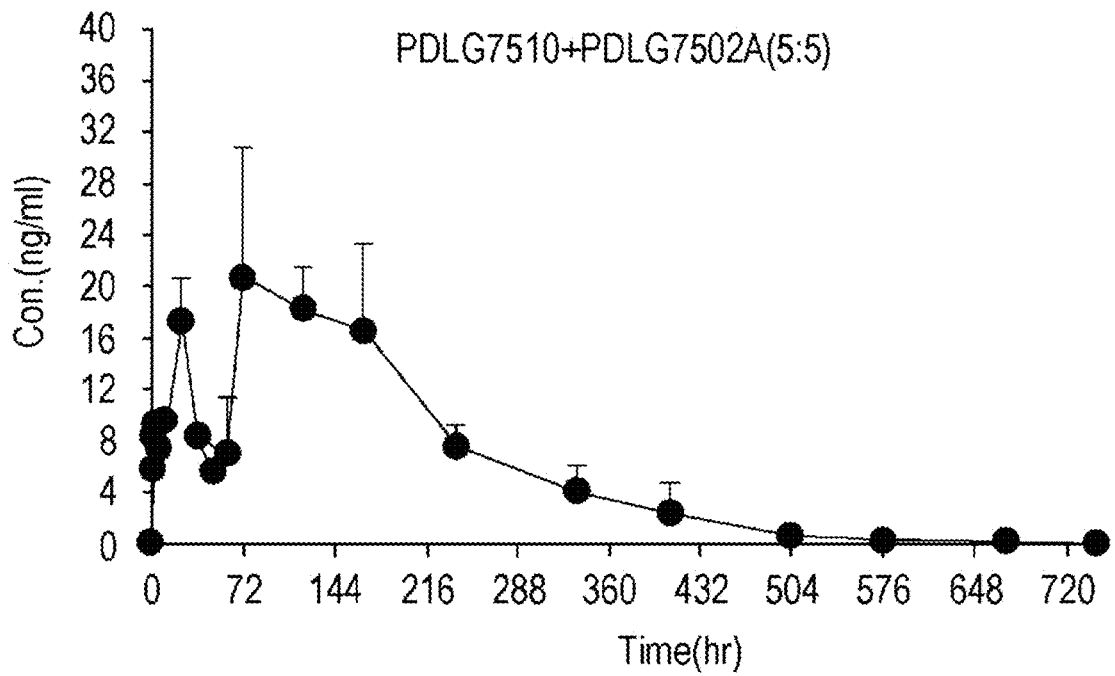

[FIG. 1E]
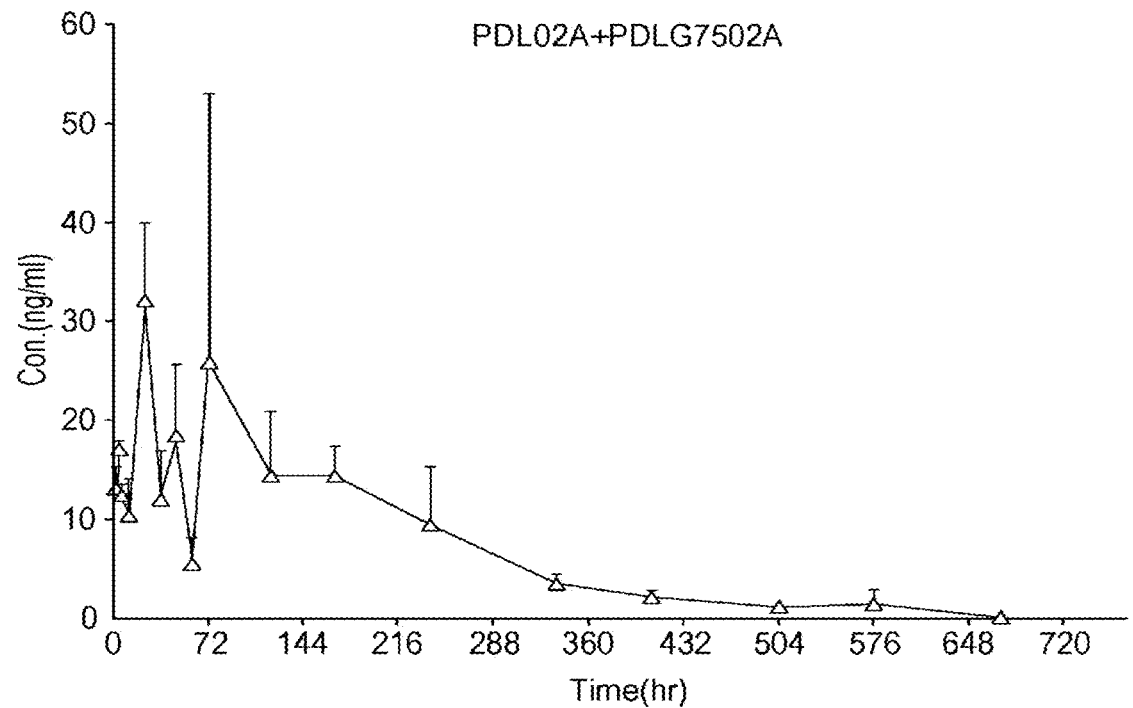
[FIG. 1F]
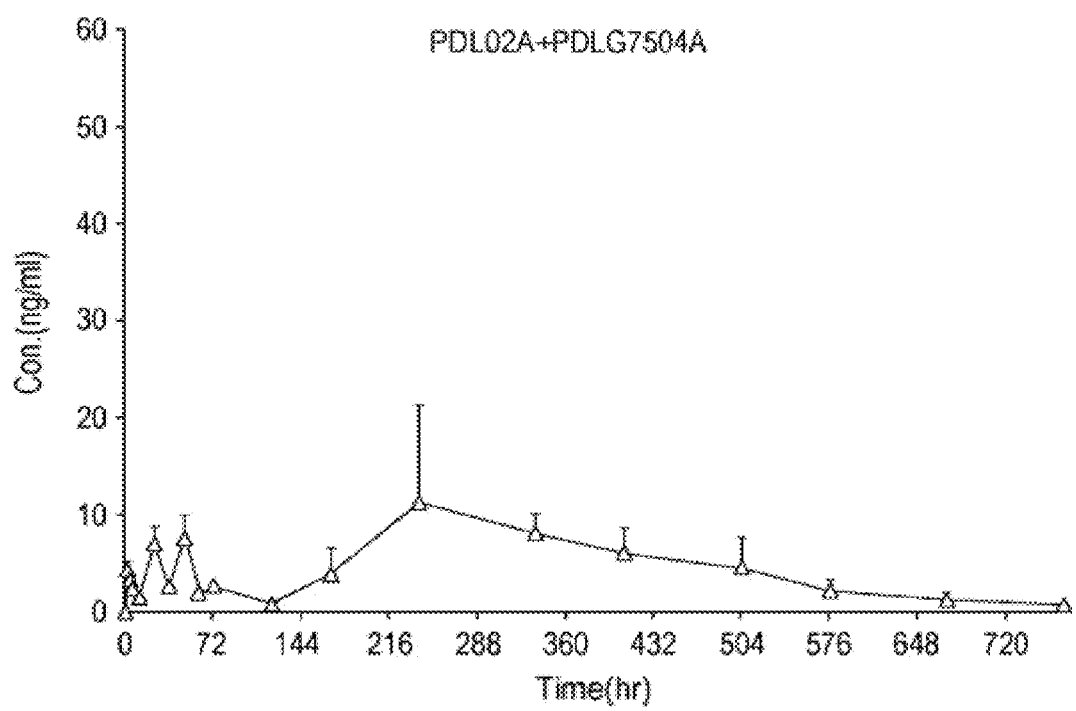

[FIG. 2A]
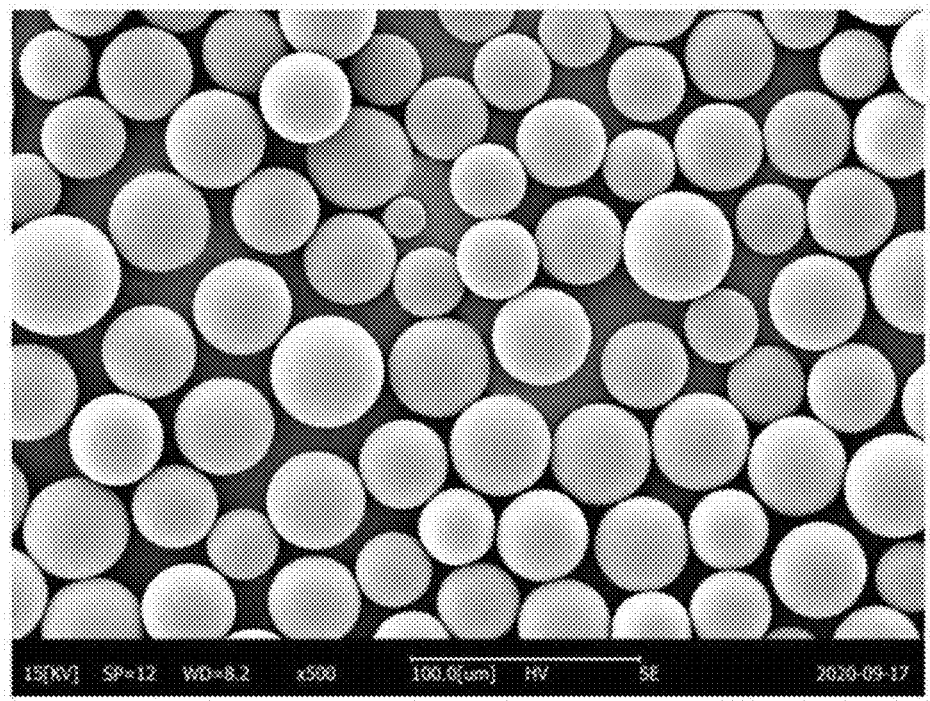
[FIG. 2B]
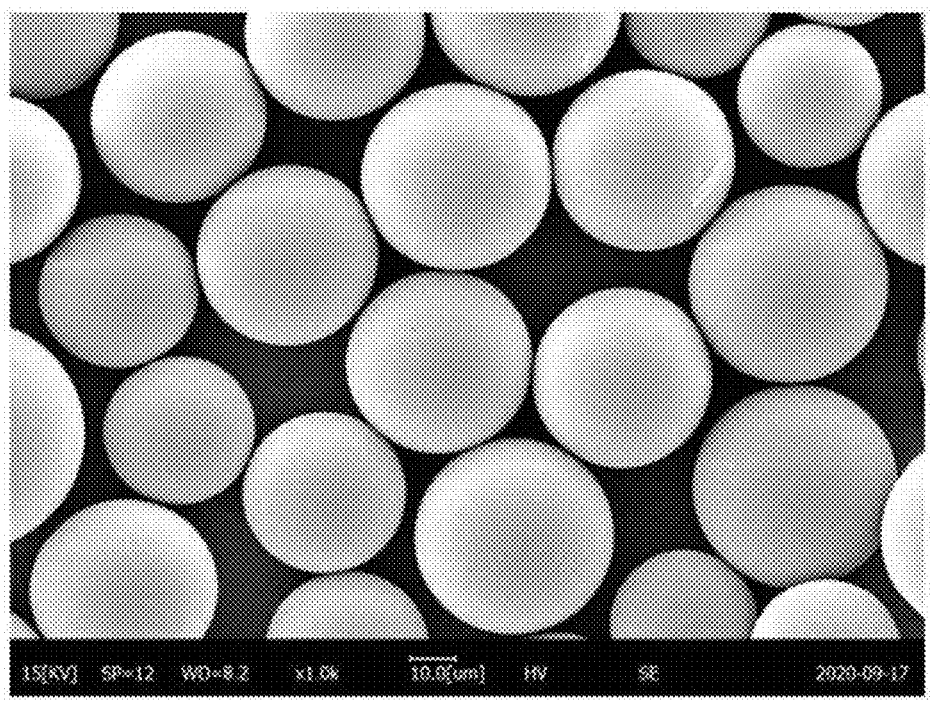

[FIG. 2C]
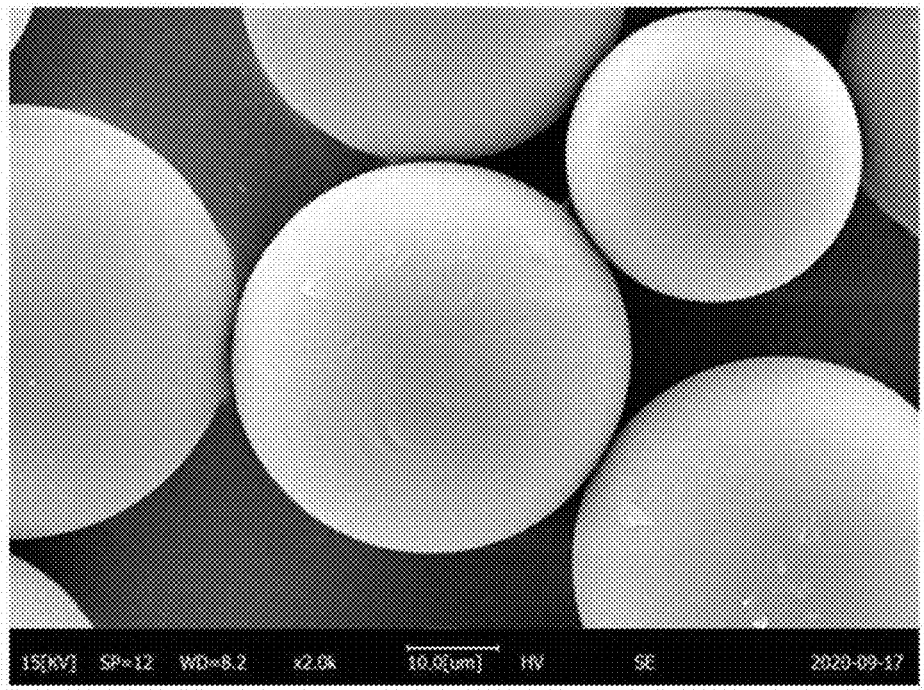

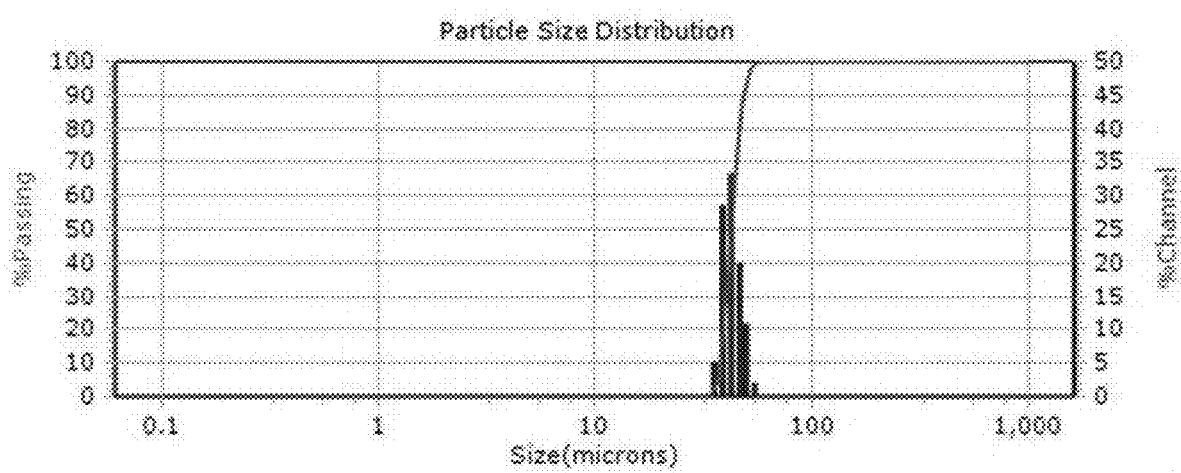
[FIG. 2D]

[FIG. 2E]
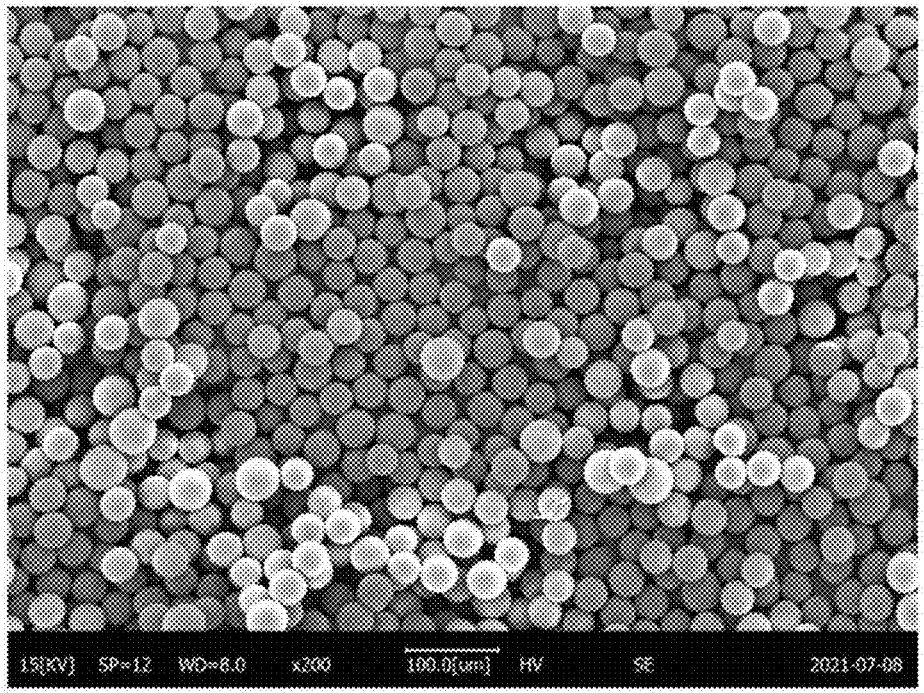
[FIG. 2F]
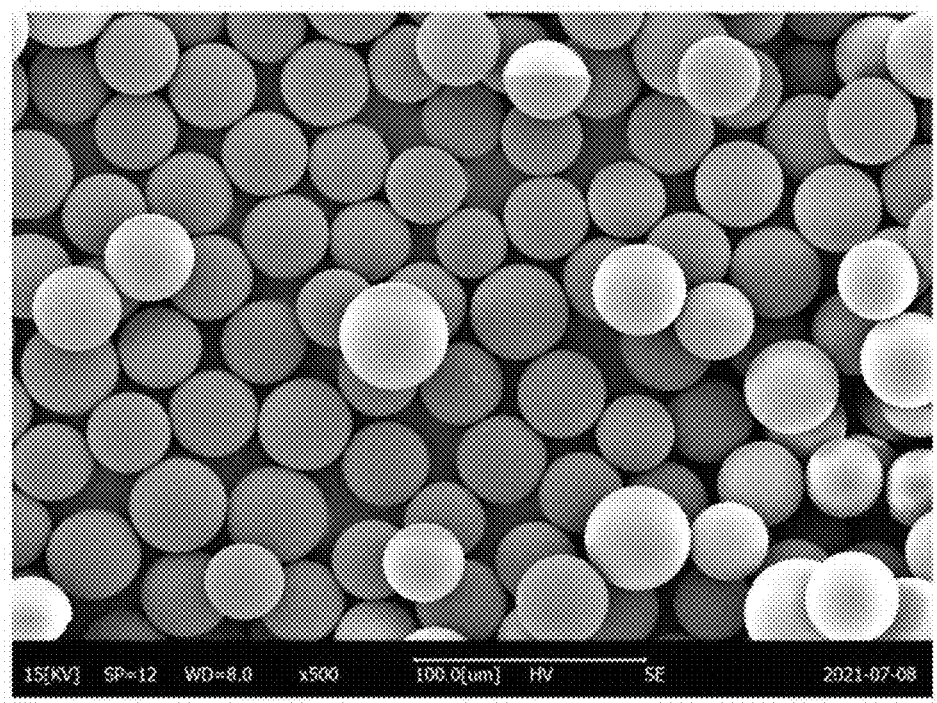

[FIG. 2G]
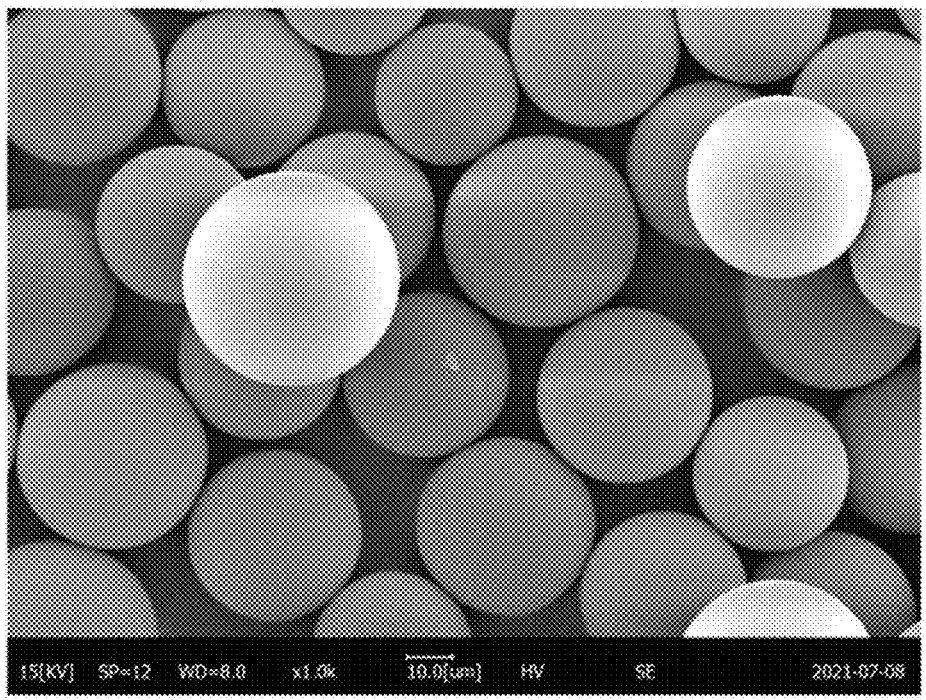
[FIG. 2H]
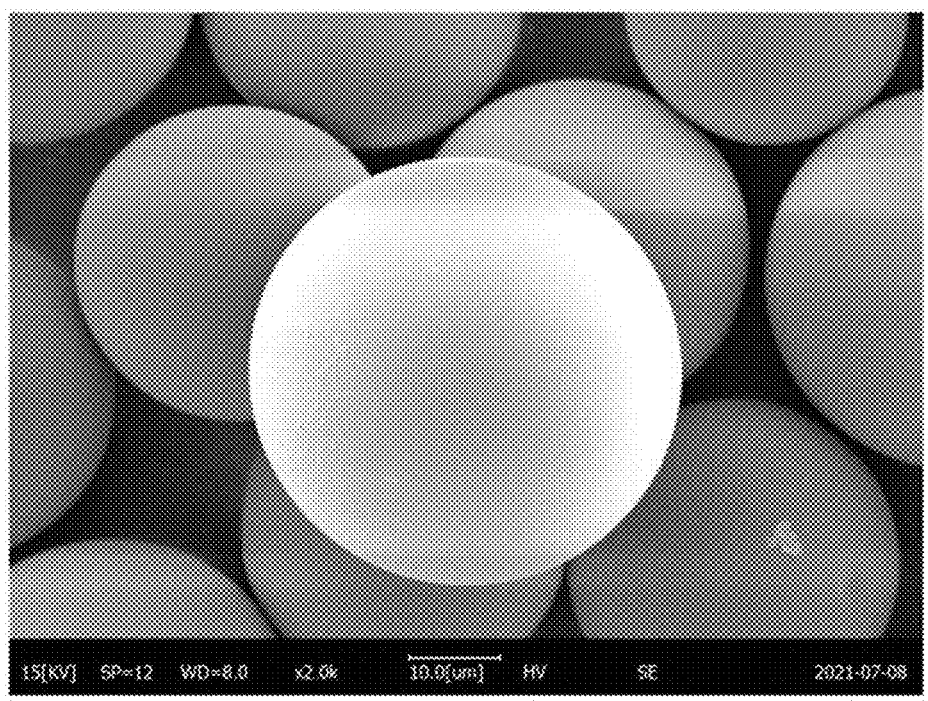

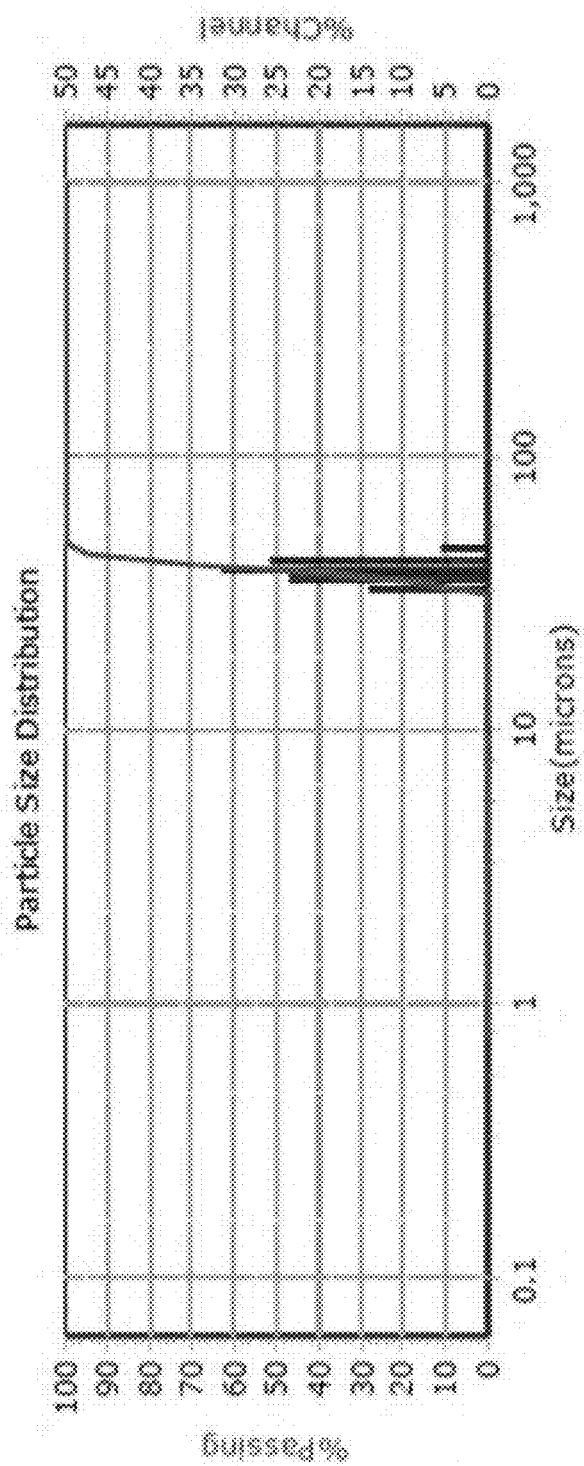
[FIG. 2I]

[FIG. 3A]
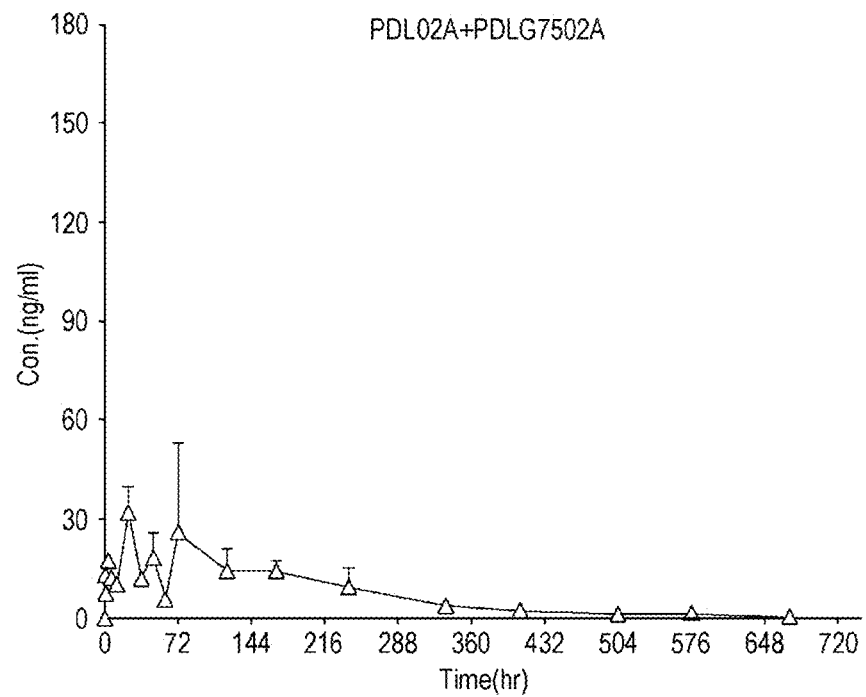
[FIG. 3B]
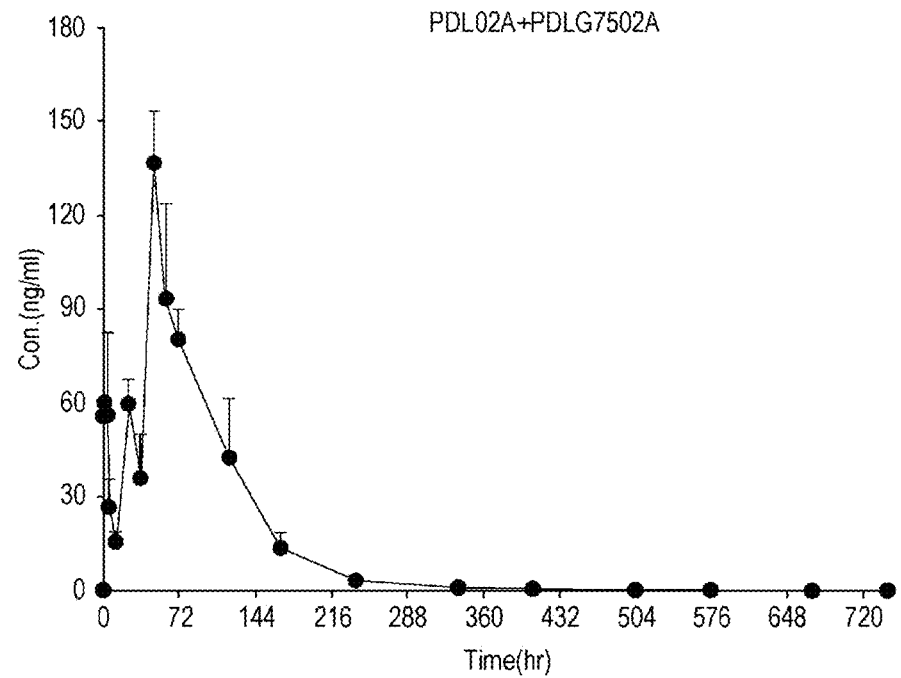

[FIG. 3C]
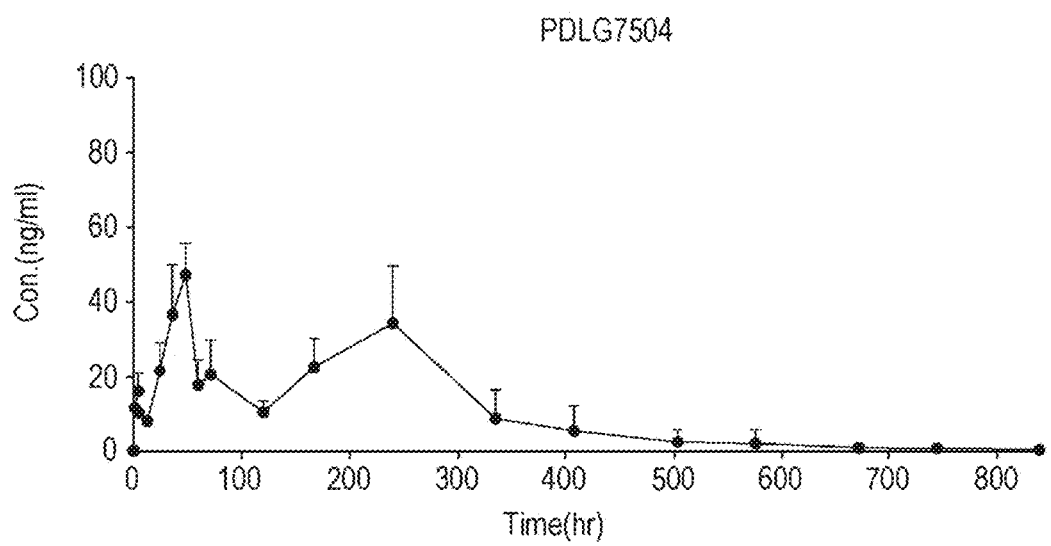
[FIG. 4A]
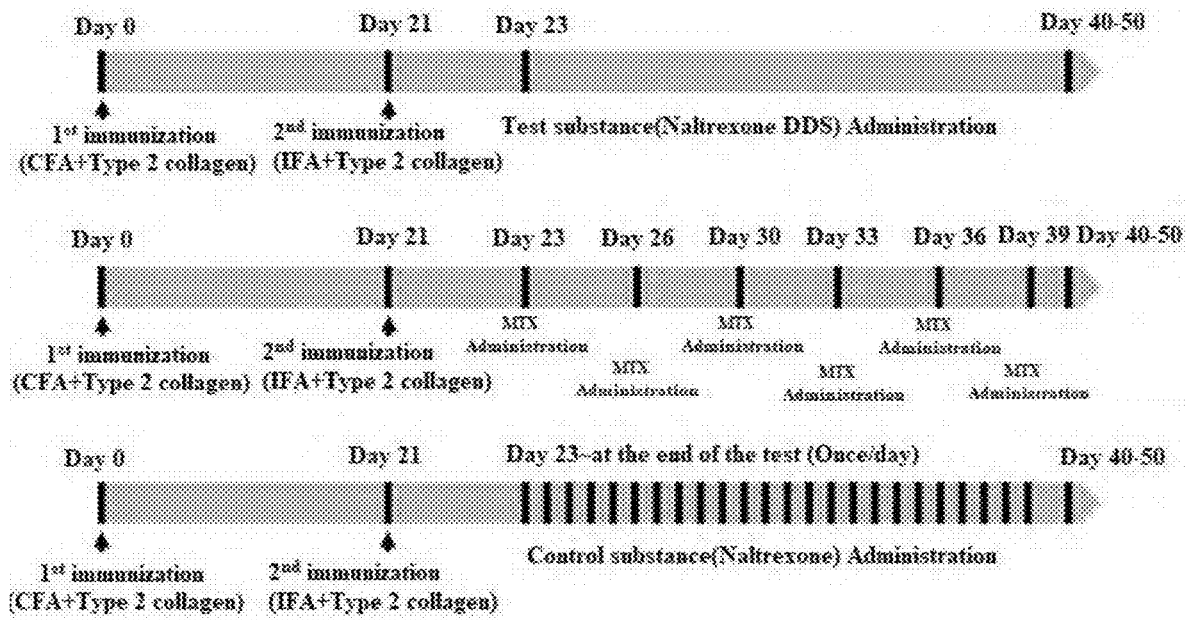

[FIG. 4B]
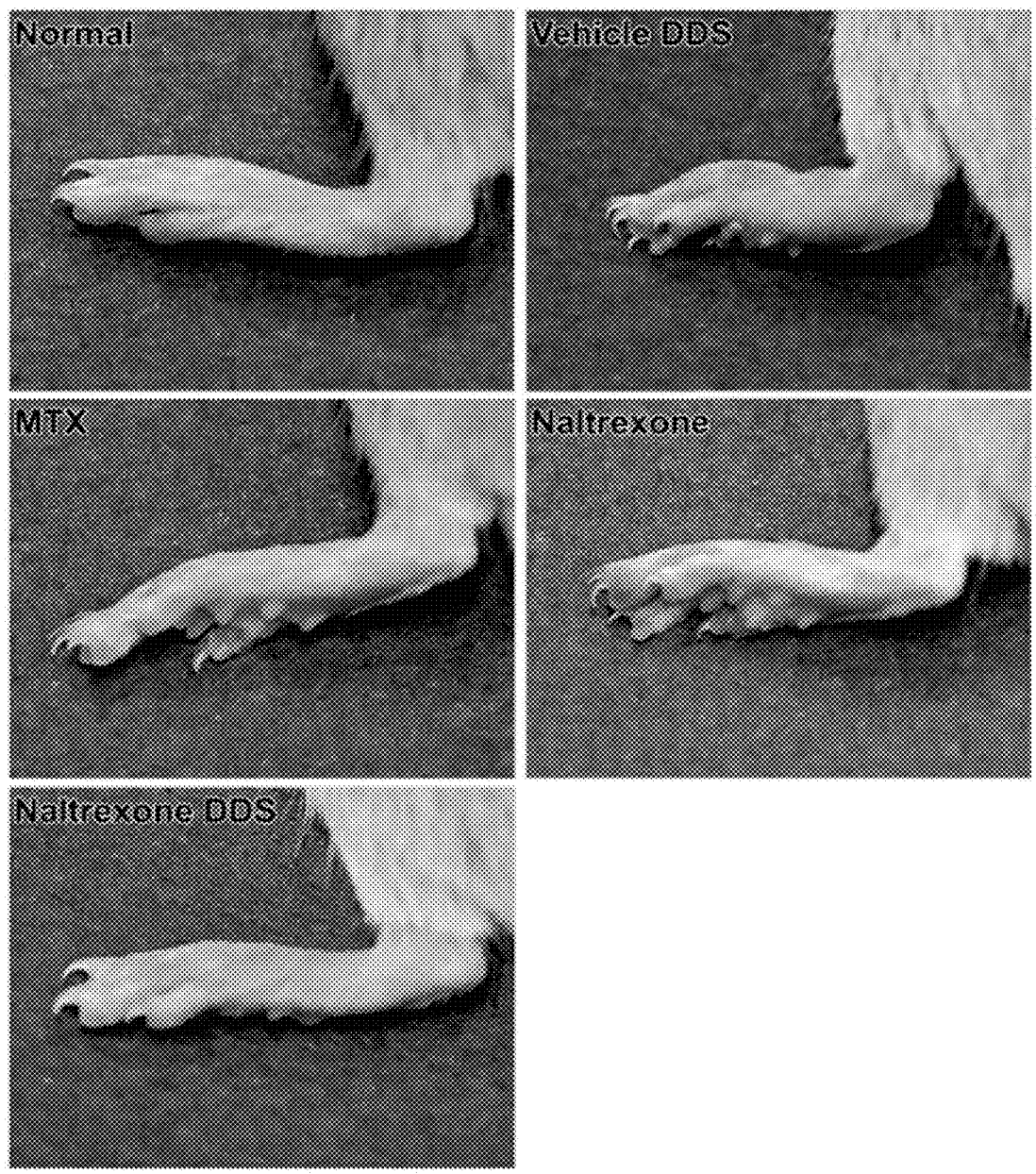

[FIG. 4C]
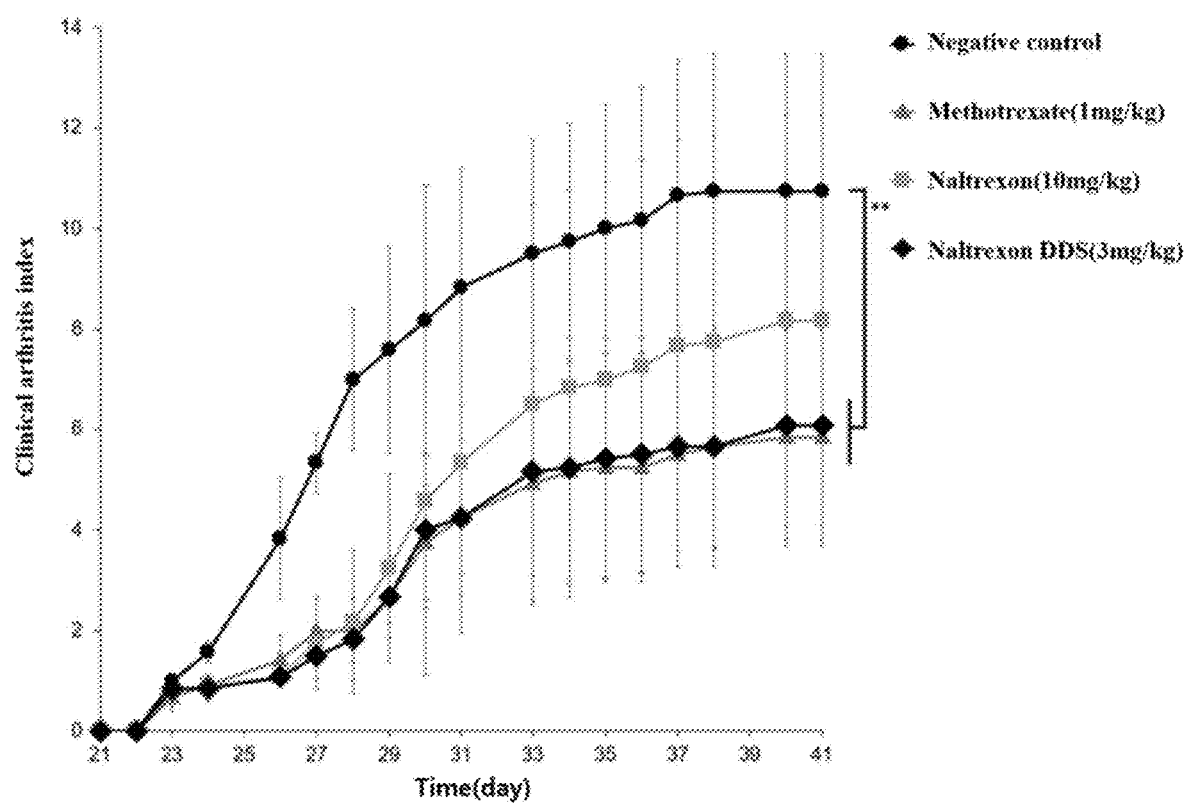

[FIG. 4D]
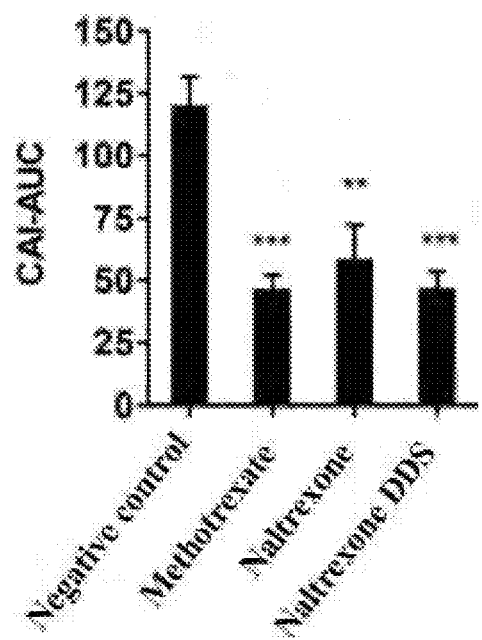

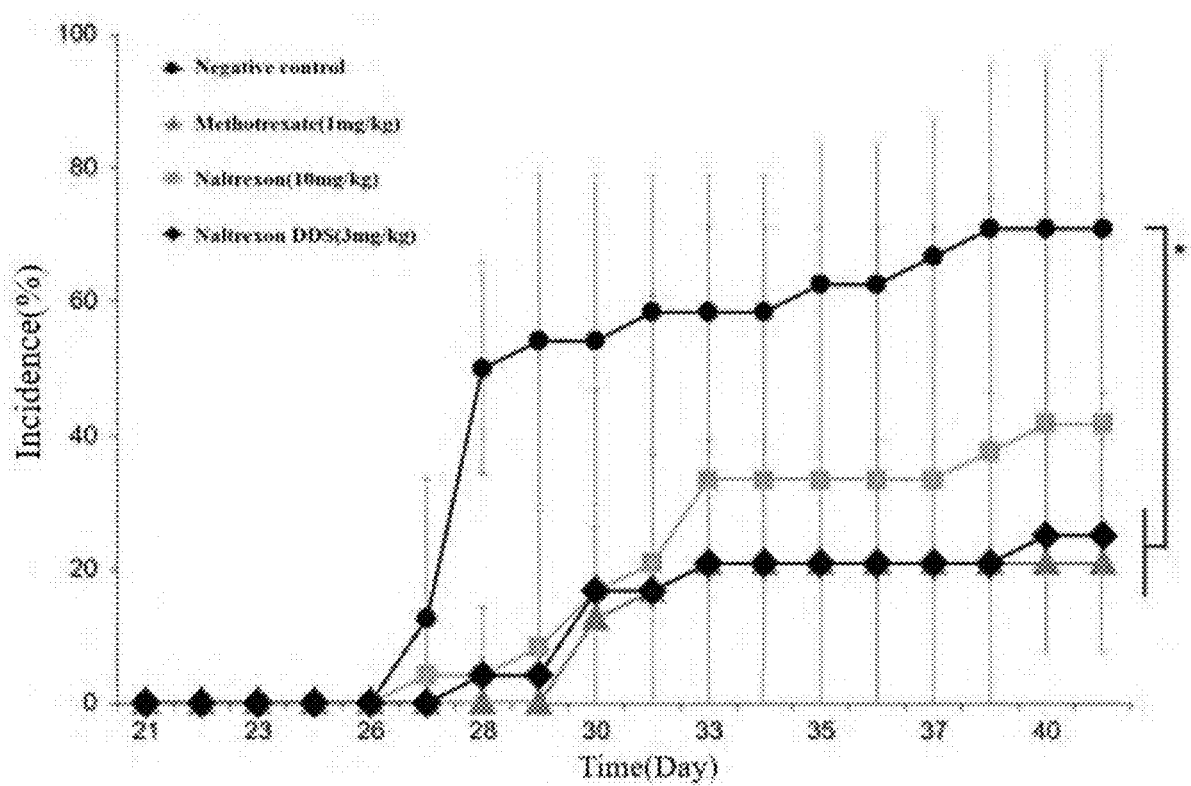
[FIG. 4E]

[FIG. 4F]
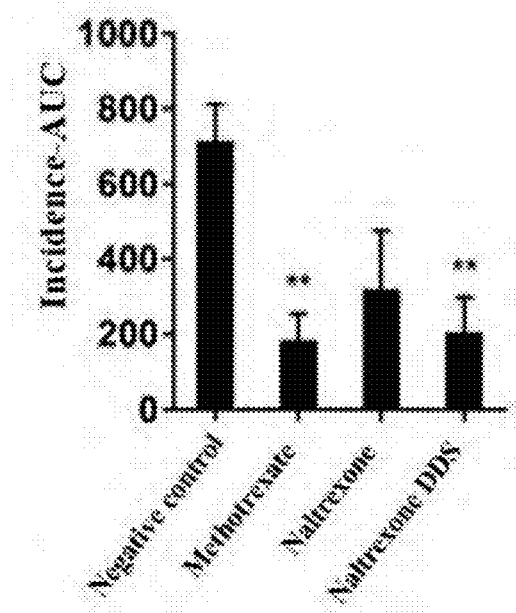
[FIG. 5A]
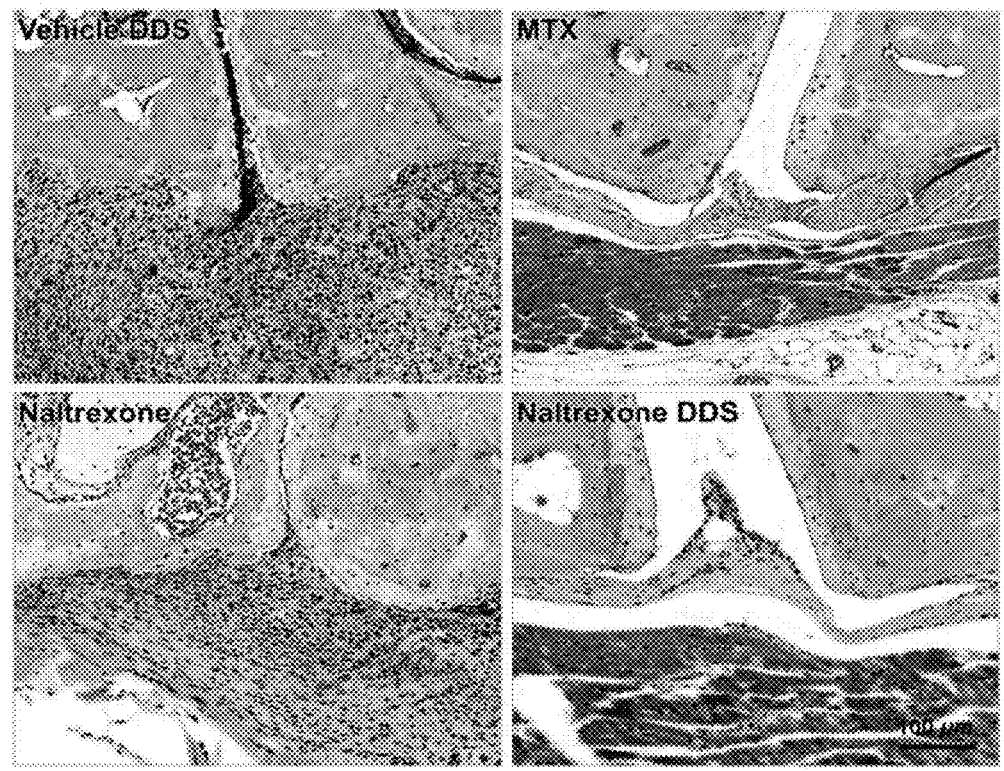

[FIG. 5B]
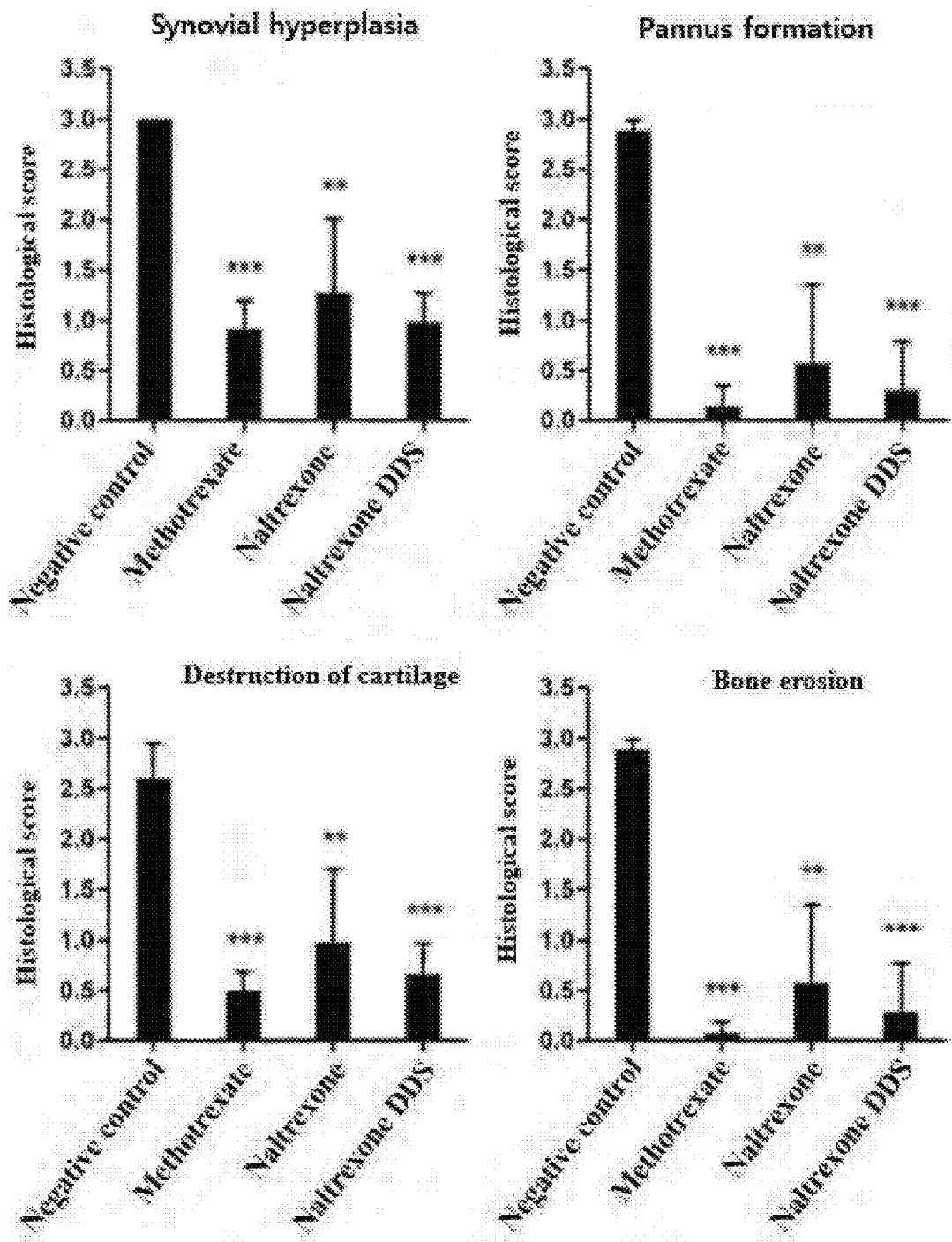

[FIG. 5C]
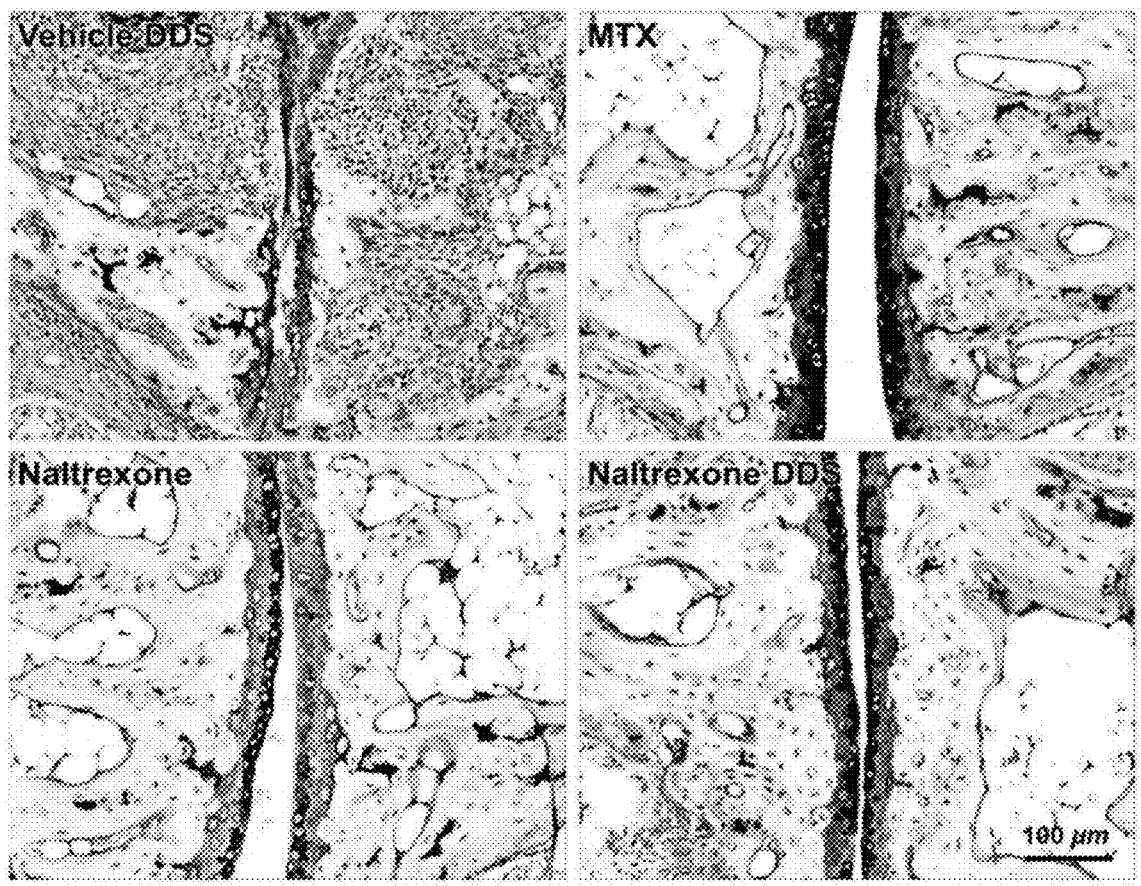

[FIG. 5D]
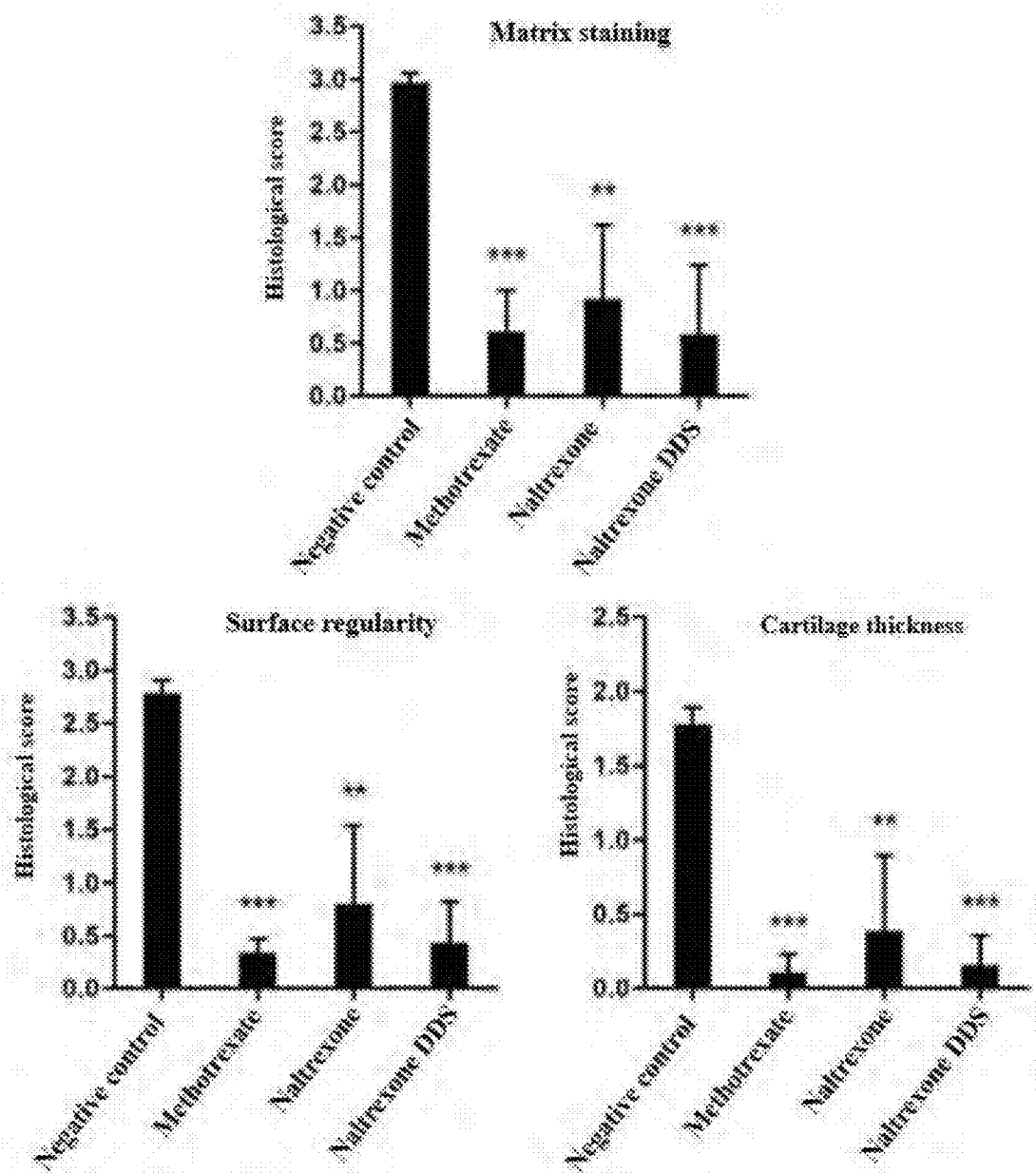

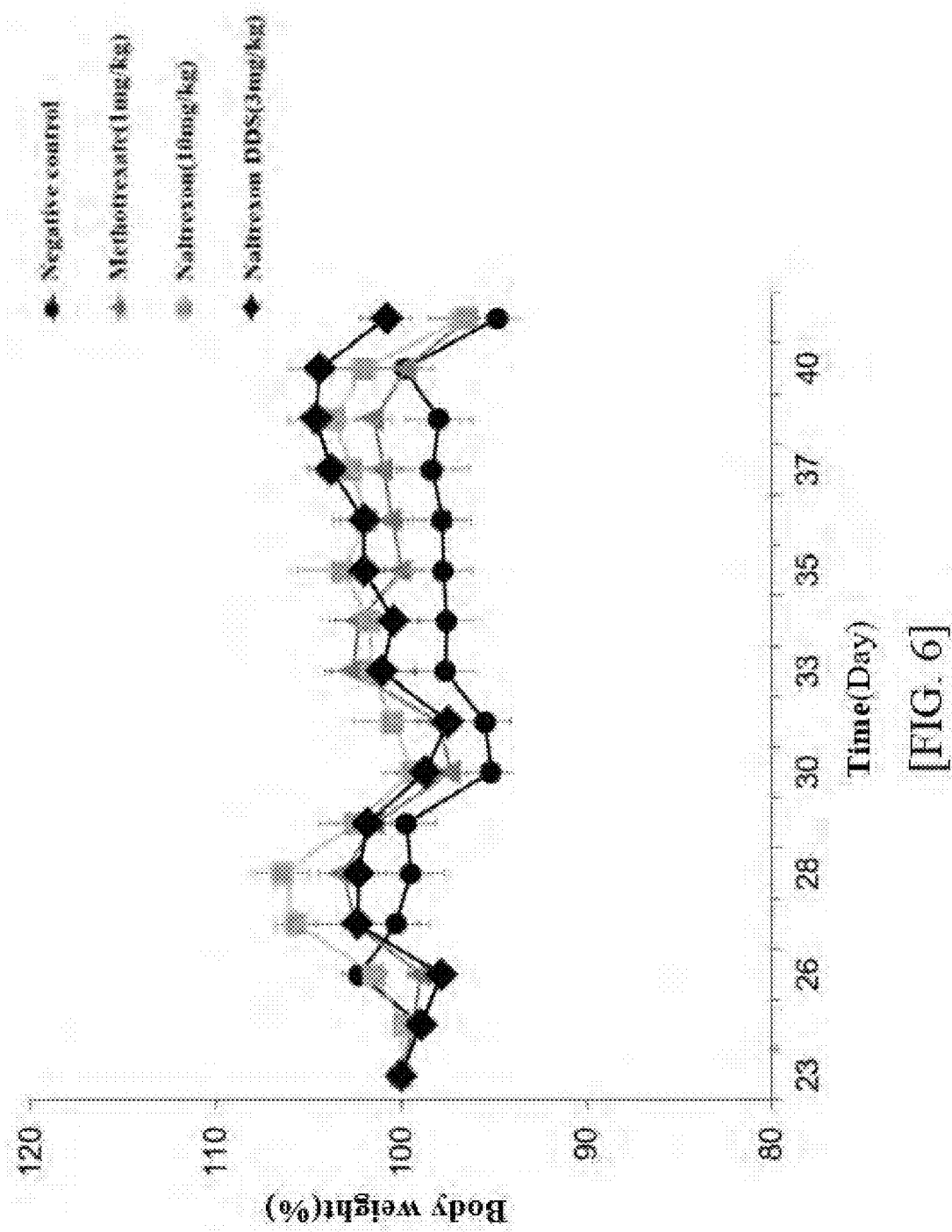
[FIG. 6]

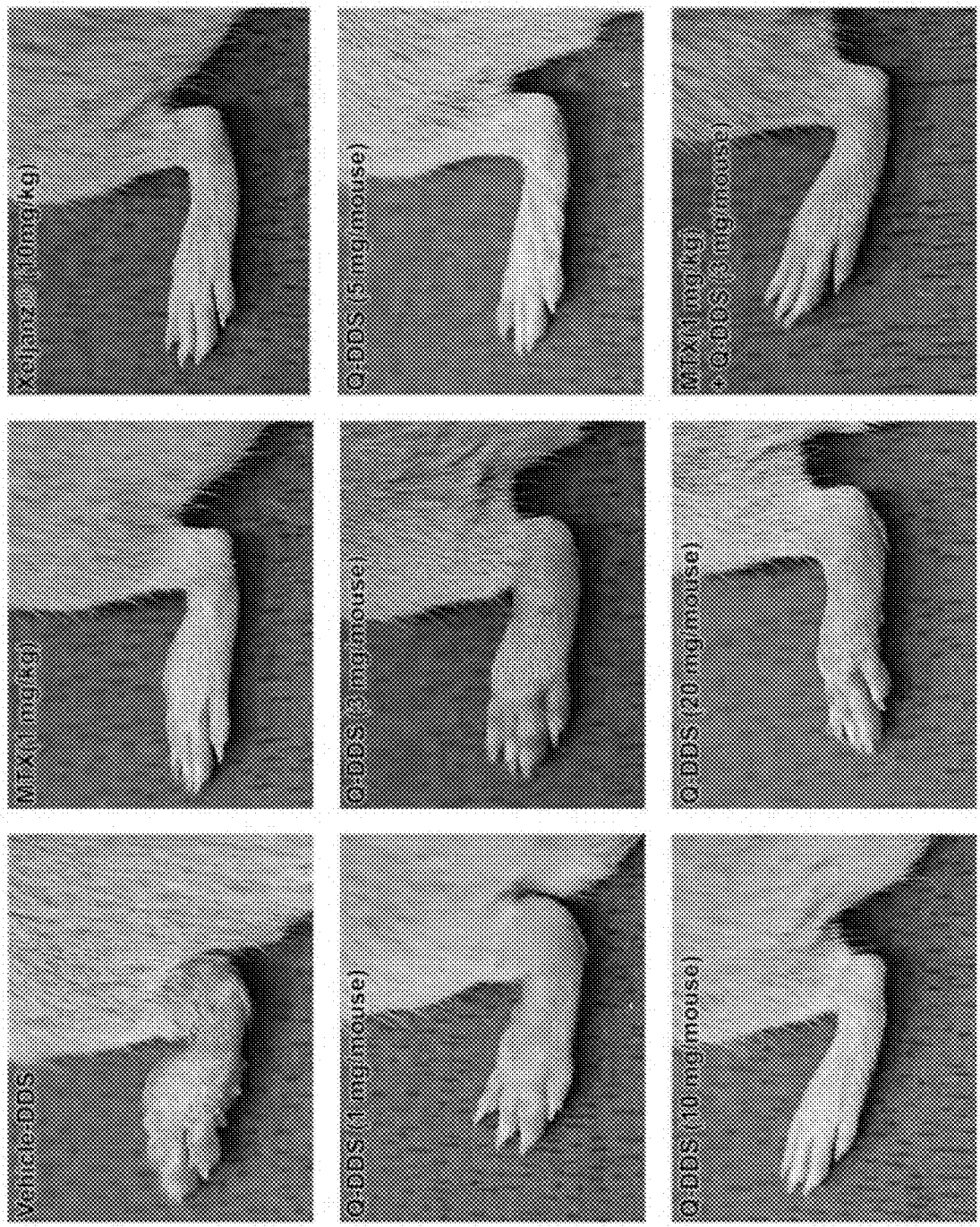
[FIG. 7A]

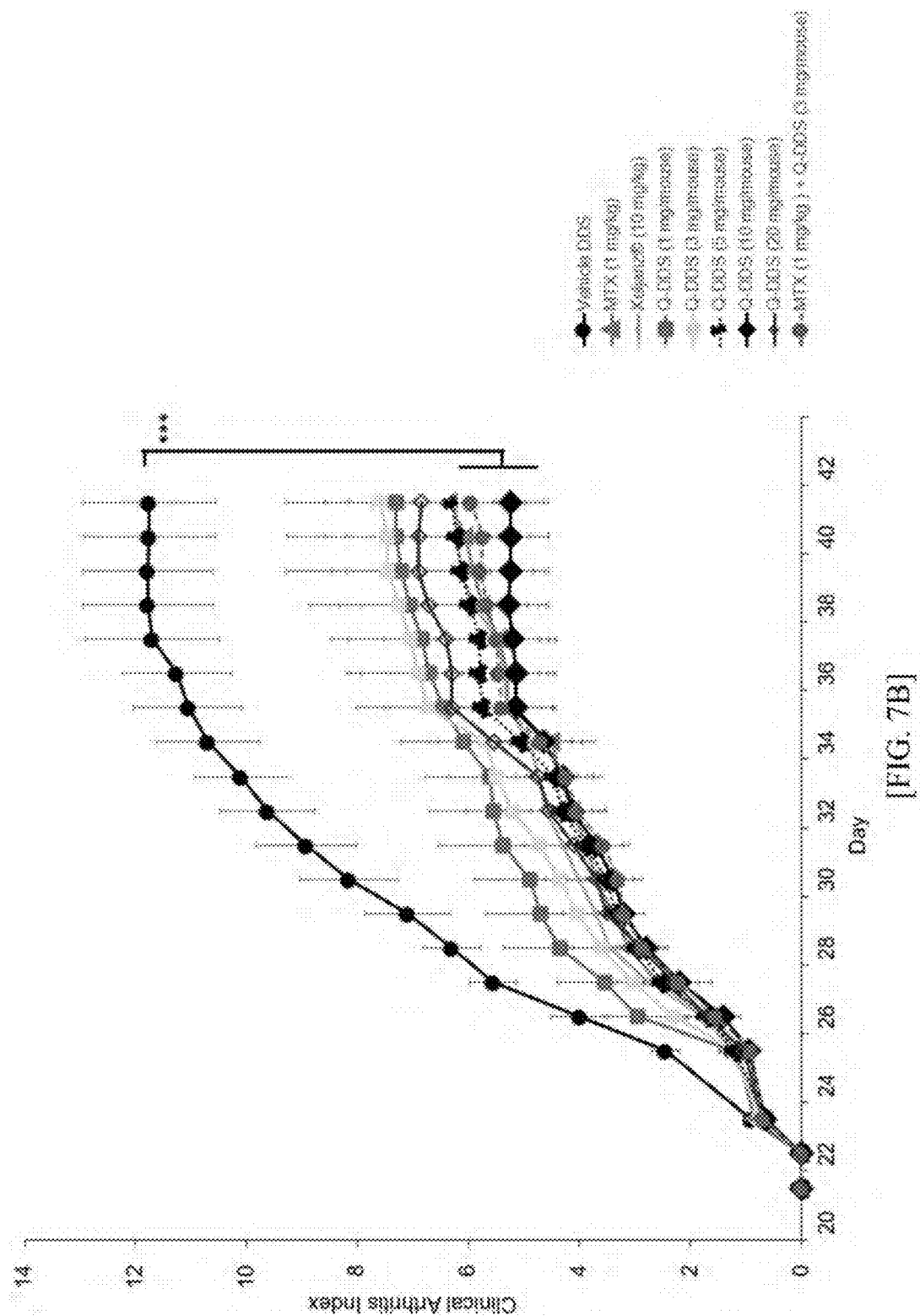
[FIG. 7B]

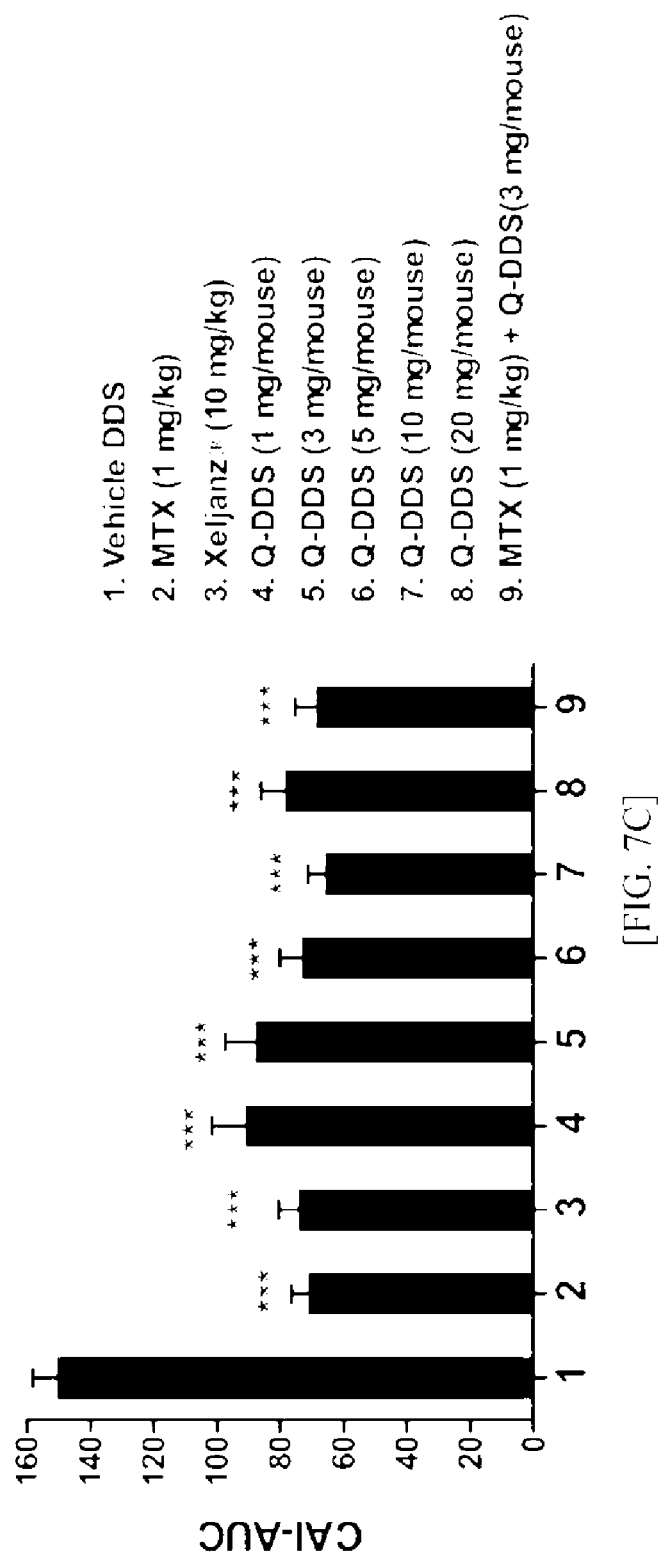

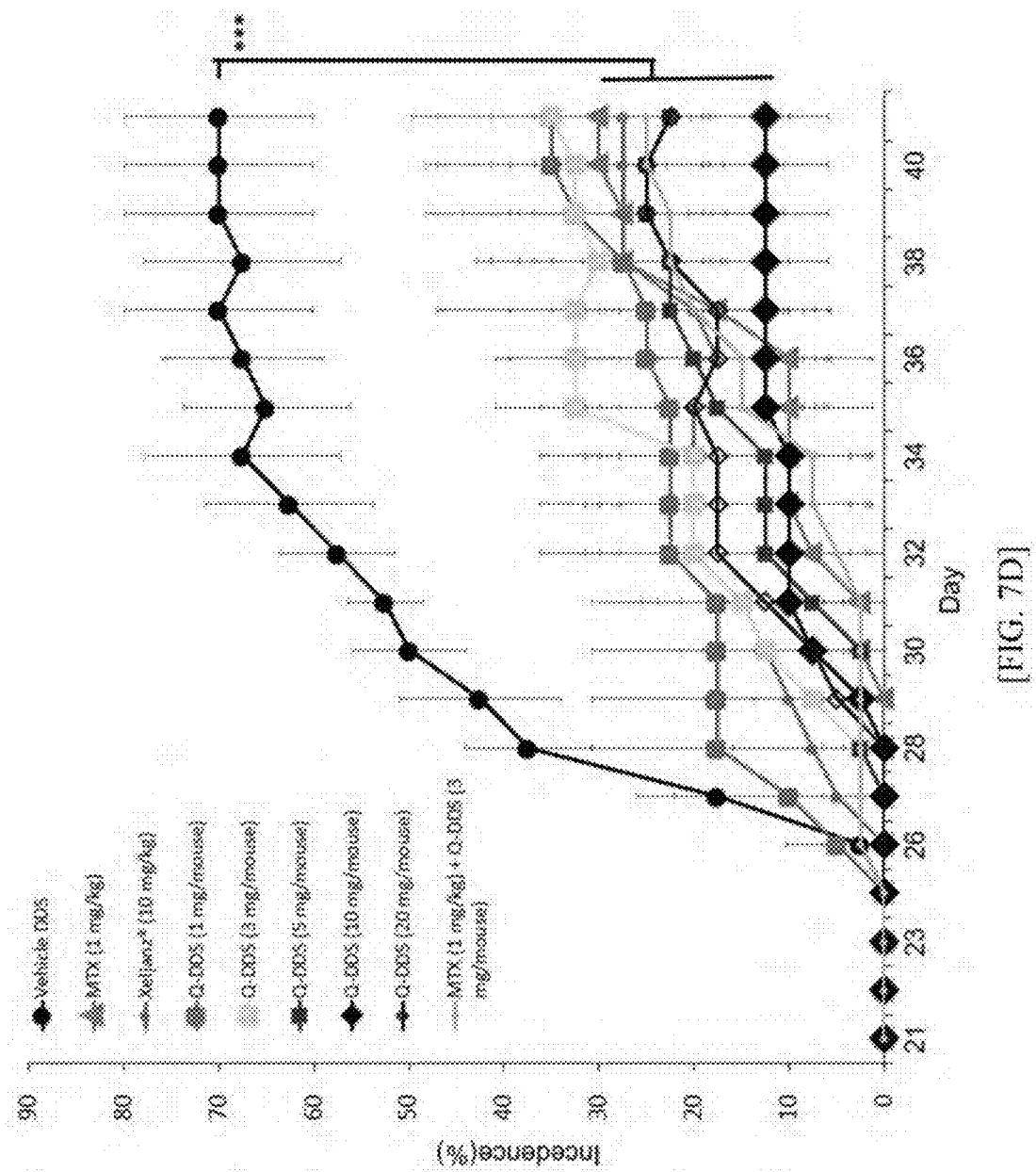
[FIG. 7D]

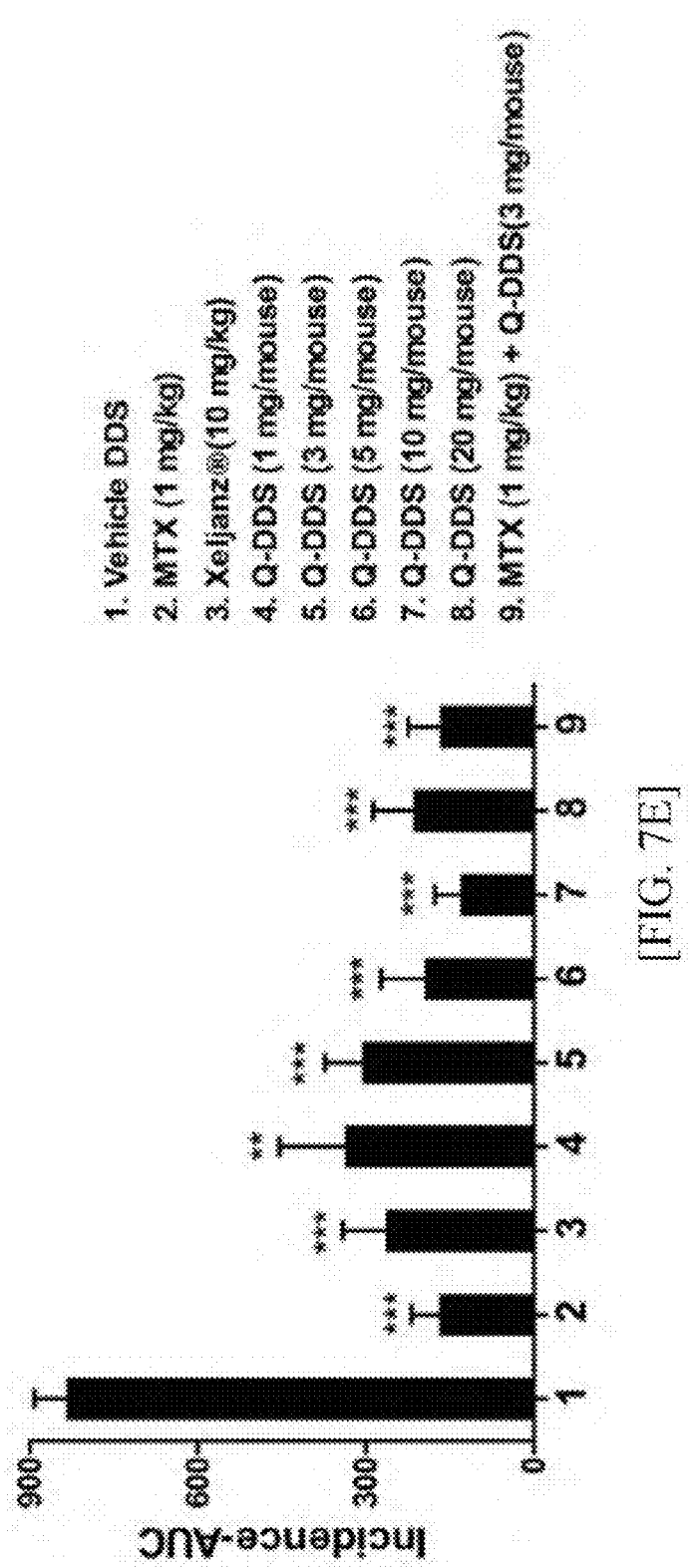
[FIG. 7E]

[FIG. 8A]
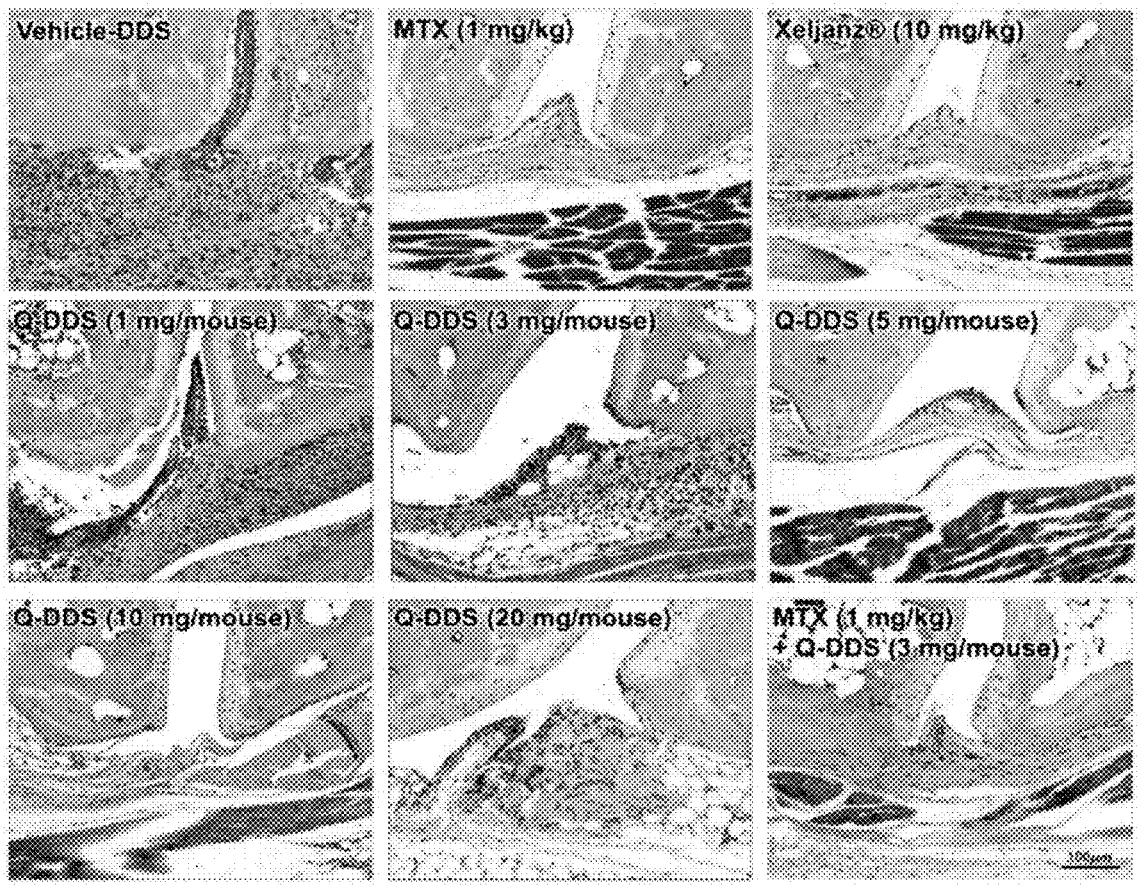

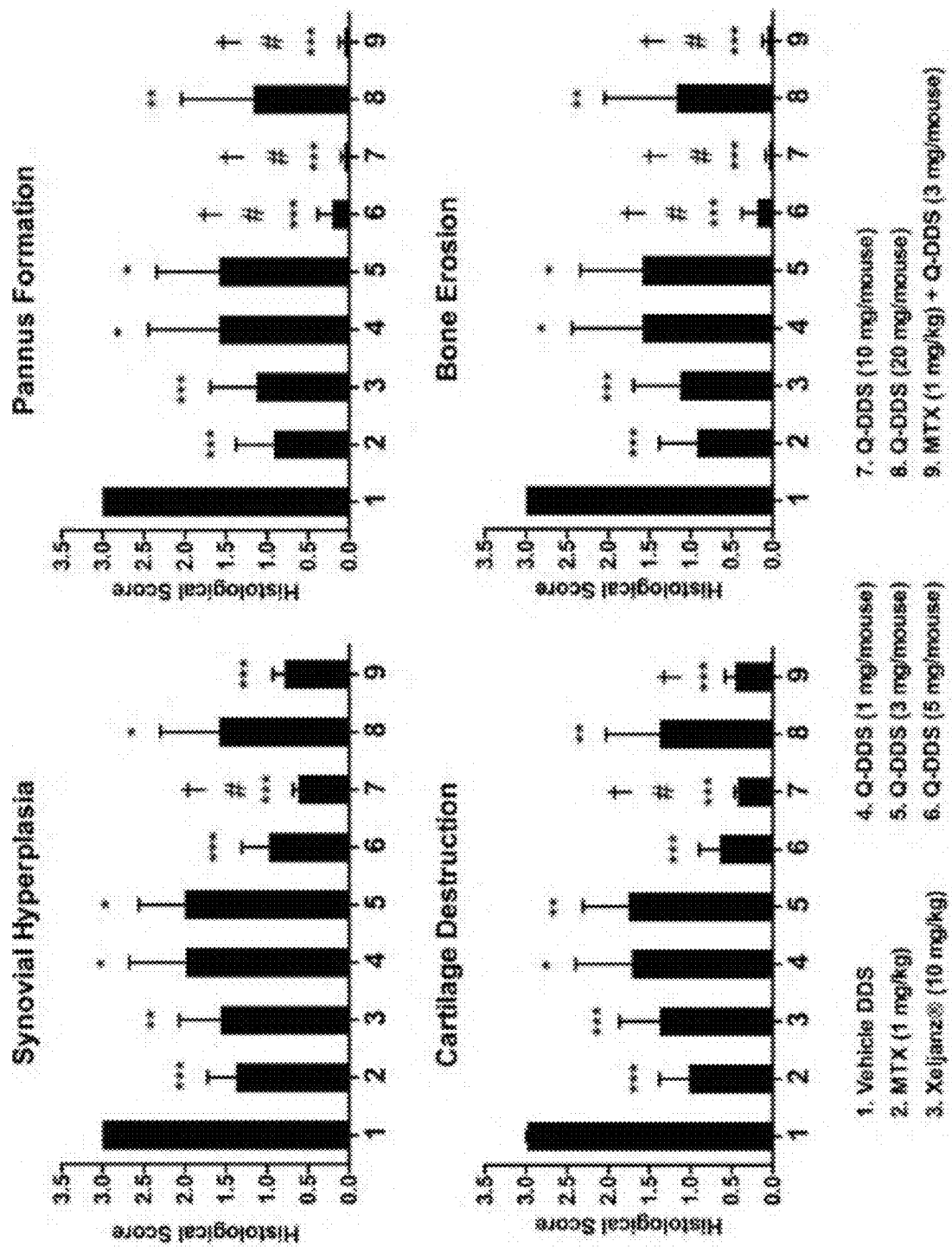
[FIG. 8B]

[FIG. 9A]
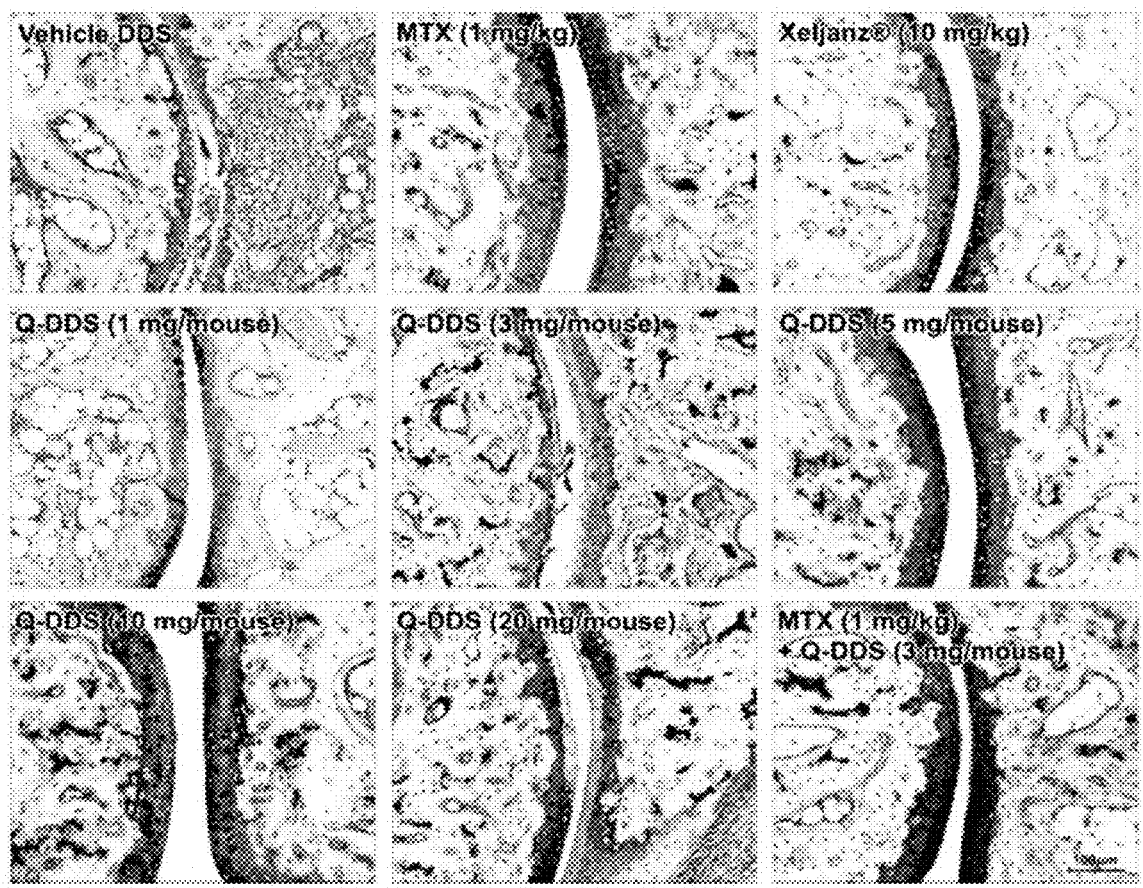

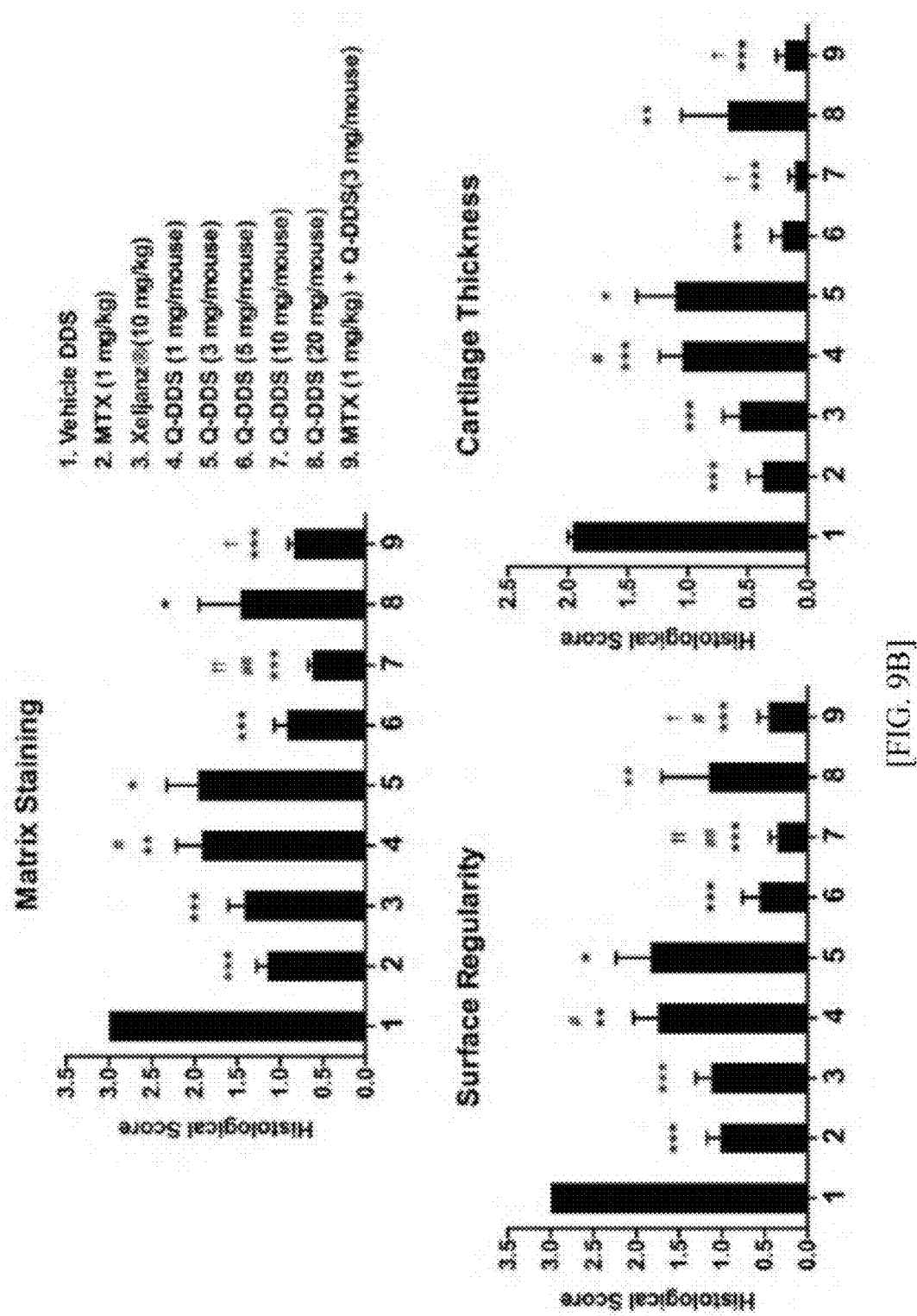
[FIG. 9B]

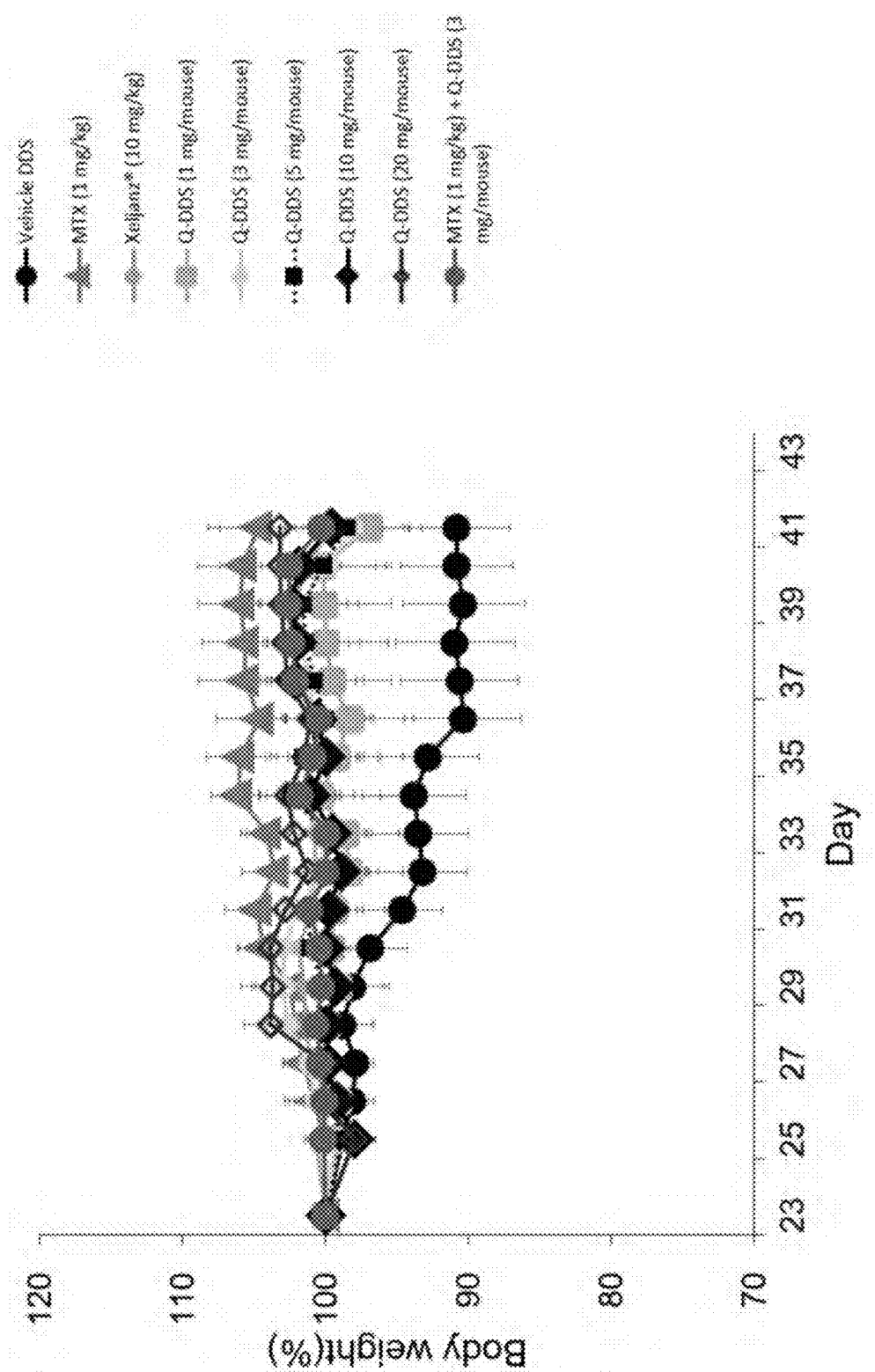
[FIG. 10]

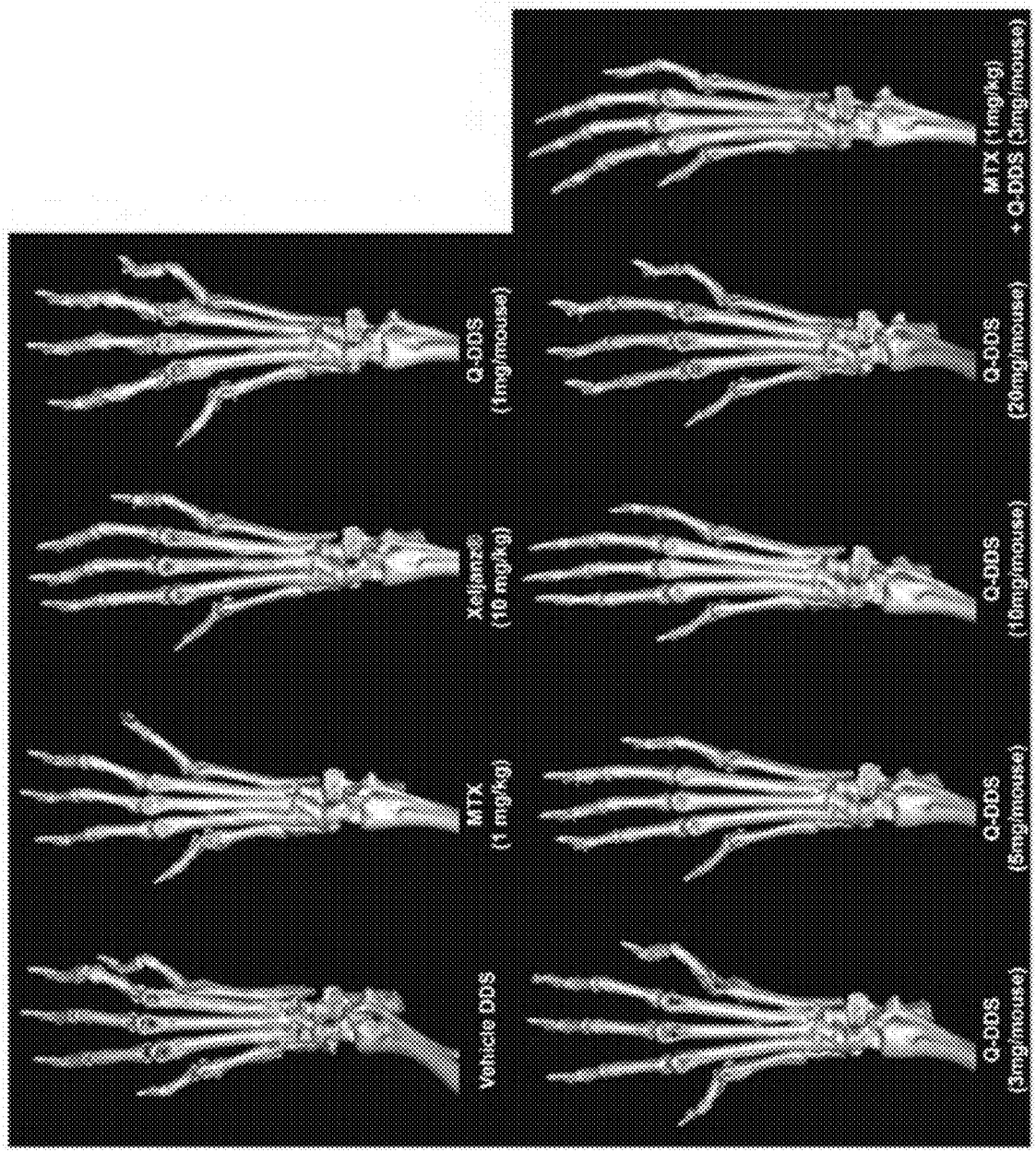
[FIG. 11A]

[FIG. 11B]
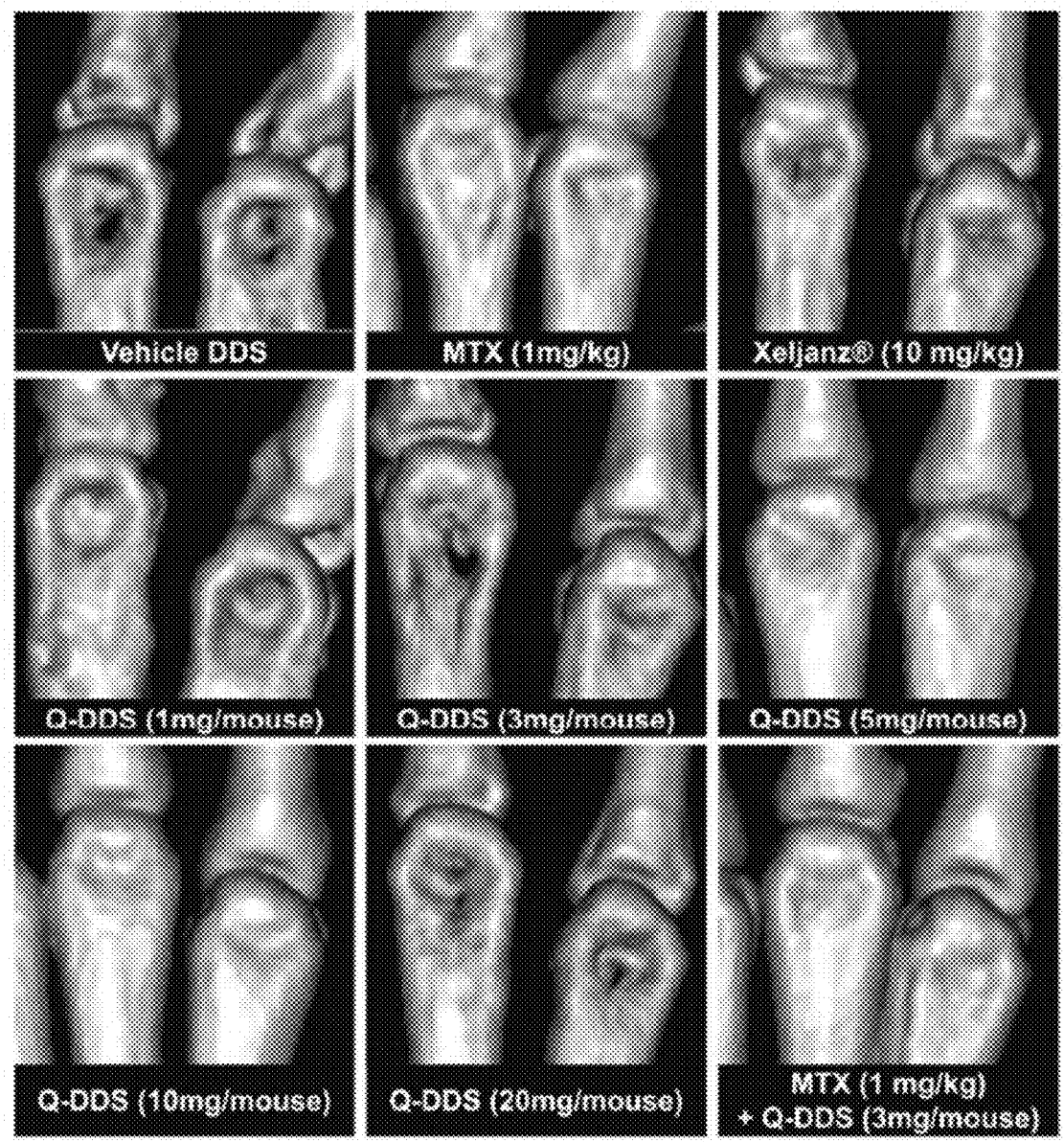

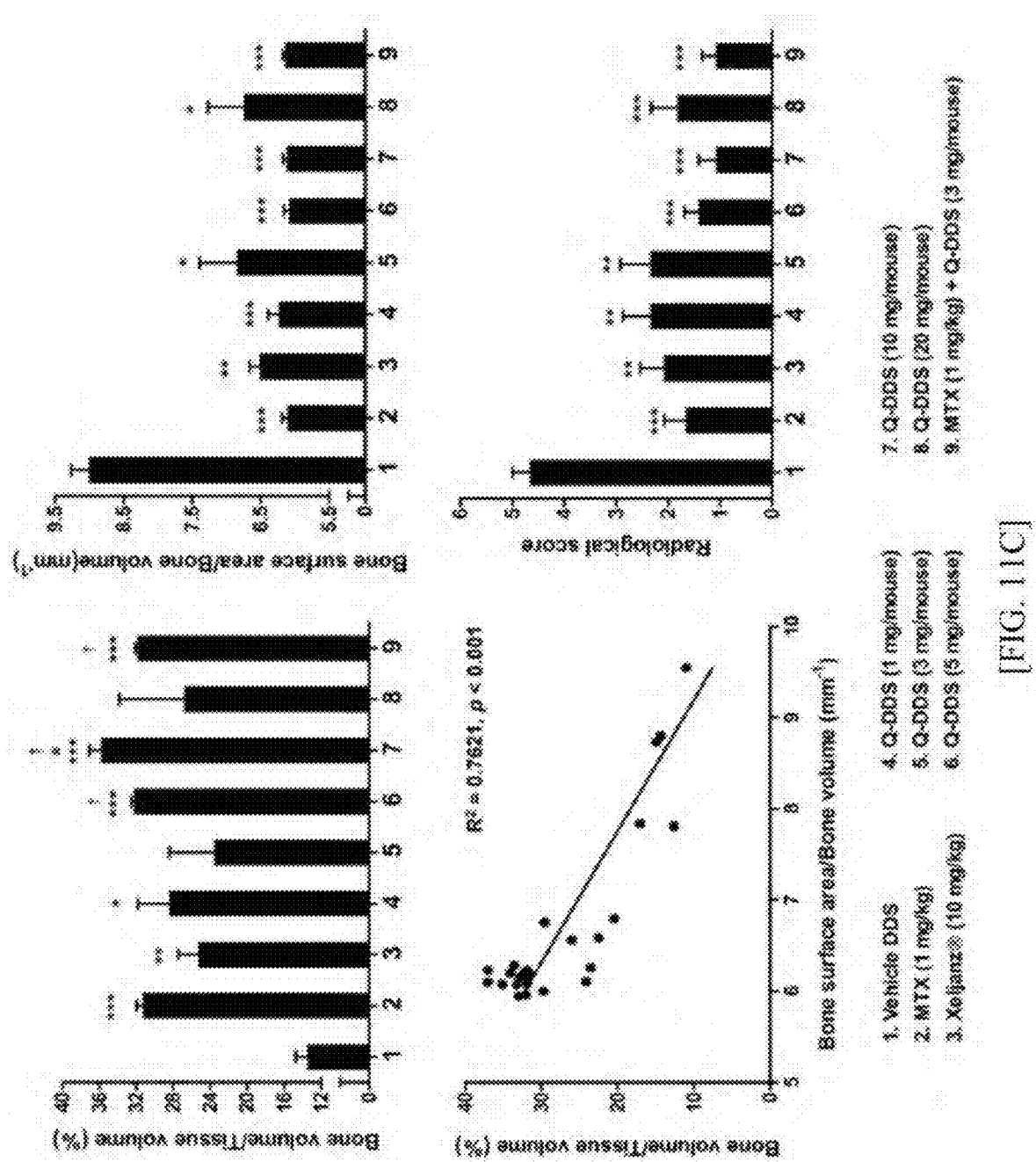
[FIG. 11C]

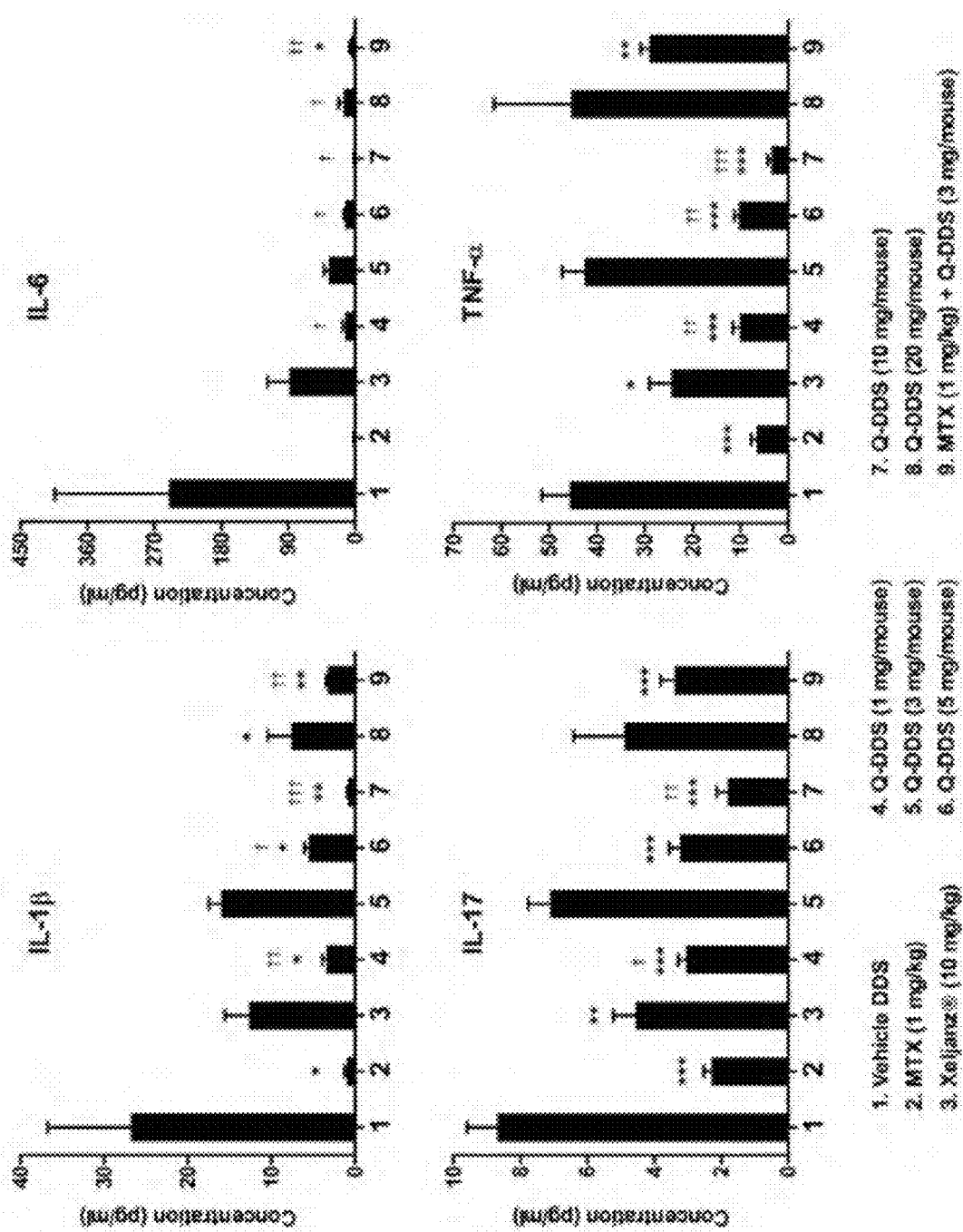
[FIG. 12A]

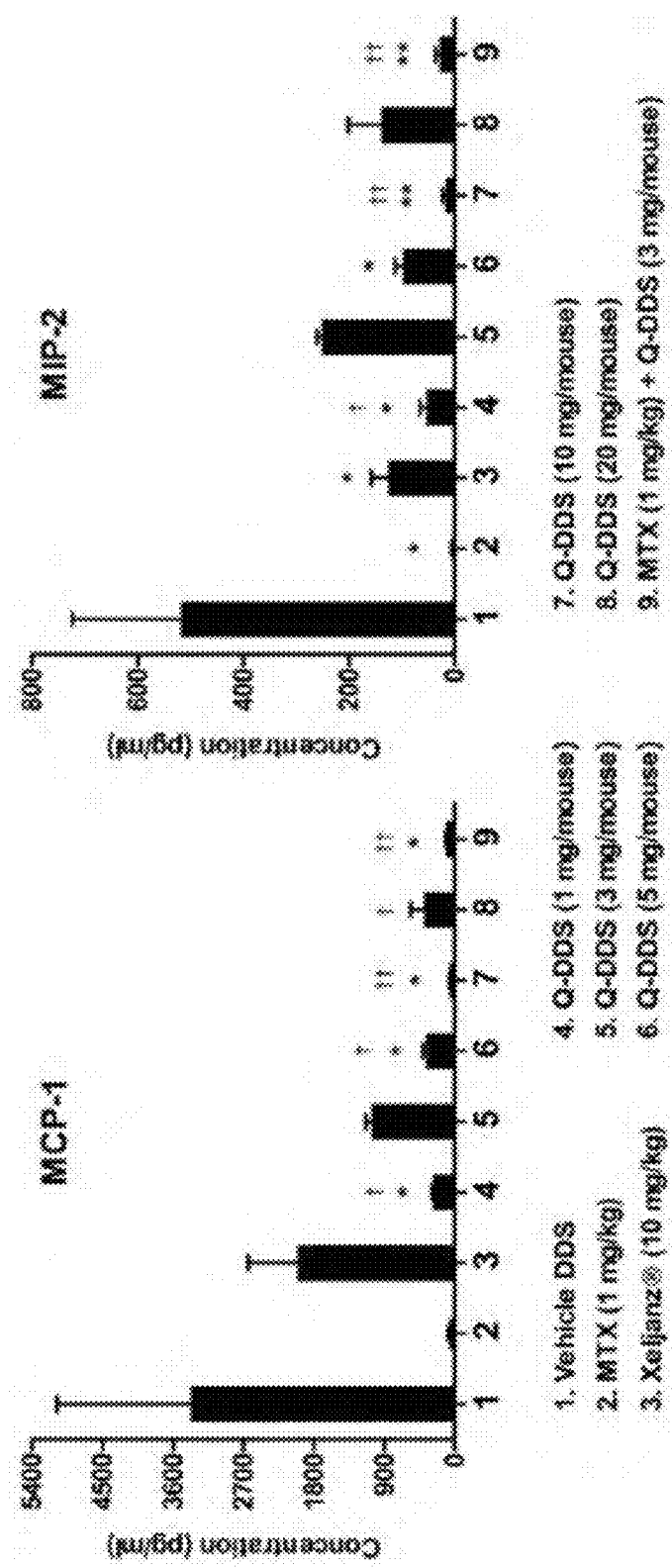
[FIG. 12B]

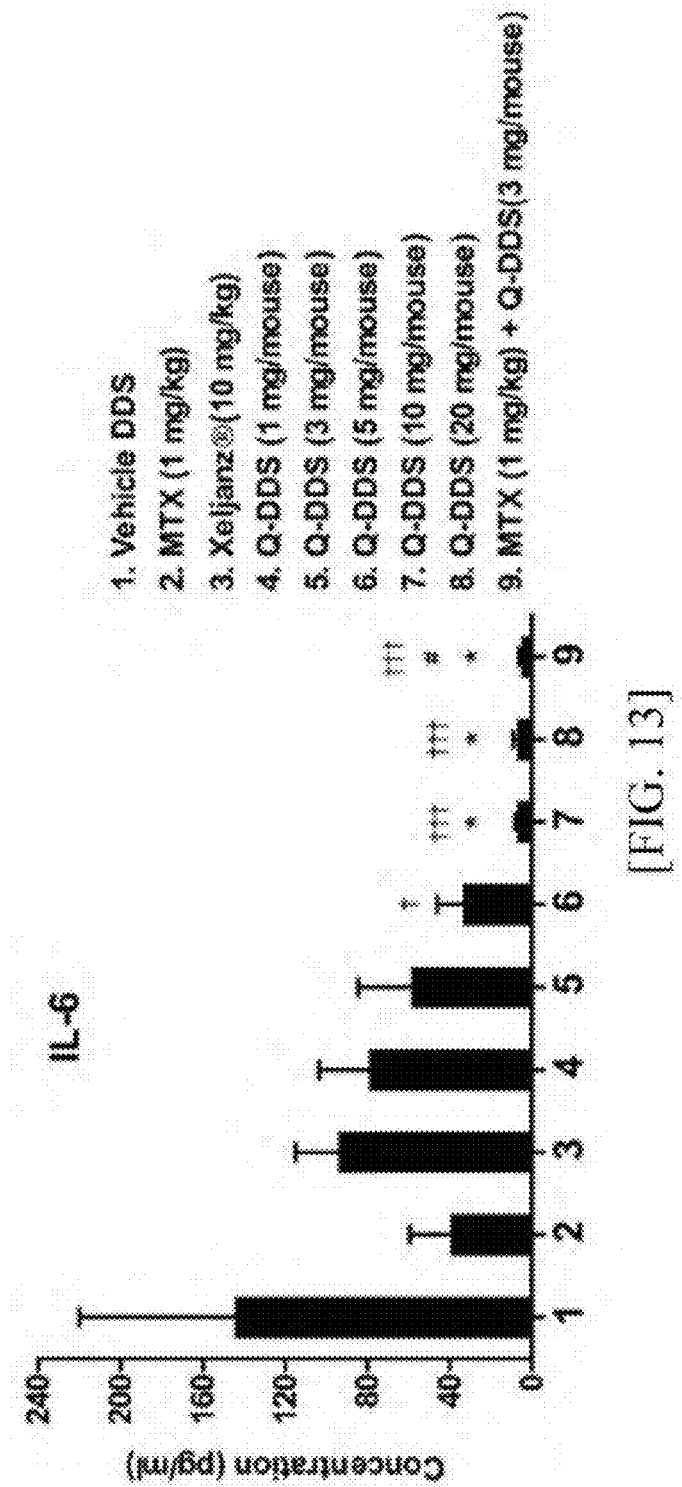
[FIG. 13]

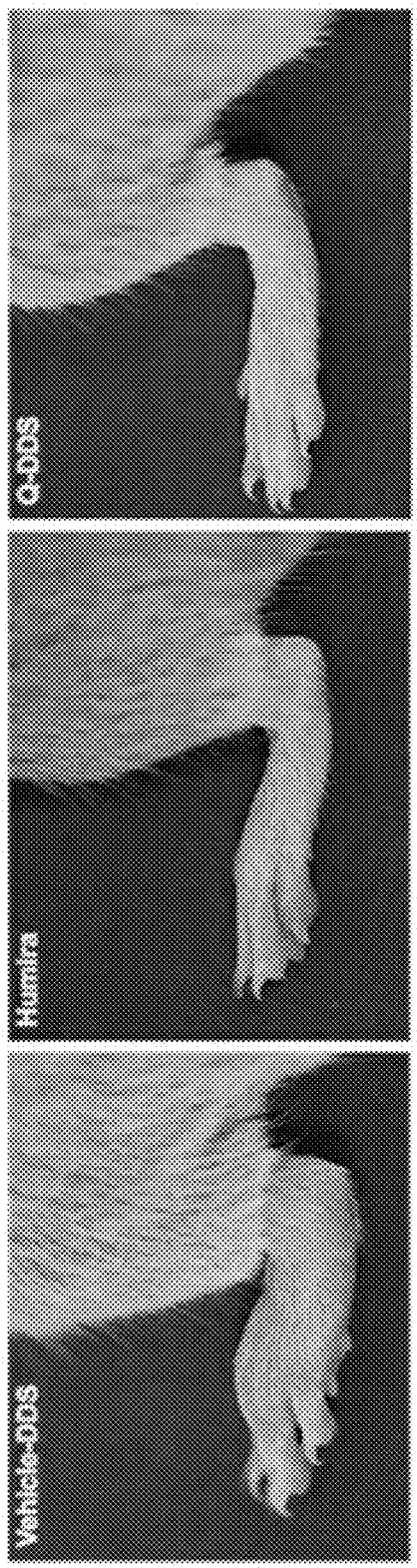
[FIG. 14A]

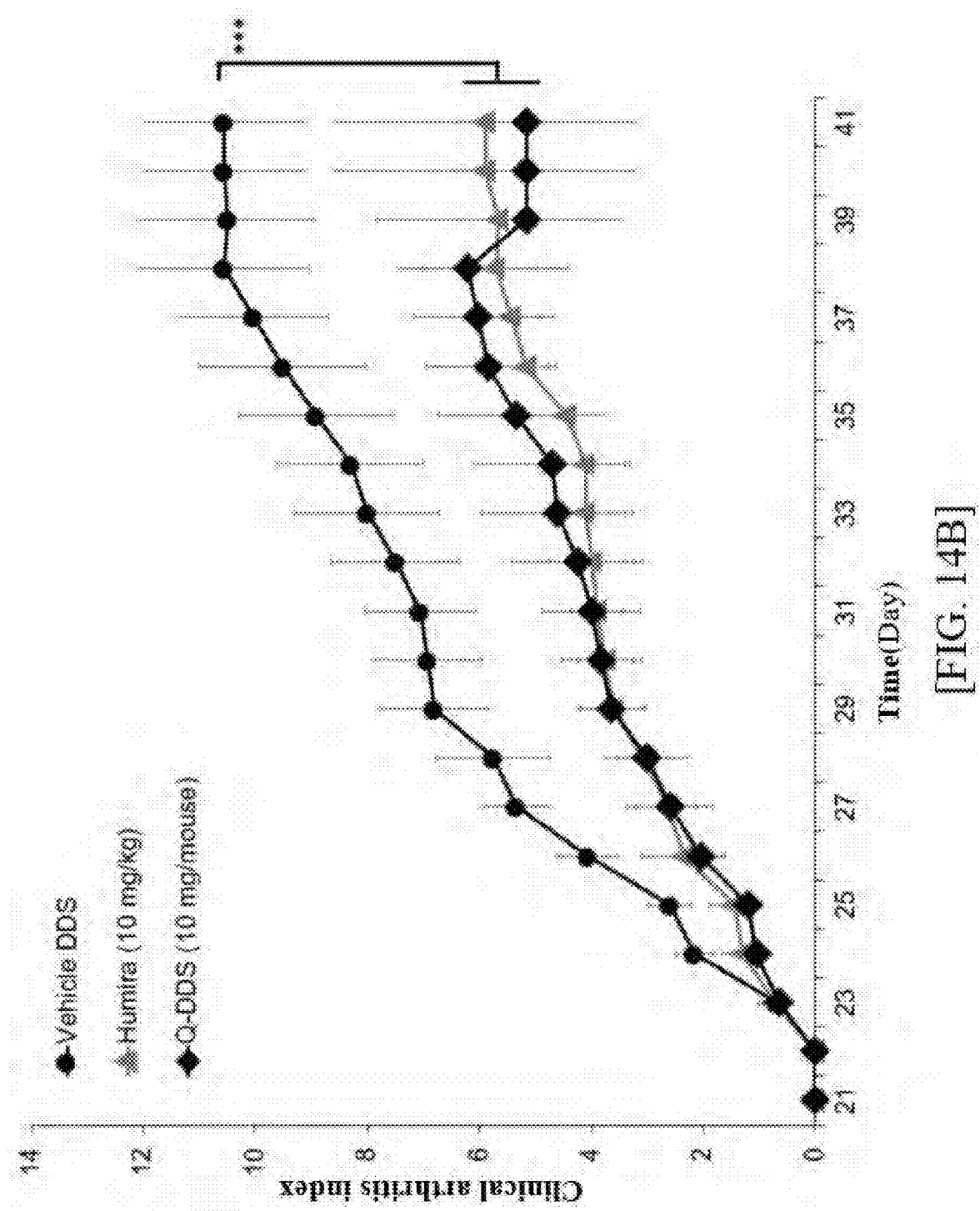
[FIG. 14B]

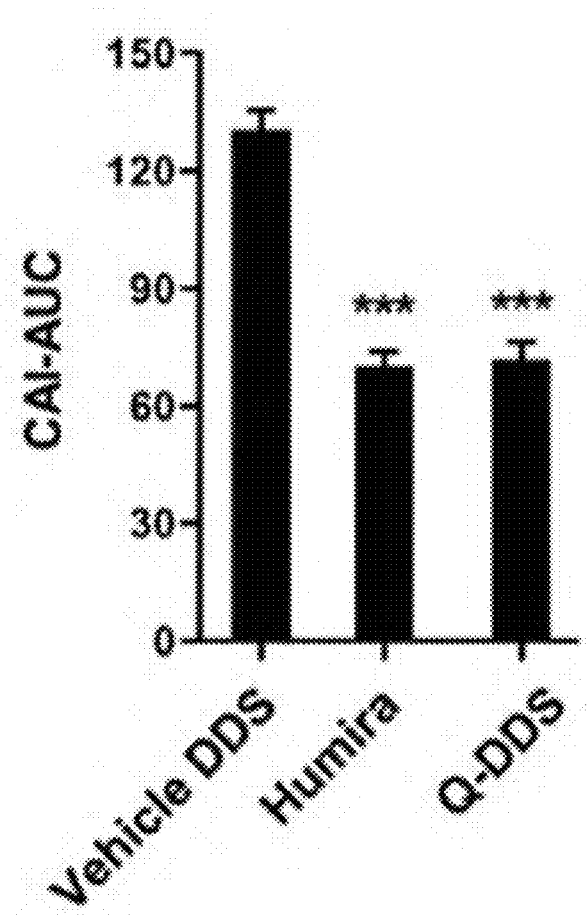
[FIG. 14C]

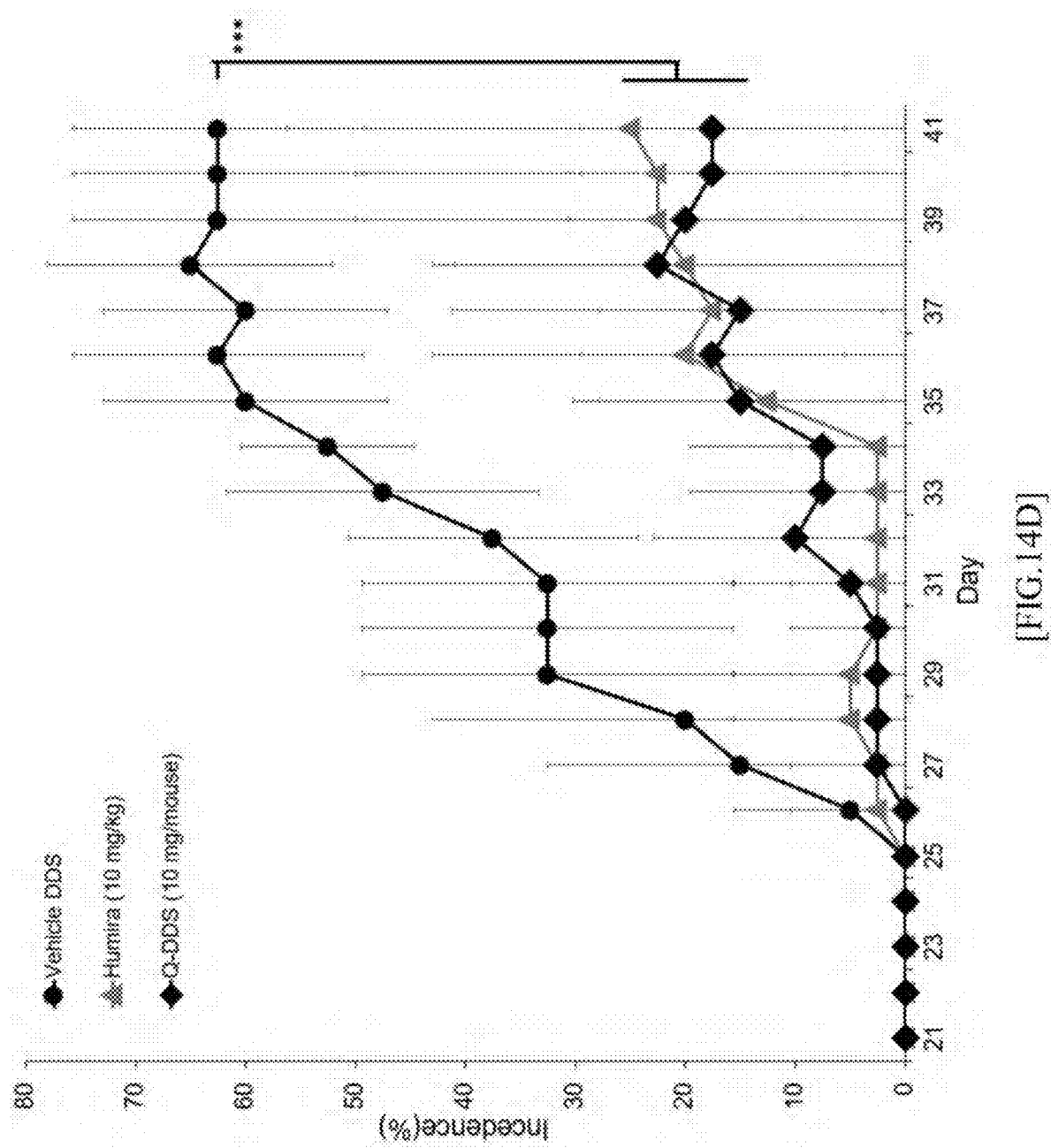
[FIG.14D]

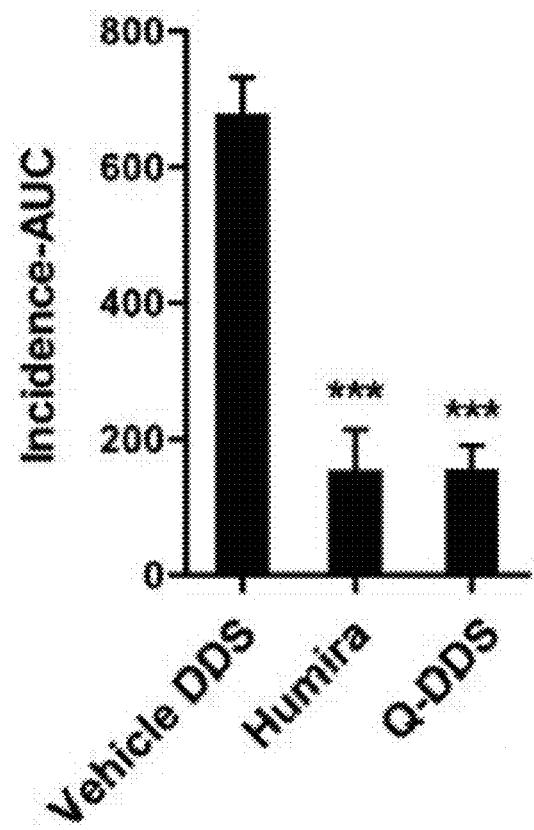
[FIG. 14E]

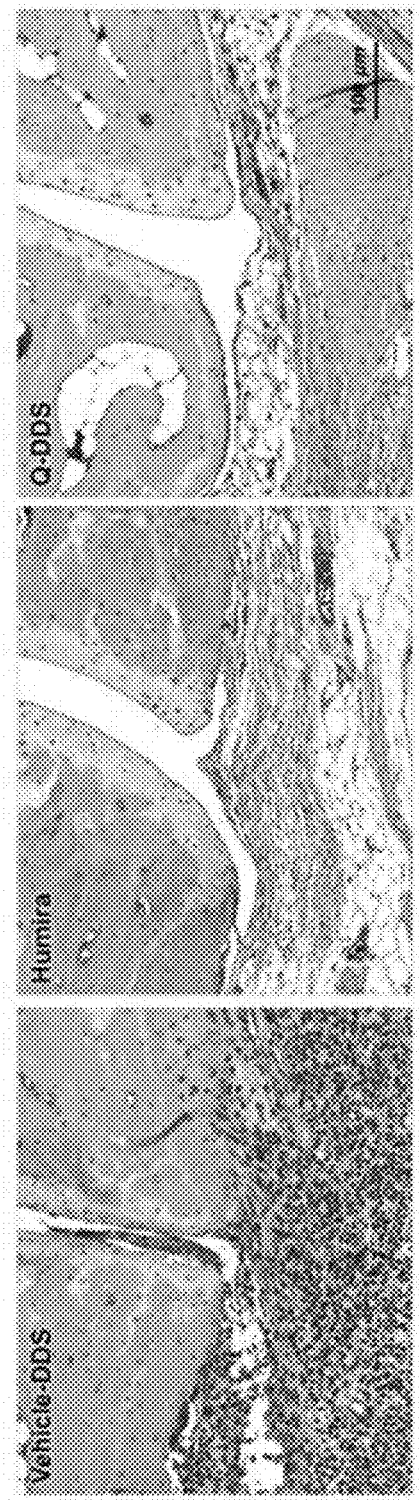
[FIG. 15A]

[FIG. 15B]
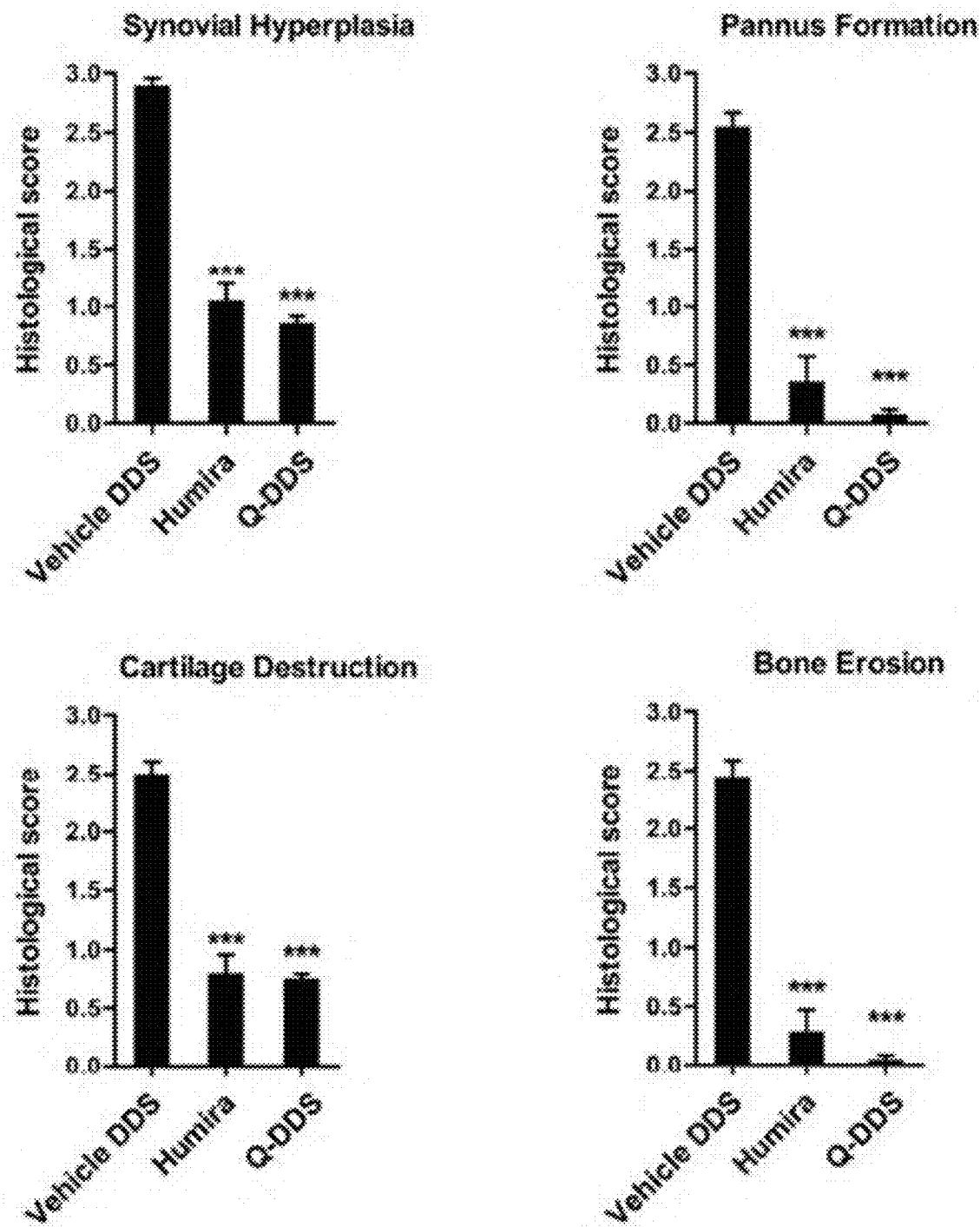

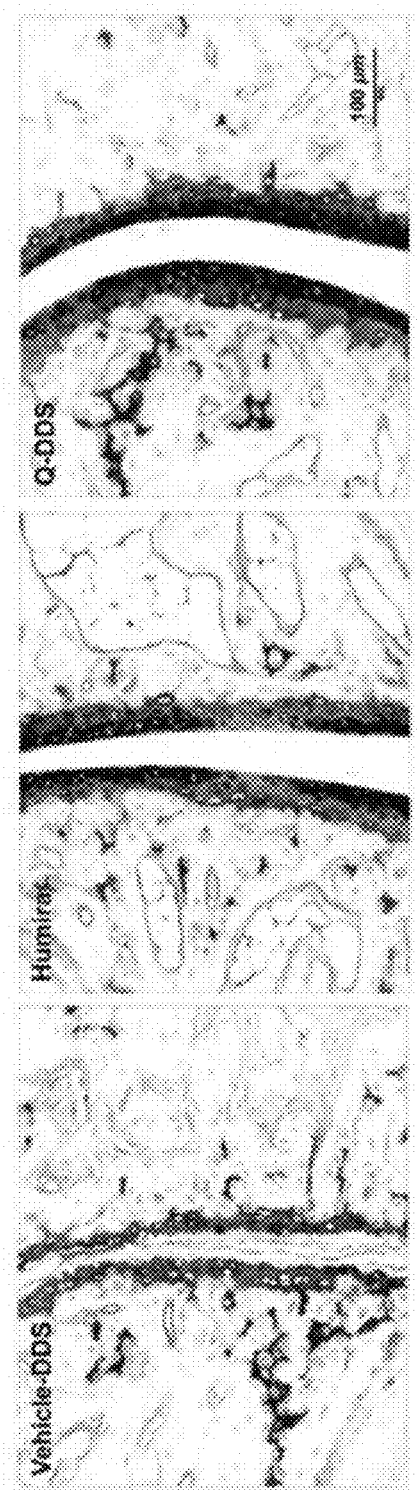
[FIG. 15C]

[FIG. 15D]
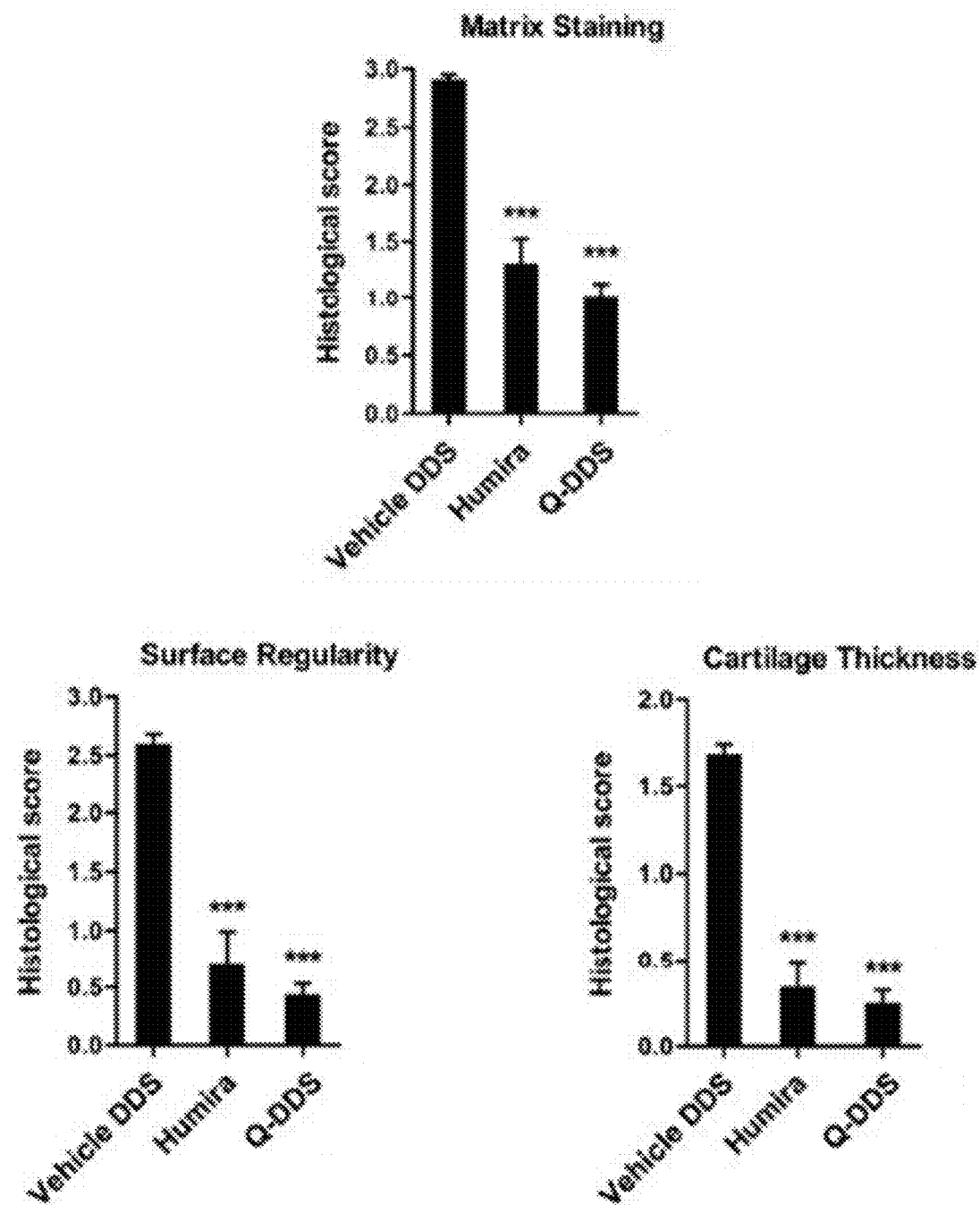

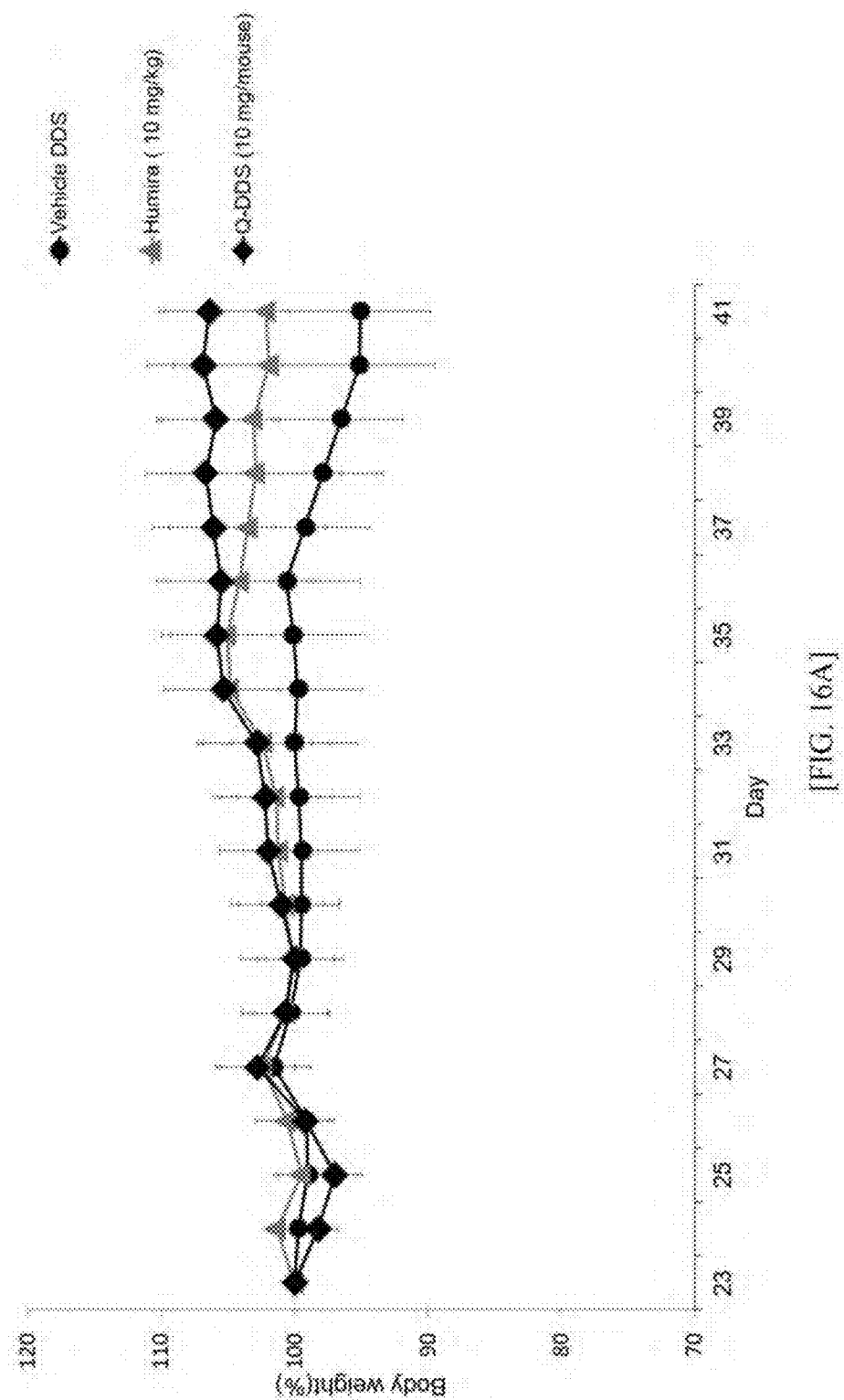
[FIG. 16A]

[FIG. 16B]
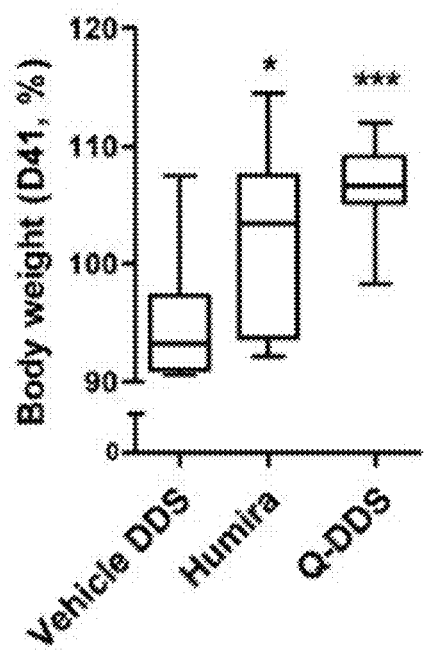
[FIG. 17A]
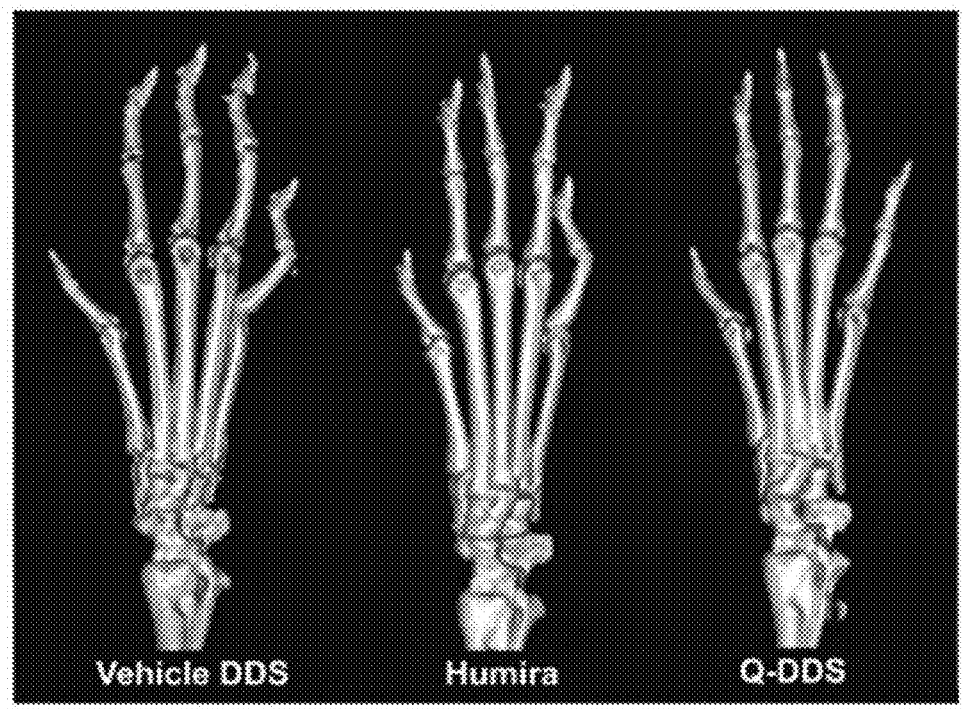

[FIG. 17B]
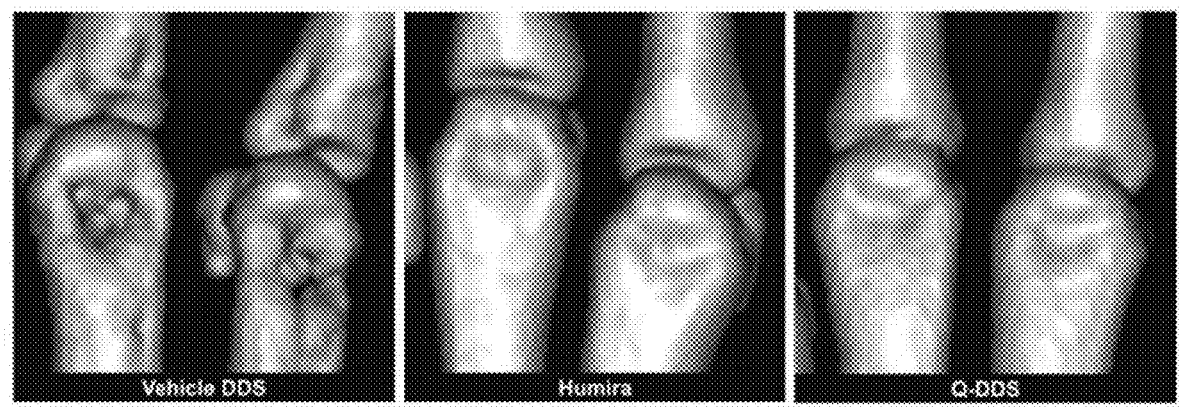

[FIG. 17C]
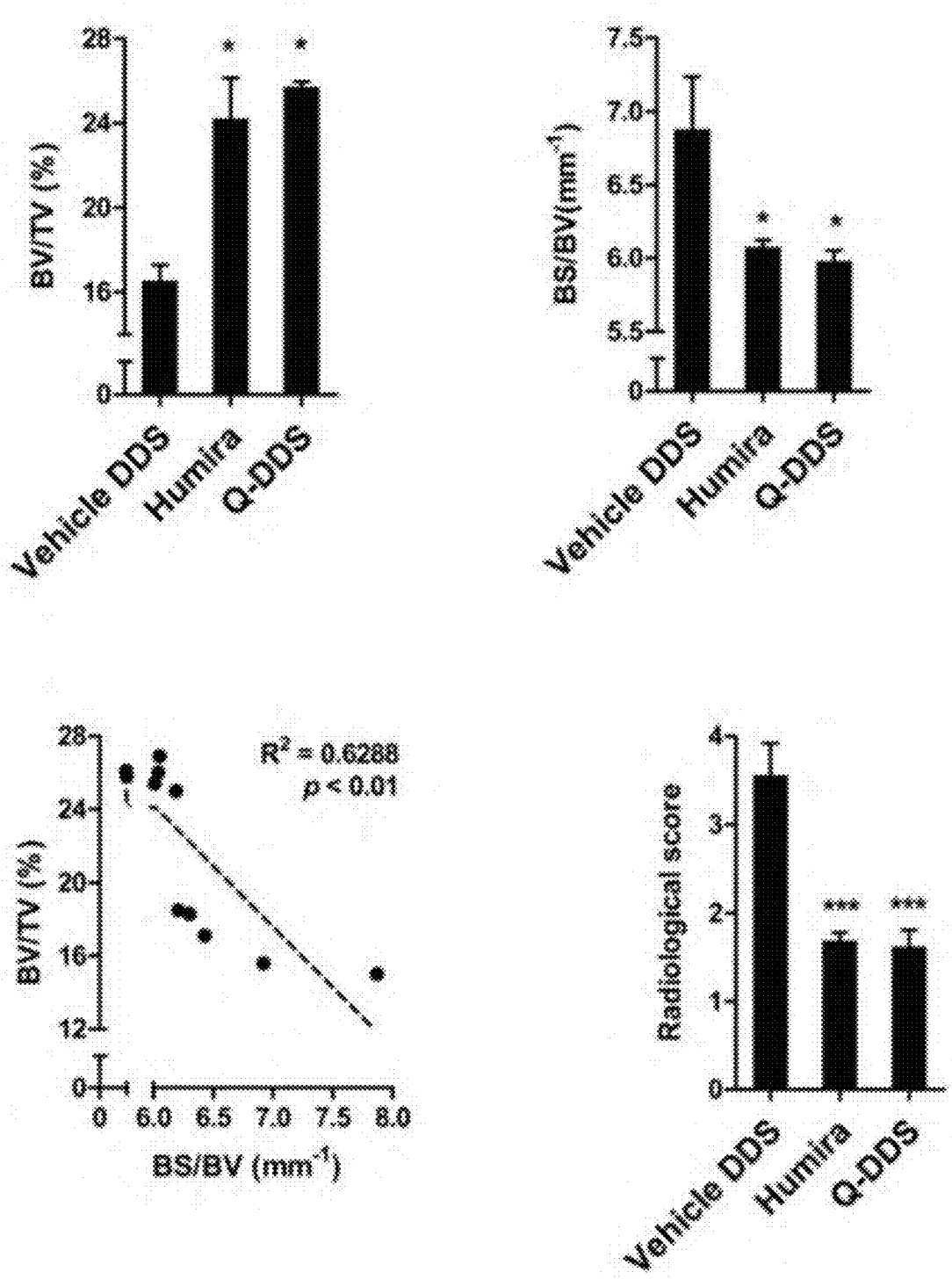

[FIG. 18A]
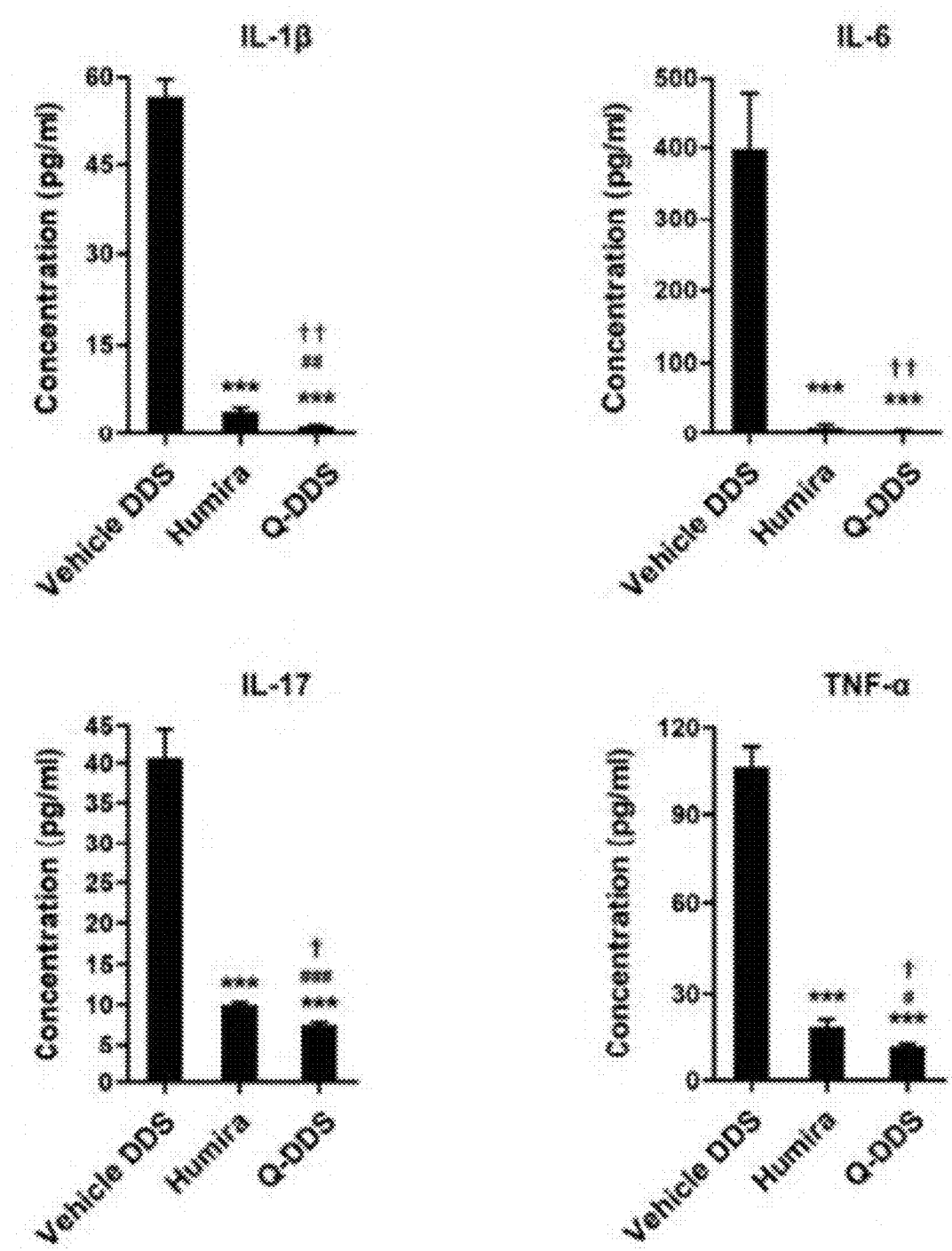

[FIG. 18B]
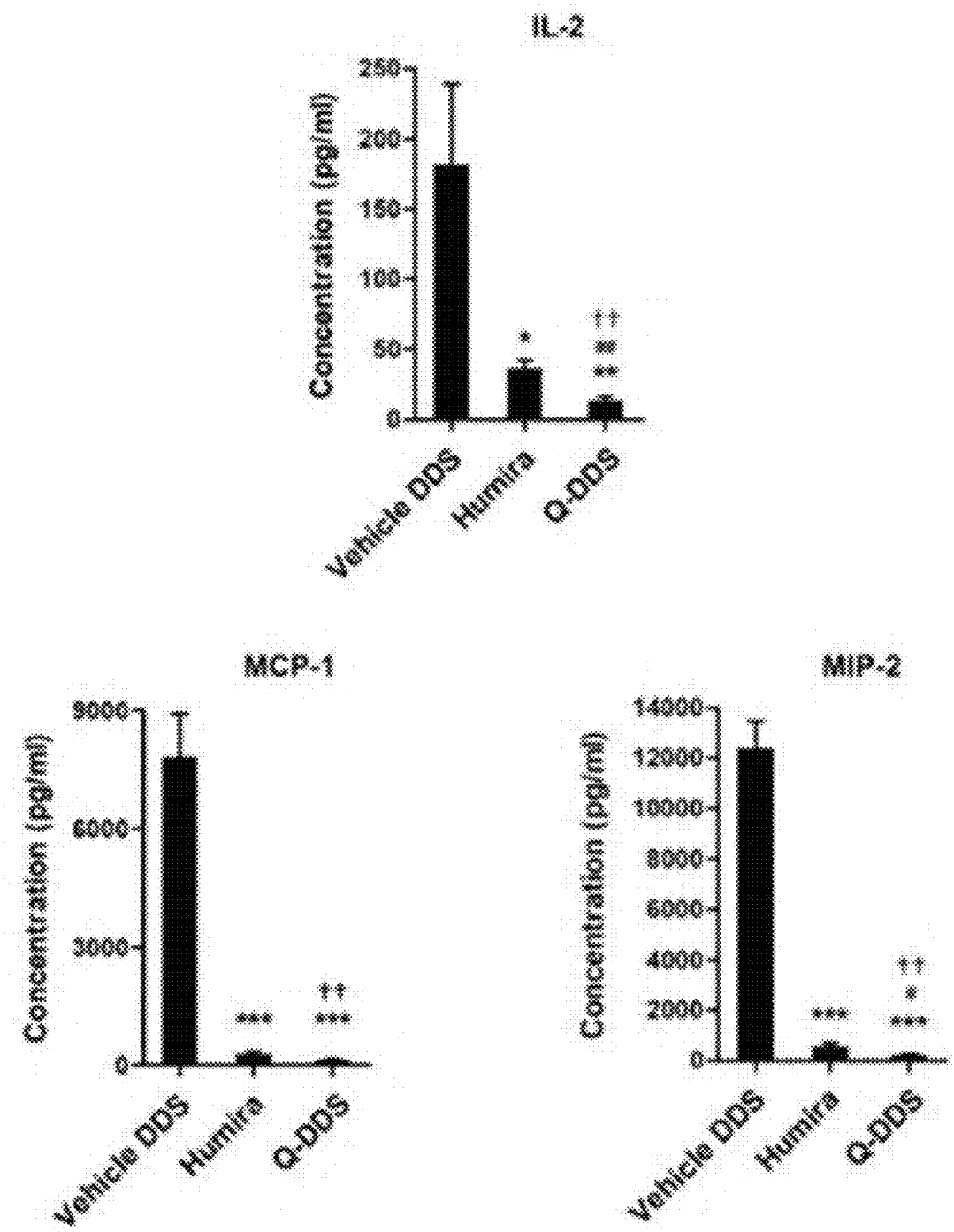

[FIG. 19]
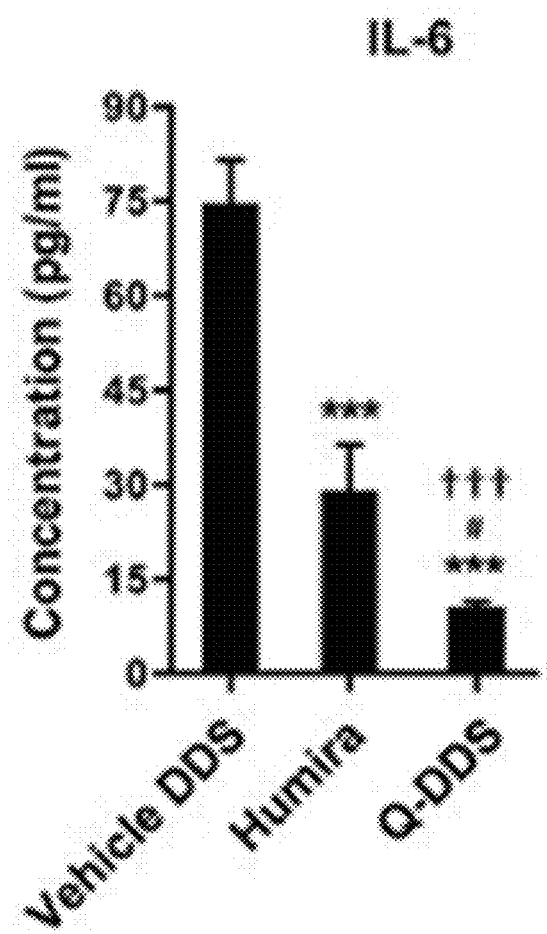

[FIG. 20A]
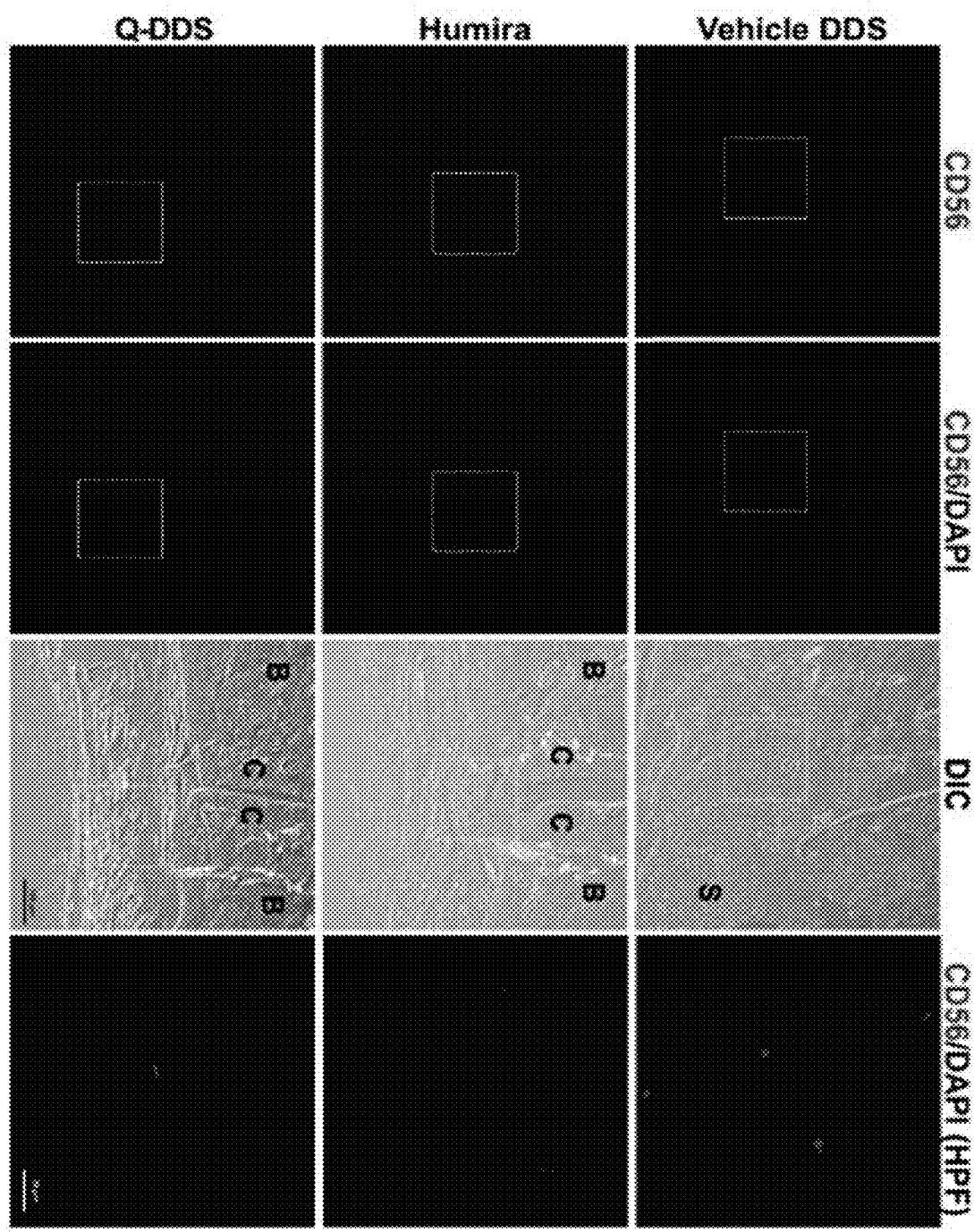

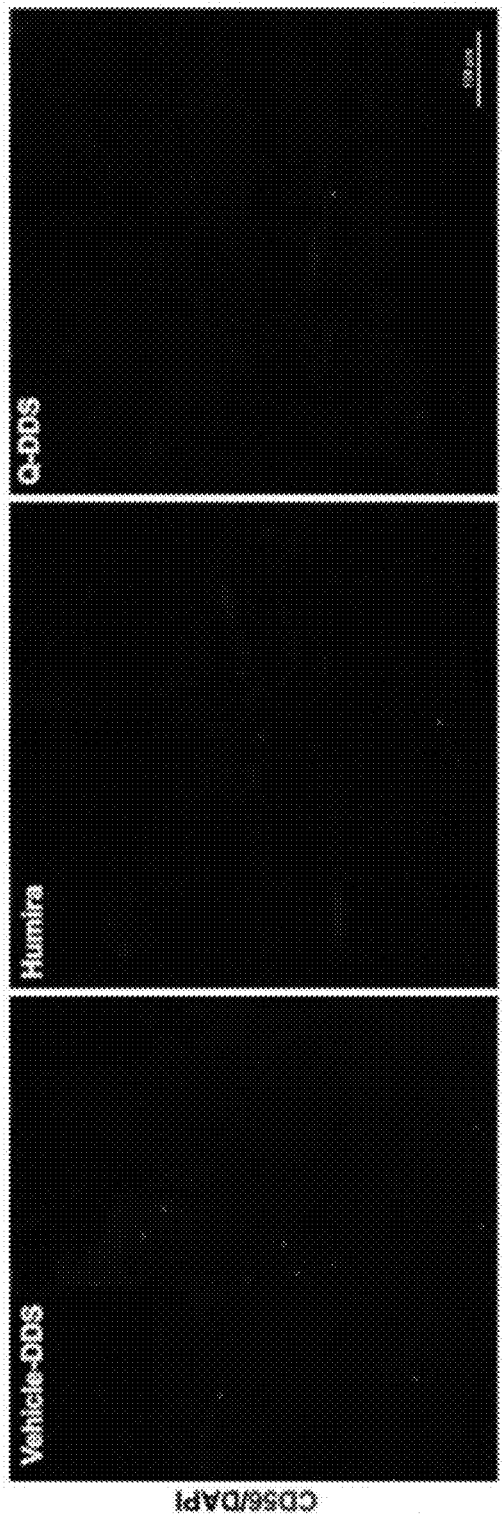
[FIG. 20B]

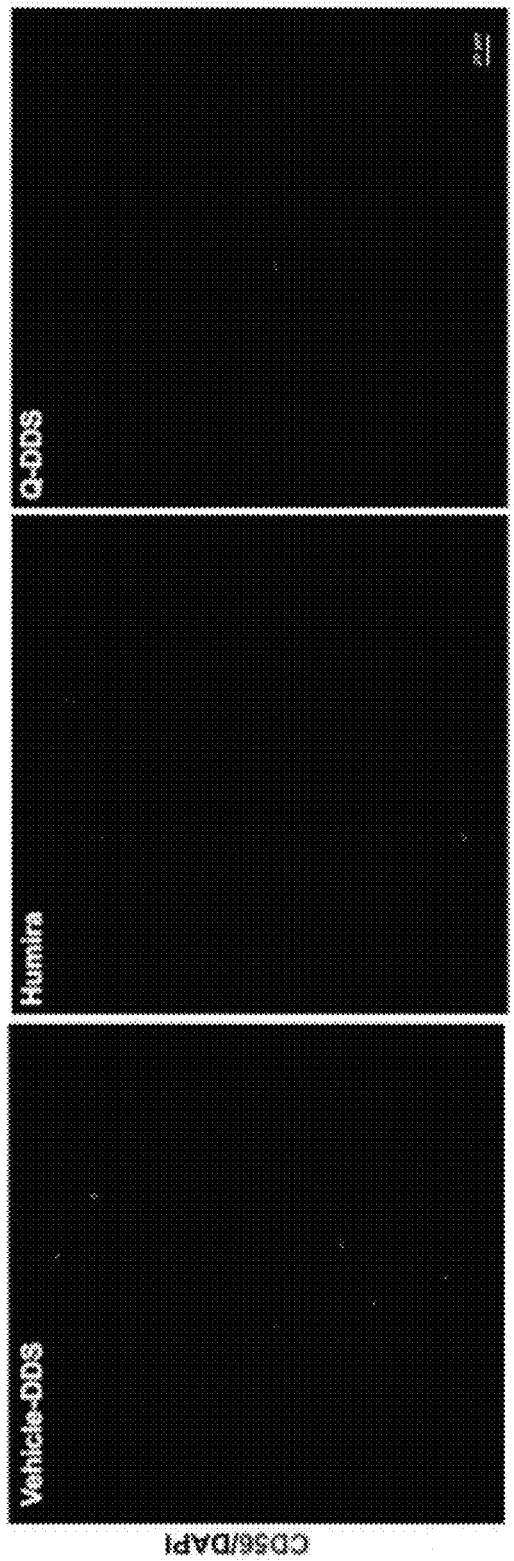
[FIG. 20C]

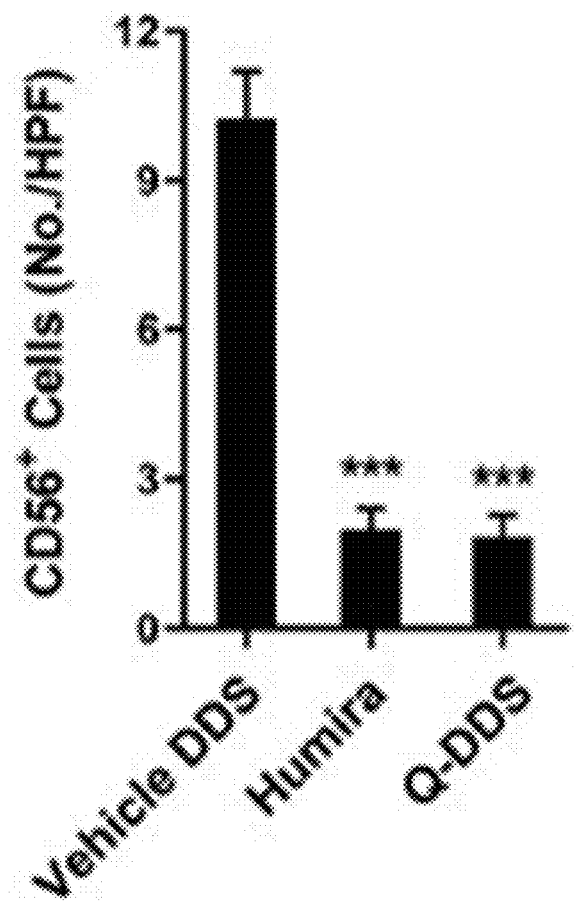
[FIG. 20D]

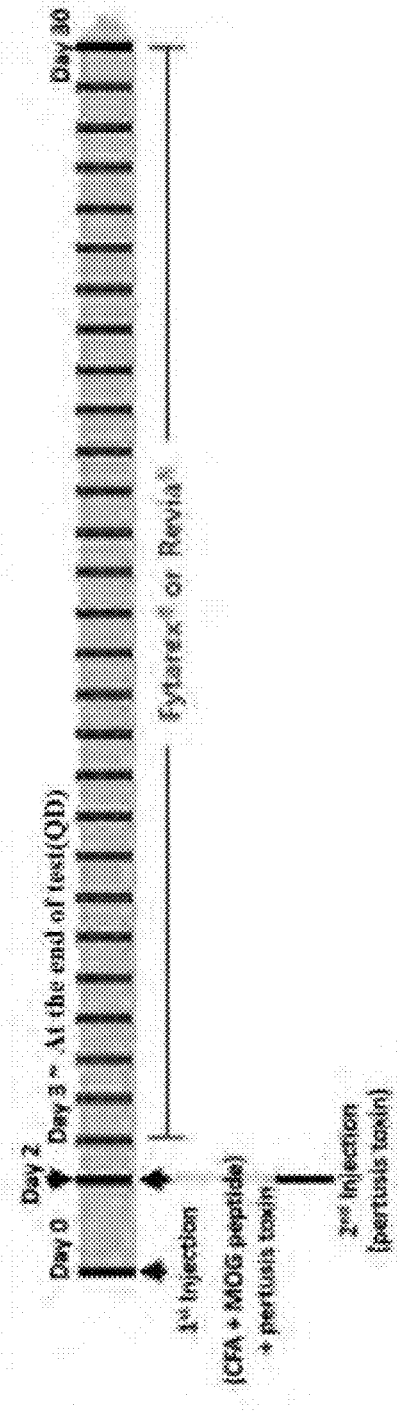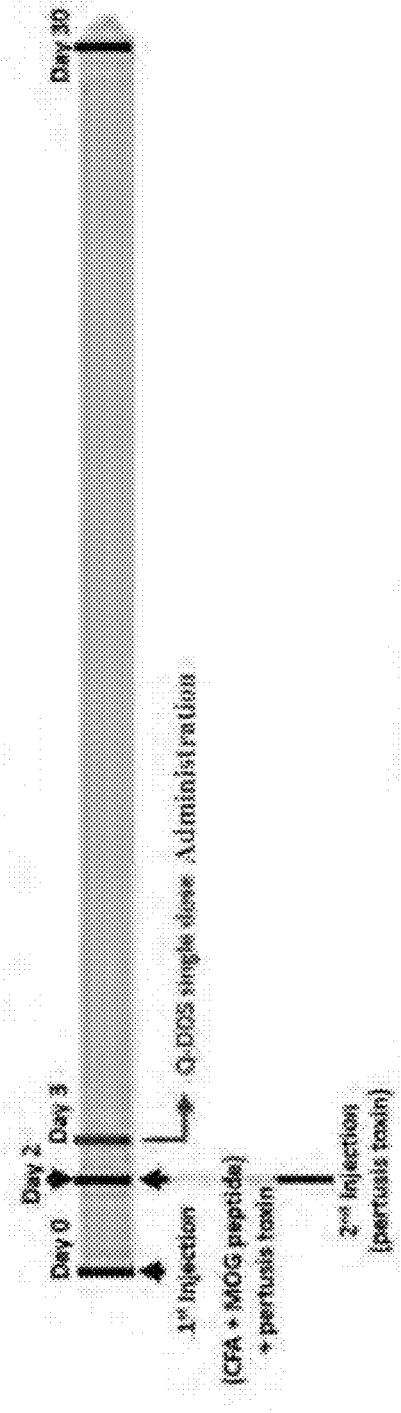
[FIG. 21A]

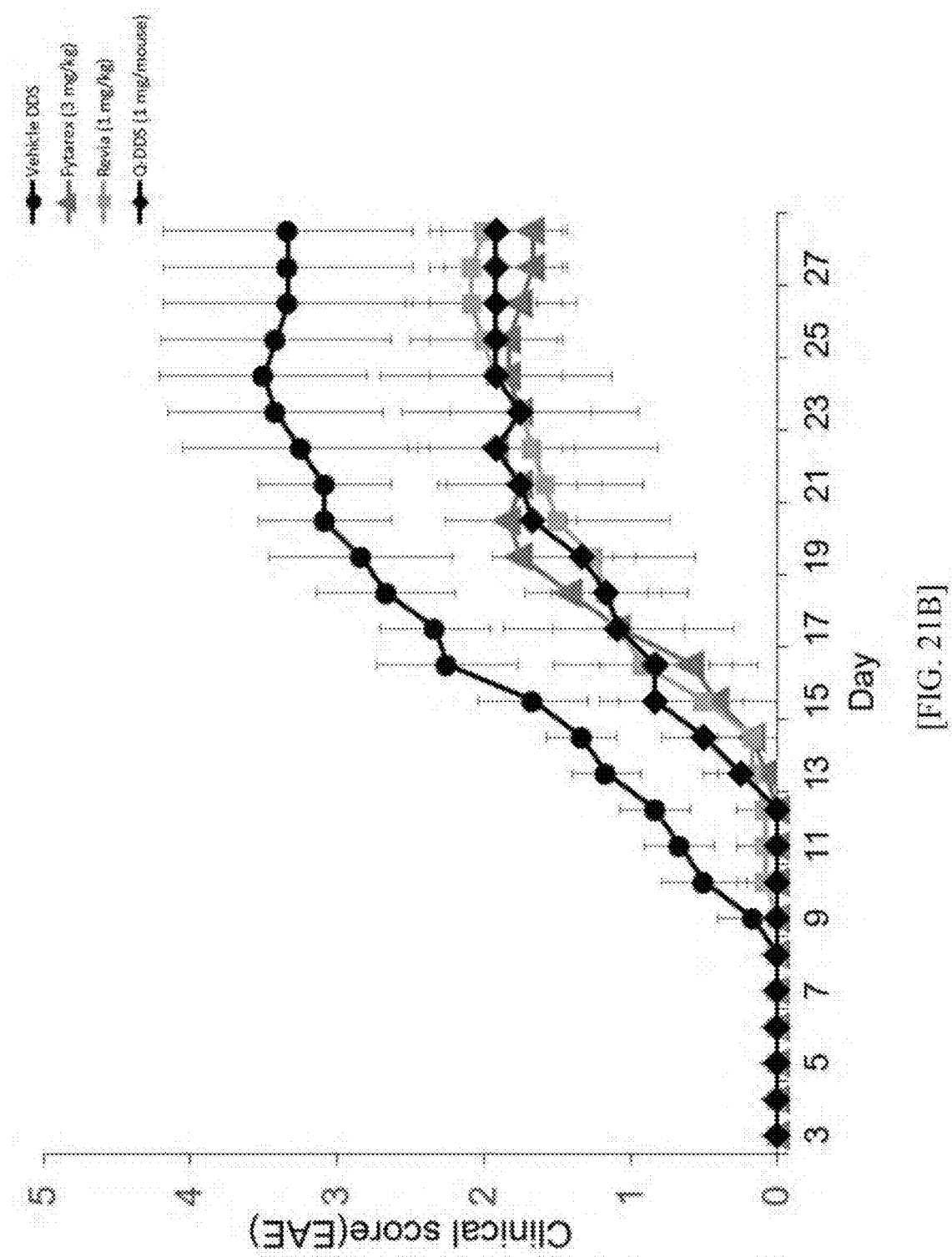
[FIG. 21B]

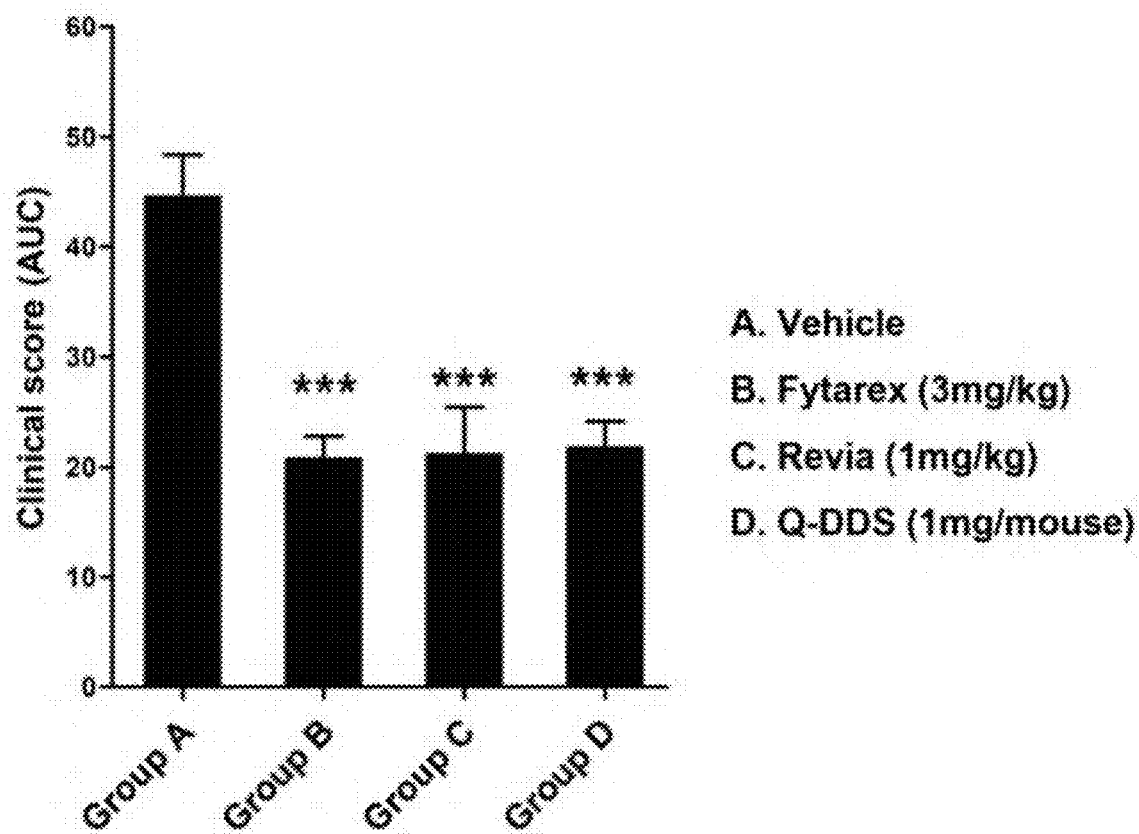
[FIG. 21C]

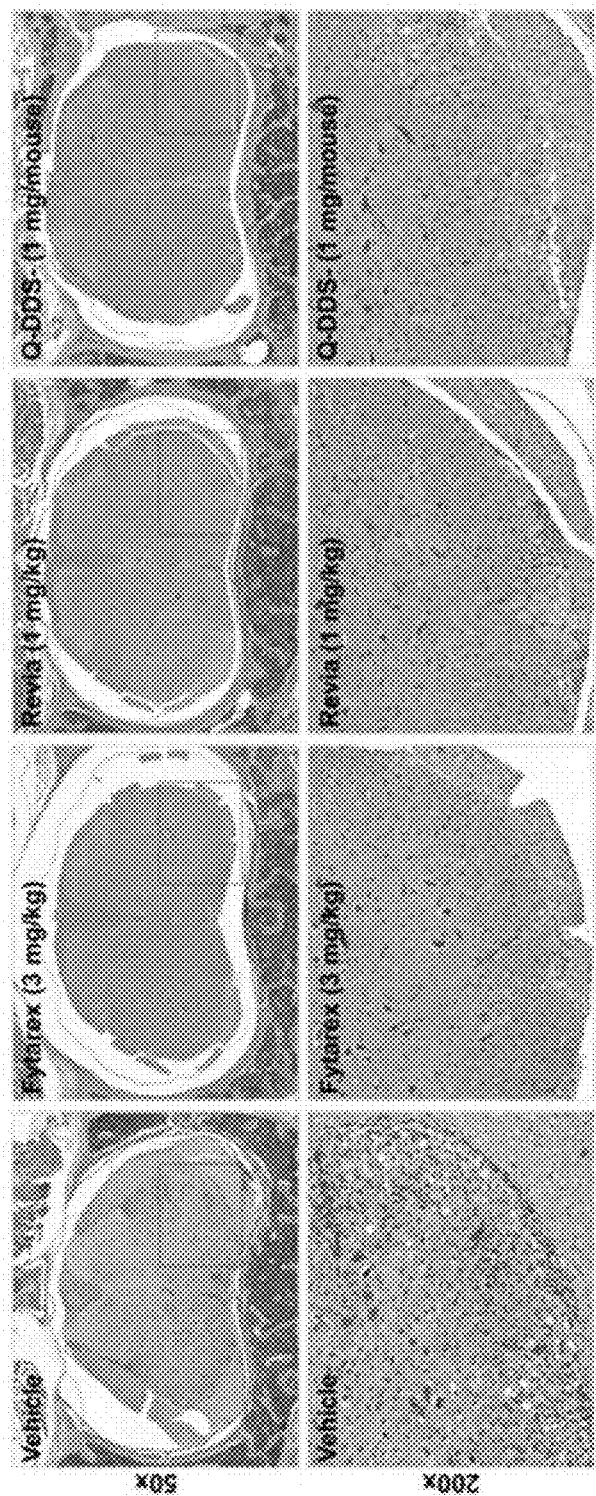
[FIG. 21D]

[FIG. 21E]
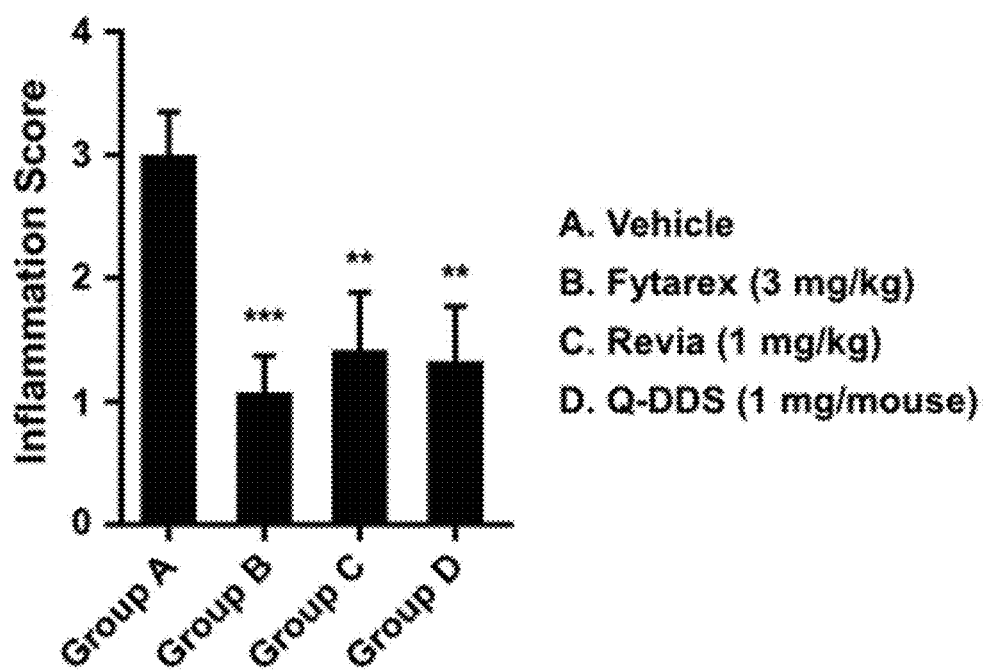

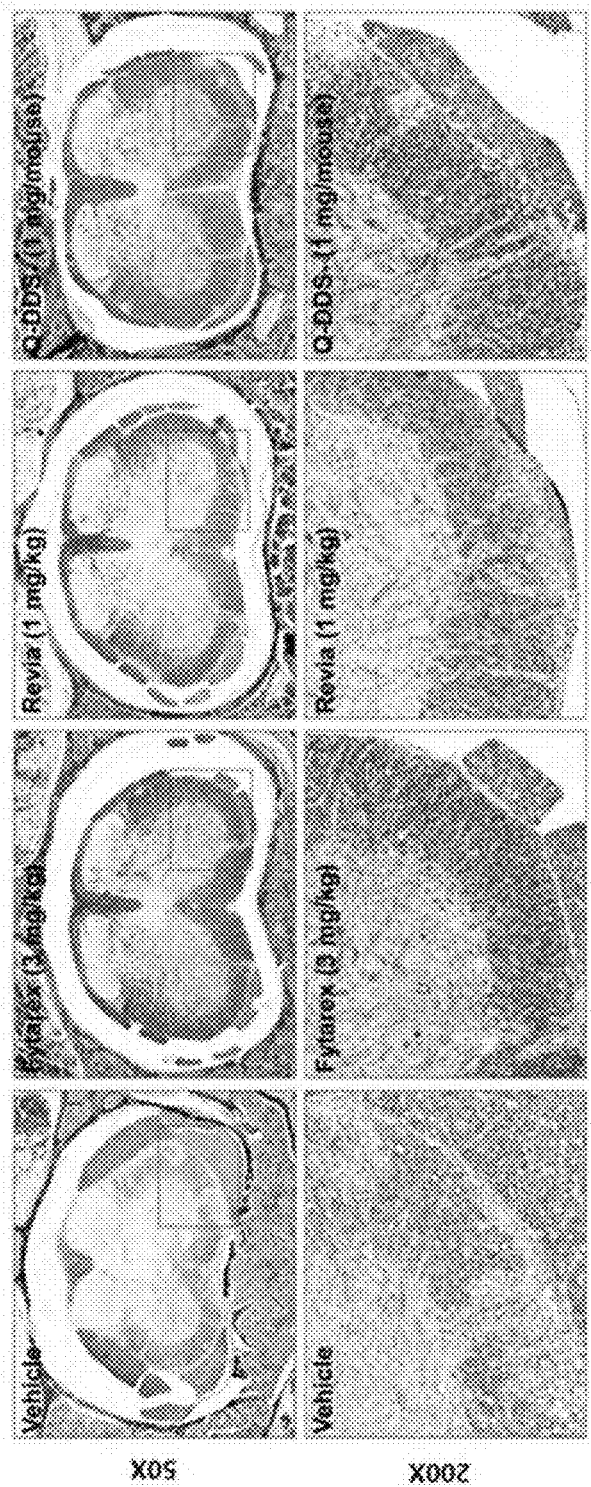
[FIG. 21F]

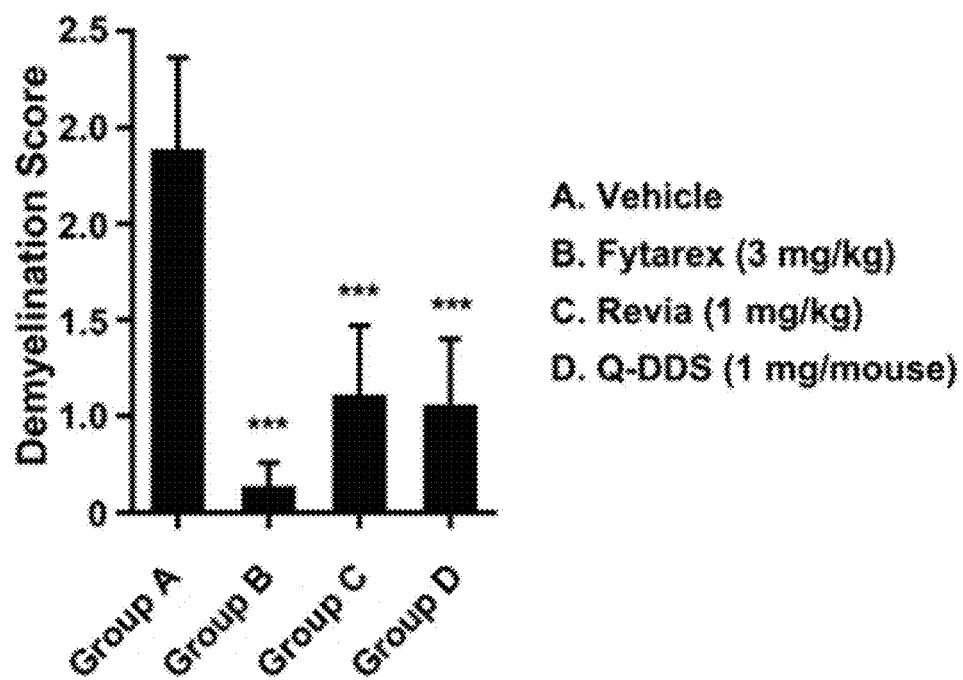
[FIG. 21G]

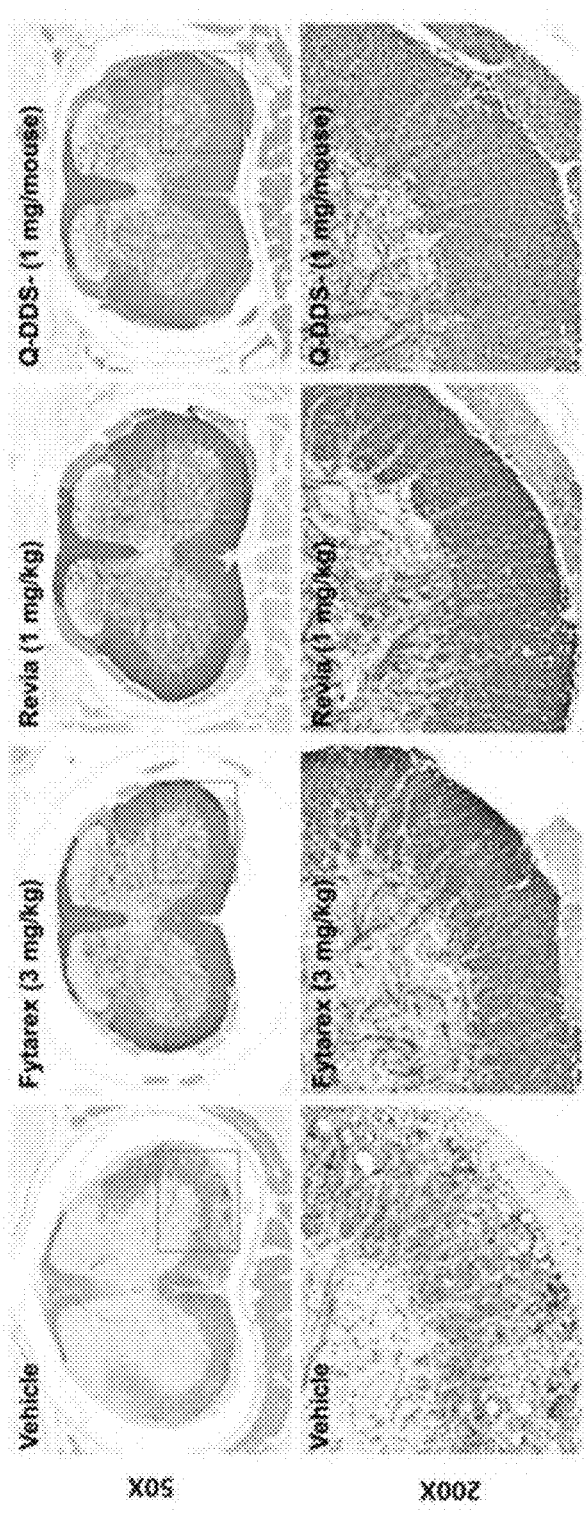
[FIG. 21H]

[FIG. 21I]
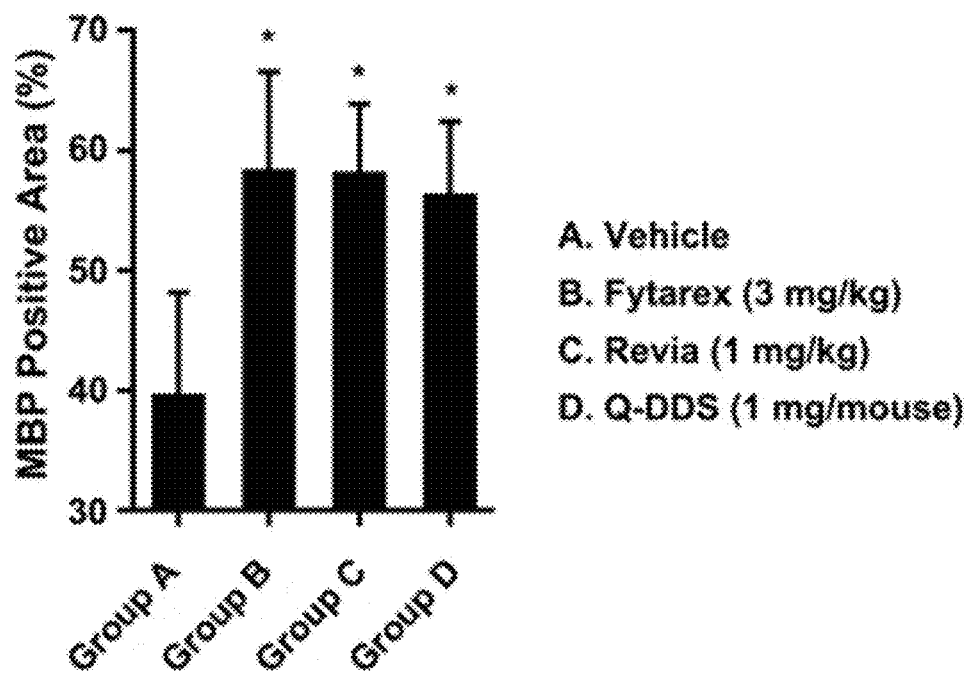

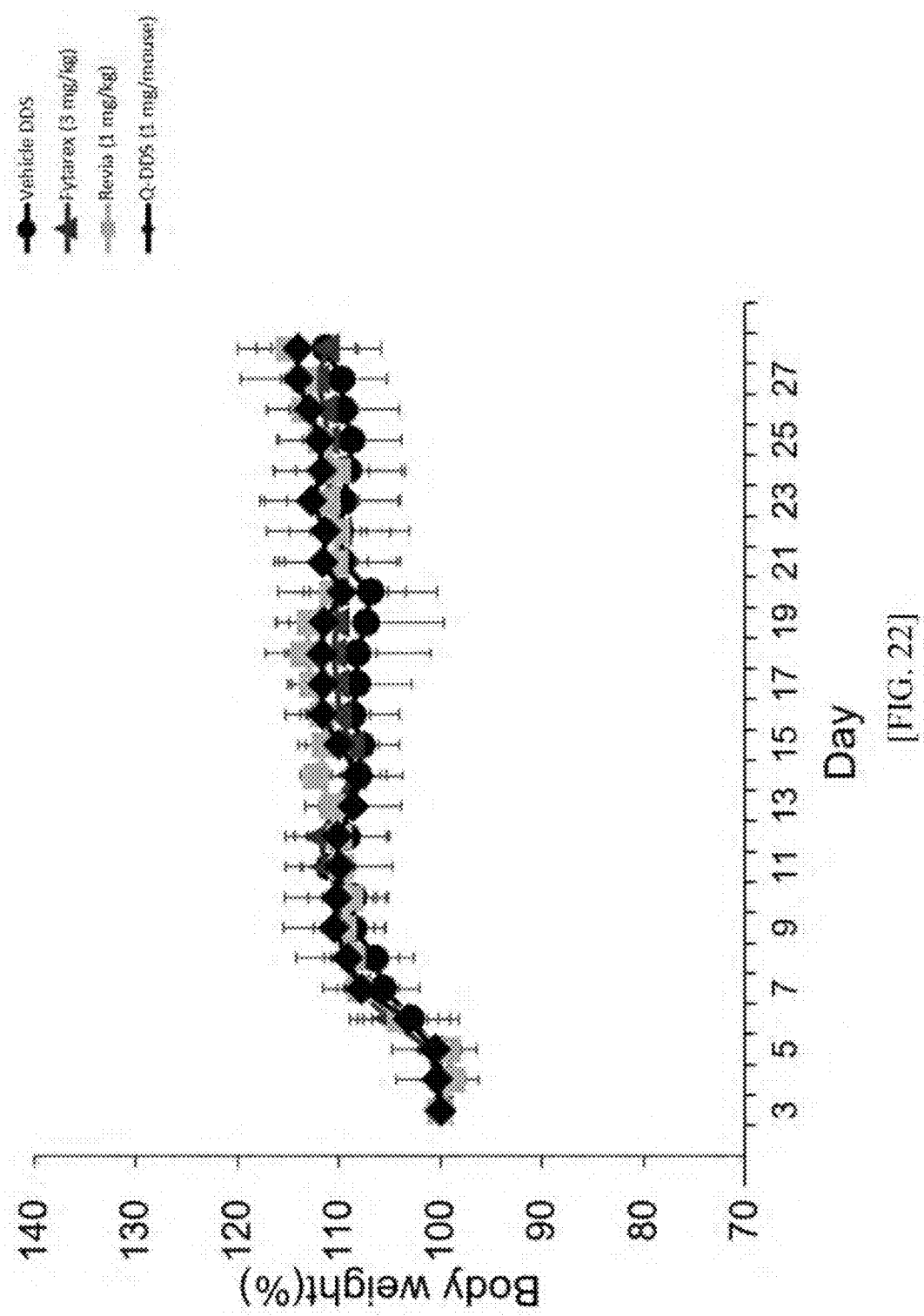
[FIG. 22]

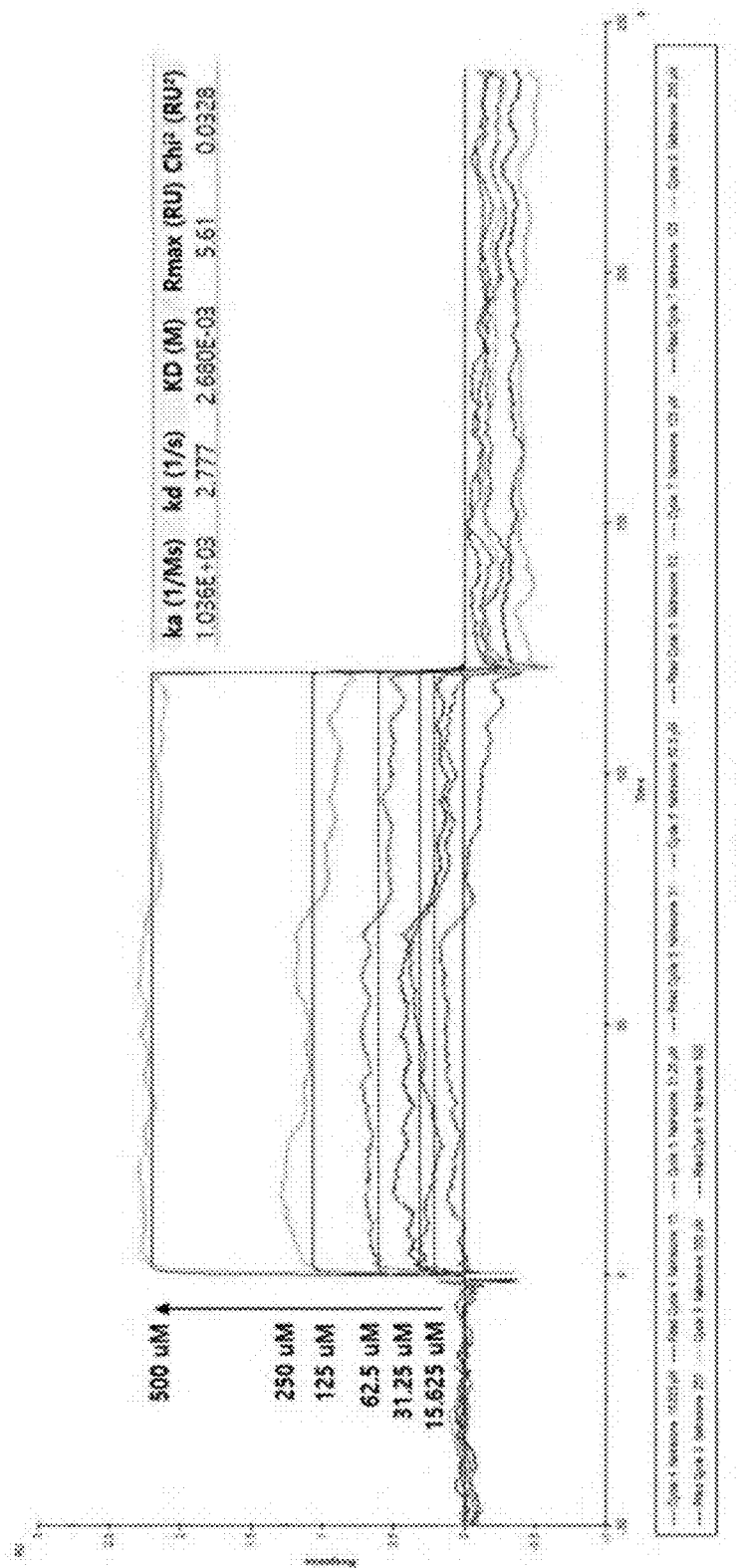
[FIG. 23]

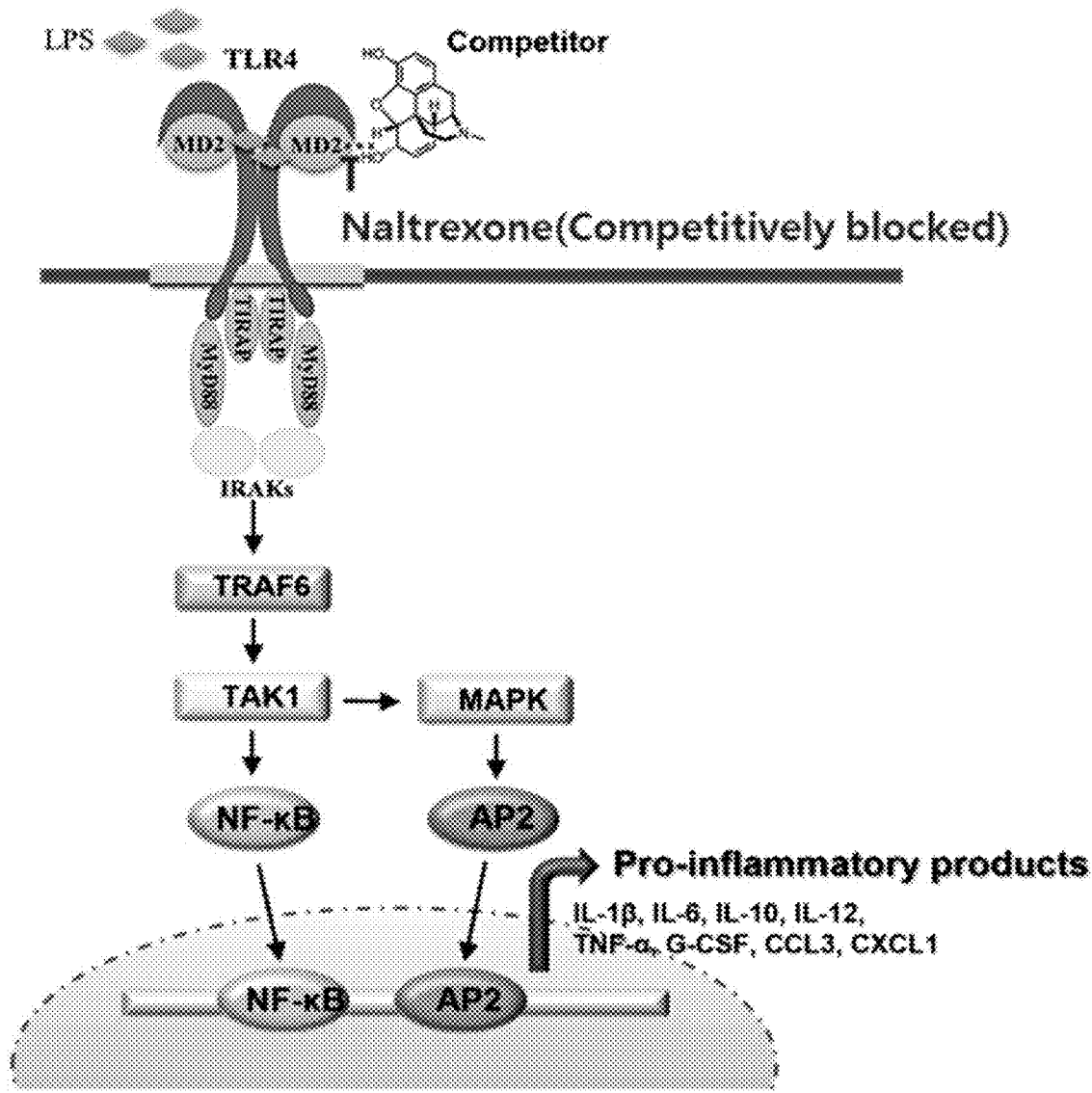
[FIG. 24]

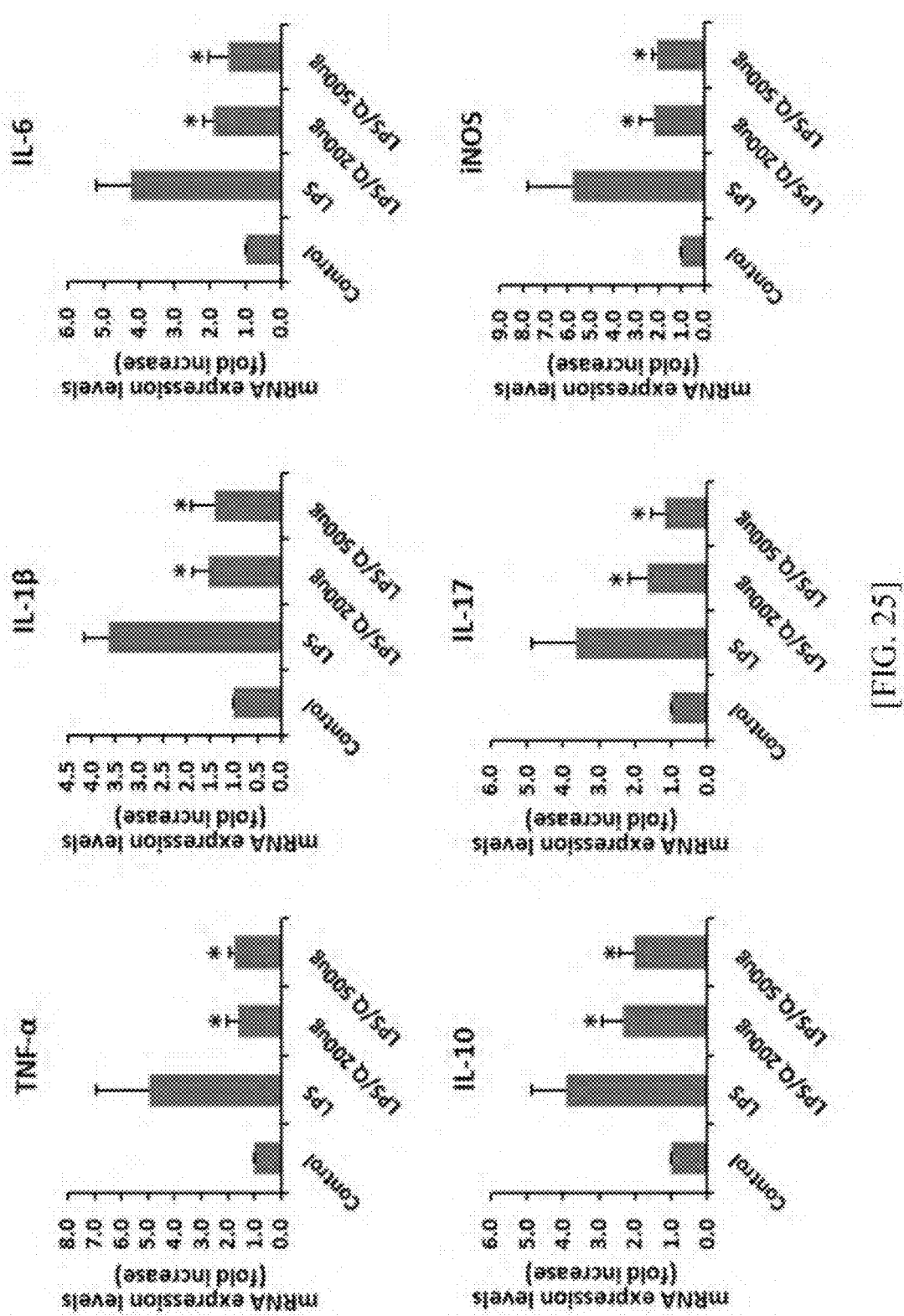
[FIG. 25]

[FIG. 26]
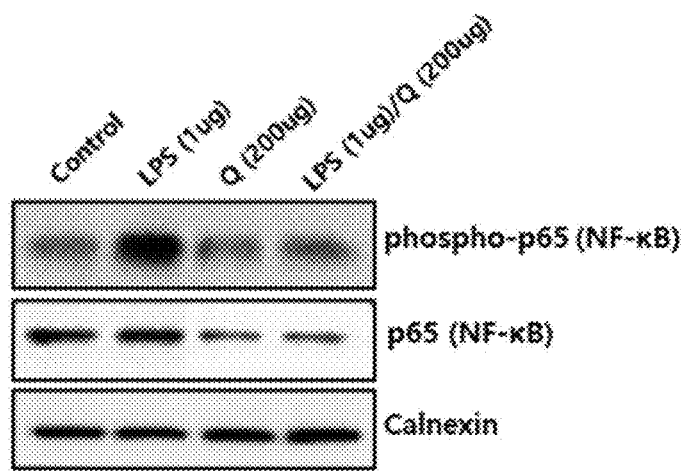
[FIG. 27]
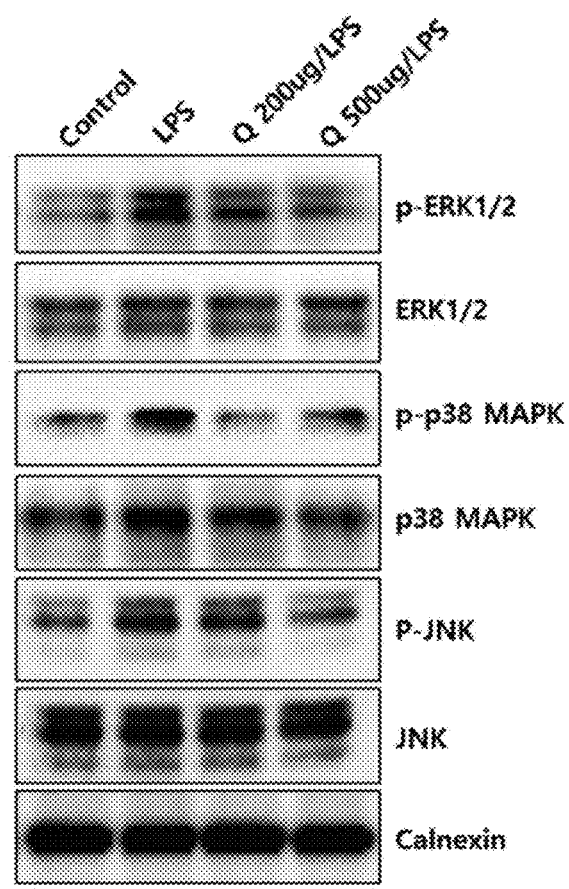

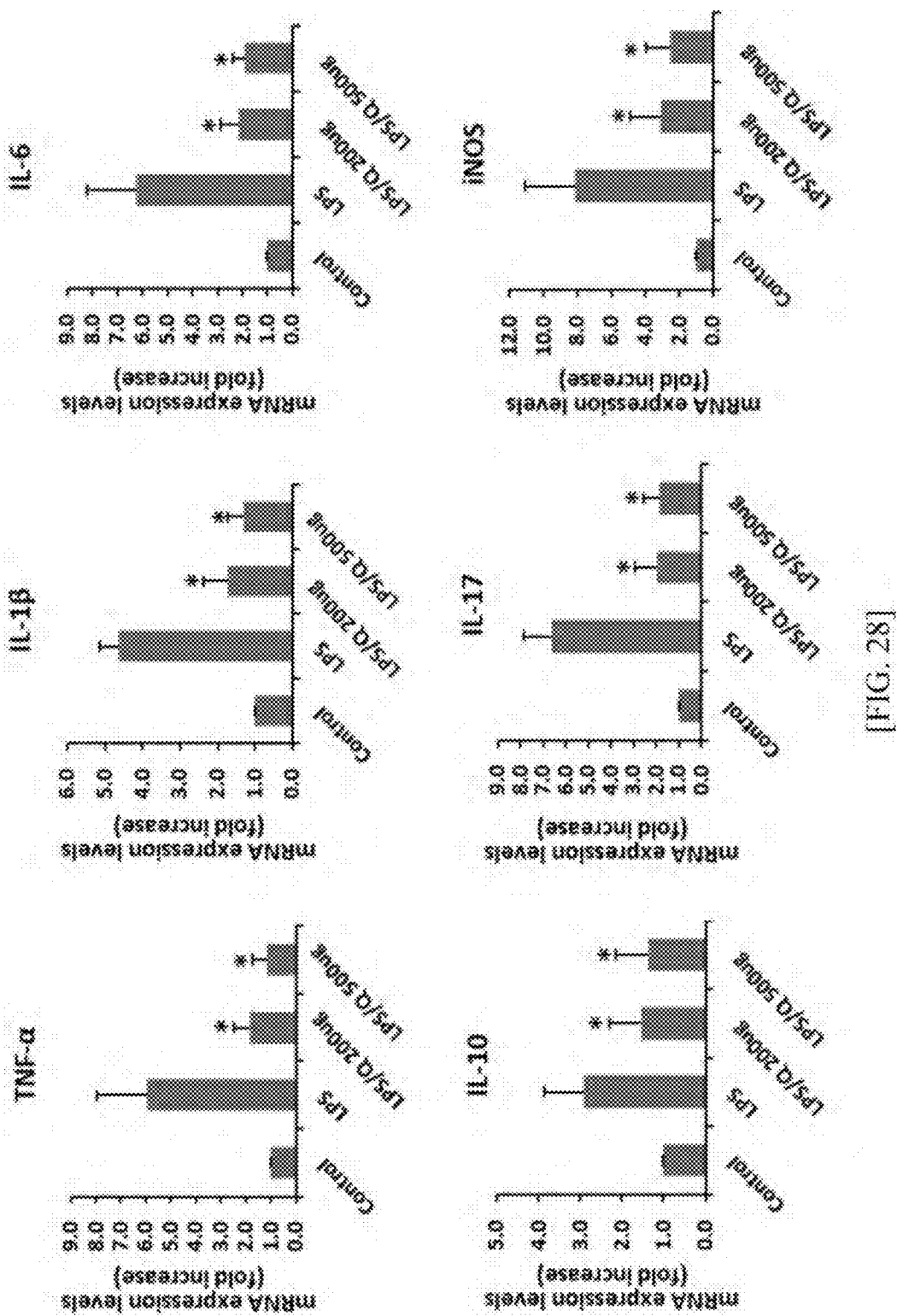
[FIG. 28]

[FIG. 29]
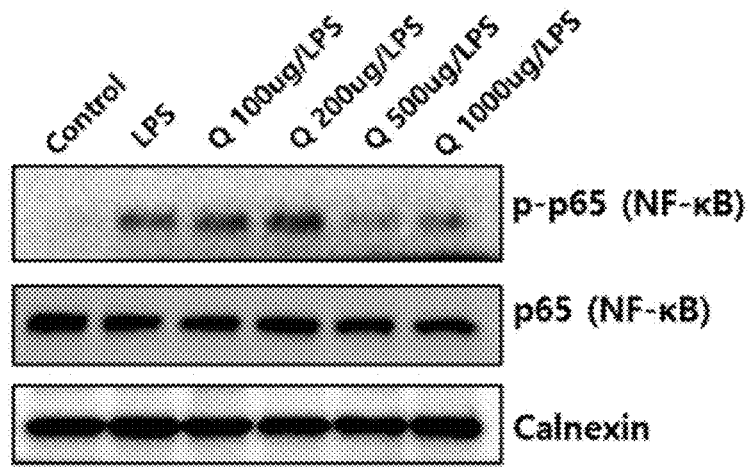
[FIG. 30]
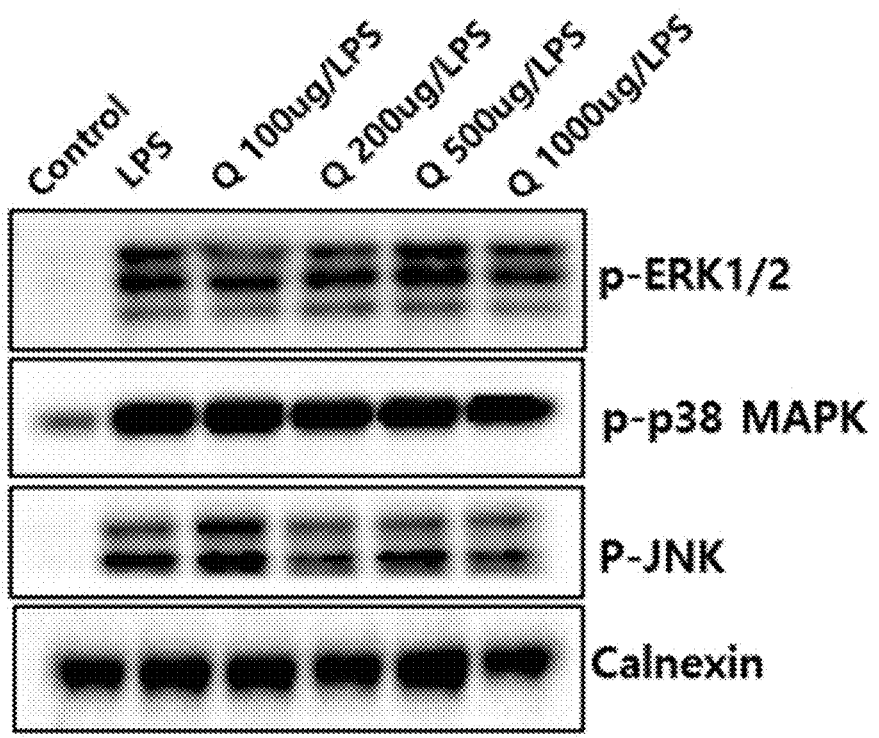

[FIG. 31]
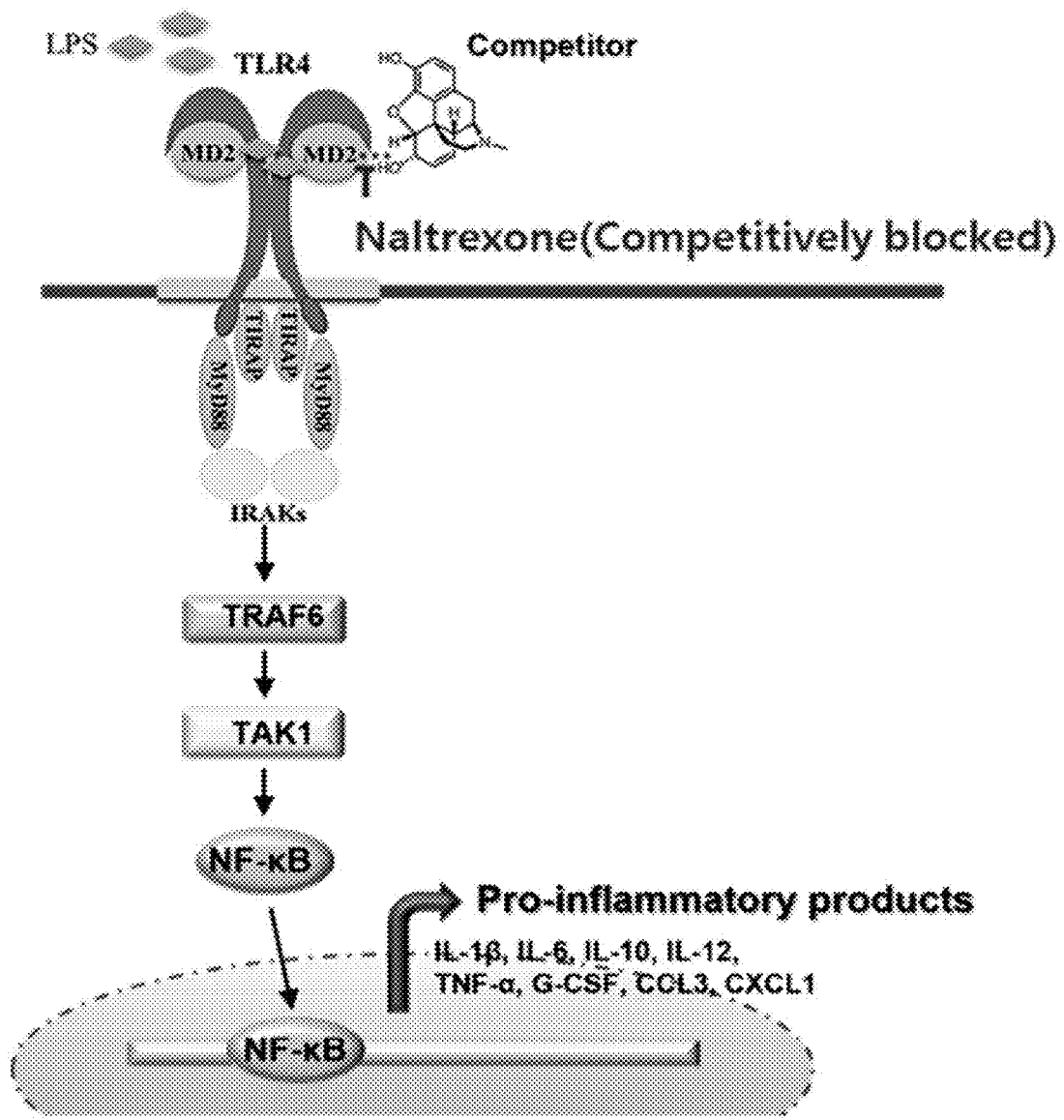

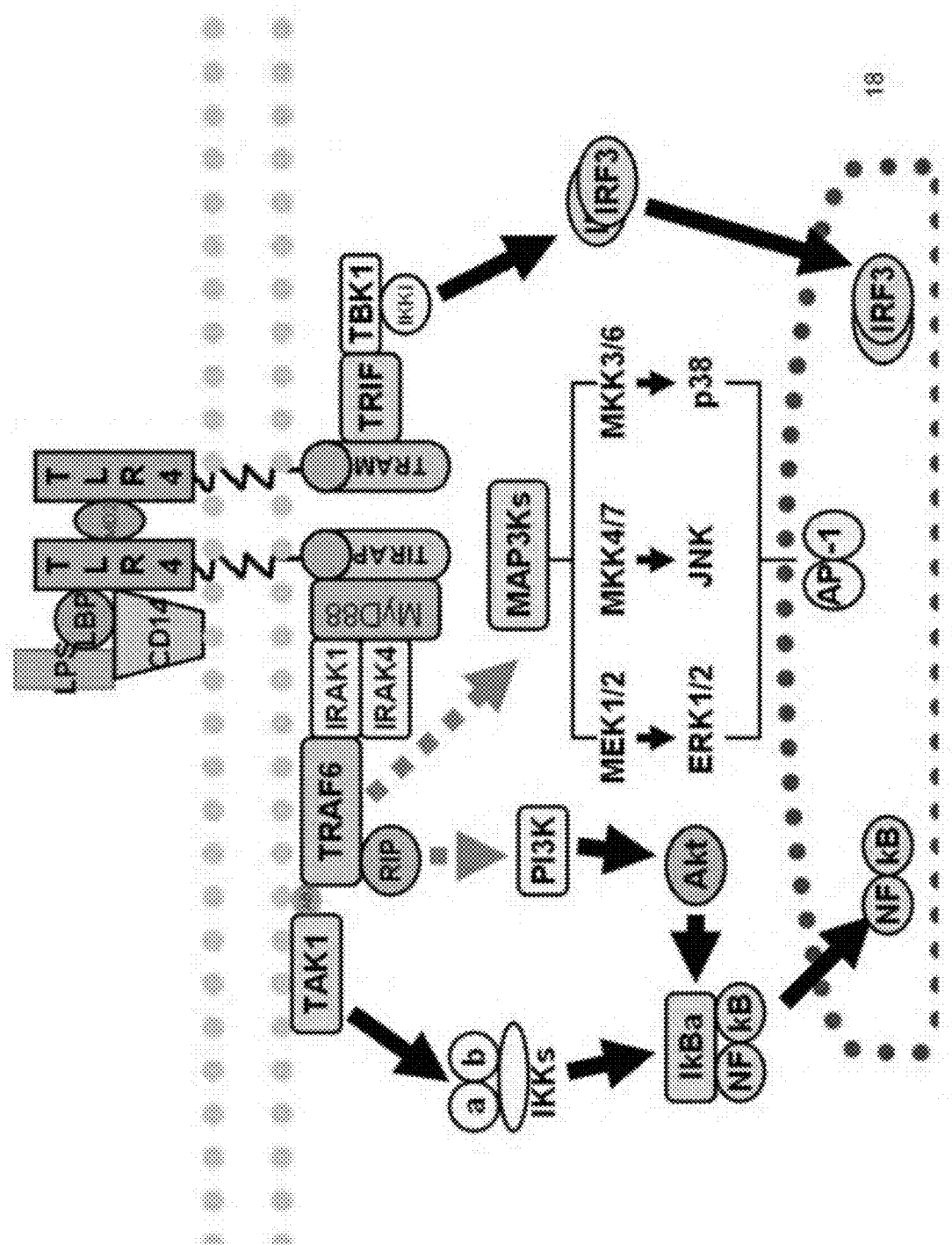
[FIG. 32]

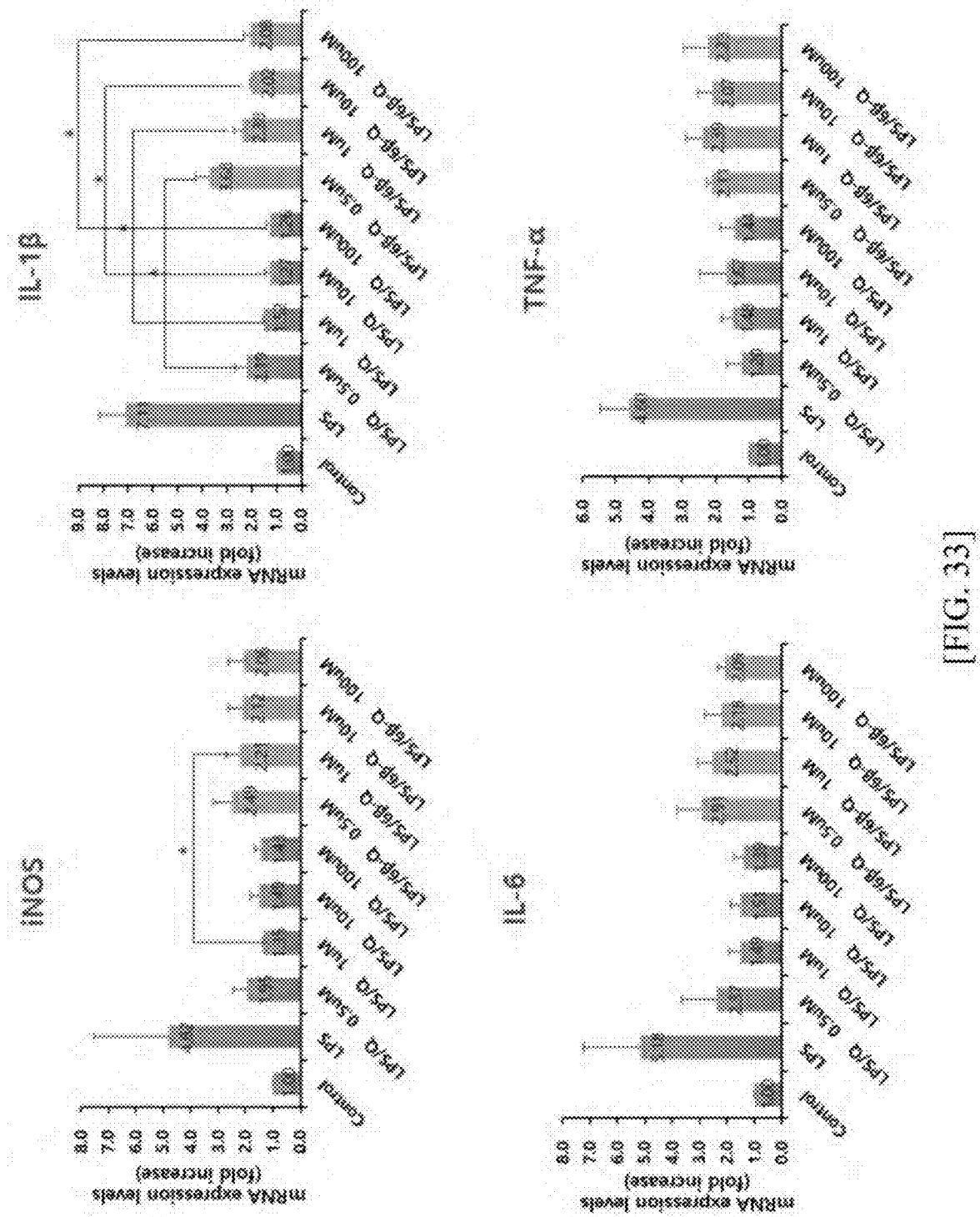
[FIG. 33]

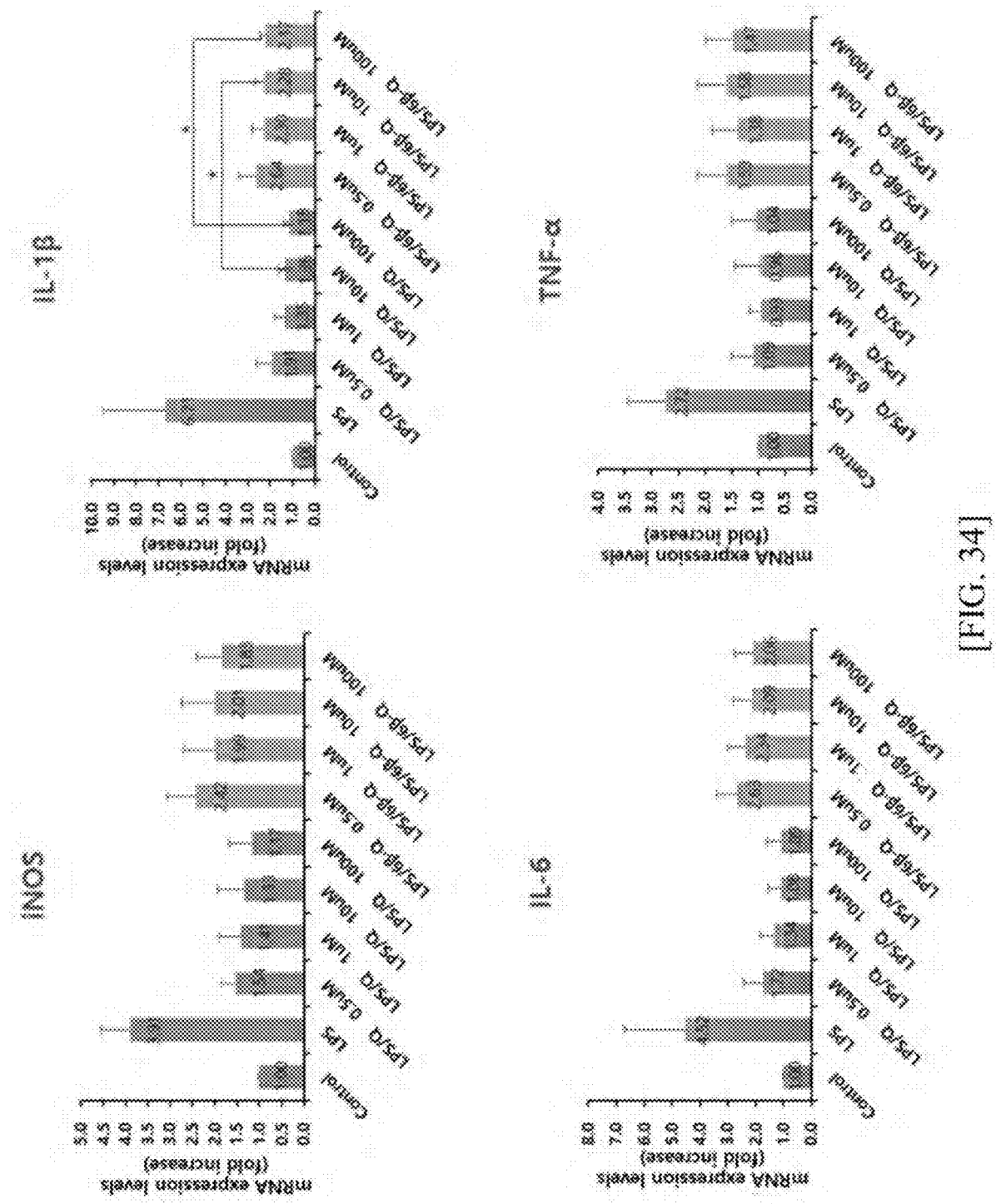
[FIG. 34]

[FIG. 35]
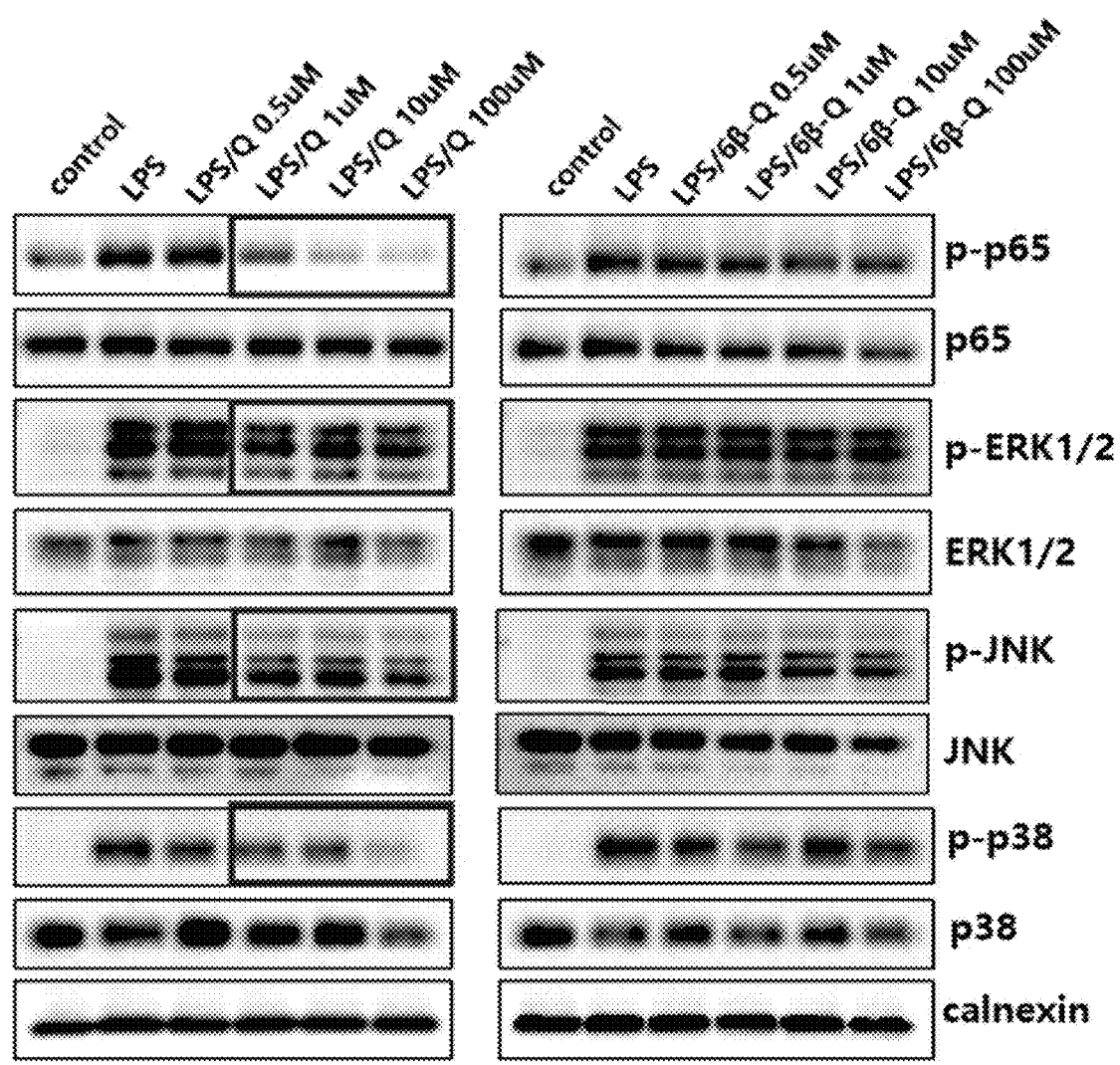

[FIG. 36]
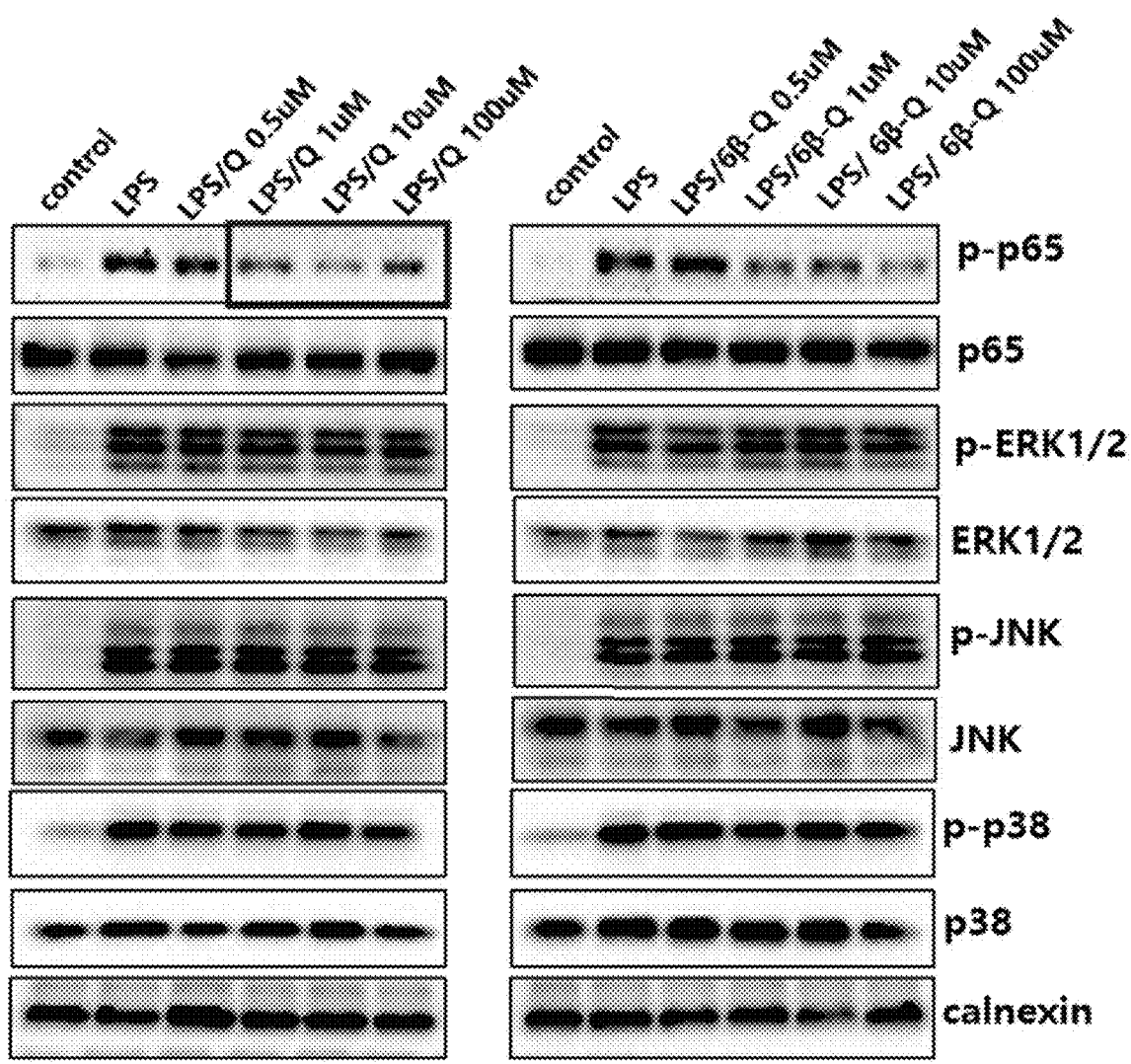

SUSTAINED FORMULATION FOR PREVENTION OR TREATMENT OF AUTOIMMUNE DISEASE CONTAINING NALTREXONE AND METHOD USING THE SAME

CROSS-REFERENCE TO RELATED APPLICATIONS

This application is a continuation of Application No. PCT/KR2022/003317 filed on Mar. 8, 2022, which in turn claims the benefit of Korean Patent Applications No. 10-2021-0030791 filed on Mar. 9, 2021, and No. 10-2022-0028995 filed on Mar. 7, 2022, the disclosures of which are incorporated by reference into the present application.

TECHNICAL FIELD

The present disclosure relates to sustained formulation for prevention or treatment of autoimmune disease containing low-dose naltrexone and method for prevention or treatment of autoimmune disease using the same.

BACKGROUND ART

Naltrexone has a similar chemical structure to that of morphine as a competitive antagonist of opioid receptors. Since naltrexone was approved by the US FDA in 1984, it has been used for the treatment of alcoholism or opioid addiction, and a fixed dose combination of naltrexone and bupropion (brand name Contrave) is used for the treatment of obesity. Recently, it has been proposed that low-dose naltrexone (LDN) has a useful effect on other diseases, but a clear therapeutic effect has not been confirmed, and there is no known pharmaceutical means for confirming this.

The naltrexone dosage form is mainly a tablet for oral administration, and is also provided as an intramuscular injection or a subcutaneous implant. Recently, sustained microparticles comprising various drugs and a method for manufacturing the same have been developed (Korean Patent Application Laid-Open No. 10-2020-0044977 (2020 Apr. 29)). However, formulations that release low-dose naltrexone for a long period of time from 3 weeks to 1 year or more have not been developed, and it has not been confirmed whether low-dose naltrexone parenteral sustained-release formulations are effective in the treatment of diseases such as autoimmune diseases.

Therefore, in order to improve the convenience of patients, it is necessary to develop a low-dose naltrexone sustained formulation capable of sustaining the medicinal effect of naltrexone for a long period of time, and to confirm the disease treatment efficacy of the low-dose naltrexone sustained formulation.

DISCLOSURE

Technical Problem

The present disclosure provides the sustained agent for prevention or treatment of autoimmune disease containing low-dose naltrexone.

The present disclosure provides a method for prevention or treatment of autoimmune disease using the sustained agent containing low-dose naltrexone.

Technical Solution

One aspect provides the sustained agent for prevention or treatment of autoimmune diseases, comprising microparticles comprising naltrexone or pharmaceutically acceptable salts thereof, and biodegradable polymer.

The present disclosure firstly confirmed through an experiment that a parenteral sustained agent containing naltrexone has the preventive or therapeutic effect on autoimmune diseases and exhibits a remarkably better effect for prevention or treatment of autoimmune disease than that of an oral formulation containing naltrexone.

Naltrexone of the present disclosure is also referred to as N-cyclopropyl-methylnoroxymorphone, N-cyclopropylmethyl-14-hydroxydihydro-morphinone, 17-(cyclopropylmethyl)-4,5α-epoxy-3,14-dihydroxymorphinan-6-one, EN-1639A, or UM-792.

In the present disclosure, naltrexone may be a compound represented by the following structural formula:

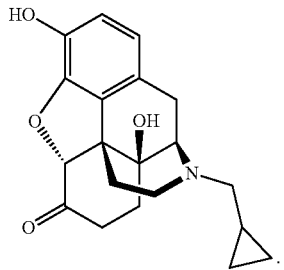

In the present disclosure, naltrexone may be a solvate, stereoisomer, prodrug, metabolite (e.g., 6β-naltrexol), or derivative (e.g., naloxone) of naltrexone. The stereoisomers refer to ones having the same molecular formula and the same sequence of bonded atoms, but having a different spatial arrangement of the atoms. The solvate refers to a compound solvated by an organic or an inorganic solvent. The solvate is, for example, a hydrate. The stereoisomer may be a diastereomer or an enantiomer. The prodrug may be a compound that is converted into a target compound in vivo after administration of the compound. The metabolite may be a compound that can be produced through an in vivo metabolic process. The derivative refers to a compound obtained by substituting a part of the structure of naltrexone with another atom or group of atoms.

In the present disclosure, the term "salt" of "pharmaceutically acceptable salt" refers to an additional salt of an inorganic acid salt, an organic acid salt, or a metal salt of a compound. The pharmaceutically acceptable salt may be a salt that does not cause serious irritation to the organism to which the compound is administered and does not impair the biological activity and physical properties of the compound. The inorganic acid salt may be hydrochloride, hydrobromide, phosphate, sulfate, or disulfate. The organic acid salts may be formate, glacial acetate, acetate, propionate, lactate, oxalate, tartrate, malate, maleate, citrate, fumarate, besylate, camsylate, edicylate, trichloroacetate, trifluoroacetate, benzoate, gluconate, methanesulfonate, glycolate, succinate, 4-toluenesulfonate, galacturonate, embonate, glutamate, methanesulfonate, ethanesulfonate, benzenesulfonate, or aspartate. The metal salt may be a calcium salt, a sodium salt, a magnesium salt, a strontium salt, or a potassium salt. The pharmaceutically acceptable salt is, for example, acetate or hydrochloride.

In the present disclosure, the biodegradable polymer may comprise at least one selected from the group consisting of polylactide, polylactic acid, polylactide-co-glycolide, polylactic-co-glycolic acid, polyphosphazine, polyiminocarbonate, polyphosphoester, polyanhydride, polyorthoester, polycaprolactone, polyhydroxyvalate, polyhydroxybutyrate, and polyamino acid.

In the present disclosure, the molar ratio of glycolide to lactide in polylactide-co-glycolide may be about 50:50 to about 90:10, about 60:40 to about 90:10, about 60:40 to about 85:15, about 60:40 to about 80:20, about 60:40 to about 75:25, about 65:35 to about 90:10, about 70:30 to about 90:10, about 75:25 to about 90:10, from about 65:35 to about 85:15, or about 70:30 to about 80:20. The molar ratio of glycolide to lactide in the polylactide-co-glycolide may be about 75:25.

In the present disclosure, the biodegradable polymer may comprise two or more types among one or more type of polylactide and one or more type of polylactide-co-glycolide. In the present disclosure, the biodegradable polymer may comprise, for example, two types of polylactide, one type of polylactide, one type of polylactide-co-glycolide, two types of polylactide-co-glycolide, three types of polylactide, a combination of two types of polylactide and one polylactide-co-glycolide, etc., one polylactide and two polylactide-co-glycolide, etc., and in particular, may comprise one type of polylactide and one type of polylactide-co-glycolide or two types of polylactide-co-glycolides, but the present disclosure is not limited thereto.

The biodegradable polymer may comprise polylactide and polylactide-co-glycolide. The weight ratio of polylactide and polylactide-co-glycolide may be about 1:10 to about 10:1, about 1:9 to about 9:1, about 1:8 to about 8:1, about 1:7 to about 7:1, about 1:6 to about 6:1, about 1:5 to about 5:1, about 1:4 to about 4:1, about 1:3 to about 3:1, about 1:2 to about 2:1, or about 1:1 to about 2:1. The weight ratio of the polylactide and polylactide-co-glycolide may be about 1:1.

In the present disclosure, the biodegradable polymer may comprise two or more types of polylactide-co-glycolide.

In the case that two or more types of polylactide-co-glycolide are a combination of two types of polylactide-co-glycolide, the weight ratio of each of polylactide-co-glycolide may be about 1:10 to about 10:1, about 1:9 to about 9:1, about 1:8 to about 8:1, about 1:7 to about 7:1, about 1:6 to about 6:1, about 1:5 to about 5:1, about 1:4 to about 4:1, about 1:3 to about 3:1, about 1:2 to about 2:1, or about 1:1 to about 2:1. The weight ratio of two types of polylactide-co-glycolide may be about 1:1.

The term "intrinsic viscosity (IV)" refers to a value obtained by extrapolating the reduced viscosity or the inherent viscosity of a diluted polymer solution to polymer concentration 0. The intrinsic viscosity may be the viscosity modulus when the interaction between the solute particles was eliminated.

In the present disclosure, the intrinsic viscosity (IV) of the polylactide may be about 0.1 dl/g to about 0.5 dl/g, about 0.1 dl/g to about 0.4 dl/g, about 0.1 dl/g to about 0.3 dl/g, about 0.1 dl/g to about 0.2 dl/g, about 0.2 dl/g to about 0.5 dl/g, about 0.2 dig to about 0.4 dl/g, or about 0.2 dl/g to about 0.3 dl/g.

In the present disclosure, the intrinsic viscosity of polylactide-co-glycolide may be about 0.1 dl/g to 1.5 dl/g, about 0.1 dl/g to 1.0 dl/g, about 0.1 dl/g to 0.8 dl/g, about 0.1 dl/g to 0.6 dl/g, about 0.1 dl/g to 0.4 dl/g, about 0.1 dl/g to 0.2 dl/g, about 0.2 dl/g to 1.5 dl/g, about 0.2 dl/g to 1.5 dl/g, about 0.2 dl/g to 1.0 dl/g, about 0.4 dl/g to 1.5 dl/g, about 0.6 dl/g to 1.5 dl/g, about 0.8 dl/g to 1.5 dl/g, or about 1.0 dl/g to 1.5 dl/g.

In the biodegradable polymer comprising polylactide and polyactide-co-glycolide of the present disclosure, the intrinsic viscosity of the polylactide may be about 0.1 dl/g to about 0.5 dl/g, about 0.1 dl/g to about 0.4 dl/g, about 0.1 dl/g to about 0.3 dl/g, about 0.1 dl/g to about 0.2 dl/g, about 0.2 dl/g to about 0.5 dl/g, about 0.2 dl/g to about 0.4 dl/g, or about 0.2 dl/g to about 0.3 dl/g. In the biodegradable polymer comprising polylactide and polyactide-co-glycolide, the intrinsic viscosity of the polylactide-co-glycolide may be about 0.1 dl/g to about 0.5 dl/g, about 0.1 dl/g to about 0.4 dl/g, about 0.1 dl/g to about 0.3 dl/g, about 0.1 dl/g to about 0.2 dl/g, about 0.2 dl/g to about 0.5 dl/g, about 0.2 dl/g to about 0.4 dl/g, or about 0.2 dl/g to about 0.3 dl/g. In the biodegradable polymer comprising polylactide and polylactide-co-glycolide, the intrinsic viscosity of polylactide may be about 0.2 dl/g and the intrinsic viscosity of polylactide-co-glycolide may be about 0.2 dl/g or about 0.4 dl/g.

In the biodegradable polymer comprising two or more types of polylactide-co-glycolide, the intrinsic viscosity of one type of polylactide-co-glycolide may be about 0.1 dl/g to about 0.3 dl/g, about 0.2 dl/g to about 0.3 dl/g, or about 0.1 dl/g to about 0.2 dl/g. In the biodegradable polymer comprising two or more types of polylactide-co-glycolide, the intrinsic viscosity of another type of polylactide-co-glycolide may be about 0.1 dl/g to 1.5 dl/g, about 0.2 dl/g to 1.5 dl/g, about 0.4 dl/g to 1.5 dl/g, about 0.6 dl/g to 1.5 dl/g, about 0.8 dl/g to 1.5 dl/g, about 0.8 dl/g to 1.2 dl/g, or about 0.8 dl/g to 1.0 dl/g. The biodegradable polymer may comprise, for example, two types of polylactide-co-glycolide having an intrinsic viscosity of about 0.2 dl/g and a polylactide-co-glycolide having an intrinsic viscosity of about 1.0 dl/g.

In the present disclosure, the biodegradable polymer may be one in which the end of the polymer is capped or uncapped (i.e., not capped). The end of the biodegradable polymer may be capped with an acid moiety. The end of the biodegradable polymer may be capped with a carboxyl group or an ester group.

The polylactide may have an end capped with an acid moiety.

The polylactide-co-glycolide may have an end capped with an acid moiety.

The two or more types of polylactide-co-glycolides may be a mixture of a polylactide-co-glycolide with an acid end-cap and two or more types of uncapped polylactide-co-glycolides.

The residual amount of the solvent in microsphere of the present disclosure may be about 1000 ppm or less, about 900 ppm or less, about 800 ppm or less, about 700 ppm or less, about 600 ppm or less, about 500 ppm or less, about 400 ppm or less, about 300 ppm or less, about 200 ppm or less, about 100 ppm or less, about 10 ppm or less, or about 1 ppm or less. The residual amount of the solvent in microsphere may be about 800 ppm to about 100 ppm, about 750 ppm to about 100 ppm, about 700 ppm to about 100 ppm, about 650 ppm to about 100 ppm, about 800 ppm to about 150 ppm, about 800 ppm to about 200 ppm, about 800 ppm to about 250 ppm, about 800 ppm to about 300 ppm, about 800 ppm to about 350 ppm, about 800 ppm to about 400 ppm, about 800 ppm to about 450 ppm, about 800 ppm to about 500 ppm, about 800 ppm to about 550 ppm, about 800 ppm to about 600 ppm, about 750 ppm to about 600 ppm, about 700 ppm to about 600 ppm, or about 650 ppm to about 600 ppm.

The solvent may be dichloromethane.

In the present disclosure, the biodegradable polymer may be one obtained by removing the solvent while stirring at about 10° C. to about 20° C. at about 200 to about 400 rpm for about 30 minutes to about 2 hours. The biodegradable polymer may be one obtained by removing the solvent while stirring at about 25° C. to about 35° C. at about 200 to about 400 rpm for about 30 minutes to about 2 hours. The biodegradable polymer may be one obtained by removing the solvent while stirring at about 35° C. to about 45° C. at about 200 to about 400 rpm for about 30 minutes to about 4 hours. The biodegradable polymer may be one obtained by removing the solvent while stirring at about 15° C. at about 300 rpm for about 1 hour. The biodegradable polymer may be one obtained by removing the solvent while stirring at about 30° C. at about 300 rpm for about 2 hours. The biodegradable polymer may be one obtained by removing the solvent while stirring at about 40° C. at about 300 rpm for about 3 hours.

In the present disclosure, microparticles may also be referred to as microspheres.

The microparticles may comprise biodegradable polymers and naltrexone or its pharmaceutically acceptable salt thereof in a weight ratio of about 1:1 to about 10:1, from about 2:1 to about 10:1, from about 2:1 to about 5:1, or about 1:1 to about 2:1.

The contents of naltrexone in the microparticles may be about 10% (w/w) to about 50% (w/w), about 15% (w/w) to about 50% (w/w), about 50% (w/w) to about 50% (w/w), about 25% (w/w) to about 50% (w/w), about 30% (w/w) to about 50% (w/w), about 10% (w/w) to abut 45% (w/w), about 10% (w/w) to about 40% (w/w), about 10% (w/w) to about 35% (w/w), about 15% (w/w) to about 45% (w/w), about 20% (w/w) to about 40% (w/w), about 25% (w/w) to about 35% (w/w), or about 30% (w/w) to about 35% (w/w), based on a total weight of the microparticles.

A median particle size distribution (D50) of the microparticles may be about 25 μm to about 100 μm, about 25 μm to about 95 μm, about 25 μm to about 90 μm, about 25 μm to about 80 μm, about 25 μm to about 70 μm, about 30 μm to about 65 μm, about 30 μm to about 60 μm, about 30 μm to about 55 μm, about 30 μm to about 50 μm, about 35 μm to about 65 μm, about 40 μm to about 65 μm, about 45 μm to about 65 μm, about 35 μm to about 60 μm, about 40 μm to about 55 μm, or about 45 μm to about 50 μm.

The microparticles may have a particle size distribution in the range of ±5 μm, ±7 μm, ±10 μm, ±12 μm, or ±15 μm, based on the median particle size distribution (D50). In addition, the microparticle may be present with 60% by weight or more, 65% by weight or more, 70% by weight or more, 75% by weight or more, 80% by weight or more, 85% by weight or more, 90% by weight or more, 95 wt % or more, or 99 wt % or more, based on the total microparticles within this particle size distribution range.

High-dose sustained formulation using conventional microparticles (e.g., Vivitrol®) has difficulty in controlling microparticle size range, and thus has a problem in that the particle size deviation was very high based on the median particle size distribution (D50) by having wide particle size distribution (that is, non-uniform particle size distribution). In the case of such a wide particle size distribution, it is difficult to ensure a constant release of the drug because each of the microparticles has a different sizes, and in particular, has a high possibility to develop adverse effects as the blood concentration of the drug rises abruptly due to the phenomenon called initial burst effect wherein all drugs are released at the same time from the microparticles in the initial point of an administration of drug. In contrast, the microparticles of the present disclosure have a narrow particle size distribution (that is, a uniform particle size distribution), and thus exhibit constant pharmacokinetic properties and effects wherein the drug may be constantly released in the body and blood concentration of the drug is maintained constantly. In addition, the present disclosure has found that these properties contribute to the remarkable and excellent effect for the prevention or treatment of autoimmune diseases. Naltrexone or a pharmaceutically acceptable salt thereof may be homogeneously distributed in the microparticles. Biodegradable polymers may be uniformly distributed in the microparticles.

The microparticles may be oval to spherical.

The term "autoimmune disease" refers to a disease wherein an abnormality occurs in immune function, and immune cells in the body attack organs or tissues of the self. The autoimmune disease may be divided into organ-specific autoantibody-related diseases and organ non-specific (systemic) diseases. In the present disclosure, the autoimmune disease may be a disease related to toll-like receptor (TLR) protein, in particular a disease related to toll-like receptor 2/4 (TLR2/4) signaling. The autoimmune disease may be selected from, for example, the group consisting of rheumatoid arthritis, multiple sclerosis, hemophagocytic lymphohistiocytosis, systemic lupus erythematosus, Kikuchi disease, vasculitis, adult onset Still's disease, inflammatory myositis, Behcet disease, IgG4-associated disease, Sjogren syndrome, giant cell arteritis, temporal arteritis, type 1 diabetes, atopic dermatitis, Crohn's disease, systemic sclerosis, psoriasis, Grave's hyperthyroidism, Hashimoto's disease, pernicious anemia, ankylosing spondylitis, myasthenia, vitiligo, Guillain-Barre syndrome, glomerulonephritis, ANCA-associated vasculitis (AAV), antiphospholipid syndrome, pemphigus, cancer, autoimmune hepatitis, encephalomyelitis, fibromyalgia, and psoriatic arthritis, but the present disclosure is not limited thereto.

The term "prevention" refers to any action that suppresses the onset of autoimmune disease or delays the onset of an autoimmune disease by administration of the agent. The term "treatment" refers to any action that improves or alters beneficially the symptom of autoimmune disease by administration of the agent.

The term "sustained" refers to properties wherein an active ingredient of drug is slowly released. The term "sustained" may be used interchangeably with terms "long-acting" or "extended".

In the present disclosure, the agent refers to a pharmaceutical composition prepared in a form and appearance suitable for administering a drug.

The agent may comprise a pharmaceutically acceptable carrier. The carrier comprises excipients, diluents or adjuvants. The carrier may be selected from, for example, the group consisting of lactose, dextrose, sucrose, sorbitol, mannitol, xylitol, erythritol, maltitol, starch, gum acacia, alginate, gelatin, calcium phosphate, calcium silicate, cellulose, methyl cellulose, polyvinyl pyrrolidone, water, physiological saline, buffers such as PBS, methylhydroxy benzoate, propylhydroxy benzoate, talc, magnesium stearate, and mineral oil. The agent may comprise a filler, an anti-agglomeration agent, a lubricant, a wetting agent, a flavoring agent, an emulsifying agent, a preservative, or a combination thereof.

The agent may be prepared in any formulation according to a conventional method. The agent may be formulated, for example, in oral dosage forms (e.g., powders, tablets, capsules, syrups, pills, or granules), or parenteral preparations (e.g., injections, patches, or implants). In addition, the formulation may be prepared for a systemic formulation or for a local formulation. The agent may be an injection for subcutaneous administration or intramuscular administration. The agent may be a patch or implant for subcutaneous administration.

The agent may comprise naltrexone as an active ingredient or a pharmaceutically acceptable salt thereof in an effective amount. The term "effective amount" refers to an amount sufficient to exhibit the effect of prevention or treatment when administered to a subject in need thereof. The effective amount may be appropriately selected by those skilled in the art depending on the individual. It may be determined depending on a severity of disease, patient's age, weight, health, sex, patient's sensitivity to drug, administration time, administration route and excretion rate, duration of treatment, factors including drugs used in combination with or concurrently with the composition used, and factors well-known to other medical fields. The effective amount may be about 0.5 µg to about 2 g, about 1 µg to about 1 g, about 10 µg to about 500 mg, about 100 µg to about 100 mg, or about 1 mg to about 50 mg per the agent.

The agent may comprise low-dose naltrexone as an active ingredient or a pharmaceutically acceptable salt thereof. The term "low-dose" may refer to a dose within a range wherein an effect following the administration of low-dose naltrexone is exhibited, when naltrexone is administered as an injection. Low-dose naltrexone (LDN) in the existing oral dosage form means a dose of 1 mg to 7.5 mg or a dose of 5 mg or less per unit dosage form, but when naltrexone is administered as an injection, this definition may not be applied, and it may mean a capacity sufficient to achieve the effect of the present disclosure. For example, low-dose naltrexone may mean (i) a dose that effectively inhibits the TLR4 receptor in the body while maintaining a normal immune response and immune system in the patient without causing a sudden decline in the patient's immunity, as described in Example 6, or (ii) a dose that exhibits the same or better effect for the prevention or treatment of autoimmune disease as that of Humira®, even though it is administered at a lower dose and less frequently than Humira. For example, in a sustained injection of naltrexone, a low dose may be for example a range of less than about 160 mg, about 150 mg or less, about 140 mg or less, about 120 mg or less, about 100 mg or less, about 80 mg or less, about 60 mg or less, about 40 mg or less, about 20 mg or less, about 10 mg or less, about 5 mg or less, about 1 mg or less.

The agent may comprise about 0.1 mg to about 1 g, about 0.5 mg to about 500 mg, about 1 mg to about 400 mg, about 1 mg to about 300 mg, about 1 mg to about 200 mg, about 1 mg to about 100 mg, about 1 mg to about 80 mg, about 1 mg to about 60 mg, about 1 mg to about 50 mg, about 1 mg to about 30 mg, about 5 mg to about 50 mg, about 10 mg to about 40 mg, about 15 mg to about 30 mg, about 25 mg to about 40 mg, or about 55 mg to about 50 mg of naltrexone or a pharmaceutically acceptable salt thereof per unit dosage form.

The agent may be administered subcutaneously, intramuscularly, or intradermally. The agent may be administered one time every about 1 week to about 2 years, about 1 week to about 1 year and 6 months, about 1 week to about 1 year, about 1 week to about 11 months, about 1 week to about 10 months, about 1 week to about 9 months, about 1 week to about 8 months, about 1 week to about 7 months, about 1 week to about 6 months, about 1 week to about 5 months, about 1 week to about 4 months, about 1 week to about 3 months, about 1 week to about 2 months, about 1 week to about 1 month, about 2 weeks to about 1 month, or about 3 weeks to about 1 month. The agent may be administered one time at about 25 days to about 30 days, about 26 days to about 30 days, about 27 days to about 30 days, about 28 days to about 30 days, about 25 days to about 29 days, or about 25 days to about 28 days.

The agent may be administered in an amount of about 0.1 mg/kg to about 1 g/kg, about 0.2 mg/kg to about 1 g/kg, about 0.5 mg/kg to about 1 g/kg, about 1 mg/kg to about 1 g/kg, about 1 mg/kg to about 900 mg/kg, about 1 mg/kg to about 800 mg/kg, about 1 mg/kg to about 700 mg/kg, about 1 mg/kg to about 600 mg/kg, about 1 mg/kg to about 500 mg/kg, about 1 mg/kg to about 400 mg/kg, about 1 mg/kg to about 300 mg/kg, about 1 mg/kg to about 200 mg/kg, about 1 mg/kg to about 100 mg/kg, about 5 mg/kg to about 100 mg/kg, about 10 mg/kg to about 100 mg/kg, about 10 mg/kg to about 80 mg/kg, about 10 mg/kg to about 60 mg/kg, or about 10 mg/kg to about 50 mg/kg.

The agent of the present disclosure may be administered in combination with one or more therapeutic agents for autoimmune diseases. According to the standard administration method of naltrexone and one or more therapeutic agents for autoimmune diseases, it may be administered simultaneously, sequentially, or in a separate administration interval and manner with the agent of the present disclosure. The therapeutic agents for autoimmune diseases that may be administered in combination with the naltrexone agent of the present disclosure may be at least one selected from the group consisting of Methotrexate, Hydroxychloroquine, Sulfasalazine, Leflunomide, Adalimumab, Etanercept, Infliximab, Golimumab, Tocilizumab, Abatacept, Rituximab, Tofacitinib, Baricitinib, Peficitinib, Upadacitinib, Glatiramer acetate, Dimethyl fumarate, Interferon β-1a, Interferon β-1b, Ocrelizumab, Fingolimod, Natalizumab, Ozanimod, Siponimod, Alemtuzumab, Teriflunomide, Cladribine, Mitoxantrone and Cyclophosphamide, but the present disclosure is not limited thereto.

One aspect may be related to a sustained agent for improving the clinical or radiological status of a rheumatoid arthritis patient, comprising microparticles comprising naltrexone or a pharmaceutically acceptable salt thereof, and biodegradable polymers. One aspect may be related to a sustained agent for treating inflammation of arthritis in rheumatoid arthritis patients or inhibiting the progression of joint destruction, comprising microparticles comprising naltrexone or a pharmaceutically acceptable salt thereof, and biodegradable polymers.

One aspect may be related to a sustained agent for reducing inflammatory mediators in patients with autoimmune diseases, comprising microparticles comprising naltrexone or a pharmaceutically acceptable salt thereof, and biodegradable polymers. Here, the autoimmune disease may be rheumatoid arthritis, and the inflammatory mediator may be one or more of a pro-inflammatory cytokine group A (IL-1β, IL-6, IL-17, and TNF-α) and a chemokine group B (MCP-1 and MIP-2).

One aspect may be related to a sustained agent for improving the clinical status of a multiple sclerosis patient, comprising microparticles comprising naltrexone or a pharmaceutically acceptable salt thereof, and biodegradable polymers.

One aspect may be related to a sustained agent for reducing cellular infiltration in the spinal cord tissue or for inhibiting inflammation of the spinal cord, comprising microparticles comprising naltrexone or a pharmaceutically acceptable salt thereof, and biodegradable polymers. One aspect may be related to a sustained agent for reducing demyelination in spinal tissue, comprising microparticles comprising naltrexone or a pharmaceutically acceptable salt thereof, and biodegradable polymers. One aspect may be related to a sustained agent for inhibiting an expression of myelin basic protein (MBP), comprising microparticles comprising naltrexone or a pharmaceutically acceptable salt thereof, and biodegradable polymers.

One aspect may be related to a sustained agent for inhibiting a TLR4 signaling, comprising microparticles comprising naltrexone or a pharmaceutically acceptable salt thereof, and biodegradable polymers. Here, the inhibition of TLR4 signaling may be the inhibition from naltrexone by binding to the MD2 protein present at the TLR4 receptor. Also, here, the sustained agent may be a sustained agent to inhibit TLR4 signaling in a patient with an autoimmune disease.

One aspect may be related to a sustained agent to inhibit an expression of pro-inflammatory cytokine, comprising microparticles comprising naltrexone or a pharmaceutically acceptable salt thereof, and biodegradable polymers. Here, the inhibition of the expression of pro-inflammatory cytokines may be the inhibition of the expression of pro-inflammatory cytokines in a mechanism mediated by the TLR4 receptor. Also, here, the sustained agent may be a sustained agent to inhibit an expression of pro-inflammatory cytokine in a patient with an autoimmune disease. The pro-inflammatory cytokine may be one or more selected from the group consisting of TNF-α, IL-1β, IL-6, IL-17 and iNOS.

One aspect may be related to a sustained agent to inhibit an activity of NF-κB, comprising microparticles comprising naltrexone or a pharmaceutically acceptable salt thereof, and biodegradable polymers. Here, the inhibition of the activity of NF-κB may be the inhibition of the activity of NF-κB in a mechanism mediated by the TLR4 receptor. Also, here, the sustained agent may be a sustained agent for inhibiting the activity of NF-κB in a patient with an autoimmune disease.

In one aspect of the present disclosure, a method for preparing naltrexone microparticles is provided, the method comprising 1) preparing a drug solution by dissolving naltrexone or a pharmaceutically acceptable salt thereof in a first solvent; 2) preparing a polymer solution by dissolving biodegradable polymers in a second solvent; 3) mixing and stirring the drug solution and the polymer solution prepared in steps 1) and 2) to prepare an oily solution; 4) preparing microparticles by applying the oil phase solution and the aqueous phase solution prepared in step 3) to a microparticle (microsphere) production module; and 5) removing the solvent by stirring the microparticles prepared in step 4).

In this aspect, naltrexone, a pharmaceutically acceptable salt, biodegradable polymers, and microparticles (microspheres) are as described above.

In step 1), the first solvent may be dichloromethane, methyl acetate, ethyl acetate, diethyl ether, benzyl alcohol, or a combination thereof, and in step 2), the second solvent may be methyl acetate, ethyl acetate, dichloromethane or a combination thereof, but is not limited thereto. In addition, steps 1) and 2) may be performed sequentially, simultaneously, or in reverse order.

In step 3), the drug solution and the polymer solution may be mixed so that the drug to polymer ratio is 1:0.5 to 1:10, specifically, the drug to polymer ratio is 1:0.5 (2:1) to 1:5, more specifically, 1:2 to 1:5, and in particular, may be mixed so that the drug and polymer ratio is 1:2.

In step 4), the aqueous phase solution may be polyethylene glycol sorbitan monooleate, sorbitan oleate, sodium lauryl sulfate or polyvinyl alcohol (PVA) solution, specifically, 0.5% (w/v) of PVA solution.

In step 5), the stirring may be carried out at 10° C. to 20° C. at 200 to 400 rpm for 30 minutes to 2 hours, at 25° C. to 35° C. at 200 to 400 rpm for 30 minutes to 3 hours, and at 35° C. to 45° C. at 200 to 400 rpm for 30 minutes to 4 hours, specifically, at 13° C. to 17° C. at 250 to 350 rpm for 30 minutes to 2 hours, at 28° C. to 32° C. at 250 to 350 rpm for 1 hour to 3 hours, and at 38° C. to 42° C. at 250 to 350 rpm for 2 hours to 4 hours, more specifically at 15° C. at 300 rpm for 1 hour, at 30° C. at 300 rpm for 2 hours, and at 40° C. at 300 rpm for 3 hours, but is not limited thereto, and may be carried out under conditions that may remove the solvent as much as possible for an appropriate time.

The residual amount of the solvent in naltrexone microparticles prepared according to a method for the preparation above may be about 1000 ppm or less, about 900 ppm or less, about 800 ppm or less, about 700 ppm or less, about 600 ppm or less, about 500 ppm or less, about 400 ppm or less, about 300 ppm or less, about 200 ppm or less, about 100 ppm or less, about 10 ppm or less, or about 1 ppm or less. Also, the residual amount of the solvent in naltrexone microparticles prepared according to a method for the preparation above may be about 800 ppm to about 100 ppm, about 750 ppm to about 100 ppm, about 700 ppm to about 100 ppm, about 650 ppm to about 100 ppm, about 800 ppm to about 150 ppm, about 800 ppm to about 200 ppm, about 800 ppm to about 250 ppm, about 800 ppm to about 300 ppm, about 800 ppm to about 350 ppm, about 800 ppm to about 400 ppm, about 800 ppm to about 450 ppm, about 800 ppm to about 500 ppm, about 800 ppm to about 550 ppm, about 800 ppm to about 600 ppm, about 750 ppm to about 600 ppm, about 700 ppm to about 600 ppm, or about 650 ppm to about 600 ppm.

The method for the preparation above may further comprise 6) step of freeze-drying the microparticles.

Another aspect provides microparticles prepared by the method for preparing naltrexone microparticles of the present disclosure.

Another aspect provides a method for preventing or treating autoimmune disease, the method comprising: administering a sustained agent for preventing or treating autoimmune disease to an individual with an injection one time per one week to two years, comprising microparticles comprising naltrexone or a pharmaceutically acceptable salt thereof, and biodegradable polymers according to one aspect.

Naltrexone, pharmaceutically acceptable salts, biodegradable polymers, microparticles, autoimmune diseases, prevention, treatment, sustained, and formulations are as described above.

The individual may be a mammalian, for example, a human, a dog, a mouse, a rat, a guinea pig, a cow, a horse, a pig, a sheep, a goat, a cat, or a simian, in particular, a mammalian including a human, or non-human mammalian, but is not limited thereto. The individual may be suffering from or at risk of suffering from an autoimmune disease.

The method of administration may be a parenteral administration, for example, an administration via subcutaneous, intramuscular, or intradermal routes. The agents may be administered systemically or locally, alone or in combination with other pharmaceutically active compounds.

Normally, naltrexone is administered at a dose of 25 mg to 50 mg once per day when administered orally, and administered once a month at a dose of 380 mg when administered intramuscularly. Naltrexone may cause liver damage when administered at dose higher than recommended doses. The sustained agent according to one aspect contains a low dose of naltrexone and may be administered once from about 1 week to about 1 year, from about 2 weeks to about 1 year, or from about 3 weeks to about 1 year. The sustained agent may be administered once on about 28 days. The sustained agent has the same effect as the methotrexate administered once a week even when administered once for about 3 weeks to about one year, and may achieve a significantly superior effect compared to the oral naltrexone agent administered once a day.

Another aspect relates to a pharmaceutical composition for preventing or treating an autoimmune disease comprising naltrexone or a pharmaceutically acceptable salt thereof, and the pharmaceutical composition may be administered parenterally. The pharmaceutical composition may be an injection for subcutaneous administration or intramuscular administration. The injection comprises naltrexone or a pharmaceutically acceptable salt thereof, and may further comprise water for injection. The water for injection is a solvent used in the preparation of injections, is not limited to the above examples, and may be used without limitation as long as it is readily available to those skilled in the art. The pharmaceutical composition may comprise 0.1 mg to 1 g of naltrexone or a pharmaceutically acceptable salt thereof per unit dosage form. The pharmaceutical composition includes a low-dose naltrexone or a pharmaceutically acceptable salt thereof, and is administered at a dose of 0.1 mg/kg body weight to 1 g/kg body weight, and is administered at a dose of 10 mg/kg body weight to 500 mg/kg body weight, but, is not limited to the above example. The matters described or defined with respect to the sustained agent in the present specification may be applied to the pharmaceutical composition as well. In one aspect, the agent may be a pharmaceutical composition.

Advantageous Effects

According to a sustained agent for preventing or treating autoimmune diseases comprising microparticles containing naltrexone or a pharmaceutically acceptable salt thereof, and biodegradable polymers and a method using the same, it may be used for long-lasting prevention or treatment of autoimmune diseases by a single administration.

BRIEF DESCRIPTION OF DRAWINGS

FIG. 1A, FIG. 1B, FIG. 1C, FIG. 1D, FIG. 1E and FIG. 1F are graphs showing the pharmacokinetic profile of microspheres prepared by varying lactide ratio and intrinsic viscosity of the microspheres.

FIG. 2A, FIG. 2B and FIG. 2C are images of scanning electron microscopy of microspheres prepared according to Preparation Example 1, and FIG. 2D is a graph showing the particle size distribution of the microspheres. FIG. 2E. FIG. 2F, FIG. 2G and FIG. 2H are images of scanning electron microscopy of microspheres prepared according to Preparation Example 4, and FIG. 2I is a graph showing the particle size distribution of the microspheres.

FIGS. 3A and 3B are graphs showing the blood concentration (ng/mL) of naltrexone over time after administration (hour) when microspheres prepared according to Preparation Example 1 were administered to dogs by subcutaneous injection and intramuscular injection, respectively. FIG. 3C is a graph showing the blood concentration (ng/mL) of naltrexone over time after administration (hour) when microspheres prepared according to Preparation Example 4 were administered to dogs by intramuscular injection.

FIG. 4A is a schematic diagram of animal model construction and administration schedule, FIG. 4B is images of the mouse toes for test substance administration groups (Vehicle DDS: negative control group, MTX: methotrexate administration group, Naltrexone: naltrexone administration group, Naltrexone DDS: naltrexone DDS administration group), FIG. 4C is a graph showing the clinical arthritis index of mouse over time (days) after administration of the test substance, FIG. 4D is a graph showing the area under the curve (AUC) of the clinical arthritis index, and FIG. 4E is a graph showing the incidence (%) of arthritis over time (day) after administration of the test substance and FIG. 4F is a graph showing the area under the curve (AUC) of the incidence (mean±SEM,: p-value<0.01,*: p-value<0.001).

FIG. 5A, FIG. 5B, and FIG. 5C are images of tissues stained with hematoxylin/eosin and toluidine blue, respectively (Vehicle DDS: negative control group, MTX: methotrexate administration group, Naltrexone: naltrexone administration group, Naltrexone DDS: naltrexone DDS administration group, 200 times magnification, bar: 100 μm), FIGS. 5B and 5D are graphs showing histomorphological scores for each administration group in hematoxylin/eosin-stained tissues and toluidine-stained tissues, respectively (mean±SEM,: p-value<0.01,*: p-value<0.001).

FIG. 6 is a graph showing the body weight (%) of mouse for each administration group over the time (days) after administration of the test substance.

FIG. 7A is a toe image of mouse by test substance administration groups (Vehicle DDS: negative control group, MTX: methotrexate administration group, Xeljanz®: Xeljanz® administration group, Q-DDS: naltrexone DDS administration group, MTX+Q-DDS: methotrexate+ naltrexone DDS combination administration group), FIG. 7B is a graph showing the clinical arthritis index of mouse according to the time (days) after administration of the test substance, FIG. 7C is a graph showing the area under the curve (AUC) of the clinical arthritis index, FIG. 7D is a graph showing the incidence (%) of arthritis according to time (days) after administration of the test substance, and FIG. 7E is a graph showing the area under the curve (AUC) of the incidence of arthritis (mean±SEM,: p-value<0.01,*: p-value<0.001).

FIG. 8A is an image of tissue stained with hematoxylin/eosin (Vehicle DDS: negative control group, MTX: methotrexate administration group, Xeljanz®: Xeljanz® administration group, Q-DDS: naltrexone DDS administration group, MTX+Q-DDS: methotrexate+ Naltrexone DDS combination administration group, 200-fold magnification, bar: 100 μm), FIG. 8B is a graph showing histomorphological scores for each administration group in hematoxylin/eosin-stained tissues (mean±SEM,: p-value<0.01,*: p-value<0.001).

FIG. 9A is an image of tissue stained with toluidine blue (Vehicle DDS: negative control group, MTX: methotrexate administration group, Xeljanz®: Xeljanz® administration group, Q-DDS: naltrexone DDS administration group, MTX+Q-DDS: methotrexate+ Naltrexone DDS combination administration group, 200-fold magnification, bar: 100 μm), FIG. 9B is a graph showing histomorphological scores for each administration group in toluidine-stained tissues (mean±SEM,: p-value<0.01,*: p-value<0.001).

FIG. 10 is a graph showing the body weight (%) of mouse for each administration group according to the time (days) after administration of the test substance.

FIG. 11A is a representative image of each group taken by micro-CT (Vehicle DDS: negative control group, MTX: methotrexate administration group, Xeljanz®: Xeljanz® administration group, Q-DDS: naltrexone DDS administration group, MTX+Q-DDS: methotrexate+Naltrexone DDS combination administration group, 200-fold magnification, bar: 100 μm), FIG. 11B is particularly an enlarged image of the joint. FIG. 11C is a graph showing radiographic scores.

FIGS. 12A and 12B are the results of analysis of the concentration of inflammatory mediator protein in the arthritis tissue for each administration group and show the respective result of measuring the amount of proteins of pro-inflammatory cytokine group A (IL-1β, IL-6, IL-17, and TNF-α) (FIG. 12A) and chemokine group B (MCP-1 and MIP-2) (FIG. 12B) of the inflammatory mediator, through the Luminex technology-based multi-analyte-ELISA (multi-analyte-ELISA) method, respectively.

FIG. 13 is the result of analysis of the concentration of inflammatory mediator protein in the blood for each administration group, and shows the result of measuring the amount of IL-6 protein through the Luminex technology-based multi-analyte-ELISA (multi-analyte-ELISA) method.

FIG. 14A is a toe image of mouse for test substance administration group (Vehicle DDS: negative control group, Humira: Humira administration group, Q-DDS: naltrexone DDS 10 mg/mouse administration group), FIG. 14B is a graph showing the clinical arthritis index of mouse according to the time (days) after administration of the test substance, FIG. 14C is a graph showing the area under the curve (AUC) of the clinical arthritis index, FIG. 14D is a graph showing the incidence (%) of arthritis over time (days) after administration of the test substance, and FIG. 14E is a graph showing the area under the curve (AUC) of the incidence of arthritis (mean±SEM,: p-value<0.01,*: p-value<0.001).

FIGS. 15A, FIG. 15B and FIG. 15C are images of tissues stained with hematoxylin/eosin and toluidine blue, respectively (Vehicle DDS: negative control group, Humira: Humira administration group, Q-DDS: Naltrexone DDS 10 mg/mouse administration group, 200-fold magnification, bar: 100 μm), FIGS. 15B and 15D are graphs showing histomorphological scores for each administration group in hematoxylin/eosin-stained tissues and toluidine-stained tissues, respectively (mean±SEM,***: p-value<0.001).

FIG. 16A is a graph showing the body weight (%) of mouse for each administration group over the time (days) after administration of the test substance, and FIG. 16B is a graph showing the body weight (% vs. 23 days) on the 41st day.

FIG. 17A is a representative image of each group taken by micro-CT (Vehicle DDS: negative control group, Humira: Humira administration group, Q-DDS: naltrexone DDS 10 mg/Mice administration group, 200-fold magnification, bar: 100 μm), FIG. 17B is particularly an enlarged image of the joint. FIG. 17C is a graph showing radiographic scores.

FIG. 18A and FIG. 18B are the results of analyzing the concentration of inflammatory mediator protein in the arthritis tissue for each administration group and show the respective result of measuring an amount of proteins of pro-inflammatory cytokine group A (IL-1β, IL-6, IL-17, and TNF-α) (FIG. 18A) and chemokine group B (MCP-1 and MIP-2, +IL-2) (FIG. 18B) of the inflammatory mediator, through the Luminex technology-based multi-analyte-ELISA (multi-analyte-ELISA) method, respectively.

FIG. 19 is a result of analyzing the concentration of inflammatory mediator protein in the blood for each administration group, and shows the result of measuring the amount of IL-6 protein through the Luminex technology-based multi-analyte-ELISA (multi-analyte-ELISA) method.

FIG. 20A, FIG. 20B, and FIG. 20C are images taken at each magnification by NK cell immunostaining (CD56+) in arthritis tissue (×200, ×200, ×400). FIG. 20D is a graph quantitatively evaluating the number of NK cells.

FIG. 21A is a schematic diagram summarizing the production, the substance to be administered, administration schedule of an experimental autoimmune encephalomyelitis mouse model (Mouse Experimental Autoimmune Encephalomyelitis: EAE), which is an animal model of multiple sclerosis.

FIG. 21B is a graph showing the EAE clinical score of mouse over time (days) after administration of the test substance, and FIG. 21C is a graph showing the area under the curve of the clinical score (mean±standard error mean (SEM),***: p-value<0.001).

FIG. 21D is an image of tissue stained with hematoxylin/eosin (Vehicle: negative control group, Fytarex: Fytarex administration group, Revia: Revia administration group, Q-DDS: naltrexone DDS administration group, 50-fold and 200-fold magnification), FIG. 21E is a graph showing histomorphological scores for each administration group in hematoxylin/eosin-stained tissues (mean±standard error mean (SEM),: p-value compared to negative control<0.01,*: p-value compared to negative control) <0.001).

FIG. 21F is an image of tissue stained with Luxol fast blue (Vehicle: negative control group, Fytarex: Fytarex administration group, Revia: Revia administration group, Q-DDS: naltrexone DDS administration group, 50-fold and 200-fold magnification), FIG. 21G is a graph showing histomorphological scores for each administration group in Luxol fast blue-stained tissues (mean±standard error mean (SEM),: p-value compared to negative control<0.01,*: p-value compared to negative control<0.001).

FIG. 21H is an image of tissue stained with immunohistochemistry (Vehicle: negative control group, Fytarex: Fytarex administration group, Revia: Revia administration group, Q-DDS: naltrexone DDS administration group, 50-fold and 200-fold magnification), FIG. 21I is a graph showing the results of quantification of the stained area for each administration group in the stained tissue based on the total spinal cord cross-sectional area (mean±standard error of mean (SEM),: p-value compared to negative control<0.01,*: p-value compared to negative control) <0.001).

FIG. 22 is a graph showing the body weight (%) of mouse for each administration group over the time (days) after administration of the test substance.

FIG. 23 is a result confirming the concentration-dependent binding of naltrexone to MD2 protein during TLR4 signaling through surface plasmon resonance analysis.

FIG. 24 is a schematic diagram of the mechanism by which naltrexone affects TLR4 signaling in the human synovial cell line SW982 cells.

FIG. 25 is a result confirming with RT-qPCR that the expression of pro-inflammatory cytokines is inhibited when human synovial cell line SW982 cells are treated with LDN (indicated by "Q" in the figure) and then treated with lipopolysaccharide ("LPS").

FIG. 26 is a result confirming the activity of NF-03 through Western blotting when the human synovial cell line SW982 cells were treated with LDN (indicated by "Q" in the figure) and then treated with LPS.

FIG. 27 is a result of confirming the phoshorylation level of ERK, JNK, p38 through Western blotting to examine the activity of MAPK when human synovial cell line SW982 cells are treated with LDN (indicated by "Q" in the figure) and then treated with LPS.

FIG. 28 is a result confirming with RT-qPCR that the expression of pro-inflammatory cytokines is inhibited when mouse macrophage line, Raw 264.7 cells are treated with LDN (indicated by "Q" in the figure) and then treated with lipopolysaccharide ("LPS").

FIG. 29 is a result confirming the activity of NF-κ13 through Western blotting when mouse macrophage line, Raw 264.7 cells were treated with LDN (indicated by "Q" in the figure) and then treated with LPS.

FIG. 30 is a result of the phoshorylation level of ERK, JNK, p38 through Western blotting to examine the activity of MAPK when mouse macrophage line, Raw 264.7 cells are treated with LDN (indicated by "Q" in the figure) and then treated with LPS.

FIG. 31 is a schematic diagram of the mechanism by which naltrexone affects TLR4 signaling in mouse macrophage line, Raw 264.7 cells.

FIG. 32 is a schematic diagram showing the signaling or activation mechanism of TLR4 in cells.

FIG. 33 is a result confirmed by RT-qPCR that the expression of pro-inflammatory cytokines is inhibited when human synovial cell line SW982 cells are treated with naltrexone (indicated by "Q" in the figure) or 6β-naltrexol (indicated by "6β-Q" in the figure) and then treated with lipopolysaccharide ("LPS"). In the figure,*means p<0.05.

FIG. 34 is a result confirmed by RT-qPCR that the expression of pro-inflammatory cytokines is inhibited when mice macrophage line, Raw 264.7 cells are treated with naltrexone (indicated by "Q" in the figure) or 6β-naltrexol (indicated by "6β-Q" in the figure) and then treated with lipopolysaccharide ("LPS"). In the figure.*means p<0.05.

FIG. 35 is a result of confirming the activity of signaling factor (NF-κB or MAPKs) of TLR4 through Western blotting when human synovial cell line SW982 cells are treated with naltrexone (indicated by "Q" in the figure) or 6β-naltrexol (indicated by "6β-Q" in the figure) and then treated with lipopolysaccharide ("LPS").

FIG. 36 is a result of the activity of signaling factor (NF-κB or MAPKs) of TLR4 through Western blotting when mice macrophage line, Raw 264.7 cells are treated with naltrexone (indicated by "Q" in the figure) or 6β-naltrexol (indicated by "6β-Q" in the figure) and then treated with lipopolysaccharide ("LPS").

BEST MODE

Hereinafter, one or more specific embodiments will be described in more detail through examples. However, these examples are for illustrative purposes only and the scope of the present disclosure is not limited to these examples.

Example 1. Preparation of Injectable Composition Containing Low-Dose Sustained-Naltrexone 1. Preparation of Naltrexone-Containing Microspheres (1) Confirmation of Pharmacokinetic Profile According to Lactide Ratio and Intrinsic Viscosity Differences in the release of active ingredients contained in microspheres depending on the type of polymers, the composition of polylactide and polylactide/glycolide copolymer, and the intrinsic viscosity (IV) of the polymer were confirmed by pharmacokinetic profiles.

For the preparation of the oily solution, naltrexone Base Anhydrous (manufactured by Mallinckrodt, hereinafter the same shall apply) and a polymer was prepared. As a polymer, PDL02A, PDLG7510, PDLG7504A, PDLG7502A, and a combination thereof were used as shown in Table 1 below.

TABLE 1

| Polymer | | Intrinsic viscosity (dl/g) | Molecular weight (kg/mol) |
|---|---|---|---|
| Poly (DL-lactide) | PDL02A | 0.2 | 17 |
| 75/25 DL-lactide/glycolide co-polymer | PDLG7510 | 1.0 | 153 |
| | PDLG7504A | 0.4 | 44 |
| | PDLG7502A | 0.2 | 17 |

A single polymer (Corbion) or a mixture thereof listed in Table 1 was dissolved in dichloromethane to prepare 18.29% (w/w) of a polymer solution. For the polymer mixture, a mixture of PDLG7510+ PDLG7502A (weight ratio 5:5), PDL02A+PDLG7502A (weight ratio 5:5), and PDL02A+PDLG7504A (weight ratio 5:5) was used. A drug solution of 29.41% (w/w) was prepared by dissolving naltrexone base in benzyl alcohol. The ratio of drug and polymer was 1:2, and the final oil phase solution was prepared by mixing and stirring the polymer solution and the drug solution.

As an aqueous solution, a 0.5% (w/v) of polyvinyl alcohol (PVA) solution was prepared.

A 100 μm of microchannel was assembled into a microsphere manufacturing module, and an oil phase solution and an aqueous phase solution were connected to an oil phase line and an aqueous phase line, respectively. A pressure of 400 mbar for the oil phase solution and 2500 mbar for aqueous phase solution was applied, and the oil phase solution and the aqueous phase solution were allowed to flow at a temperature of 17'C. Microspheres were to be prepared at the point where the flows of the oil phase solution and the aqueous phase solution met. After the preparation of microspheres was completed, the product was stirred at 300 rpm at 15° C. for 1 hour, 300 rpm at 30° C. for 2 hours, and 300 rpm at 40° C. for 3 hours to remove the solvent. Microspheres having a diameter between 25 μm and 63 μm were obtained by filtration through a sieve of 25 μm and 63 μm. The obtained microspheres were lyophilized then stored until use.

The prepared microspheres were dispersed in a diluent to prepare an injection formulation. The microspheres of the injection formulation were administered to the beagle dog once by subcutaneous injection at a dose of 190 mg/2 mL (based on naltrexone) (microspheres, 570 mg). The concentration (ng/mL) of naltrexone in the blood over the administration time (hour) was measured, and the results were shown in FIGS. 1A to 1F.

In general, the degradation rate of PDL02A-based microspheres is about 6 months to about 9 months, and the degradation rate of PDLG7502A-based microspheres is about 2 months to about 3 months. This means that the degradation rate of microspheres is decreased and the microspheres are maintained for a longer period in poly lactide compared to poly lactide-glycolide copolymer.

According to the results of FIGS. 1A to 1C, as the ratio and intrinsic viscosity of lactide increased, the decomposition rate of microspheres decreased, and the microspheres are maintained for a longer period (see FIGS. 1A to 1C).

In consideration of the naltrexone release pattern, initial release, and maintenance period of microsphere according to the results of FIGS. 1A to 1F, PDLG7510+ PDLG7502A (weight ratio 5:5) (FIG. 1D) and PDL02A+PDLG7502A (weight ratio 5:5) (FIG. 1E) were selected and used as a polymer of microsphere suitable for the naltrexone sustained injection.

(2) Change in Dichloromethane Residual Amount According to Stirring Conditions

Changes in the residual amount of dichloromethane (DCM) according to the stirring conditions during the preparation of microspheres were confirmed.

PDLG7510+ PDLG7502A (weight ratio 5:5) and PDL02A+PDLG7502A (weight ratio 5:5)-based microspheres were prepared by a method described in Example 1.1(2). The residual amount of dichloromethane according to the stirring conditions was shown in Table 2 below.

TABLE 2

| Conditions | PDLG7510 + PDLG7502A (5:5) | | PDL02A + PDLG7502A (5:5) | |
|---|---|---|---|---|
| Size of a particle ($\mu$l)(X50) | 46.92 | 109.5 | 50.25 | 51.38 |
| Amount in an aqueous (Reservoir, mL) | 5000 | 5000 | 5000 | 5000 |
| 15° C./rpm | 1 H/150 | 1 H/300 | 1 H/300 | 1 H/300 |
| 30° C./rpm | 2 H/300 | 3 H/600 | 2 H/300 | 2 H/300 |
| 40° C./rpm | 3 H/600 | — | 1 H/300 | 3 H/300 |
| Residual amount (ppm) of DCM | 644.6 | 530,027.1 | 7,596.3 | 619.0 |

As shown in Table 2, if PDL02A+PDLG7502A (5:5)-based microspheres were stirred at 300 rpm at 15° C. for 1 hour, at 300 rpm at 30° C. for 2 hours, and at 300 rpm at 40° C. for 3 hours, the residual amount of dichloromethane was the lowest.

2. Preparation of Microsphere-Based Low-Dose Naltrezone Injection Composition and Confirmation of its Particle Size Distribution.

2-1. Preparation of Microsphere-Based Low-Dose Naltrexone Injection Composition (Preparation Example 1)

Microspheres containing low dose naltrexone were prepared according to the method described in Example 1.1.

Specifically, for the preparation of the oil phase solution, a polymer solution of 18.29% (w/w) was prepared by dissolving PDL02A and PDLG7502A (5:5) mixture in dichloromethane. A drug solution of 29.41% (w/w) was prepared by dissolving naltrexone base in benzyl alcohol. The final oil phase solution was prepared by mixing and stirring the polymer solution and the drug solution, so that the ratio of drug and polymer was 1:2.

As an aqueous phase solution, a 0.5% (w/v) of polyvinyl alcohol (PVA) solution was prepared.

A 100 µm microchannel was assembled into a microsphere manufacturing module, and an oil phase solution and an aqueous phase solution were connected to an oily line and an aqueous line, respectively. A pressure of 400 mbar for the oil phase solution and 2500 mbar for aquious phase solution was applied, and the oil phase solution and the aqueous phase solution were allowed to flow at a temperature of 17° C. Microspheres were allowed to be prepared at the point where the flow of the oil phase solution and the flow of the aqueous phase solution met. After the preparation of microspheres was completed, the product was stirred at 300 rpm at 15° C. for 1 hour, 300 rpm at 30° C. for 2 hours, and 300 rpm at 40° C. for 3 hours to remove the solvent. Microspheres having a diameter between 25 µm and 63 µm were obtained by filtration through a sieve of 25 µm and 63 µm. The obtained microspheres were lyophilized and stored until use.

The prepared microspheres were confirmed with a scanning electron microscope (SEM), and the images were shown in FIGS. 2A to 2C. The particle size distribution of the microspheres was measured, and the results were shown in FIG. 2D. As shown in FIGS. 2A to 2D, it was confirmed that the microspheres were well prepared. As a result, the median particle size (D50) of the microspheres was 42.0 µm, the width was 8.82 µm, the encapsulation rate of the active ingredient was 91.36%, and the residual amount of dichloromethane was 19.5 ppm. The ratio of polymer to naltrexone was about 1:2. Here, the median particle size may mean an average particle size, and the width may mean a deviation.

2-2. Preparation of Microsphere-Based Low-Dose Naltrexone Injection Composition (Preparation Example 2)

Microspheres containing low dose naltrexone were prepared according to the method described in Example 1.1.

Specifically, for the preparation of an oil phase solution, PDLG7504 was dissolved in ethyl acetate and benzyl alcohol, and a drug solution was prepared by dissolving naltrexone base. The final oil phase solution was prepared by mixing and stirring the polymer solution and the drug solution, so that the ratio of drug and polymer was 1:2.

As an aqueous phase solution, a 1.0% (w/v) of polyvinyl alcohol (PVA) solution was prepared.

A 100 µm of microchannel was assembled into a microsphere manufacturing module, and an oil phase solution and an aqueous phase solution were connected to an oily line and an aqueous line, respectively. A pressure of 400 mbar for the oil phase solution and 2500 mbar for aquious phase solution was applied, and the oil phase solution and the aqueous phase solution were allowed to flow at a temperature of 7° C. Microspheres were allowed to be prepared at the point where the flows of the oil phase solution and the aqueous phase solution met. After the preparation of the microspheres was completed, the solvent was removed by extracting the solvent from an aqueous ethanol solution at 10° C. for 10 hours. Microspheres having a diameter between 25 µm and 63 µm were obtained by filtration through a sieve of 25 µm and 63 µm. The obtained microspheres were lyophilized and stored until use.

2-3. Preparation of Microsphere-Based Low-Dose Naltrexone Injection Composition (Preparation Example 3)

Microspheres containing low dose naltrexone were prepared according to the method described in Example 1.1.

Specifically, for the preparation of an oily solution, PDLG7504 was dissolved in dichloromethane, and a drug solution was prepared by dissolving naltrexone base. The final oil phase solution was prepared by mixing and stirring the polymer solution and the drug solution, so that the ratio of drug and polymer was 1:2.

As an aqueous solution, a 0.5% (w/v) of polyvinyl alcohol (PVA) solution was prepared.

A 100 µm of microchannel was assembled into a microsphere manufacturing module, and an oil phase solution and an aqueous phase solution were connected to an oily line and an aqueous line, respectively. A pressure of 600 mbar for the oil phase solution and 3000 mbar for aquious phase solution was applied, and the oil phase solution and the aqueous phase solution allowed to flow at a temperature of 10° C. Microspheres allowed to be prepared at the point where the flows of the oil phase solution and the aqueous phase solution met. The product was stirred at 300 rpm at 10° C. for 1 hour, at 300 rpm at 30° C. for 2 hours, and at 300 rpm at 40'C for 3 hours to remove the solvent. Microspheres having a diameter between 25 µm and 63 µm were obtained by filtration through a sieve of 25 µm and 63 µm. The obtained microspheres were lyophilized and then stored until use.

2-4. Preparation of Microsphere-Based Low-Dose Naltrexone Injection Composition (Preparation Example 4)

Microspheres containing low dose naltrexone were prepared according to the method described in Example 1.1.

Specifically, for the preparation of an oily solution, PDLG7504 was dissolved in dichloromethane and diethylether, and a drug solution was prepared by dissolving naltrexone base. The final oil phase solution was prepared by mixing and stirring the polymer solution and the drug solution, so that the ratio of drug and polymer was 1:2.

As an aqueous solution, a 0.5°% (w/v) of polyvinyl alcohol (PVA) solution was prepared.

A 100 µm of microchannel was assembled into a microsphere manufacturing module, and an oil phase solution and an aqueous phase solution were connected to an oily line and an aqueous line, respectively. A pressure of 600 mbar for the oil phase solution and 3000 mbar for the aqueous phase solution was applied, and the oil phase solution and the aqueous phase solution were allowed to flow at a temperature of 10'C. Microspheres were allowed to be prepared at the point where the flows of the oil phase solution and the aqueous phase solution met. The product was stirred at 300 rpm at 10° C. for 1 hour, at 300 rpm at 30° C. for 2 hours, and at 300 rpm at 40'C for 3 hours to remove the solvent. Microspheres having a diameter between 25 µm and 63 µm were obtained by filtration through a sieve of 25 µm and 63 µm. The obtained microspheres were lyophilized and stored until use.

The prepared microspheres were confirmed with a scanning electron microscope (SEM), and the images were shown in FIGS. 2E to 2H. The particle size distribution of the microspheres was measured, and the results were shown in FIG. 2I. As shown in FIGS. 2E to 2H, it was confirmed that the microspheres were well prepared. As a result, the median particle size (D50) of the microspheres was 38.34 µm, the width was 8.08 µm, the encapsulation rate of the active ingredient was 98.03%, and the residual amount of dichloromethane was 105.7 ppm and the residual amount of diethyl ether was 89.3 ppm. The ratio of polymer to naltrexone was about 1:2. Here, the median particle size may mean an average particle size, and the width may mean a deviation.

3. Pharmacokinetic Properties of Naltrexone-Containing Microspheres

The microspheres prepared as described in Example 1.2-1 (Preparation Example 1) were dispersed in a diluent to prepare an injection formulation. The microspheres of the injection formulation were administered to the beagle dog once by subcutaneous injection at a dose of 190 mg/2 mL (naltrexone base) (microspheres, 570 mg). The concentration (ng/mL) of naltrexone in the blood over the administration time (hour) was measured, and the results were shown in FIG. 3A.

The microspheres of the injection formulation were administered once by intramuscular injection at a dose of 300 mg/4 mL (based on naltrexone) (microspheres, 900 mg). Blood of beagle dogs was obtained regularly until 31 days after administration. The concentration (ng/mL) of naltrexone in the blood according to the administration time (hour) was measured, and the results were shown in FIG. 3B.

As shown in FIGS. 3A and 3B, even when administered once by subcutaneous or intramuscular injection, the sustaining effect of the test substance was shown for up to 28 days. Therefore, it was confirmed that the prepared microspheres can be used as long-acting and sustained-injections as a polymer drug delivery system (DDS).

Further, the microspheres prepared as described in Example 1.2-4 (Preparation Example 4) were dispersed in a diluent to prepare an injection formulation. The microspheres of the injection formulation were administered to the beagle dog once by intramuscular injection at a dose of 300 mg/head (based on naltrexone) (microspheres, 900 mg). The concentration (ng/mL) of naltrexone in the blood over the administration time (hour) was measured, and the results were shown in FIG. 3C.

As shown in FIG. 3C, even when administered once by intramuscular injection, the lasting effect of the test substance was shown up to 28 days. Therefore, it was confirmed that the prepared microspheres can be used as long-acting and sustained-injections as a polymer drug delivery system (DDS).

Example 2. Efficacy Evaluation of Naltrexone-Containing Microspheres for Rheumatoid Arthritis (First)

1. In Vivo Testing Method of Naltrexone-Containing Microspheres for Rheumatoid Arthritis In vivo efficacy was evaluated to determine whether naltrexone-containing microspheres, i.e., the naltrexone drug delivery systems, have therapeutic efficacy for rheumatoid arthritis.

As a model of murine collagen-induced arthritis (CIA), 6 to 10 week-old male mice of DBA/1 J strain was prepared. Mice were kept and tested in a specific pathogen free (SPF) laboratory under an environment of a temperature of 21° C. to 23° C. and a relative humidity of 40% to 45%. The number of experimental animals per cage was kept under 6, and a cage was exchanged twice a week and feed was supplied.

A 2 mg/mL collagen solution was prepared by dissolving bovine type 2 collagen in 10 mM acetic acid. After emulsifying by mixing 2 mg/mL of Complete Freund's adjuvant and collagen solution in a 1:1 (v/v) ratio, it was intradermally injected into the tail of mouse at a dose of 100 µl/animal (first immunization, day 0). After emulsifying by mixing incomplete Freund's adjuvant (WA) and collagen solution in a 1:1 (v/v) ratio on the $21^{th}$ day, it was intradermally injected into the tail of mouse at a dose of 100 µl/animal (the secondary immunization, on the $21^{th}$ day). After that, mice were randomly divided into groups and assigned to experimental groups.

As a material to be tested, naltrexone DDS prepared as described in Preparation Example 1 was prepared. Since the ratio of polymer to active ingredient in naltrexone DDS is about 1:2, 9 mg of microspheres contains about 3 mg of naltrexone as an active ingredient. As a negative control, DDS containing a carrier was used instead of naltrexone, and as a positive control, methotrexate (MTX, MTX injection, 50 mg/2 mL, JW Pharmaceutical) and naltrexone (Revia Tablet) were used. The refrigerated test substance was standed at room temperature 1 hour before administration and dissolved in 0.15 mL of water for injection. 0.15 mL of the test substance was filled using a syringe with a 21 G needle. The needle was changed to 23 G within 2 minutes after filling and the mice were injected.

Administration information for each administration group is as described in Table 3 below.

TABLE 3

| Administration group (Each group, n = 6) | Administration drug | Route of administration | Regimen and dose of administration (Baseline of the active ingredient) | Administration volume (μl) |
|---|---|---|---|---|
| 1 (Negative control) | Carrier-containing DDS | Subcutaneous injection | one dose on the 23rd day, N/A | 150 |
| 2 (Positive control) | metho-trexate | intra-peritoneal injection | Twice/week, 1 mg/kg body weight/each time | 100 |
| 3 (Positive control) | Naltrexone | Oral | Once/day, 10 mg/kg body weight/each time | 200 |
| 4 (Test group) | Naltrexone DDS | Sub-cutaneously | Administration once on the 23rd day, 3 mg/mouse | 150 |

Based on the blind evaluation data for each evaluation index, statistical analysis between the negative control group and the test group or between the two test groups was performed using SPSS. Student's t-test was used for comparison between the two groups. To compare differences between treatment groups at multiple time points, repeated measures ANOVA with Turkey's post-hoc test was used. The significance level was defined as a p-value of 0.05 or less.

2. Clinical Evaluation of Arthritis Activity

After administration of the test substance to the collagen-induced arthritis mouse model, the occurrence and level of inflammation were regularly observed from the date of group separation to the end of the experiment (the 41st day). Inflammation level was given a score of 0 to 4 for each paw according to the criteria in Table 4 below, and the sum was used as a clinical arthritis index (CAI).

TABLE 4

| Score | Symptom |
|---|---|
| 0 | Asymptomatic |
| 1 | Inflammation on one toe |
| 2 | Inflammation on two toes |
| 3 | Inflammation on three or more toes and sole |
| 4 | Inflammation on all toes and sole |

When the clinical index of each paw was 2 score or higher, it was determined that arthritis occurred, and the incidence was defined as 100% when arthritis occurred in four toes.

Toe images of normal mouse to which the test substance was not administered, and each administration group was shown in FIG. 4B (Normal: normal group, Vehicle DDS: negative control group, MTX: methotrexate administration group, Naltrexone: naltrexone administration group, Naltrexone DDS: naltrexone DDS administration group). The clinical arthritis index (CM) of mouse over the time (days) after administration of the test substance was shown in FIG. 4C, and a graph showing the area under the curve (AUC) of the clinical arthritis index was shown in FIG. 4D (mean±standard error of mean (SEM),: p-value<0.01,*: p-value<0.001). The results of the clinical arthritis index and the area under the curve were summarized in Table 5 below.

TABLE 5

| | CAI | | | CAI-AUC | | |
|---|---|---|---|---|---|---|
| Group | Mean | SEM | p-value vs Vehicle | Mean | SEM | p-value vs Vehicle |
| Vehicle DDS | 10.75 | 2.73 | — | 120.3 | 27.9 | — |
| Methotrexate (1 mg/kg) | 5.92 | 2.15 | 0.0057 | 46.6 | 13.8 | 0.0002 |
| Naltrexone (10 mg/kg) | 8.25 | 4.06 | 0.0572 | 59.0 | 32.5 | 0.0057 |
| Naltrexone DDS (3 mg/mouse) | 6.25 | 2.46 | 0.0064 | 46.8 | 16.5 | 0.0002 |

As shown in FIGS. 4C, 4D, and Table 5, the naltrexone DDS-administration group (test group) showed a decrease in the clinical arthritis index compared to the carrier-containing DDS-administration group (negative control group), and a similar level of decrease to the methotrexate-administration group (positive control group). The area under the curve for the clinical arthritis index showed a decrease in both the positive control group and the naltrexone DDS administration group compared to the carrier-containing DDS administration group. In particular, the clinical arthritis index was lower in the naltrexone DDS-administration group compared to the oral naltrexone (10 mg/kg) administration group, and the difference was consistently maintained during the arthritis progression.

The frequency (%) of arthritis over the time (days) after administration of the test substance was shown in FIG. 4E, and a graph showing the area under the curve (AUC) of the incidence was shown in FIG. 4F (mean±standard error mean (SEM),: p-value<0.01 versus negative control,*: p-value<0.001 versus negative control). The results of the incidence and the area under the curve were summarized in Table 6 below.

TABLE 6

| | Incidence (%) | | | Incidence-AUC | | |
|---|---|---|---|---|---|---|
| Group | Mean | SEM | p-value | Mean | SEM | p-value |
| Vehicle DDS | 70.83 | 24.58 | — | 714.6 | 28.3 | — |
| Methotrexate (1 mg/kg) | 20.83 | 18.82 | 0.0120 | 185.4 | 169.8 | 0.0013 |
| Naltrexone (10 mg/kg) | 41.67 | 34.16 | 0.0813 | 320.8 | 377.5 | 0.0561 |
| Naltrexone DDS (3 mg/mouse) | 25.00 | 22.36 | 0.0159 | 204.2 | 229.8 | 0.0036 |

As shown in FIGS. 4E, 4F, and Table 6, the naltrexone DDS-administration group showed a decrease in the incidence of arthritis compared to the carrier-containing DDS-administration group, and showed a similar level of decrease to the methotrexate-administration group. Also, in area under the curve for the incidence of arthritis, the naltrexone DDS-administration group showed a decrease compared to the carrier-containing DDS-administered group, and decrease similar to the methotrexate-administration group.

Therefore, it was confirmed that naltrexone DDS showed superior therapeutic efficacy compared to naltrexone for oral administration, and showed an effect similar to that of methotrexate, which is a standard treatment used in clinical practice.

3. Histological Estimation

Mice were sacrificed on the 41st day, which is the end of the experiment, and the tissues of the hind paws were stained with hematoxylin/eosin. Hematoxylin/eosin staining was used to evaluate the activity of inflammation in the arthritic tissue, and toluidine blue staining was performed to confirm the histological therapeutic effect on cartilage destruction.

(1) Hematoxylin/Eosin Staining

The hind paw tissue of the mouse was stained with hematoxylin/eosin, and 4 sites (100 magnification) for each tissue were photographed. Two or more investigators evaluated the items of synovial hyperplasia, pannus formation, cartilage destruction, and bone erosion for hematoxylin/eosin staining. The scoring criteria for each item were described in Table 7, and the average score of 4 sites was calculated as the score of each tissue.

TABLE 7

| Score | Synovial hyperplasia | Pannus formation | Cartilage destruction | Bone erosion |
|---|---|---|---|---|
| 0 | None | None | None | None |
| 1 | Very few inflammatory cells are found in the synovium Mild hyperplastic synovium | Pannus formation is not distinct | Catilage surface is not smooth. Focal erosion of cartilage surface region | Bone surface is not smooth |
| 2 | Inflammatory cellular proliferation is well marked leading to thichkened synovium | Pannus is weakly invaded in the bone | Catilage surface takes a corrugated shape | Cell invasion in bone is Found. Marked loss of bone surface integrity |
| 3 | Extensive proliferation of inflammatory cell along with severely thickening of synovium | Pannus is strongly invaded in the bone | More than 50% of cartilage of either joint counterpart is destroyed | Bone conformation is almost disrupted |

The image of the tissue stained with hematoxylin/eosin was shown in FIG. 5A (Vehicle DDS: negative control group, MTX: methotrexate administration group, Naltrexone: naltrexone administration group, Naltrexone DDS: naltrexone DDS administration group, 200 times magnification, bar: 100 μm). Histological scores were shown in FIG. 5B and the results were summarized in Table 8 below (mean±standard error mean (SEM),: p-value compared to negative control<0.01,*: p-value compared to negative control<0.001).

TABLE 8

| Histochromatographic parameters | | Vehicle DDS | MTX (1 mg/kg) | Naltrexone (10 mg/kg) | Naltrexone DDS (3 mg/mouse) |
|---|---|---|---|---|---|
| Synovial hyperplasia | Mean | 3.00 | 0.91 | 1.27 | 0.98 |
| | SEM | 0.00 | 0.28 | 0.74 | 0.29 |
| | p-value vs Vehicle | — | <0.0001 | 0.0045 | <0.0001 |
| Pannus formation | Mean | 2.89 | 0.14 | 0.58 | 0.30 |
| | SEM | 0.10 | 0.21 | 0.77 | 0.49 |
| | p-value vs Vehicle | — | <0.0001 | 0.0014 | 0.0001 |
| Cartilage destruction | Mean | 2.61 | 0.50 | 0.98 | 0.66 |
| | SEM | 0.34 | 0.18 | 0.72 | 0.31 |
| | p-value vs Vehicle | — | <0.0001 | 0.0052 | <0.0001 |
| Bone erosion | Mean | 2.89 | 0.08 | 0.58 | 0.28 |
| | SEM | 0.10 | 0.11 | 0.77 | 0.49 |
| | p-value vs Vehicle | — | <0.0001 | 0.0014 | 0.0001 |

As shown in FIGS. 5A, 5B, and Table 8, in the negative control group, cartilage destruction and bone erosion were clearly observed due to the increase of the pannus tissue along with the over proliferation of synovial cells. In the methotrexate-administration group, proliferation of synovial tissue was observed, but it showed a marked decrease compared to the negative control group, and the level of destruction of cartilage and bone was also decreased. The naltrexone DDS administration group showed a decrease compared to the negative control group in all four parameters, and showed a decrease similar to that of the methotrexate administration group.

(2) Toluidine Blue Staining

The hind paw tissue of the mouse was stained with toluidine blue, and 4 sites (100 magnification) for each tissue were photographed. Two or more investigators evaluated the items of matrix staining, surface regularity, and cartilage thickness. The scoring criteria for each item was described in Table 9, and the average score of 4 sites was calculated as the score of each

TABLE 9

| Score | Matrix staining | Surface regularity | Cartilage thickness |
|---|---|---|---|
| 0 | Normal | Smooth; 75% to 100% | >2/3 depth relative to av. GC* depth |
| 1 | Slightly reduced | Moderate; 50% to 75% | 1/2 to 2/3 depth relative to av. GC |
| 2 | Markedly reduced | Irregular; <50% | <1/2 depth relative to av. GC |
| 3 | Not staining | Severely irregular | |

The image of the tissue stained with toluidine blue was shown in FIG. 5C (Vehicle DDS: negative control group, MTX: methotrexate administration group, Naltrexone: naltrexone administration group, Naltrexone DDS: naltrexone DDS administration group, 200 times magnification, bar: 100 μm). Histological scores were shown in FIG. 5D and the results were summarized in Table 10 below (mean±SEM,: p-value compared to negative control<0.01,*: p-value compared to negative control<0.001).

TABLE 10

| Histological Scoring parameters | | Vehicle DDS | MTX (1 mg/kg) | Naltrexone (10 mg/kg) | Naltrexone DDS (3 mg/mouse) |
|---|---|---|---|---|---|
| Matrix staining | Mean | 2.97 | 0.61 | 0.92 | 0.59 |
| | SEM | 0.09 | 0.39 | 0.70 | 0.65 |
| | p-value vs Vehicle | — | <0.0001 | 0.0015 | 0.0003 |
| Surface regularity | Mean | 2.78 | 0.34 | 0.80 | 0.44 |
| | SEM | 0.13 | 0.13 | 0.74 | 0.38 |
| | p-value vs Vehicle | — | <0.0001 | 0.0024 | <0.0001 |
| Cartilage thickness | Mean | 1.78 | 0.11 | 0.39 | 0.16 |
| | SEM | 0.11 | 0.12 | 0.51 | 0.20 |
| | p-value vs Vehicle | — | <0.0001 | 0.0024 | <0.0001 |

As shown in FIGS. 5C, 5D, and Table 10, the naltrexone DDS administration group showed a decrease compared to the negative control group in all three parameters, and showed a decrease similar to that of the methotrexate administration group.

Taken together with the histological estimation results, the naltrexone DDS administration group showed a level of inhibitory effect similar to the methotrexate-administered group as the positive control in the evaluation of the activity of inflammation of the arthritis tissues and the severity of joint damage, and showed a more consistent inhibitory effect compared with the oral administration group of naltrexone. Therefore, naltrexone DDS was histologically confirmed to have an arthritis treatment effect.

4. Safety Assessment In Vivo

The in vivo safety of the test substance was evaluated by measuring the body weight of mouse in each administration group of Example 2.1.

For the safety evaluation of the test substance, the body weight of mouse was measured daily from before the start of administration (The $21^{th}$ day) to just before the end of administration (The $41^{th}$ day), and the body weight (%) of the mouse for each administration group over the time (day) was shown in FIG. 6.

As shown in FIG. 6, there was a tendency for the overall body weight of the mice to decrease according to the occurrence of arthritis during the test period. The naltrexone DDS-administration group had a slight body weight loss at the beginning of the administration, but the loss was recovered afterwards and the group showed the smallest weight loss compared to the other administration groups. Therefore, it was confirmed that naltrexone DDS is safe in vivo.

Example 3. Efficacy Evaluation of Naltrexone-Containing Microspheres for Rheumatoid Arthritis (Secondary)

1. In Vivo Testing Method of Naltrexone-Containing Microspheres for Rheumatoid Arthritis Following the in vivo efficacy evaluation of naltrexone-containing microspheres for rheumatoid arthritis in Example 2, an additional efficacy experiment was conducted by giving a difference between the dose and the combination administration of methotrexate and the control group.

A model of murine collagen-induced arthritis prepared in the same manner as in Example 2 (6-10 week-old male mouse of DBA/1J strain; the first immunization on day 0 and secondary immunization on day 21) was used.

As a material to be tested, naltrexone DDS ("Q-DDS") was prepared as described in Preparation Example 1. As a negative control, vehicle DDS was used instead of naltrexone, and as a positive control, methotrexate (MTX, MTX injection, 50 mg/2 mL, JW Pharmaceutical) and Tofacitinib (Xeljanz® Tablet, 5 mg, Pfizer Korea) were used.

Administration information for each administration group is as described in Table 11 below.

TABLE 11

| Administration group (Each group, n = 6) | Administration drug | Route of administration | Regimen and dose of administration (based on the active ingredient) | Administration volume (µl) |
|---|---|---|---|---|
| 1 (Negative control) | Vehicle DDS | Subcutaneous injection | 1 dose on the $23^{th}$ day, N/A | 140 |
| 2 (Positive control) | Methotrexate (MTX) | Intraperitoneal injection | Twice/week, 1 mg/kg body weight/each time | 100 |
| 3 (Positive control) | Tofacitinib (Xeljanz ®) | Oral | Once/day, 10 mg/kg body weight/each time | 200 |
| 4 (Test group) | Q-DDS | Subcutaneous injection | Administration once on the $23^{th}$ day, 1 mg/mouse | 50 |
| 5 (Test group) | Q-DDS | Subcutaneous injection | Administration once on the $23^{th}$ day, 3 mg/mouse | 160 |
| 6 (Test group) | Q-DDS | Subcutaneous injection | Administration once on the $23^{th}$ day, 5 mg/mouse | 260 |
| 7 (Test group) | Q-DDS | Subcutaneous injection | Administration once on the $23^{th}$ day, 10 mg/mouse | 500 |
| 8 (Test group) | Q-DDS | Subcutaneous injection | Administration once on the $23^{th}$ day, 20 mg/mouse | 1000 |
| 9 (Test group) | MTX + Q-DDS | Intraperitoneal + subcutaneous injection | MTX: Twice/week, 1 mg/kg body weight/each time Q-DDS: Administration once on the $23^{th}$ day, 3 mg/mouse | 160 |

Based on the blind evaluation data for each evaluation index, statistical analysis between the negative control group and the test group or between the two test groups was performed using SPSS. For comparison between the two groups, Student's t-test or Mann Whitney U test was used. To compare differences between treatment groups at multiple time points, repeated measures ANOVA with Turkey's post-hoc test was used. The significance level was defined as a p-value of 0.05 or less.

2. Clinical Evaluation of Arthritis Activity

After administration of the test substance to the collagen-induced arthritis mouse model, the occurrence and level of inflammation were regularly observed from the date of group separation to the end date of the experiment (the $41^{th}$ day). Inflammation level was given a score of 0 to 4 for each paw according to the criteria in Table 4 above, and the sum was used as a clinical arthritis index (CAI).

When the clinical index of each paw was 2 score or higher, it was determined that arthritis occurred, and the incidence was defined as 100% when arthritis occurred in four toes.

Toe Images for each administration group were shown in FIG. 7 (Vehicle DDS: negative control, MTX: methotexate administration group, Xeljanz®: Xeljanz® administration group, Q-DDS: naltrexone DDS administration group, MTX+Q-DDS: methotrexate+naltrexone DDS combination administration group). The clinical arthritis index (CAI) of mouse over the time (days) after administration of the test substance was shown in FIG. 7B, and a graph showing the area under the curve (AUC) of the clinical arthritis index was shown in FIG. 7C (mean±standard error mean (SEM), : p-value<0.01,*: p-value<0.001). The results of the clinical arthritis index and the area under the curve were summarized in Table 12 below.

TABLE 12

| Group | CAI (D41) | | | CAI-AUC | | |
|---|---|---|---|---|---|---|
| | Mean | SEM | P value vs Vehicle | Mean | SEM | P value vs Vehicle |
| Vehicle DDS | 11.75 | 1.20 | — | 150.65 | 12.03 | — |
| Methotrexate (1 mg/kg) | 6.35 | 1.05 | <0.0001 | 71.20 | 8.19 | <0.0001 |
| Xeljanz ® (10 mg/kg) | 6.25 | 0.75 | <0.0001 | 74.50 | 9.63 | <0.0001 |
| Q-DDS (1 mg/mouse) | 7.30 | 1.28 | <0.0001 | 91.13 | 16.43 | <0.0001 |
| Q-DDS (3 mg/mouse) | 7.60 | 1.69 | <0.0001 | 88.05 | 14.86 | <0.0001 |
| Q-DDS (5 mg/mouse) | 6.30 | 1.32 | <0.0001 | 73.30 | 10.77 | <0.0001 |
| Q-DDS (10 mg/mouse) | 5.25 | 0.69 | <0.0001 | 66.08 | 8.09 | <0.0001 |
| Q-DDS (20 mg/mouse) | 6.85 | 1.30 | <0.0001 | 78.63 | 11.93 | <0.0001 |
| Methotrexate (1 mg/kg) + Q-DDS (3 mg/mouse) | 5.95 | 1.30 | <0.0001 | 63.60 | 10.75 | <0.0001 |

As shown in FIGS. 7B, 7C, and Table 12, the positive control group, the naltrexone DDS administration group (test group), and the MTX+ naltrexone DDS administration group (combination test group) showed a decrease of a clinical arthritis index compared to the Vehicle DDS administration group (negative control group). In particular, the naltrexone DDS 10 mg/mouse administration group and the combination administration group showed the lowest clinical arthritis index, which was lower than the methotrexate administration group and Xeljanz® administration group (tofacitinib administration group; positive control group). The area under the curve for the clinical arthritis index also showed a decrease in both the positive control group and the naltrexone DDS administration group, and a combination administration group compared to the Vehicle DDS administration group. Between the doses of naltrexone DDS 1 mg/mouse and 10 mg/mouse administration, a concentration-dependent effect of lowering the clinical arthritis index was confirmed as the dose increased, but the effect of treating arthritis in naltrexone DDS 20 mg/mouse administration group appeared to decrease, compared to the administration dose. In addition, the group administered with methotrexate and naltrexone DDS 3 mg/mouse (combination test group) showed a lower clinical arthritis index than the group administered with methotrexate alone or naltrexone DDS 3 mg/mouse, and its synergistic effect could be confirmed since the area under the curve for the clinical arthritis index shows the lowest value. Through the above results, it was confirmed that the naltrexone DDS of the present disclosure exhibited an effect of reducing the clinical arthritis index to a degree similar to that of the standard therapeutic agent used in clinical practice and it was confirmed that there was a concentration-dependence in a treatment dose between the administration dose of naltrexone DDS 1 mg/mouse to 10 mg/mouse, and synergistic effect between naltrexone and methotrexate.

The incidence (%) of arthritis over the time (days) after administration of the test substance was shown in FIG. 7D, and a graph showing the area under the curve (AUC) of the incidence was shown in FIG. 7E (mean±standard error mean (SEM),: p-value<0.01 versus negative control,*: p-value<0.001 versus negative control). The results of the incidence and the area under the curve were summarized in Table 13 below.

TABLE 13

| Group | Incidence (%) | | | Incidence-AUC | | |
|---|---|---|---|---|---|---|
| | Mean | SEM | P value vs Vehicle | Mean | SEM | P value vs Vehicle |
| Vehicle DDS | 70.0 | 9.9 | — | 835.0 | 89.2 | — |
| Methotrexate (1 mg/kg) | 30.0 | 11.5 | <0.0001 | 170.0 | 77.1 | <0.0001 |
| Xeljanz ® (10 mg/kg) | 27.5 | 9.2 | <0.0001 | 263.8 | 122.7 | <0.0001 |
| Q-DDS (1 mg/mouse) | 35.0 | 12.1 | 0.0002 | 337.5 | 185.4 | 0.0012 |
| Q-DDS (3 mg/mouse) | 35.6 | 14.7 | 0.0001 | 307.5 | 103.3 | <0.0001 |
| Q-DDS (5 mg/mouse) | 22.5 | 12.4 | <0.0001 | 196.3 | 121.3 | <0.0001 |
| Q-DDS (10 mg/mouse) | 12.5 | 6.6 | <0.0001 | 131.3 | 71.9 | <0.0001 |
| Q-DDS (20 mg/mouse) | 22.5 | 12.4 | <0.0001 | 216.3 | 112.1 | <0.0001 |
| Methotrexate (1 mg/kg) + Q-DDS (3 mg/mouse) | 25.0 | 11.8 | <0.0001 | 167.5 | 90.9 | <0.0001 |

As shown in FIGS. 7D, 7E, and Table 13, the positive control group, the naltrexone DDS administration group (test group), and the MTX+naltrexone DDS administration group (combination administration group) showed a decrease of an incidence of arthritis, compared to the Vehicle DDS administration group. Further, in the case of the naltrexone DDS 10 mg/mouse administration group and the combination administration group, the incidence of arthritis was decreased compared to the methotrexate administration group. In the area under the curve for the incidence of arthritis, a concentration-dependent effect according to the administration dose was confirmed between the administration dose of naltrexone DDS 1 mg/mouse and 10 mg/mouse. In particular, the naltrexone DDS 10 mg/mouse administration group showed the most significant decrease, and showed a more significant decrease than the methotrexate administration group and Xeljanz® administration group.

In addition, since the group administered with methotrexate and naltrexone DDS 3 mg/mouse (combination test group) had a lower incidence of arthritis than the group administered with methotrexate alone or naltrexone DDS 3 mg/mouse, a synergistic effect could be confirmed.

3. Histological Estimation

Mice were sacrificed on the 41$^{th}$ day, which is the end of the experiment, and the tissues of the hind paws were stained with hematoxylin/eosin. Hematoxylin/eosin staining was used to evaluate the activity of inflammation in the arthritic tissue, and toluidine blue staining was performed to confirm the histological therapeutic effect on cartilage destruction.

(1) Hematoxylin/Eosin Staining

Hematoxylin/eosin staining was performed and evaluated in the same manner as in Example 2.3. (1) above, and the score for items of synovial hyperplasia, pannus formation, cartilage destruction, and bone erosion was calculated by scoring each tissue as the average of the score of 4 sites based on Table 7 above.

Images for tissues stained with hematoxylin/eosin were shown in FIG. 8A (Vehicle DDS: negative control, MTX: methotexate administration group, Xeljanz®: Xeljanz® administration group, Q-DDS: naltrexone DDS administration group, MTX+Q-DDS: methotexate+naltrexone DDS combination administration group, 200 times magnification, bar: 100 μm). Histological scores were shown in FIG. 8B and the results were summarized in Table 14 below (mean±standard error mean (SEM),: p-value compared to negative control<0.01,*: p-value compared to negative control<0.001).

TABLE 14

| | | | | p-value | | |
|---|---|---|---|---|---|---|
| | Histological Scorning Value | Mean | SEM | vs Vehicle | vs MTX | vs Xeljanz ® |
| Synovial hyperplasia | Negative control (Vehicle DDS) | 3.00 | 0.00 | — | <0.0001 | 0.0012 |
| | MTX | 1.38 | 0.29 | <0.0001 | — | 0.6489 |
| | Xeljanz ® | 1.56 | 0.39 | 0.0012 | 0.6489 | — |
| | Q-DDS (1 mg/mouse) | 1.98 | 0.54 | 0.0441 | 0.2564 | 0.4634 |
| | Q-DDS (3 mg/mouse) | 2.00 | 0.43 | 0.0183 | 0.1737 | 0.3825 |
| | Q-DDS (5 mg/mouse) | 0.98 | 0.27 | <0.0001 | 0.2485 | 0.1658 |
| | Q-DDS (10 mg/mouse) | 0.63 | 0.10 | <0.0001 | 0.0127 | 0.0175 |
| | Q-DDS (20 mg/mouse) | 1.58 | 0.56 | 0.0108 | 0.6942 | 0.9720 |
| | MTX + Q-DDS (3 mg/mouse) | 0.79 | 0.18 | <0.0001 | 0.0599 | 0.0529 |
| Pannus formation | Negative control (Vehicle DDS) | 3.00 | 0.00 | — | <0.0001 | 0.0004 |
| | MTX | 0.92 | 0.36 | <0.0001 | — | 0.6608 |
| | Xeljanz ® | 1.13 | 0.44 | 0.0004 | 0.6608 | — |
| | Q-DDS (1 mg/mouse) | 1.58 | 0.67 | 0.0273 | 0.3075 | 0.5004 |
| | Q-DDS (3 mg/mouse) | 1.58 | 0.59 | 0.0147 | 0.2627 | 0.4629 |
| | Q-DDS (5 mg/mouse) | 0.21 | 0.14 | <0.0001 | 0.0489 | 0.0358 |
| | Q-DDS (10 mg/mouse) | 0.06 | 0.05 | <0.0001 | 0.0165 | 0.0150 |
| | Q-DDS (20 mg/mouse) | 1.17 | 0.68 | 0.0079 | 0.6985 | 0.9529 |
| | MTX + Q-DDS (3 mg/mouse) | 0.06 | 0.08 | <0.0001 | 0.0175 | 0.0156 |
| Cartilage destruction | Negative control (Vehicle DDS) | 2.98 | 0.03 | — | <0.0001 | 0.0004 |
| | MTX | 1.02 | 0.30 | <0.0001 | — | 0.3907 |
| | Xeljanz ® | 1.38 | 0.38 | 0.0004 | 0.3907 | — |
| | Q-DDS (1 mg/mouse) | 1.71 | 0.56 | 0.0199 | 0.2157 | 0.5592 |
| | Q-DDS (3 mg/mouse) | 1.75 | 0.45 | 0.0071 | 0.1294 | 0.4519 |
| | Q-DDS (5 mg/mouse) | 0.65 | 0.20 | <0.0001 | 0.2356 | 0.0627 |
| | Q-DDS (10 mg/mouse) | 0.42 | 0.06 | <0.0001 | 0.0380 | 0.0117 |
| | Q-DDS (20 mg/mouse) | 1.38 | 0.51 | 0.0033 | 0.4839 | 0.9975 |
| | MTX + Q-DDS (3 mg/mouse) | 0.46 | 0.14 | <0.0001 | 0.0654 | 0.0187 |
| Bone erosion | Negative control (Vehicle DDS) | 3.00 | 0.00 | — | <0.0001 | 0.0004 |
| | MTX | 0.92 | 0.36 | <0.0001 | — | 0.6608 |
| | Xeljanz ® | 1.13 | 0.44 | 0.0004 | 0.6608 | — |
| | Q-DDS (1 mg/mouse) | 1.58 | 0.678 | 0.0273 | 0.3075 | 0.5004 |
| | Q-DDS (3 mg/mouse) | 1.58 | 0.59 | 0.0147 | 0.2627 | 0.4629 |
| | Q-DDS (5 mg/mouse) | 0.19 | 0.15 | <0.0001 | 0.0445 | 0.0330 |

TABLE 14-continued

| Histological Scorning Value | Mean | SEM | p-value vs Vehicle | p-value vs MTX | p-value vs Xeljanz ® |
|---|---|---|---|---|---|
| Q-DDS (10 mg/mouse) | 0.04 | 0.05 | <0.0001 | 0.0145 | 0.135 |
| Q-DDS (20 mg/mouse) | 1.17 | 0.68 | 0.079 | 0.6985 | 0.9529 |
| MTX + Q-DDS (3 mg/mouse) | 0.06 | 0.08 | <0.0001 | 0.0175 | 0.0156 |

As shown in FIGS. 8A, 8B, and Table 14, in the negative control group, cartilage destruction and bone erosion were evident due to the increase of the panus tissue along with the overproliferation of synovial cells, and in MTX or Xeljanz® administration group as the positive control group, other parameters showed a marked decrease compared to the negative control group except for the proliferation of some synovial tissue. In the case of the naltrexone DDS administration group, the proliferation of synovial tissue was observed in the 1, 3, and 20 mg/mouse administration groups, and the initiation of some cartilage destruction and bone erosion were observed. In the case of the naltrexone DDS 5 mg/mouse and 10 mg/mouse administration group, and the combination administration group, all four indicators were shown to be decreased compared to the negative control group, and also shown to be decreased compared with the MTX and Xeljanz® administration group as the positive control group.

(2) Toluidine Blue Staining

In the same manner as in Example 2.3. (2), the hind paw tissue of the mouse was stained with toluidine blue, and items such as photographing and matrix staining, surface regularity, and cartilage thickness were evaluated. The scoring criteria for each item were described in Table 9, and the average score of 4 sites was calculated as the score of each tissue.

Images for tissues stained with toluidine blue were shown in FIG. 9A (Vehicle DDS: negative control, MTX: methotexate administration group, Xeljanz®: Xeljanz® administration group, Q-DDS: naltrexone DDS administration group, MTX+Q-DDS: methotrexate+ naltrexone DDS combination administration group, 200 times magnification, bar: 100 μm). Histological scores were shown in FIG. 9B and the results were summarized in Table 15 below (mean±SEM,: p-value compared to negative control<0.01,*: p-value compared to negative control<0.001).

TABLE 15

| Histochromatographic parameters | | Mean | SEM | p-value vs Vehicle | p-value vs MTX | p-value vs Xeljanz ® |
|---|---|---|---|---|---|---|
| Matrix staining | Negative control (Vehicle DDS) | 3.00 | 0.00 | — | <0.0001 | <0.0001 |
| | MTX | 1.15 | 0.16 | <0.0001 | — | 0.2676 |
| | Xeljanz ® | 1.42 | 0.23 | <0.0001 | 0.2676 | — |
| | Q-DDS (1 mg/mouse) | 1.92 | 0.36 | 0.0040 | 0.0366 | 0.1814 |
| | Q-DDS (3 mg/mouse) | 1.96 | 0.45 | 0.0177 | 0.0639 | 0.2198 |
| | Q-DDS (5 mg/mouse) | 0.92 | 0.18 | <0.0001 | 0.2767 | 0.0659 |
| | Q-DDS (10 mg/mouse) | 0.63 | 0.06 | <0.0001 | 0.0037 | 0.0023 |
| | Q-DDS (20 mg/mouse) | 1.46 | 0.60 | 0.0104 | 0.5517 | 0.9384 |
| | MTX + Q-DDS (3 mg/mouse) | 0.83 | 0.09 | <0.0001 | 0.0612 | 0.0163 |
| Surface regularity | Negative control (Vehicle DDS) | 3.00 | 0.00 | — | <0.0001 | <0.0001 |
| | MTX | 1.02 | 6.19 | <0.0001 | — | 0.6652 |
| | Xeljanz ® | 1.13 | 0.22 | <0.0001 | 0.6652 | — |
| | Q-DDS (1 mg/mouse) | 1.75 | 0.34 | 0.0011 | 0.0442 | 0.0868 |
| | Q-DDS (3 mg/mouse) | 1.83 | 0.49 | 0.0159 | 0.0886 | 0.1383 |
| | Q-DDS (5 mg/mouse) | 0.56 | 0.24 | <0.0001 | 0.0946 | 0.0587 |
| | Q-DDS (10 mg/mouse) | 0.35 | 0.10 | <0.0001 | 0.0032 | 0.0027 |
| | Q-DDS (20 mg/mouse) | 1.15 | 0.68 | 0.0074 | 0.8321 | 0.9721 |
| | MTX + Q-DDS (3 mg/mouse) | 0.46 | 0.14 | <0.0001 | 0.0147 | 0.0101 |
| Cartilage thickness | Negative control (Vehicle DDS) | 1.96 | 0.05 | — | <0.0001 | <0.0001 |
| | MTX | 0.38 | 0.15 | <0.0001 | — | 0.3341 |
| | Xeljanz ® | 0.56 | 6.17 | <0.0001 | 0.3341 | — |

TABLE 15-continued

| Histochromatographic parameters | Mean | SEM | p-value vs Vehicle | vs MTX | vs Xeljanz ® |
|---|---|---|---|---|---|
| Q-DDS (1 mg/mouse) | 1.04 | 0.24 | 0.0009 | 0.0150 | 0.0719 |
| Q-DDS (3 mg/mouse) | 1.10 | 0.39 | 0.0245 | 0.0589 | 0.1521 |
| Q-DDS (5 mg/mouse) | 0.21 | 0.12 | <0.0001 | 0.3035 | 0.0625 |
| Q-DDS (10 mg/mouse) | 0.10 | 0.06 | <0.0001 | 0.0652 | 0.0115 |
| Q-DDS (20 mg/mouse) | 0.67 | 0.47 | 0.0075 | 0.4855 | 0.8040 |
| MTX + Q-DDS (3 mg/mouse) | 0.19 | 0.09 | <0.0001 | 0.2094 | 0.0375 |

As shown in FIGS. 9A, 9B, and Table 15, the naltrexone DDS administration group showed a decrease in histological scores than the negative control group in all three parameters, and in particular, 5 mg/mouse and 10 mg/mouse administration group, and the combination administration group showed a lower histological score than the MTX and Xeljanz® administration groups.

Taken together with the histological estimation results, naltrexone DDS 5 mg/mouse administration group and 10 mg/mouse administration group, and combination administration group not only had an anti-inflammatory effect compared to the negative control group in the evaluation of the activity of inflammation of arthritic tissues and the severity of joint damage but also showed a more effective arthritis inhibitory effect than the positive control group, such as the standard antirheumatic drugs methotrexate or Xeljanz® administration group. Therefore, it was confirmed that naltrexone DDS is histologically effective for treating arthritis, and when administered in an appropriate amount, it has a superior effect to existing standard antirheumatic agents.

4. Safety Assessment In Vivo

The in vivo safety of the test substance was evaluated by measuring the body weight of mouse in each administration group of Example 3.1.

For the safety evaluation of the test substance, the body weight of mouse was measured daily from before the start of administration (The 21$^{th}$ day) to just before the end of administration (The 41$^{th}$ day), and the body weight (%) of the mouse for each administration group over the time (day) was shown in FIG. 10 and Table 16.

TABLE 16

| Change of body weight | D23 body weight | | D41 body weight | | Change of body weight (%, D23 body weight 100%) | |
|---|---|---|---|---|---|---|
| | Mean | SEM | Mean | SEM | Mean | SEM |
| Negative control (Vehicle DDS) | 22.6 | 0.3 | 20.5 | 1.0 | 90.8 | 3.7 |
| MTX | 22.7 | 6.5 | 23.8 | 1.2 | 104.7 | 3.5 |
| Xeljanz ® | 21.7 | 0.5 | 21.6 | 0.8 | 99.6 | 2.5 |
| Q-DDS (1 mg/mouse) | 21.4 | 0.6 | 20.7 | 0.9 | 96.9 | 3.6 |
| Q-DDS (3 mg/mouse) | 22.2 | 0.9 | 21.7 | 0.6 | 98.2 | 4.0 |
| Q-DDS (5 mg/mouse) | 22.8 | 0.6 | 22.5 | 1.3 | 98.5 | 4.3 |
| Q-DDS (10 mg/mouse) | 22.6 | 0.5 | 22.5 | 0.8 | 99.6 | 2.0 |
| Q-DDS (20 mg/mouse) | 22.7 | 0.7 | 23.4 | 1.1 | 103.2 | 4.3 |
| MTX + Q-DDS (3 mg/mouse) | 22.2 | 0.5 | 22.3 | 1.0 | 100.3 | 2.8 |

As shown in FIG. 10 and Table 16, there was a tendency for the body weight of the mouse to be decreased if severity of arthritis was high during the test period. In contrast to the 9.2% body weight loss in the negative control group, the naltrexone DDS administration group showed little body weight loss. Therefore, it was confirmed that naltrexone DDS is safe in vivo.

5. Imaging Evaluation of Arthritis Using Micro-CT

After treatment with the test substance in Example 3.1, and fixing the paw tissue representing the results of each group, micro-CT scanners (Quantum FX, Perkin Elmer, MA) were used to photograph it. The radiographs were 3D rendered using the Quantum FX μCT imaging system (Perkin Elmer, MA), and then the radiological score was evaluated, and the bone volume ratio (Bone volume [BV]/Tissue volume [Tissue volume; TV]) and bone surface density (Bone surface area (BS)/Bone volume (BV)) were also measured. Two or more investigators performed blind evaluation for joint destruction, and the indicators in Table 17 below were used as the scoring criteria. The average value of the researchers' blind evaluation data was used as the score, and the average score of the paw tissue was calculated as the score of each group.

TABLE 17

| score | Joint destruction |
|---|---|
| 0 | No damage |
| 1 | Minor bone destruction observed in one enlightened spot |
| 2 | Moderate change, 2-4 spots in one area |
| 3 | Marded change, 2-4 spots in more area |
| 4 | Severe erosion afflicting the joint |
| 5 | Complete destruction of the joints |

Representative images for each group photographed with micro-CT were shown in FIG. 11A, and in particular, images magnifying joint portions were shown in FIG. 11B (Vehicle DDS: negative control, MTX: methotexate administration group, Xeljanz®: Xeljanz® administration group, Q-DDS: naltrexone DDS administration group, MTX+Q-DDS: methotrexate+ naltrexone DDS combination administration group, 200 times magnification, bar: 100 μm). The radiological score was shown in FIG. 11C and the results were summarized in Table 18 below (mean±standard error mean (SEM),*: p-value<0.05 compared to negative control group, : p-value<0.01 compared to negative control group,*: p-value<0.001 compared to negative control group, #: p-value compared to MTX administration group<0.05, †: p-value<0.05 compared to MTX administration group).

TABLE 18

| | | | | p-value | | |
|---|---|---|---|---|---|---|
| Radiological analysis | value | Mean | SEM | vs Vehicle | vs MTX | vs Xeljanz® |
| Bone volume/ tissue volume (%) | Negative control group (Vehicle DDS) | 13.50 | 1.06 | — | 0.0002 | 0.0097 |
| | MTX | 31.25 | 0.62 | 0.0002 | — | 0.0624 |
| | Xeljanz® | 25.27 | 1.92 | 0.0097 | 0.0624 | — |
| | Q-DDS (1 mg/mouse) | 28.46 | 2.92 | 0.0141 | 0.4652 | 0.4730 |
| | Q-DDS (3 mg/mouse) | 23.57 | 4.18 | 0.1131 | 0.1906 | 0.7653 |
| | Q-DDS (5 mg/mouse) | 32.24 | 0.27 | 0.0001 | 0.2726 | 0.0358 |
| | Q-DDS (10 mg/mouse) | 35.82 | 1.09 | 0.0002 | 0.0341 | 0.0144 |
| | Q-DDS (20 mg/mouse) | 26.81 | 6.10 | 0.1363 | 0.5654 | 0.8444 |
| | MTX + Q-DDS (3 mg/mouse) | 31.93 | 0.16 | 0.0001 | 0.4119 | 0.0403 |
| Bone surface area/bone volume (mm$^{-1}$) | Negative control group (Vehicle DDS) | 9.00 | 0.23 | — | 0.0004 | 0.0011 |
| | MTX | 6.12 | 0.06 | 0.0004 | — | 0.0703 |
| | Xeljanz® | 6.52 | 0.13 | 0.0011 | 0.0703 | — |
| | Q-DDS (1 mg/mouse) | 6.23 | 0.14 | 0.0008 | 0.5389 | 0.2600 |
| | Q-DDS (3 mg/mouse) | 6.84 | 0.47 | 0.0233 | 0.2578 | 0.5947 |
| | Q-DDS (5 mg/mouse) | 6.09 | 0.06 | 0.0004 | 0.8030 | 0.0587 |
| | Q-DDS (10 mg/mouse) | 6.12 | 0.04 | 0.0004 | 0.9423 | 0.0639 |
| | Q-DDS (20 mg/mouse) | 6.75 | 0.45 | 0.0180 | 0.2981 | 0.6934 |
| | MTX + Q-DDS (3 mg/mouse) | 6.14 | 0.03 | 0.0004 | 0.7847 | 0.0673 |
| Radiological score | Negative control group (Vehicle DDS) | 4.67 | 0.41 | — | 0.0002 | 0.0010 |
| | MTX | 1.67 | 0.49 | 0.0002 | — | 0.5078 |
| | Xeljanz® | 2.08 | 0.56 | 0.0010 | 0.5078 | — |
| | Q-DDS (1 mg/mouse) | 2.33 | 0.66 | 0.0044 | 0.3466 | 0.7314 |
| | Q-DDS (3 mg/mouse) | 2.33 | 0.72 | 0.0062 | 0.3705 | 0.7433 |
| | Q-DDS (5 mg/mouse) | 1.42 | 0.33 | <0.0001 | 0.6171 | 0.2368 |
| | Q-DD (10 mg/mouse) | 1.08 | 0.40 | <0.0001 | 0.2862 | 0.1046 |
| | Q-DDS (20 mg/mouse) | 1.83 | 0.61 | 0.0008 | 0.7989 | 0.7176 |
| | MTX + Q-DDS (3 mg/mouse) | 1.08 | 0.33 | <0.0001 | 0.2563 | 0.0884 |

As noted in FIGS. 11A and 11B, as a result of the micro-CT scan, in the case of the negative control group, bone volume was decreased, and bone erosion of the paw joint was clearly observed in several joints, and in MTX administration group and Xeljanz® administration group as a control, a decrease in volume was observed in some joint portions, but the degree of the decrease was smaller than that of the negative control group. In the naltrexone DDS administration group, the joint morphology of the 5 mg/mouse, 10 mg/mouse, and combination administration group was maintained at a level similar to that of normal paw tissue, and no bone erosion was observed.

As a result of measurement of bone volume ratio, the naltrexone DDS 10 mg/mouse administration group showed a higher value than the negative control group (Vehicle DDS vs Q-DDS 10 mg/mouse, 13.50%±1.06% vs 35.82%±1.09%, p<0.001) and showed increased values compared to the positive control group (MTX vs Xeljanz® vs Q-DDS 10 mg/mouse, 31.25%±0.62% vs 25.27%±1.92% vs 35.82%±1.09%, p<0.05). As a result of measurement of bone surface density, it was lower in all treatment groups compared to the negative control group, and in particular, in the naltrexone DDS 5 mg/mouse administration group, 10 mg/mouse administration group, and the combination administration group, the MTX administration group, it was similar to the normal joint at a level similar to that of the MTX administration group among the positive control groups (Vehicle DDS vs Q-DDS 5 mg/mouse vs Q-DDS 10 mg/mouse vs MTX+Q-DDS, 9.00 mm$^{-1}$±0.23 mm$^{-1}$ vs 6.09 mm$^{-1}$±0.06 mm$^{-1}$ vs 6.12 mm$^{-1}$±0.04 mm$^{-1}$ vs 6.14 mm$^{-1}$±0.03 mm$^{-1}$, p<0.001), and showed lower level compared to Xeljanz® administration group. As a result of radiographic score for joint destruction, when compared with the negative control group, the radiographic score was decreased in the naltrexone DDS administration group including the positive control group, and showed a decrease in radiological score compared to the positive control group, in particular, in the naltrexone DDS administration group, 5 mg/mouse administration group and 10 mg/mouse administration group and a combination administration group. In the end, it was confirmed that naltrexone DDS not only treats the inflammation of arthritis, but also inhibits the progression of joint destruction as a result.

6. Multiplex Protein Immunoassay on Arthritic Tissue and Serum

In order to evaluate the inflammatory activity and confirm the mode of action of the test substance through quantitative analysis of inflammatory substances in mouse arthritis tissue and blood, inflammatory mediators were investigated at the protein level. In order to overcome the limitation of the amount of sample that can be extracted for protein analysis, a multi-analyte-ELISA (multi-analyte-ELISA) method based on Luminex technology was used to analyze the largest amount of protein in a small sample.

(1) Biomarker Evaluation Through Analysis of Protein Concentration of Inflammation Mediators in Arthritic Tissues The mouse joint tissue obtained after treatment with the test substance in the method of Example 3.1 was pulverized through ceramic beads, and all proteins were extracted using a lysis buffer (Cat. 1713040111, Bio-Rad). Using Pro-reagent kit V, the same amount of protein (2.7 mg/mL) for each administration group was diluted ¼ and reacted with the target-binding beads in a culture dish for 30 minutes. After washing with a wash buffer, it was reacted with the target-measurement antibody for 30 minutes, and after washing with a wash buffer again, it was reacted with streptavidin-PE for 10 minutes. Thereafter, the target protein is quantitatively measured for each administration group using the Bio-Plex® 200 system (Bio-Rad). The target-binding beads were composed of a set that can be combined as needed from Bio-Plex Mouse cytokine 4-plex (IL-1β, IL-6, IL-17A, TNF-α; Cat. 171G5002M), Bio-Plex Pro Mouse Cytokine 1-plex (MCP1; Cat. 171G5019M), Bio-Plex Pro Mouse Cytokine II 1-plex (MIP2; Cat 171G6006M), and Bio-Plex Pro Mouse Cytokine 1-plea (IL-6; Cat. 171 G5007M) (all products are from Bio Rad) and were used for measurement.

For the measurement result, paw tissue weight of the mouse was corrected for the quantified target protein. For each target joint, the hind paw was mainly used, and in order to overcome the limitation of the amount of protein extracted from the joint tissue, up to 4 inflammatory mediators were measured in one well.

On the other hand, as the target protein to be measured, a representative inflammation-promoting cytokine group A (IL-1β, IL-6, IL-17, and TNF-α) among inflammatory mediators, and a chemokine group B (MCP-1 and MIP-2) among inflammatory mediators was selected to carry out the experiment. The measurement results were summarized in FIGS. 12A and 12B, and Tables 19 and 20 below.

TABLE 19

| ELISA values in Arthritis Paw (pg/mL) | | Mean | SEM | p-value vs Vehicle | p-value vs MTX | p-value vs Xeljanz ® |
|---|---|---|---|---|---|---|
| IL-1β | Negative control (Vehicle DDS) | 26.77 | 12.21 | — | 0.0276 | 0.1321 |
| | MTX | 1.05 | 0.31 | 0.0276 | — | 0.0069 |
| | Xeljanz ® | 12.68 | 4.38 | 0.1321 | 0.0069 | — |
| | Q-DDS (1 mg/mouse) | 3.44 | 0.79 | 0.0122 | 0.0034 | 0.0067 |
| | Q-DDS (3 mg/mouse) | 15.98 | 2.27 | 0.2112 | <0.0001 | 0.3297 |
| | Q-DDS (5 mg/mouse) | 5.52 | 0.94 | 0.0201 | 0.0001 | 0.0289 |
| | Q-DDS (10 mg/mouse) | 0.83 | 0.25 | 0.0064 | 0.4583 | 0.0009 |
| | Q-DDS (20 mg/mouse) | 7.64 | 4.29 | 0.0473 | 0.0867 | 0.2340 |
| | MTX + Q-DDS (3 mg/mouse) | 3.28 | 0.31 | 0.0034 | <0.0001 | 0.0014 |

TABLE 19-continued

| ELISA values in Arthritis Paw (pg/mL) | | Mean | SEM | p-value vs Vehicle | p-value vs MTX | p-value vs Xeljanz ® |
|---|---|---|---|---|---|---|
| IL-6 | Negative control (Vehicle DDS) | 250.8 | 187.0 | — | 0.1341 | 0.2264 |
| | MTX | 1.8 | 0.7 | 0.1341 | — | 0.0359 |
| | Xeljanz ® | 88.6 | 44.8 | 0.2264 | 0.0359 | — |
| | Q-DDS (1 mg/mouse) | 14.0 | 4.4 | 0.0750 | 0.0057 | 0.0246 |
| | Q-DDS (3 mg/mouse) | 35.3 | 10.3 | 0.1023 | 0.0017 | 0.1019 |
| | Q-DDS (5 mg/mouse) | 14.1 | 2.0 | 0.0749 | <0.0001 | 0.0242 |
| | Q-DDS (10 mg/mouse) | 1.5 | 0.5 | 0.0623 | 0.6586 | 0.0102 |
| | Q-DDS (20 mg/mouse) | 15.5 | 10.1 | 0.0771 | 0.1247 | 0.0298 |
| | MTX + Q-DDS (3 mg/mouse) | 6.1 | 2.4 | 0.0326 | 0.0505 | 0.0046 |
| IL-17 | Negative control (Vehicle DDS) | 8.70 | 1.11 | — | <0.0001 | 0.0022 |
| | MTX | 2.269 | 0.29 | <0.0001 | — | 0.0179 |
| | Xeljanz ® | 4.57 | 0.99 | 0.0022 | 0.0179 | — |
| | Q-DDS (1 mg/mouse) | 3.06 | 0.35 | <0.0001 | 0.0459 | 0.0465 |
| | Q-DDS (3 mg/mouse) | 7.11 | 0.99 | 0.1690 | 0.0001 | 0.0150 |
| | Q-DDS (5 mg/mouse) | 3.21 | 0.45 | <0.0001 | 0.0419 | 0.0877 |
| | Q-DDS (10 mg/mouse) | 1.78 | 0.50 | <0.0001 | 0.2862 | 0.0018 |
| | Q-DDS (20 mg/mouse) | 4.87 | 2.29 | 0.0824 | 0.1964 | 0.8487 |
| | MTX + Q-DDS (3 mg/mouse) | 3.40 | 0.71 | <0.0001 | 0.0881 | 0.1346 |
| TNF-α | Negative control (Vehicle DDS) | 45.61 | 7.21 | — | 0.0001 | 0.0129 |
| | MTX | 6.54 | 1.60 | 0.0001 | — | 0.0077 |
| | Xeljanz ® | 24.52 | 6.78 | 0.0129 | 0.0077 | — |
| | Q-DDS (1 mg/mouse) | 10.14 | 2.15 | <0.0001 | 0.1037 | 0.0080 |
| | Q-DDS (3 mg/mouse) | 42.60 | 6.97 | 0.6925 | <0.0001 | 0.0131 |
| | Q-DDS (5 mg/mouse) | 10.42 | 1.28 | <0.0001 | 0.0213 | 0.0075 |
| | Q-DDS (10 mg/mouse) | 3.54 | 1.10 | <0.0001 | 0.0504 | 0.0003 |
| | Q-DDS (20 mg/mouse) | 45.37 | 24.23 | 0.9915 | 0.0748 | 0.2310 |
| | MTX + Q-DDS (3 mg/mouse) | 29.01 | 3.11 | 0.0032 | <0.0001 | 0.3208 |

TABLE 20

| ELISA values in Arthritis Paw (pg/mL) | | Mean | SEM | p-value vs Vehicle | p-value vs Vehicle | p-value vs Vehicle |
|---|---|---|---|---|---|---|
| MCP-1 | Negative control (Vehicle DDS) | 3371.1 | 2096.6 | — | 0.0831 | 0.4044 |
| | MTX | 76.1 | 11.5 | 0.0831 | — | 0.0294 |
| | Xeljanz ® | 207.9 | 954.6 | 0.4044 | 0.0294 | — |
| | Q-DDS (1 mg/mouse) | 281.8 | 22.6 | 0.0421 | <0.0001 | 0.0154 |
| | Q-DDS (3 mg/mouse) | 1062.6 | 120.1 | 0.1168 | <0.0001 | 0.1599 |
| | Q-DDS (5 mg/mouse) | 366.9 | 57.0 | 0.0473 | <0.0001 | 0.0204 |
| | Q-DDS (10 mg/mouse) | 69.8 | 9.4 | 0.0316 | 0.5709 | 0.0077 |
| | Q-DDS (20 mg/mouse) | 398.3 | 247.0 | 0.0514 | 0.1389 | 0.0262 |
| | MTX + Q-DDS (3 mg/mouse) | 111.8 | 12.9 | 0.0134 | 0.0112 | 0.0026 |

TABLE 20-continued

| ELISA values in Arthritis Paw (pg/mL) | | Mean | SEM | p-value vs Vehicle | p-value vs Vehicle | p-value vs Vehicle |
|---|---|---|---|---|---|---|
| MIP-2 | Negative control (Vehicle DDS) | 519.3 | 249.7 | — | 0.0301 | 0.0359 |
| | MTX | 4.4 | 1.7 | 0.0301 | — | 0.0077 |
| | Xeljanz ® | 126.8 | 46.9 | 0.0359 | 0.0077 | — |
| | Q-DDS (1 mg/mouse) | 3.9 | 18.0 | 0.0139 | 0.0055 | 0.0452 |
| | Q-DDS (3 mg/mouse) | 251.5 | 13.3 | 0.1257 | <0.0001 | 0.0015 |
| | Q-DDS (5 mg/mouse) | 98.1 | 23.2 | 0.0236 | 0.000 | 0.4237 |
| | Q-DDS (10 mg/mouse) | 17.4 | 8.5 | 0.0089 | 0.0908 | 0.0034 |
| | Q-DDS (20 mg/mouse) | 139.2 | 92.7 | 0.0550 | 0.1021 | 0.8596 |
| | MTX + Q-DDS (3 mg/mouse) | 28.2 | 12.9 | 0.0029 | 0.0423 | 0.0024 |

Through the above process, as a result of measuring the protein amount of four representative inflammation-promoting cytokines (IL-1β, IL-6, IL-17, and TNF-α) in arthritis tissues, IL-1β and IL-6 showed similar patterns, and the naltrexone DDS administration group entirely showed results similar to CAI, a clinical indicator of arthritis activity. In particular, in the naltrexone DDS 5 mg/mouse administration group, the 10 mg/mouse administration group, and the combination administration group, it was shown that pro-inflammatory cytokines were decreased compared to the negative control group, and also compared to the Xeljanz® administration group as a positive control group (FIG. 12A and Table 19).

In the case of IL-17 and TNF-α, the naltrexone DDS administration group showed a decrease compared to the negative control group, and in particular, the naltrexone DDS 5 mg/mouse administration group and 10 mg/mouse administration group showed a decrease compared to the negative control group, and also showed a decrease when compared with the Xeljanz® administration group, which is a positive control. (IL 17: Xeljanz® vs 10 mg/mouse, 4.57 pg/ml±0.99 pg/ml vs 1.78 pg/ml±0.50 pg/ml, p<0.01; TNF-α: Xeljanz® vs 5 mg/mouse vs 10 mg/mouse, 24.52 pg/ml±6.78 pg/ml vs 10.42 pg/ml±1.28 pg/ml vs 3.54 pg/ml±1.10 pg/ml, p<0.01).

In addition, as a result of measurement of the chemokines MCP-1 and MIP-2, both naltrexone DDS 5 mg/mouse administration group and 10 mg/mouse administration group and the combination administration group showed a decrease compared to the negative control group (Vehicle DDS vs 5 mg/mouse vs 10 mg/mouse vs MTX+Q-DDS, MCP 1:3371.1 pg/ml f 2096.6 pg/ml vs 366.9 pg/ml±57.0 pg/ml vs 69.8 pg/ml±9.4 pg/ml vs 111.8 pg/ml±12.9 pg/ml, p<0.05; MIP-2:519.3 pg/ml±249.7 pg/ml vs 98.1 pg/ml±23.2 pg/ml vs 17.4 pg/ml±8.5 pg/ml vs 28.2 pg/ml±12.9 pg/ml, p<0.05), and also showed a decrease when compared with the Xeljanz® administration group, which is a positive control (Xeljanz® vs 10 mg/mouse vs MTX+Q-DDS, MCP 1:207.9 pg/ml±954.6 pg/ml vs 69.8 pg/ml±9.4 pg/ml vs 111.8 pg/ml f 12.9 pg/ml, p<0.01; MIP-2:126.8 pg/ml±46.9 pg/ml vs 17.4 pg/ml±8.5 pg/ml vs 28.2 pg/ml±12.9 pg/ml, p<0.01).

As a result, the major inflammatory mediators measured in the arthritic tissue showed a pattern very similar to the clinical indicators, especially in the naltrexone DDS 10 mg/mouse administration group, the pro-inflammatory cytokine group A (IL-1β, IL-6, IL). −17, and TNF-α) and all of the inflammatory mediators belonging to the chemokine B group (MCP-1 and MIP-2) showed a decrease compared to the negative control group, and also showed a decrease compared to the Xeljanz® administration group, the standard clinical treatment.

(2) Biomarker Evaluation Through Analysis of Protein Concentration of Inflammation Mediators in Serum Using the Pro-reagent kit V, the mouse blood (serum) obtained after treatment with the test substance in the method of Example 3.1. above was diluted to ¼ with the same amount of protein (2.7 mg/mL) for each administration group, and then incubated in target-binding beads (IL-6 target) and a culture dish for 30 min. After washing with a wash buffer, it was reacted with the target-measurement antibody for 30 minutes, and after washing with a wash buffer again, it was reacted with streptavidin-PE for 10 minutes. Thereafter, the target protein is quantitatively measured for each administration group using the Bio-Plex® 200 system (Bio-Rad). As the target-binding beads, the beads described in Example 3.6. (1) were used.

For the measurement result, paw tissue weight of the mouse was corrected for the quantified amount of IL-6 protein. For each target joint, the hind paw was mainly used, and in order to overcome the limitation of the amount of protein extracted from the joint tissue, up to 4 inflammatory mediators were measured in one well.

The measured results were summarized in FIG. 13 and Table 21.

TABLE 21

| ELISA values in Serum (pg/mL) | | Mean | SEM | p-value vs Vehicle | p-value vs MTX | p-value vs Xeljanz ® |
|---|---|---|---|---|---|---|
| IL-6 | Negative control (Vehicle DDS) | 144.7 | 92.2 | — | 0.2065 | 0.4558 |
| | MTX | 39.6 | 24.3 | 0.2065 | — | 0.093 |
| | Xeljanz ® | 94.5 | 30.8 | 0.4558 | 0.0903 | — |
| | Q-DDS (1 mg/mouse) | 79.5 | 36.1 | 0.3494 | 0.2594 | 0.6416 |
| | Q-DDS (3 mg/mouse) | 58.8 | 38.4 | 0.2293 | 0.5972 | 0.2933 |
| | Q-DDS (5 mg/mouse) | 33.5 | 19.1 | 0.0974 | 0.7898 | 0.0224 |
| | Q-DDS (10 mg/mouse) | 7.2 | 1.7 | 0.0400 | 0.0636 | 0.0006 |

TABLE 21-continued

| ELISA values in Serum (pg/mL) | Mean | SEM | p-value vs Vehicle | vs MTX | vs Xeljanz® |
|---|---|---|---|---|---|
| Q-DDS (20 mg/mouse) | 7.2 | 2.8 | 0.0400 | 0.0648 | 0.0006 |
| MTX + Q-DDS (3 mg/mouse) | 5.2 | 1.9 | 0.0156 | 0.0233 | 0.0001 |

As can be seen in FIG. 13 and Table 21, as a result of measuring the amount of IL-6 protein among the inflammatory mediators, the amount was decreased in all of the naltrexone DDS dose administration groups in a concentration-dependent mode, but in particular, a significant decrease at the dose concentration of not less than naltrexone DDS 5 mg/mouse was shown. In particular, the naltrexone DDS 10 mg/mouse administration group, 20 mg/mouse administration group, and combination administration group showed the lowest IL-6 concentration, and the concentration was decreased compared to the negative control group, and decreased even when compared to the Xeljanz® administration group, a positive control group.

In conclusion, the blood concentration of IL-6 presents in the downstream of the inflammatory response cascade showed results consistent with the histologic and clinical findings of arthritis in the naltrexone DDS 10 mg/mouse administration group and the combination administration group.

Example 4. Efficacy Evaluation of Naltrexone-Containing Microspheres for Rheumatoid Arthritis (Tertiary)

1. In Vivo Testing Method of Naltrexone-Containing Microspheres for Rheumatoid Arthritis Following the efficacy evaluation in vivo of naltrexone-containing microspheres for rheumatoid arthritis in Example 2 and Example 3, an additional efficacy experiment was conducted by giving a difference to the positive control group.

A model of murine collagen-induced arthritis prepared in the same manner as in Example 2 (6-10 week-old male mouse of DBA/1J strain; the first immunization on day 0 and secondary immunization on day 21) was used.

As a material to be tested, naltrexone DDS prepared as described in preparation example 1 was prepared. As a negative control, DDS containing a carrier was used instead of naltrexone, and Humira® (Humira®, Humira® prefilled syringe, 40 mg/0.4 mL, Abbott Korea), a treatment for rheumatoid arthritis, was used as a positive control.

Administration information for each administration group is as described in Table 22 below.

TABLE 22

| Administration group (Each group, n = 10) | Administration drug | Route of administration | Regimen and dose of administration (based on the active ingredient) | Administration volume (μl) |
|---|---|---|---|---|
| 1 (Negative control) | Vehicle DDS | Subcutaneous injection | Administration once on the 23$^{th}$ day, 3 mg/mouse, N/A | 140 |
| 2 (Positive control) | Humira® | Subcutaneous injection | Twice/week, 10 mg/kg body weight/each time | 100 |
| 3 (Test group) | Q-DDS | Subcutaneous injection | Administration once on the 23$^{th}$ day, 10 mg/mouse | 500 |

Based on the blind evaluation data for each evaluation index, statistical analysis between the negative control group and the test group or between the two test groups was performed through SPSS. For comparison between the two groups, Student's t-test or Mann Whitney U test was used. To compare differences between treatment groups at multiple time points, repeated measures ANOVA with Turkey's post-hoc test was used. The significance level was defined as a p-value of 0.05 or less.

2. Clinical Evaluation of Arthritis Activity

After administration of the test substance to the collagen-induced arthritis mouse model, the occurrence and level of inflammation were regularly observed from the date of group separation to the end of the experiment (the 41$^{th}$ day). Inflammation level was given a score of 0 to 4 for each paw according to the criteria in Table 4 above, and the sum was used as a clinical arthritis index (CAI).

When the clinical index of each paw was 2 or more scores, it was found that arthritis occurred, and the incidence was defined as 100% when arthritis occurred in the four toes.

Toe images of each administration group were shown in FIG. 14A (Vehicle DDS: negative control group, Humira: Humira administration group, Q-DDS: naltrexone DDS 10 mg/mouse administration group). The clinical arthritis index (CAI) of mouse over the time (days) after administration of the test substance was shown in FIG. 14B, and a graph showing the area under the curve (AUC) of the clinical arthritis index was shown in FIG. 14C (mean±standard error mean (SEM),***: p-value<0.001). The results of the clinical arthritis index and the area under the curve were summarized in Table 23 below.

TABLE 23

| Group | CAI | | | CAI-AUC | | |
|---|---|---|---|---|---|---|
| | Mean | SEM | p-value | Mean | SEM | p-value |
| Vehicle DDS | 10.55 | 1.44 | — | 130.48 | 15.24 | — |
| Humira® | 5.90 | 2.67 | <0.0001 | 70.28 | 11.61 | <0.0001 |
| Q-DDS (10 mg/mouse) | 5.15 | 1.27 | <0.0001 | 71.88 | 14.38 | <0.0001 |

As shown in FIGS. 14A, 14B, and Table 23, the positive control group and the naltrexone DDS administration group (test group) showed a decrease of a clinical arthritis index compared to the carrier-containing DDS administration group (negative control group). In particular, the naltrexone DDS administration group showed the lowest clinical arthritis index on the 41$^{th}$ day (Vehicle DDS vs Q-DDS, 10.55±1.44 vs 5.15±1.27, p<0.001). As a result of analyzing the area under the curve for the clinical arthritis index (FIG. 14C and Table 23), a similar pattern to the numerical results of clinical arthritis was observed, and both the positive control group and the naltrexone DDS administration group showed a decrease compared to the carrier-containing DDS administration group. Through the above results, the effectiveness of naltrexone DDS of the present disclosure as a therapeutic agent for chronic inflammatory arthritis was confirmed by exhibiting an arthritis inhibitory effect similar to that of Humira, a representative biological antirheumatic agent used in clinical practice.

The incidence (%) of arthritis over the time (days) after administration of the test substance was shown in FIG. 14D, and a graph showing the area under the curve (AUC) of the incidence was shown in FIG. 14E (mean±standard error mean (SEM),: p-value<0.01 versus negative control,*: p-value<0.001 versus negative control). The results of the incidence and the area under the curve were summarized in Table 24 below.

TABLE 24

| Group | Incidence (%) | | | Incidence-AUC | | |
|---|---|---|---|---|---|---|
| | Mean | SEM | p-value | Mean | SEM | p-value |
| Vehicle DDS | 62.50 | 13.18 | — | 678.8 | 167.7 | — |
| Humira ® | 25.00 | 31.18 | <0.0001 | 155.0 | 186.1 | <0.0001 |
| Q-DDS (10 mg/mouse) | 17.50 | 12.08 | <0.0001 | 156.3 | 108.1 | <0.0001 |

As shown in FIGS. 14D, 14E, and Table 24, the positive control group and the naltrexone DDS administration group (test group) showed a decrease of an incidence of arthritis, compared to the carrier-containing DDS administration group. In particular, the naltrexone DDS 10 mg/mouse administration group showed a more decreased result than the positive control group (Humira vs Q-DDS, 25.00 f 26.35 vs 17.50±12.08). In the area under the curve for the frequency of arthritis incidence, the positive control group and the naltrexone DDS administration group showed a clear decrease compared to the negative control group, and the naltrexone DDS administration group showed a similar decrease to the Humira administration group.

3. Histological Estimation

Mice were sacrificed on the 41$^{th}$ day, which is the end of the experiment, and the tissues of the hind paws were stained with hematoxylin/eosin. Hematoxylin/eosin staining was used to evaluate the activity of inflammation in the arthritic tissue, and toluidine blue staining was performed to confirm the histological therapeutic effect on cartilage destruction.

(1) Hematoxylin/Eosin Staining

Hematoxylin/eosin staining was performed and evaluated in the same manner as in Example 2.3. (1) above, and the score for items of synovial hyperplasia, pannus formation, cartilage destruction, and bone erosion was calculated by scoring each tissue as the average of the score of 4 sites based on Table 7 above.

The image of the tissue stained with hematoxylin/eosin was shown in FIG. 15A (Vehicle DDS: negative control group, Humira: Humira administration group, Q-DDS: Naltrexone DDS 10 mg/mouse administration group, 200 times magnification, bar: 100 μm). Histological scores were shown in FIG. 15B and the results were summarized in Table 25 below (mean±standard error mean (SEM),***: p-value compared to negative control group<0.001).

TABLE 25

| Histochromatographic parameters | | Mean | SEM | p-value | |
|---|---|---|---|---|---|
| | | | | vs Vehicle | vs Q-DDS |
| Synovial hyperplasia | Negative control (Vehicle DDS) | 2.89 | 0.17 | — | <0.0001 |
| | Humira ® | 1.05 | 0.41 | <0.0001 | 0.2498 |
| | Q-DDS (10 mg/mouse) | 0.86 | 0.17 | <0.0001 | — |
| Pannus formation | Negative control (Vehicle DDS) | 2.55 | 0.32 | — | <0.0001 |
| | Humira ® | 0.36 | 0.60 | <0.0001 | 0.2166 |
| | Q-DDS (10 mg/mouse) | 0.08 | 0.11 | <0.0001 | — |
| Cartilage destruction | Negative control (Vehicle DDS) | 2.50 | 0.29 | — | <0.0001 |
| | Humira ® | 0.80 | 0.44 | <0.0001 | 0.7799 |
| | Q-DDS (10 mg/mouse) | 0.75 | 0.12 | <0.0001 | — |
| Bone erosion | Negative control (Vehicle DDS) | 2.45 | 0.38 | — | <0.0001 |
| | Humira ® | 0.28 | 0.52 | <0.0001 | 0.2315 |
| | Q-DDS (10 mg/mouse) | 0.05 | 0.09 | <0.0001 | — |

As shown in FIGS. 15A, 15B, and Table 25, in the negative control group, cartilage destruction and bone erosion were evident due to the increase of the panus tissue along with the overproliferation of synovial cells, and all of positive control group and naltrexone DDS administration group showed a marked decrease compared to the negative control group in all parameters including overproliferation of synovial tissue. In the case of the naltrexone DDS administration group, when compared with the positive control group, items of the synovial hyperplasia and cartilage destruction were decreased to similar levels, but items of the pannus formation and bone erosion showed a lower index than the Humira-administration group.

(2) Toluidine Blue Staining

In the same manner as in Example 2.3. (2) above, the hind paw tissue of the mouse was stained with toluidine blue, and items such as photographing and matrix staining, surface regularity, and cartilage thickness were evaluated. The scoring criteria for each item is described in Table 9, and the average score of 4 sites was calculated as the score of each tissue.

The image of the tissue stained with toluidine blue was shown in FIG. 15C (Vehicle DDS: negative control group, Humira: Humira administration group, Q-DDS: Naltrexone DDS 10 mg/mouse administration group, 200 times magnification, bar: 100 μm). Histological scores were shown in FIG. 15D and the results were summarized in Table 26 below (mean±SEM,***: p-value compared to negative control group<0.001).

TABLE 26

| Histochromatographic parameters | | Mean | SEM | p-value | |
|---|---|---|---|---|---|
| | | | | vs Vehicle | vs Q-DDS |
| Matrix staining | Negative control (Vehicle DDS) | 2.91 | 0.11 | — | <0.0001 |
| | Humira ® | 1.31 | 0.59 | <0.0001 | 0.2249 |
| | Q-DDS (10 mg/mouse) | 1.00 | 0.37 | <0.0001 | — |
| Surface regularity | Negative control (Vehicle DDS) | 2.59 | 0.24 | — | <0.0001 |
| | Humira ® | 0.72 | 0.76 | <0.0001 | 0.3335 |
| | Q-DDS (10 mg/mouse) | 0.44 | 0.25 | <0.0001 | — |

TABLE 26-continued

| Histochromatographic parameters | | Mean | SEM | p-value vs Vehicle | p-value vs Q-DDS |
|---|---|---|---|---|---|
| Cartilage thickness | Negative control (Vehicle DDS) | 1.69 | 0.15 | — | <0.0001 |
| | Humira ® | 0.34 | 0.43 | <0.0001 | 0.5824 |
| | Q-DDS (10 mg/mouse) | 0.25 | 0.16 | <0.0001 | — |

As shown in FIGS. 15C, 15D, and Table 26, the positive control group and the naltrexone DDS administration group showed a decrease compared to the negative control group in all three parameters, and in particular, the naltrexone DDS administration group showed a lower histological score than Humira administration group.

Taken together with the histological estimation results, naltrexone DDS 10 mg/mouse administration group not only had an anti-inflammatory effect compared to the negative control group in the evaluation of the activity of inflammation of arthritic tissues and the severity of joint damage but also showed a more effective arthritis inhibitory effect rather than that of Humira which is an antirheumatic agent used in a clinic.

4. Safety Assessment In Vivo

The safety in vivo of the test substance was evaluated by measuring the body weight of mouse in each administration group of Example 4.1.

For the safety evaluation of the test substance, the body weight of mouse was measured daily from before the start of administration (The 23$^{th}$ day) to just before the end of administration (The 41$^{th}$ day), and the body weight (%) of the mouse for each administration group over the time (day) and the body weight on the 41$^{th}$ day were shown in FIG. 16A, FIG. 16B and Table 27.

TABLE 27

| Change of body weight | D23 body weight | | D41 body weight | | Change of body weight (%, D23 body weight 100%) | | p-value (vs Vehicle) |
|---|---|---|---|---|---|---|---|
| | Mean | SEM | Mean | SEM | Mean | SEM | |
| Negative control (Vehicle DDS) | 22.3 | 1.2 | 21.2 | 0.9 | 95.06 | 5.29 | — |
| Humira ® | 22.2 | 1.6 | 22.6 | 1.9 | 102.11 | 7.67 | 0.0279 |
| Q-DDS (10 mg/mouse) | 23.6 | 1.4 | 24.4 | 1.8 | 106.39 | 3.79 | <0.0001 |

As shown in FIG. 16A, FIG. 168 and Table 27, there was a tendency for the body weight of the mouse to be decreased if severity of arthritis is high during the test period. In contrast to 4.94% weight loss in the negative control group, no body weight loss was observed in the naltrexone DDS administration group and the positive control group.

5. Imaging Evaluation of Arthritis Using Micro-CT

The paw tissue representing each group's results was fixed after the treatment with the test substance in Example 4.1 and was photographed with micro-CT scanners (Quantum FX, Perkin Elmer, MA). The radiographs were 3D rendered using the Quantum FX µCT imaging system (Perkin Elmer, MA), and then the radiological score was evaluated, and the bone volume ratio (Bone volume [BV]/Tissue volume; TV) and bone surface density (Bone surface area (BS)/Bone volume (BV)), and cortical bone thickness were also measured. Two or more researchers performed blind evaluation for joint destruction, and the indicators in Table 17 above were used as the scoring criteria. The average value of the researchers' blind evaluation data was used as the score, and the average score of the paw tissue was calculated as the score of each group.

Representative images for each group photographed with micro-CT were shown in FIG. 17A, and in particular, images magnifying joint portions were shown in FIG. 17B (Vehicle DDS: negative control, MTX: methotexate administration group, Xeljanz®: Xeljanz® administration group, Q-DDS: naltrexone DDS administration group, MTX+Q-DDS: methotrexate+ naltrexone DDS combination administration group, 200 times magnification, bar: 100 µm). The radiological score was shown in FIG. 17C and the results were summarized in Table 28 below (mean±standard error mean (SEM),*: p-value<0.05 compared to negative control group, : p-value<0.01 compared to negative control group,*: p-value<0.001 compared to negative control group, #: p-value compared to MTX administration group<0.05, †: p-value<0.05 compared to MTX administration group).

TABLE 28

| Radiological analysis values | | Mean | SEM | p-value vs Vehicle | p-value vs Q-DDS |
|---|---|---|---|---|---|
| Bone volume/ tissue volume (%) | Negative control (Vehicle DDS) | 16.53 | 1.50 | — | 0.0209 |
| | Humira ® | 24.21 | 3.83 | 0.0209 | 0.8845 |
| | Q-DDS (10 mg/mouse) | 25.71 | 0.48 | 0.0209 | — |
| Bone surface width/Bone volume (mm$^{-1}$) | Negative control group (Carrier) | 6.88 | 0.71 | — | 0.0202 |
| | Humira ® | 6.08 | 0.09 | 0.0202 | 0.2944 |
| | Q-DDS (10 mg/mouse) | 5.97 | 0.15 | 0 0202 | — |

TABLE 28-continued

| Radiological analysis values | | Mean | SEM | p-value vs Vehicle | p-value vs Q-DDS |
|---|---|---|---|---|---|
| Cortical bone thickness (mm) | Negative control group (Carrier) | 0.62 | 0.06 | — | 0.0209 |
| | Humira ® | 0.78 | 0.03 | 0.0202 | 0.7674 |
| | Q-DDS (10 mg/mouse) | 0.78 | 0.03 | 0.0209 | — |

As noted in FIGS. 17A and 17B, as a result of micro-CT scan, in the case of the negative control group, bone volume decreased, and bone erosion of the paw joint was clearly observed in several joints, and the reduction of a joint volume in the Humira administration group as the positive control group was less compared to the negative control group. In the naltrexone DDS administration group, the bone volume ratio was higher than in the negative control group, and slightly higher than in the Humira administration group (Vehicle DDS vs Q-DDS, 16.53%±1.50% vs 25.71%±0.48%, p<0.05).

As a result of measurement of bone surface density, the positive control group and the naltrexone DDS administration group showed lower levels than the negative control group, and the naltrexone DDS administration group showed a level similar to the positive control group (Vehicle DDS vs Humira vs Q-DDS, 6.88 mm$^{-1}$±0.71 mm$^{-1}$ vs 6.08 mm$^{-1}$±0.09 mm$^{-1}$ vs 5.97 mm$^{-1}$±0.15 mm$^{-1}$, p<0.05).

As a result of quantification of cortical bone thickness, it was found that the negative control group had a thinner cortical bone thickness due to bone erosion, but the positive control group showed a greater thickness than the negative control group. The naltrexone DDS administration group was thicker than the negative control group (Vehicle DDS vs Q-DDS, 0.62 mm±0.06 mm vs 0.78 mm±0.03 mm p<0.05), and exhibited a thickness similar to the Humira administration group.

In the radiological score, the positive control group and the naltrexone DDS administration group showed a decrease compared to the negative control group, and as a result, through imaging analysis, it was confirmed that naltrexone DDS not only treats arthritis inflammation, but also inhibits the progression of joint destruction as a result.

6. Multiplex Protein Immunoassay on Arthritic Tissue and Serum

In order to evaluate the inflammatory activity and confirm the mode of action of the test substance through quantitative analysis of inflammatory substances in mouse arthritis tissue and serum, inflammatory mediators were investigated at the protein level. The same multi-analyte-ELISA (multi-analyte-ELISA) method based on Luminex technology as in Example 3.6. above was used.

(1) Biomarker Evaluation Through Analysis of Protein Concentration of Inflammation Mediators in Arthritic Tissues The mouse joint tissue obtained after treatment with the test substance in the method of Example 4.1. above was pulverized through ceramic beads, and all proteins were extracted using a lysis buffer (Cat. 1713040111, Bio-Rad). Using Pro-reagent kit V, the same amount of protein (2.7 mg/mL) for each administration group was diluted ¼ and reacted with the target-binding beads in a culture dish for 30 minutes. After washing with a wash buffer, it was reacted with the target-measurement antibody for 30 minutes, and after washing with a wash buffer again, it was reacted with streptavidin-PE for 10 minutes. Thereafter, the target protein is quantitatively measured for each administration group using the Bio-Plex® 200 system (Bio-Rad). The target-binding beads were composed of a set that can be combined as needed from Bio-Plex Mouse cytokine 4-plex (IL-1β, IL-6, IL-17A, TNF-α; Cat. 171 G5002M), Bio-Plex Pro Mouse Cytokine 1-plex (MCP1; Cat. 171G5019M), Bio-Plex Pro Mouse Cytokine II 1-plex (MIP2; Cat. 171 G6006M), and Bio-Plex Pro Mouse Cytokine 1-plex (IL-6; Cat. 171G5007M) (all products are from Bio Rad) and were used for measurement.

For the measurement result, paw tissue weight of the mouse was corrected for the quantified target protein. For each target joint, the hind paw was mainly used, and in order to overcome the limitation of the amount of protein extracted from the joint tissue, up to 4 inflammatory mediators were measured in one well.

On the other hand, as the target protein to be measured, a representative inflammation-promoting cytokine group A (IL-1β, IL-6, IL-17, and TNF-α) among inflammatory mediators, and IL-2 and a chemokine group B (IL-2, MCP-1 and MIP-2) among inflammatory mediators were selected to carry out the experiment. The measurement results were summarized in FIGS. 18A and 18B, and Tables 29 and 30 below.

TABLE 29

| ELISA values in Arthritis | | | | p-value | |
|---|---|---|---|---|---|
| Paws (pg/mL) | | Mean | SEM | vs Vehicle | vs Q-DDS |
| IL-1β | Negative control (Vehicle DDS) | 56.80 | 8.43 | — | <0.0001 |
| | Humira ® | 4.09 | 1.90 | <0.0001 | 0.0018 |
| | Q-DDS (10 mg/mouse) | 1.67 | 0.42 | <0.0001 | — |
| IL-6 | Negative control (Vehicle DDS) | 397.25 | 247.40 | — | 0.0002 |
| | Humira ® | 10.75 | 12.57 | 0.0003 | 0.0589 |
| | Q-DDS (10 mg/mouse) | 2.20 | 1.02 | 0.0002 | — |
| IL-17 | Negative control (Vehicle DDS) | 40.56 | 11.83 | — | <0.0001 |
| | Humira ® | 9.93 | 1.01 | <0.0001 | 0.0001 |
| | Q-DDS (10 mg/mouse) | 7.50 | 1.02 | <0.0001 | — |
| TNF-α | Negative control (Vehicle DDS) | 105.64 | 20.60 | — | <0.0001 |
| | Humira ® | 18.93 | 7.64 | <0.0001 | 0.0299 |
| | Q-DDS (10 mg/mouse) | 12.49 | 2.77 | <0.0001 | — |

TABLE 30

| ELISA values in Arthritis | | | | p-value | |
|---|---|---|---|---|---|
| Paws (pg/mL) | | Mean | SEM | vs Vehicle | vs Q-DDS |
| IL-2 | Negative control (Vehicle DDS) | 182.26 | 170.68 | — | 0.0093 |
| | Humira ® | 36.59 | 16.19 | 0.0215 | 0.0016 |
| | Q-DDS (10 mg/mouse) | 14.00 | 7.56 | 0.0093 | — |
| MCP-1 | Negative control (Vehicle DDS) | 7808.4 | 3280.5 | — | <0.0001 |
| | Humira ® | 281.3 | 204.6 | <0.0001 | 0.0536 |
| | Q-DDS (10 mg/mouse) | 138.4 | 22.4 | <0.0001 | — |
| MIP-2 | Negative control (Vehicle DDS) | 12373.11 | 3255.29 | — | <0.0001 |
| | Humira ® | 564.83 | 393.77 | <0.0001 | 0.0165 |
| | Q-DDS (10 mg/mouse) | 211.31 | 43.55 | <0.0001 | — |

Through the above process, as a result of measuring the protein amount of four representative pro-inflammative cytokines (IL-1β, IL-6, IL-17, and TNF-α) in the arthritic tissue, the positive control group and the naltrexone DDS administration group showed a decrease compared to the negative control group, and in particular, for IL-1β, IL-17, and TNF-α, the naltrexone DDS administration group showed a decrease even when compared to the Humira-administered group, a positive control group (IL 1β: Humira vs Q-DDS, 4.09 pg/ml±1.90 pg/ml vs 1.67 pg/ml±0.42 pg/ml, p<0.01; IL-17: Humira vs Q-DDS, 9.93 pg/ml±1.01 pg/ml vs 7.50 pg/ml±1.02 pg/ml, p<0.05; TNF-α: Humira vs Q-DDS, 18.9.3 pg/ml±7.64 pg/ml vs 12.49 pg/ml±2.77 pg/ml, p<0.05).

In the case of IL-6, the naltrexone DDS administration group showed a decrease compared to the negative control group.

In addition, as a result of measurement of the chemokines MCP-1 and MIP-2, a pattern similar to that of pro-inflammatory cytokines of group A was found. Specifically, the IL-2 concentration in the naltrexone DDS administration group was lower than that of the negative control group and was measured at a lower level than Humira-administered group as the positive control group (Humira vs Q-DDS, 36.59 pg/ml±16.19 pg/ml vs. 14.00 pg/ml±7.56 pg/ml, p<0.01). MIP-2 and MCP-1 measurement results also showed a decrease in the naltrexone DDS administration group compared to the negative control group.

As a result, the major inflammatory mediators measured in arthritic tissues showed a pattern very similar to the previously measured clinical indicators, and in the naltrexone DDS administration group, all of IL-1β, IL-6, IL-17, TNF-α, IL-2, MCP-1, and MIP-2 not only showed a decrease compared to the negative control group, but also showed an inhibition compared to Humira, a standard treatment. The major inflammatory cytokines and chemokines in these arthritic tissues are important biomarkers of arthritis. Therefore, from the above result that the main causative agents of inflammation were more inhibited in the naltrexone DDS administration group than in the Humira administration group, it could be confirmed that the naltrexone DDS of the present disclosure effectively inhibits, alleviates, or modulates both the symptoms and inflammation of arthritis in the treatment of arthritis.

(2) Biomarker Evaluation Through Analysis of Protein Concentration of Inflammation Mediators in Serum Using the Pro-reagent kit V, the mouse blood (serum) obtained after treatment with the test substance in the method of Example 4.1. above was diluted to ¼ with the same amount of protein (2.7 mg/mL) for each administration group, and then incubated with target-binding beads (IL-6 target) and a culture dish for 30 min. After washing with a wash buffer, it was reacted with the target-measurement antibody for 30 minutes, and after washing with a wash buffer again, it was reacted with streptavidin-PE for 10 minutes. Thereafter, the target protein is quantitatively measured for each administration group using the Bio-Plex® 200 system (Bio-Rad). As the target-binding beads, the beads described in Example 4.6. (1) were used.

For the measurement result, paw tissue weight of the mouse was corrected for the quantified amount of IL-6 protein. For each target joint, the hind paw was mainly used, and in order to overcome the limitation of the amount of protein extracted from the joint tissue, up to 4 inflammatory mediators were measured in one well.

The measured results were summarized in FIG. 19 and Table 31.

TABLE 31

| ELISA values in serum (pg/mL) | | Mean | SEM | p-value vs Vehicle | vs Q-DDS |
|---|---|---|---|---|---|
| IL-6 | Negative control (Vehicle DDS) | 74.72 | 20.33 | — | <0.0001 |
| | Humira ® | 29.02 | 21.74 | 0.0003 | 0.0219 |
| | Q-DDS (10 mg/mouse) | 10.45 | 2.85 | <0.0001 | — |

As can be seen in FIG. 19 and Table 31, as a result of measuring the amount of IL-6 protein among inflammatory mediators, the positive control group and the naltrexone DDS administration group showed a decrease compared to the negative control group and in particular, the naltrexone DDS administration group showed the lowest level of concentration and a decrease compared to the positive control group, Humira administration group. (Vehicle DDS vs Q-DDS, 74.72 pg/ml±20.33 pg/ml vs 10.45 pg/ml±2.85 pg/ml, p<0.001; Humira vs Q-DDS, 29.02 pg/ml±21.74 pg/ml vs 10.45 pg/ml±2.85 pg/ml, p<0.05).

In conclusion, the blood concentration of IL-6 consists of the downstream of the inflammatory response cascade was shown to be decreased, consistent with the histological and clinical findings of arthritis in the naltrexone DDS administration group. The naltrexone DDS of the present disclosure exhibits more reducing effect on the concentration of IL-6 in the blood compared to the positive control Humira, which means that the present disclosure reduces IL-6 not only in arthritic tissues but also in a systemic level. In addition, since IL-6 is a cytokine substantially showing high levels in the serum of arthritis patients and reflects disease activity, this result means that naltrexone DDS can be effective in the treatment of arthritis.

7. NK Cell Immunostaining in Arthritic Tissue

In order to verify the etiological mechanism according to the severity of arthritis, the infiltration of NK cells in the mouse paw tissue was measured after administration of the test substance in the method of Example 4.1.

Specifically, after de-paraffinization and rehydration on a paraffin-embedded tissue piece slide, the antigen in the tissue is exposed through heat-induced antigen retrieval. After the serum blocking step, the slides were reacted with a CD56 target the first antibody (rabbit anti-CD56 antibody, Abcam, ab220360) for 1 hour, and then peroxidase blocking was performed for 15 minutes. After reacting with horseradish peroxidase-conjugated secondary antibody (goat anti-rabbit IgG-HRP, Jackson lab, #111-035-144) for 30 minutes, OPAL 690 solution pack (Akoya Biosciences, CA) was reacted for 10 minutes to proceed with binding to the secondary antibody. After nuclear staining by reaction with DAPI for 3 minutes, the slides were mounted with Vector Shield (Vector Lab, CA) medium having a fluorescence preservation formula, and photographed with confocal microscopy; C2 plus Ti2-E, Nikon, NY). After photographing 3 areas per slide (400 magnification), the number of cells stained with CD56 antibody (NK cells) was quantitatively evaluated. The images taken according to the magnification were shown in FIGS. 20A, 20B, and 20C, and the quantitatively evaluated values were shown in FIG. 20D and Table 32 below.

TABLE 32

| The number of CD56+ cell (number/HPF) | Mean | SEM | p-value vs Vehicle | vs Q-DDS |
|---|---|---|---|---|
| Negative control (Vehicle DDS) | 10.25 | 3.25 | — | <0.0001 |
| Humira ® | 2.00 | 1.41 | <0.0001 | 0.7841 |
| Q-DDS (10 mg/mouse) | 1.83 | 1.53 | <0.0001 | — |

As can be seen in FIGS. 20A, 20B, 20C, and Table 32, a large number of CD56+ cells were observed in the proliferated synovial tissue in the negative control group, but very little CD56+ cell infiltration occurred in the positive control group and the naltrexone DDS administration group (Vehicle DDS vs Q-DDS, 10.25±3.25 vs 1.83±1.53, p<0.001). The naltrexone DDS administration group showed more decrease compared to the positive control group.

As a result, in the case of CD56-positive NK cells in the development of arthritis, infiltration into the inflamed tissue occurs as the arthritis becomes worse, but it was confirmed that the infiltration is clearly inhibited by administration of naltrexone DDS, and compared to Humira as an antirheumatic agent used in clinical practice, it was further inhibited.

Example 5. Efficacy Evaluation of Naltrexone-Containing Microspheres for Multiple Sclerosis 1. In Vivo Test Method of Naltrexone-Containing Microspheres for Multiple Sclerosis In vivo efficacy was evaluated to determine whether naltrexone-containing microspheres, i.e., the naltrexone drug delivery systems, have therapeutic efficacy for multiple sclerosis.

As an experimental autoimmune encephalomyelitis mouse model (Mouse Experimental Autoimmune Encephalomyelitis: EAE), 6 to 10 week-old female mice of C57BL/6 strain were prepared. Mice were kept and tested in a specific pathogen free (SPF) laboratory under an environment of a temperature of 21° C. to 23° C. and a relative humidity of 40% to 50%. Experimental animals were kept per cage in the number of 4 or less, and a cage was exchanged 2 to 3 times a week and feed was supplied.

Myelin-oligodendrocyte glycoprotein (MOG) was dissolved in phosphate-buffered saline (PBS) to be 1 mg/mL, and was emulsified by mixing at 1:1 (v/v) with 5 mg/mL Complete Freund's adjuvant. 100 μl of this was subcutaneously injected into both sides of the mouse, and then 400 μl of 2 pg/mL pertussis toxin was intraperitoneally injected (first immunization, day 0). On the second day, 400 μl of 2 μg/mL pertussis toxin was intraperitoneally injected a second time. On the third day after the first immunization, the test was performed by separating the experimental group.

As a material to be tested, naltrexone DDS prepared as described in preparation example 1 was prepared. As a negative control, DDS containing a carrier was used instead of naltrexone, and as a positive control, Fingolimod (Fytarex® capsule, 0.5 mg, Novartis Korea) and naltrexone hydrochloride (Revia® tablet, 50 mg, Jell Pharmaceutical) were used.

Administration information for each administration group is as described in Table 33 below. The animal model preparation and administration schedule were shown in FIG. 21A.

TABLE 33

| Administration group (Each group, n = 6) | Administration drug | Route of administration | Regimen and dose of administration (Baseline of the active ingredient) | Administration volume (μl) |
|---|---|---|---|---|
| 1 (Negative control) | Vehicle DDS | Subcutaneous injection | Administration once on the third day, N/A | |
| 2 (Positive control) | Fytarex ® | Oral | Once/day, 3 mg/kg body weight/each time | |
| 3 (Positive control) | Revia ® | Oral | Once/day, 1 mg/kg/time | |
| 4 (Test group) | Naltrexone DDS (Q-DDS) | Subcutaneously | Administration once on the third day, 1 mg/mouse | |

Based on the blind evaluation data for each evaluation index, statistical analysis between the negative control group and the test group or between the two test groups was performed using SPSS. For comparison between the two groups, Student's t-test or Mann Whitney U test was used. The significance level was defined as a p-value of 0.05 or less.

2. Clinical Evaluation of the Occurrence and Severity of Neurological Symptoms

The experimental autoimmune encephalomyelitis mouse model was prepared, and from the third day after immunization, administered with carrier-containing DDS as a negative control, and Q-DDS as the test substance by subcutaneous injection once at 1 mg/mouse, and Fytarex® and Revia® as the positive control group were administered orally daily with the corresponding dose. Then, the occurrence and extent of clinical symptoms were regularly observed until the end of the experiment (The 30$^{th}$ day). The clinical symptom level was assigned a score of 0 to 5 after evaluating the functionality of the tail and four legs according to the criteria in Table 34 below, and was used as the EAE clinical score.

TABLE 34

| Score | Clinical neurologic findings |
|---|---|
| 0 | No obvious changes in motor function compared to non-immunized mice. |
| 0.5 | Tip of tail is limp. |
| 1 | Limp tail. |
| 1.5 | Limp tail and hind lig inhibition. |
| 2 | Limp tail and weakness of hind legs. |
| 2.5 | Limp tail and dragging of hind legs. |
| 3 | Limp tail and complete paralysis of hind legs (most common). |
| 3.5 | Limp tail and complete paralysis of hind legs. In addition to: Mouse is moving around the cage, but when placed on its side, is unable to right itself. Hind legs are together on one side of body. |
| 4 | Limp tail, complete hind leg and partial front leg paralysis. |
| 4.5 | Complete hind and partial front leg paralysis, no movement around the cage. Moue is not alert. |
| 5 | Mouse is spontaneously rolling in the cage (euthanasia is recommended). |

The clinical score of EAE mouse over the time (days) after administration of the test substance was shown in FIG. 21B, and a graph showing the area under the curve (AUC) of the clinical score was shown in FIG. 21C (mean±standard error mean (SEM),***: p-value<0.001). The results of the clinical score of EAE and the area under the curve were summarized in Table 35 below.

TABLE 35

| | Clinical score (D28) | | | Clinical score-AUC | | |
|---|---|---|---|---|---|---|
| Group | Mean | SEM | p-value vs Vehicle | Mean | SEM | p-value vs Vehicle |
| Vehicle DDS | 3.33 | 0.47 | — | 44.50 | 3.88 | — |
| Fytarex ® | 1.67 | 0.13 | 0.002 | 20.67 | 2.16 | 0.0001 |
| Revia ® | 2.00 | 0.16 | 0.008 | 21.08 | 4.37 | 0.0006 |
| Q-DDS (1 mg/mouse) | 1.92 | 0.25 | 0.008 | 21.71 | 2.42 | 0.0001 |

As shown in FIGS. 21B, 21C, and Table 35, the positive control group (Fytarex® and Revia®) and the Q-DDS 1 mg/mouse administration group showed a decrease in EAE clinical score compared to the carrier-containing DDS administration group. In particular, in the Q-DDS 1 mg/mouse administration group (Vehicle DDS vs Q-DDS 1 mg/mouse, 3.33±0.47 vs 1.92±0.25, p<0.001), a similar level of effect of the current global standard treatment, Fytarex® could be observed (3 mg/kg) (Vehicle DDS vs Fytarex® 3 mg/kg, 3.33±0.47 vs 1.67±0.13, p<0.001).

The analyzed results of the area under the curve (AUC) of the clinical scores also showed a similar pattern to the time course data of the clinical scores, and the positive control group (Fytarex® and Revia®) and Q-DDS 1 mg/mouse administration group showed a decrease compared to the carrier-containing DDS group. Through the above results, it was confirmed that a low-dose Q-DDS (1 mg/mouse) exhibited a reducing effect in clinical index similar to the standard treatment used in clinical practice. In addition, in the case of the sustained-release injection naltrexone DDS administration group, despite administration once a month, the results were almost similar to the results of Revia tablet administration group which is daily orally administered, and from this, it was confirmed that sustained-injection of the present disclosure was better in terms of formulation.

3. Histological Estimation

After mouse euthanasia, spinal cord tissue was extracted, hematoxylin/eosin staining and Luxol Fast Blue staining were performed, and MBP-targeted immunohistochemical staining was performed, and histological evaluation was performed through blind evaluation.

(1) Hematoxylin/Eosin Staining

On the 30th day which is the last day of the experiment, mouse was sacrificed, and the mouse spinal cord tissue was extracted and paraffin-embedded slides were prepared and then stained with hematoxylin/eosin, and the spinal cord tissue was photographed at 50 and 200 magnifications. Then, histological scores were measured according to the histological evaluation criteria of Table 36 below to evaluate the distribution of inflammatory cells.

TABLE 36

| Score | Inflammation scoring |
|---|---|
| 0 | No inflammation |
| 1 | Cellular infiltrate only in the perivascular areas and meninges |
| 2 | Mild cellular infiltrate in parenchyma: Less than one third part of the white matter is infiltrated with inflammatory cells |
| 3 | Moderate cellular infiltration in parenchyma: More than one third part of the white matter is infiltrated with inflammatory cells |
| 4 | Severe cellular infiltration in parenchyma: Infiltration of inflammatory cells are observed in the whole white matter |

The image of the tissue stained with hematoxylin/eosin was shown in FIG. 21D (Vehicle: negative control group, Fytarex®: Fytarex® administration group, Revia®: Revia® administration group, Q-DDS: naltrexone DDS administration group, 50 times and 200 times magnification). Histological scores were shown in FIG. 21E and the results were summarized in Table 37 below (mean±standard error mean (SEM),: p-value compared to negative control<0.01,*: p-value compared to negative control<0.001).

TABLE 37

| | | | p-value | | |
|---|---|---|---|---|---|
| Administration group | Mean | SEM | vs Vehicle | vs Fytarex | vs Revia |
| Vehicle DDS | 3.0 | 0.35 | — | | |
| Fytarex ® (3 mg/kg) | 1.08 | 0.29 | 0.0005 | | |
| Revia ® (1 mg/kg) | 1.42 | 0.46 | 0.0074 | 0.4702 | |
| Q-DDS (1 mg/mouse) | 1.13 | 0.44 | 0.0046 | 0.5737 | 0.8753 |

As shown in FIGS. 21D, 21E, and Table 37, in the case of the Vehicle DDS administration group, which is a negative control in the inflammation score evaluating the infiltration of inflammatory cells, infiltration of inflammatory cells in the entire white matter layer of the spinal cord was evident and diffuse infiltration of cells into the meninges was found, and the volume of the spinal cord was also decreased. In contrast, in the Fytarex administration group, which is a positive control group, the infiltration of inflammatory cells occurred partly in the white matter or had a limited distribution in the meninges, and when quantified by the inflammation score, it showed a decrease compared to the group administered with the carrier-containing DDS. Also, the Q-DDS 1 mg/mouse administration group showed a decrease (Vehicle DDS vs Q-DDS 1 mg/mouse, 3.00±0.35 vs 1.33±0.44, p<0.01). In addition, in the case of the sustained-injection naltrexone DDS administration group, despite administration once a month, the results were almost similar to the results of Revia tablet administration group which is daily orally administered, and from this, it was confirmed that sustained-injection of the present disclosure was better in terms of efficacy and formulation.

(2) Luau Fast Blue Staining

On the 30th day which is the last day of the experiment, mouse was sacrificed, and the mouse spinal cord tissue was extracted and paraffin-embedded slides were prepared and then stained with Luxol Fast Blue, and the spinal cord tissue was photographed at 50 and 200 magnifications. In Luxol Fast Blue staining, myelin is stained from blue to green, and nerves are stained purple, and through this, the degree of demyelination was analyzed in the EAE model by confirming the neural structure in the spinal cord. Demyelination was analyzed according to the criteria described in Table 38 below and measured as a score.

TABLE 38

| Score | Matrix staining results for demyelination scoring |
|---|---|
| 0 | No demyelination foci or lesion |
| 1 | Mild demyelination |
| 2 | Moderate demyelination |
| 3 | Severe demyelination |

The image of the tissue stained with Luxol Fast Blue was shown in FIG. 21F (Vehicle: negative control group, Fytarex®: Fytarex® administration group, Revia®: Revia administration group, Q-DDS: naltrexone DDS administration group, 50 times and 200 times magnification). Histological scores were shown in FIG. 21G and the results were summarized in Table 37 below (mean±standard error mean (SEM),: p-value compared to negative control<0.01,*: p-value compared to negative control<0.001).

TABLE 39

| | | | p-value | | |
|---|---|---|---|---|---|
| Administration group | Mean | SEM | vs Vehicle | vs Fytarex | vs Revia |
| Vehicle DDS | 1.72 | 0.51 | — | <0.0001 | <0.0001 |
| Fytarex ® (3 mg/kg) | 0.14 | 0.12 | <0.0001 | — | 0.0120 |
| Revia ® (1 mg/kg) | 0.61 | 0.36 | <0.0001 | 0.0120 | — |
| Q-DDS (1 mg/mouse) | 0.56 | 0.34 | <0.0001 | 0.0196 | 0.8136 |

As shown in FIGS. 21F, 21G, and Table 39, a lot of demyelination occurred in the carrier-containing DDS administration group with severe spinal nerve damage due to inflammation, and a decrease in histological score and demyelination in positive controls (Fytarex and Revia) and Q-DDS 1 mg/mouse administration group was observed (Vehicle DDS vs Q-DDS 1 mg/mouse, 1.72±0.51 vs 0.56±0.34, p<0.001).

As a result, in the evaluation of the inflammatory activity of myelitis tissue and the severity of myelin sheath, the Q-DDS 1 mg/mouse administration group showed a therapeutic effect compared to the negative control group, and also showed a similar level of therapeutic effect compared to Fytarex®, the clinically most widely used standard multiple sclerosis treatment. In addition, in the case of the sustained-injection naltrexone DDS administration group, despite administration once a month, the results were better than the results of Revia tablet administration group which is daily orally administered, and from this, it was confirmed that sustained injection of the present disclosure was better in terms of efficacy and formulation.

(3) Immunohistochemistry (IHC) Staining Using Anti-Myelin Basic Protein (MBP) Antibody On the 30th day which is the last day of the experiment, mouse was sacrificed, and the mouse spinal cord tissue was extracted and paraffin-embedded slides were prepared and then myelin basic protein (MBP) was stained immunohistochemically, and the spinal cord tissue was photographed at 50 and 200 magnifications. This is to confirm demyelination through immunohistochemical analysis using an antibody against myelin basic protein (MBP), a component of myelin.

The immunohistochemical staining image of the tissue was shown in FIG. 21H (Vehicle: negative control group, Fytarex®: Fytarex administration group, Revia®: Revia® administration group, Q-DDS: naltrexone DDS administration group, 50 times and 200 times magnification). The quantified result of the stained area based on the total spinal cord cross-sectional area was shown in FIG. 21I, and the results were summarized in Table 40 below (mean±standard error mean (SEM),*: p-value<0.05 versus negative control, : p-value<0.01 versus negative control,*: p-value<0.001 versus negative control).

TABLE 40

| Administration group | Mean | SEM | p-value vs Vehicle | vs Fytarex | vs Revia |
|---|---|---|---|---|---|
| Vehicle DDS | 39.72 | 8.46 | — | 0.0237 | 0.0251 |
| Fytarex ® (3 mg/kg) | 58.47 | 8.12 | 0.0237 | — | 0.9029 |
| Revia ® (1 mg/kg) | 58.23 | 5.67 | 0.0251 | 0.9029 | — |
| Q-DDS (1 mg/mouse) | 56.41 | 5.99 | 0.0454 | 0.4661 | 0.51514 |

As shown in FIGS. 21H, 21I, and Table 40, the white matter portion expressing MBP was decreased in the carrier-containing DDS administration group with severe inflammation and demyelination, and area expressing MBP in the positive control group (Fytarex® and Revia®) was conserved compared to the negative control. The ratio of MBP positive area/total spinal area was increased in the Q-DDS 1 mg/mouse administration group compared to the negative control group (Vehicle DDS vs Q-DDS 1 mg/mouse, 39.72±8.46 vs 56.41±5.99, p<0.0454). As a result, it can be confirmed that the low-dose Q-DDS administration group preserves the myelin sheath in healthy state while suppressing the inflammation of the spinal cord and thus reducing demyelination, thereby showing the therapeutic effect of multiple sclerosis. In addition, in the case of the sustained-injection naltrexone DDS administration group, despite administration once a month, the results were better than the results of Revia tablet administration group which is daily orally administered, and from this, it was confirmed that sustained-injection of the present disclosure was better in terms of efficacy and formulation.

4. Safety Assessment In Vivo

The in vivo safety of the test substance was evaluated by measuring the body weight of mouse in each administration group of Example 5.1.

For the safety evaluation of control substance, the test substance, the body weight of mouse was measured daily from before the start of administration (0 day) to just before the end of administration (The 30th day), and the body weight (%) of the mouse for each administration group over the time (day) was shown in FIG. 22.

As shown in FIG. 22, during the test period, the naltrexone DDS administration group maintained a higher body weight than the negative control group, and exhibited a level similar to that of Revia tablet, an oral administration agent. Therefore, it was confirmed that naltrexone DDS is safe in vivo.

Example 6. Study on the Mechanism of Action of Low-Dose Naltrexone-Containing Microspheres Related to Autoimmune Diseases Toll-like receptor 4 (TLR4) is closely related to innate immunity, which is the first step of the immune response in the body, and is a representative receptor responsible for regulating the initial immune response and inflammation response, when there is damage or infection in cells or the body. When TLR4 is activated due to injury or inflammatory response, NF-κB, a sub-regulator of TLR4, is activated to increase the expression of inflammatory cytokines and secrete inflammatory cytokines into the body (J. Med. Chem. 2020, 63, 22), 13466-13513).

The present inventors conducted the following experiment to confirm whether low-dose naltrexone exerts an antagonistic effect by regulating the activity of TLR4.

1. Confirmation of Direct Binding of Naltrexone to MD2

Naltrexone was purchased from USP (Rockville, Md., USA), and MD2 was purchased from R&D systems (Minneapolis, Minn., USA). It was confirmed through surface plasmon resonance analysis that naltrexone binds to the MD2 protein on TLR4 signaling. As the concentration of naltrexone increased, the binding to MD2 gradually increased (FIG. 23).

In the present disclosure, it was revealed for the first time that low-dose naltrexone binds to MD2, the major active site of TLR4, and these results show that naltrexone may inhibit TLR4 activity by directly binding to MD2, which is an active central factor in TLR4 signaling. From these results, it is expected that naltrexone has a mechanism of curing autoimmune diseases and inflammatory diseases caused by abnormal immune responses by targeting a novel target TLR4 signaling molecule and blocking immune abnormalities or immune overreaction. A schematic diagram of the mechanism by which low-dose naltrexone affects TLR4 signaling was shown in FIG. 24.

Hereinafter, it was confirmed whether a low-dose naltrexone capable of blocking TLR4 signal transduction could inhibit TLR4-mediated inflammatory factors increased by LPS in actual cells.

2. Effect of Low-Dose Naltrexone on Expression of Pro-Inflammatory Cytokines (TNF-α, IL-1β, IL-6, IL-1β, IL-17, iNOS) in Human Synovial Cell Lines The SW982 cell line (ATCC, Manassas, Va., USA), a human synovial cell line, was placed in RPM 1640 medium (Welgene, Republic of Korea) to which 10% fetal bovine serum (FBS), 50 IU/ml penicillin, and 50 µg/ml streptomycin (Thermo Fisher Scientific Inc.) was added, and cultured in a culture system (Sanyo, Japan) under 37° C. and 5% $CO_2$ conditions. Lipopolysaccharide (LPS) was purchased from Sigma-Aldrich (St. Louis, Mo., USA).

After treating SW982 cells with LPS (1 ug/ml) and naltrexone 200 or 500 ug/ml for 6 hours, RNA was extracted and cDNA was synthesized. As a result of performing RT-qPCR on the synthesized cDNA, it was confirmed that the expression of pro-inflammatory cytokines (TNF-α, IL-1β, IL-6, IL-17, iNOS) increased by LPS was significantly inhibited by 200 or 500 ug/ml of naltrexone (see FIG. 25).

3. Effect of Low-Dose Naltrexone on Activity of NF-κB in Human Synovial Cell Lines After treating SW982 cells with 200 or 500 ug/ml of naltrexone, Western blotting was performed to confirm whether the activity of NF-κB was inhibited. 1× Cell lysis buffer (Cell signaling, CA, USA) was mixed with protease and a phosphatase inhibitor and added to SW982 cells. After extracting the protein from the cells, the concentration was measured, and the same amount of protein was developed on an SDS-polyacrylamide gel, and transferred to an ECL nitrocellulose membrane (Amersham Pharmacia Biotech, Inc., Piscataway, N.J., USA) and blocked with nonfat dried milk for 1 hour. Thereafter, the reaction was performed with the first antibody (p65 NF-κB, phospho p65 NF-κB or calnexin; Cell signaling, CA, USA), while shaking at 4° C. for 24 hours. Then, after shaking and washing 3 times for 10 minutes with PBST buffer, the secondary antibody was incubated with anti-mouse or anti-rabbit HRP-conjugated secondary antibody for 1 hour at room temperature, and reacted with the protein band on the membrane using Supersignal west pico ECL solution (Thermo Fisher Scientific Inc.). The results were visualized with the Bio-Rad Gel Documentation system (Bio-Rad Laboratories, Hercules, Calif., USA), and the results were shown in FIG. 26.

As shown in FIG. 26, the phosphorylation of p65 NF-κB increased by the control LPS was inhibited by 200 ug/ml of naltrexone, confirming that the low-dose naltrexone inhibited the activity of NF-κB.

4. Effects of Low-Dose Naltrexone on Activity of Mitogen-Activated Protein Kinases (MAPKs) in Human Synovial Cell Lines After treating SW982 cells with 200 or 500 ug/ml of naltrexone, western blotting was performed to confirm whether the activity of MAPKs was inhibited. Western blotting was performed in the same manner as in Example 6.3. The first antibody used at this time is an antibody against p-ERK, ERK, p-JNK, JNK, p-p38, p38 and calnexin (Cell signaling, CA, USA), and the secondary antibody is anti-mouse or anti-rabbit HRP-binding secondary antibody. The results obtained by performing Western blotting were shown in FIG. 27.

As shown in FIG. 27, phosphorylation of MAPK increased by LPS as a control was decreased by 200 or 500 ug/ml of naltrexone. Through this, it can be confirmed that the low-dose naltrexone according to the present disclosure inhibits the activity of MAPKs induced by LPS.

5. Effect of Low-Dose Naltrexone on Expression of Pro-Inflammatory Cytokines (TNF-α, IL-1β, IL-6, IL-17, iNOS) in Murine Macrophage Cell The Raw 264.7 cell line (ATCC, Manassas, Va., USA), murine macrophage cell line, was placed in DMEM medium (Welgene, Republic of Korea) to which 10% fetal bovine serum (FBS), 50 IU/ml penicillin, and 50 µg/ml streptomycin (Thermo Fisher Scientific Inc.) was added, and cultured in a culture system (Sanyo, Japan) under 37° C. and 5% $CO_2$ conditions. Lipopolysaccharide (LPS) was purchased from Sigma-Aldrich (St. Louis, Mo., USA).

After treating Raw 264.7 cells with LPS (1 ug/ml) and naltrexone 200 or 500 ug/ml for 6 hours, RNA was extracted and cDNA was synthesized. As a result of performing RT-qPCR on the synthesized cDNA, it was confirmed that the expression of pro-inflammatory cytokines (TNF-α, IL-1β, IL-6, IL-17, iNOS) increased by LPS was significantly inhibited by 200 or 500 ug/ml of naltrexone (see FIG. 28).

6. Effect of Low-Dose Naltrexone on the Activity of NF-κB in Murine Macrophage Cell After treating Raw 264.7 cells with 100, 200, 500 or 1000 ug/ml of naltrexone, Western blotting was performed to confirm whether the activity of NF-κB was inhibited. 1× Cell lysis buffer (Cell signaling, CA, USA) was mixed with protease and a phosphatase inhibitor and added to SW982 cells. After extracting the protein from the cells, the concentration was measured, and the same amount of protein was developed on an SDS-polyacrylamide gel, and transferred to an ECL nitrocellulose membrane (Amersham Pharmacia Biotech, Inc., Piscataway, N.J., USA) and blocked with nonfat dried milk for 1 hour. Thereafter, the reaction was performed with the first antibody (p65 NF-κB, phospho p65 NF-κB or calnexin; Cell signaling, CA, USA), while shaking at 4° C. for 24 hours. Then, after shaking and washing 3 times for 10 minutes with PBST buffer, the secondary antibody was incubated with anti-mouse or anti-rabbit HRP-conjugated secondary antibody for 1 hour at room temperature, and reacted with the protein band on the membrane using Supersignal west pico ECL solution (Thermo Fisher Scientific Inc.). The results were visualized with the Bio-Rad Gel Documentation system (Bio-Rad Laboratories, Hercules, Calif., USA), and the results were shown in FIG. 29.

As shown in FIG. 29, it was confirmed that the phosphorylation of p65 NF-κB increased by the control LPS from a concentration of 500 ug/ml of naltrexone inhibits the activity of NF-κB.

7. Effects of Low-Dose Naltrexone on Activity of Mitogen-Activated Protein Kinases (MAPKs) in Murine Macrophage Cell After treating Raw 264.7 cells with 100, 200, 500 or 1000 ug/ml of naltrexone, Western blotting was performed to confirm whether the activity of MAPKs was inhibited. Western blotting was performed in the same manner as in Example 6.3. The first antibody used at this time is an antibody against p-ERK, ERK, p-JNK, JNK, p-p38, p38 and calnexin (Cell signaling, CA, USA), and the secondary antibody is anti-mouse or anti-rabbit HRP-binding secondary antibody. The results obtained by performing Western blotting were shown in FIG. 30.

As shown in FIG. 30, phosphorylation of MAPKs increased by LPS as a control group was not inhibited at all treatment concentrations of naltrexone 100, 200, 500, or 1000 ug/ml. Therefore, as shown in FIG. 31, it was confirmed that low-dose naltrexone did not inhibit the activity of MAPKs induced by LPS in murine macrophage cells, but inhibited only the activity of NF-κB in the TLR4 receptor mechanism.

Example 7. Evaluation of the Inhibitory Effect of Naltrexone and 6β-Naltrexol on Autoimmune Inflammatory Factors and the Regulation of TLR4 Signaling Factors

1. Background and Outline

When naltrexone is orally administered to humans, 6β-naltrexol as a metabolite, is produced in the body due to the first-pass effect and accordingly, in the case of oral preparations, 6β-naltrexol is relatively produced approximately 10 times more than injections. In addition, when administered orally, the deviation of naltrexone and 6β-naltrexol production rates between patients is large enough to cause a 128-fold difference between individuals (0.73 to 92.00), and when a 6β-naltrexol production rate is high, side effects including nausea and headache may occur and this has been reported to affect drug efficacy, toxicity, and patient compliance (Journal of Analytical Toxicology 2014; 38:212-217). Although 6β-naltrexol is known to be active against opioid addiction, which is currently used commercially, it has not been studied whether naltrexone and its metabolite, 6β-naltrexol show a difference in efficacy against TLR4 in relation to autoimmune diseases. Accordingly, the present inventors compared the autoimmune or inflammation inhibitory effects of naltrexone and 6β-naltrexol at the cellular level for the first time in order to confirm whether the sustained-injection of the present disclosure exhibits superior effects compared to the oral preparation, and checked whether TLR4 signaling factors (NF-κB, MAPKs) are regulated.

Toll-like receptor 4 (TLR4) is closely related to innate immunity, which is the first step of the immune response in the body, and is a representative receptor responsible for regulating the initial immune response and inflammation response, when there is damage or infection in cells or the body. When TLR4 is activated due to injury or inflammatory response, NF-κB, a sub-regulator of TLR4, is activated to increase the expression of inflammatory cytokines and secrete inflammatory cytokines into the body (J. Med. Chem. 2020, 63, 22), 13466-13513).

IL-1β and IL-6 are highly expressed in the synovial membrane, the lesion of rheumatoid arthritis, and this leads to aggravation of the disease. As a result of a recent study in muuse with multiple sclerosis, it has been found that IL-1β activates bystander T cells, which migrate to the spinal cord and release interleukin-17 and interferon-gamma, which are signaling substances that cause autoimmune diseases again and then damage the central nervous system (Nature Communications volume 10, Article number: 709 (2019)).

Recent biologics block the action of TNF-α or IL-6 receptors, directly interfering with the action of T cells or deplete B cells, and targeted therapies are being developed to prove the effect of RA treatment, T cell inhibition by abatacept and a decrease of cytokine signaling by JAK inhibitors, but unmet needs still remain.

Biological disease-modifying antirheumatic drugs (BD-MARD) developed by targeting TNF-α show excellent effects in the treatment of rheumatoid arthritis, but there are limitations that patients show only a partial response to the treatment, resistance to the treatment, and side effects. Multiple sclerosis treatments have also recently improved the treatment effect due to high efficacy and ease of administration, but they still have a problem in that they lack efficacy for neuroprotection. Because existing treatment methods block only one target among several etiological mechanisms, it is thought that the therapeutic effect decreases or resistance occurs in cases caused by a complex network of mechanisms.

On the other hand, lipopolysaccharide (LPS) is a large glycolipid molecule located in the outer membrane of Gram-negative bacteria and is a major inducer of TLR4-mediated immune responses. It was known that TLR4 induces Myd88 (myeloid differentiation first response gene 88) and TRIF (Toll/interleukin-1 receptor (TIR)-domain-containing adapter-inducing interferon-13)-dependent pathways, and when MyD88-dependent pathways are initiated, nuclear factor NF-κB and MAPKs are activated to induce the expression of cytokines related to autoimmune diseases (see FIG. 32).

The present inventors confirmed the effect of naltrexone and 6β-naltrexol on the mechanism of TLR4 activation through LPS stimulation, which is a major causative agent of immune-inflammatory mediated response.

2. Effect of Naltrexone and 6β-Naltrexol on Expression of Pro-Inflammatory Cytokines (iNOS, IL-1β, IL-6, and TNF-α) in Human Synovial Cell Lines The SW982 cell line (ATCC, Manassas, Va., USA), a human synovial cell line, was placed in RPMI 1640 medium (Welgene, Republic of Korea) to which 10% fetal bovine serum (FBS), 50 IU/ml penicillin, and 50 µg/ml streptomycin (Thermo Fisher Scientific Inc.) was added, and cultured in a culture system (Sanyo, Japan) under 37° C. and 5% $CO_2$ conditions. Lipopolysaccharide (LPS) was purchased from Sigma-Aldrich (St. Louis, Mo., USA).

After treating SW982 cells with LPS (1 ug/ml) and naltrexone (0.5, 1, 10, 100 uM) or 6β-naltrexol (0.5, 1, 10, 100 uM) for 6 hours, RNA was extracted and cDNA was synthesized. By performing RT-qPCR on the synthesized cDNA, it was confirmed whether the expression of pro-inflammatory cytokines (iNOS, IL-1β, IL-6, and TNF-α) increased by LPS was inhibited, and the results were shown in FIG. 33. As a result, it was confirmed that the expression of cytokines induced by LPS was suppressed at all concentrations of the treated naltrexone or 6β-naltrexol. In addition, naltrexone exhibited superior cytokine inhibitory activity than the metabolite 6β-naltrexol. In particular, in the case of iNOS, there was a significant difference when comparing the inhibitory effects of 1 uM of naltrexone and 1 uM of 6β-naltrexol (p=0.037), and in the case of IL-1β, when the inhibitory effect of 6β-naltrexol versus naltrexone was compared at all treatment concentrations, there was a significant difference in the cytokine inhibitory effect of naltrexone (0.5 uM p=0.032, 1 uM p=0.011, 10 uM p=0.003, 100 uM p=0.009), confirming the excellent inhibitory effect of naltrexone on autoimmune inflammation of naltrexone.

Since IL-1β is the most potent cytokine that induces autoimmune diseases and is also an important marker for clinical indicators of autoimmune diseases such as arthritis, the fact that naltrexone has a higher cytokine inhibitory effect than its metabolite 6β-naltrexol indicates that the low-dose naltrexone sustained-injection of the present disclosure exhibits superior effects compared to the oral naltrexone.

3. Effect of Naltrexone and 6β-Naltrexol on Expression of Pro-Inflammatory Cytokines (iNOS, IL-1β, IL-6, and TNF-α) in Murine Macrophage Cell Lines The Raw 264.7 cell line (ATCC, Manassas, Va., USA), murine macrophage cell line, was placed in DMEM medium (Welgene, Republic of Korea) to which 10% fetal bovine serum (FBS), 50 IU/ml penicillin, and 50 µg/ml streptomycin (Thermo Fisher Scientific Inc.) was added, and cultured in a culture system (Sanyo, Japan) under 37° C. and 5% $CO_2$ conditions. Lipopolysaccharide (LPS) was purchased from Sigma-Aldrich (St. Louis, Mo., USA).

After treating Raw 264.7 cells with LPS (1 ug/ml) and naltrexone (0.5, 1, 10, 100 uM) or 6β-naltrexol (0.5, 1, 10, 100 uM) for 6 hours, RNA was extracted and cDNA was synthesized. By performing RT-qPCR on the synthesized cDNA, it was confirmed whether the expression of pro-inflammatory cytokines (iNOS, IL-1β, IL-6, and TNF-α) increased by LPS was inhibited, and the results were shown in FIG. 34. As a result, it was confirmed that the expression of cytokines induced by LPS was suppressed at all concentrations of the treated naltrexone or 6β-naltrexol. In particular, in the case of IL-1β, when the inhibitory effect of 6β-naltrexol versus naltrexone was compared, there was a significant difference at 10 uM (p=0.028) and 100 uM (p=0.005) treatment concentrations.

4. Effects of Naltrexone and 6β-Naltresol on Activity of NF-κB or Mitogen-Activated Protein Kinases (MAPKs) in Human Synovial Cell Lines After treating SW982 cells with LPS (1 ug/ml) and naltrexone (0.5, 1, 10, 100 uM) or 6β-naltrexol (0.5, 1, 10, 100 uM) for 30 minutes, proteins were isolated from the cells, and Western blotting was performed to conform whether the activity of NF-κB and MAPKs was inhibited.

1× Cell lysis buffer (Cell signaling, CA, USA) was mixed with protease and a phosphatase inhibitor and added to SW982 cells. After extracting the protein from the cells, the concentration was measured, and the same amount of protein was developed on an SDS-polyacrylamide gel, and transferred to an ECL nitrocellulose membrane (Amersham Pharmacia Biotech, Inc., Piscataway, N.J., USA) and blocked with nonfat dried milk for 1 hour. Thereafter, the reaction was performed with the first antibody (p65 NF-κB, phospho p65 NF-κB, p-ERK, ERK, p-JNK, JNK, p-p38, p38 or calnexin; Cell signaling, CA, USA), while shaking at 4° C. for 24 hours. Then, after shaking and washing 3 times for 10 minutes with PBST buffer, the secondary antibody was incubated with anti-mouse or anti-rabbit HRP-conjugated secondary antibody for 1 hour at room temperature, and reacted with the protein band on the membrane using Supersignal west pico ECL solution (Thermo Fisher Scientific Inc.). The results were visualized with the Bio-Rad Gel Documentation system (Bio-Rad Laboratories, Hercules, Calif., USA), and the results are shown in FIG. 35.

As shown in FIG. 35, it was found that phosphorylation of p65 NF-κB and MAPKs (ERK1/2, JNK, p38), which are TLR4 signaling subfactors increased by LPS as a control group, was inhibited by 1 uM of naltrexone. However, 6β-naltrexol had no inhibitory effect on phosphorylation of p65 NF-κB and MAPKs (ERK1/2, JNK, p38).

That is, as shown in FIG. 24 or 32, naltrexone effectively regulates the phosphorylation of p65 NF-κB and MAPKs (ERK1/2, JNK, p38), which are TLR4 signaling subfactors, and thereby it was confirmed that it affects the activity of autoimmune disease-inducing cytokines and the metabolite 6β-naltrexol had no effect on the activity of the TLR4 signaling factor. That is, it could be confirmed that the autoimmune disease response due to LPS-induced TLR4 activity in human synovial cell lines was inhibited by naltrexone, and the metabolite 6β-naltrexol had no effect.

5. Effects of Naltrexone and 6O-Naltrexol on Activity of NF-κB or Mitogen-Activated Protein Kinases (MAPKs) in Murine Macrophage Cell Lines After treating Raw 264.7 cells with LPS (1 ug/ml) and naltrexone (0.5, 1, 10, 100 uM) or 6β-naltrexol (0.5, 1, 10, 100 uM) for 30 minutes, proteins were isolated from the cells, and Western blotting was performed to conform whether the activity of NF-κB and MAPKs was inhibited. Western blotting was performed in the same manner as in Example 7.4. The results obtained by performing Western blotting were shown in FIG. 36.

As shown in FIG. 36, in the experiment on the murine macrophage cell line, it was found that p65 NF-κB phosphorylation among the TLR4 signaling subfactors increased by the control LPS was inhibited not only by naltrexone but also by 6β-naltrexol. Both naltrexone and 6β-naltrexol had similar inhibitory effects on p65 NF-κB phosphorylation. However, unlike the previous human synovial cell line SW982, both naltrexone and 6β-naltrexol had no inhibitory effect on phosphorylation of MAPKs (ERK1/2, JNK, p38). That is, as shown in FIG. 31, it was found that naltrexone and its metabolite 6β-naltrexol did not inhibit LPS-induced MAPKs activity in murine macrophages, but inhibited only NF-κB activity in the TLR4 activation mechanism.

Although similar results in both of naltrexone and metabolite 6β-naltrexol were shown, a clear difference (naltrexone showed a distinct decrease compared to 6β-naltrexol) in the cytokine inhibitory effect experiment performed in the item of Example 7.4. suggests that there is an additional autoimmune suppression pathway in addition to the effect through TLR4 in the case of murine macrophage cell line.

6. Conclusion

In this experiment, the effects of naltrexone and 6β-naltrexol on the mechanism of TLR4 activation through LPS stimulation were compared to confirm whether low-dose naltrexone had an antagonist effect by regulating TLR4 activity. As a result, it was found that phosphorylation of p65 NF-κB and MAPKs (ERK1/2, JNK, p38), which are TLR4 signaling subfactors increased by LPS in human synovial cell line (SW982 cell line), was inhibited from 1 uM in the naltrexone-treated group. However, in 6β-naltrexol, an inhibitory effect on the phosphorylation of p65 NF-κB and MAPKs (ERK1/2, JNK, p38) was not observed. That is, it means that the autoimmune inhibitory effect through TLR4 by the orally administered naltrexone is due to non-metabolized naltrexone, not 6β-naltrexol.

In addition, the result of measuring the production amount of cytokines involved in autoimmunity also showed the same result. When naltrexone was treated compared to 6β-naltrexol, it showed a better inhibitory effect on cytokines such as IL-6, TNF-α, and iNOS related with autoimmune diseases such as rheumatoid arthritis, multiple sclerosis, and lupus, and was in particular confirmed that the expression of IL-1β was significantly decreased. The reduction of cytokines such as IL-1β, IL-6, TNF-α, iNOS, etc., by naltrexone treatment is an important result indicating that excellent therapeutic effects may be achieved by inhibiting disease activity of rheumatoid arthritis. Above all, the result of significantly inhibiting the expression of IL-1β means that naltrexone functions as an excellent and effective therapeutic agent for autoimmune diseases, which regulates the activation and inflammatory response of immune cells.

In addition, in an experiment conducted in murine macrophage cell line (Raw 264.7 cell), blocking of the NF-κB-mediated pathway among the mechanisms acting through TLR4 was observed in both naltrexone and 6β-naltrexol, and it was confirmed that it did not act on the MAPK-mediated pathway. However, specifically, in cytokine inhibition, there was a clear difference between the two substances, and since the distinct difference was shown in the inhibition rate in IL-1β, IL-6, TNF-α, iNOS, etc., it suggests that there are other mechanisms of action that leads to the difference of the inhibition rate between naltrexone and 6β-naltrexol. This fact also indicates that the main substance exhibiting an autoimmune inhibitory effect is naltrexone and not 6β-naltrexol.

In conclusion, it was confirmed that the substance exhibiting an autoimmune inhibitory effect through TLR4 was naltrexone and not its metabolite 6β-naltrexol, and by confirming the result that naltrexone exhibited a significantly superior autoimmune inflammatory cytokine inhibitory effect compared to 6β-naltrexol, it was found that the sustained injection of the present disclosure, may reduce the lowering of the drug efficacy due to the production of 6β-naltrexol, a representative metabolite occurring in oral drugs due to the first-pass effect, and may reduce side effects, and the difference in metabolic rate between individuals, and maximize the bioavailability and effect of naltrexone in the body, and is superior in terms of safety and effectiveness. In addition, the present disclosure has a very convenient advantage because it eliminates the discomfort and pain of daily administration when using the injection, and may achieve its purpose with a single administration.

From the results of Examples 6 and 7 above, it was confirmed that it is possible to treat various autoimmune diseases and immune diseases related to TLR4 by using the naltrexone microparticles of the present disclosure that may excellently maintain naltrexone a low dose and effective concentration for a long period of time.

In addition, if naltrexone is administered at a high dose in a situation with increased inflammation in affected lesion, such as arthritis, the activity of TLR4 in the body might be strongly inhibited and the secretion of inflammatory substances might be temporarily remarkably decreased, but a strong inhibition of TLR4 due to an administration of such a high dose of the naltrexone might decrease all of the inflammatory responses in the body, resulting in a sudden loss of immunity. Unlike high-dose administration, the low-dose naltrexone sustained formulation of the present disclosure does not cause a sudden decrease in immunity and maintains a normal immune response and immune system in the patient, even when administered to a patient with an autoimmune disease such as arthritis, while inhibiting TLR4 in the body since it may effectively inhibit the inflammatory response, and thus it will be a safe and excellent method for treating autoimmune diseases.

From the above description, those skilled in the art to which the present invention pertains will be able to understand that the present disclosure may be embodied in other specific forms without changing the technical spirit or essential characteristics thereof. In this regard, it should be understood that the embodiments described above are illustrative in all respects and not restrictive. The scope of the present disclosure should be construed as including all changes or modifications derived from the meaning and scope of the claims to be described later rather than the above detailed description, and equivalent concepts thereof.

The invention claimed is:

1. A sustained formulation, comprising microparticles comprising naltrexone or pharmaceutically acceptable salts thereof, and biodegradable polymers, wherein the end of the biodegradable polymer is capped or uncapped and a median particle size (D50) of the microparticles is 25 μm to 100 μm.

2. The formulation of claim 1, wherein the biodegradable polymer comprises one or more selected from the group consisting of polylactide, polylactic acid, polylactide-co-glycolide, polylactic-co-glycolic acid, polyphosphazine, polyiminocarbonate, polyphosphoester, polyanhydride, polyorthoester, polycaprolactone, polyhydroxyvalate, polyhydroxybutyrate, and polyamino acids.

3. The formulation of claim 2, wherein the molar ratio of glycolide to lactide in the polylactide-co-glycolide is 50:50 to 90:10.

4. The formulation of claim 2, wherein the biodegradable polymer comprises one or more of polylactide and polylactide-co-glycolide.

5. The formulation of claim 2, wherein the biodegradable polymer comprises one or more polylactide and one or more of polylactide-co-glycolide.

6. The formulation of claim 5, wherein the weight ratio of polylactide and polylactide-co-glycolide is 1:10 to 10:1.

7. The formulation of claim 5, wherein the weight ratio of polylactide and polylactide-co-glycolide is 1:1 to 2:1.

8. The formulation of claim 2, wherein the biodegradable polymer comprises two or more of polylactide-co-glycolide.

9. The formulation of claim 8, wherein the two or more polylactide-co-glycolides are polylactide-co-glycolides in a weight ratio of 1:10 to 10:1.

10. The formulation of claim 9, wherein the two or more of polylactide-co-glycolides are polylactide-co-glycolides in a weight ratio of 1:1 to 2:1.

11. The formulation of claim 2, wherein an intrinsic viscosity (IV) of the polylactide is 0.1 dl/g to 0.5 dl/g.

12. The formulation of claim 2, wherein an intrinsic viscosity of the polylactide-co-glycolide is 0.1 dl/g to 1.5 dl/g.

13. The formulation of claim 4, wherein an intrinsic viscosity of the polylactide is 0.1 dl/g to 0.5 dl/g.

14. The formulation of claim 4, wherein an intrinsic viscosity of the polylactide-co-glycolide is 0.1 dl/g to 1.0 dl/g.

15. The formulation of claim 1, wherein the residual amount of the solvent in the microsphere is 1000 ppm or less.

16. The formulation of claim 15, wherein the residual amount of the solvent in the microsphere is 800 ppm or less.

17. The formulation of claim 15, wherein the solvent is dichloromethane.

18. The formulation of claim 1, wherein the biodegradable polymer is stirred with 200 to 400 rpm at 100° C. to 20° C. for 30 minutes to 2 hours, with 200 to 400 rpm at 25° C. to 35° C. for 30 minutes to 2 hours, and with 200 to 400 rpm at 35° C. to 45° C. for 30 minutes to 4 hours to remove the solvent.

19. The formulation of claim 1, wherein the microparticle comprises biodegradable polymers and naltrexone or a pharmaceutically acceptable salt thereof in a weight ratio of 1:1 to 10:1.

20. The formulation of claim 1, wherein naltrexone or a pharmaceutically acceptable salt thereof is homogenously dispersed in the microparticles.

21. The formulation of claim 1, wherein the formulation is a parenteral formulation.

22. The formulation of claim 1, wherein the formulation is an injection for subcutaneous administration or intramuscular administration.

23. The formulation of claim 1, wherein the formulation comprises 0.1 mg to 1 g of naltrexone or a pharmaceutically acceptable salt thereof per unit dosage form.

24. The formulation of claim 1, wherein the formulation is administered once a day to once a year.

25. The formulation of claim 24, wherein the formulation is administered once every 1 week to 2 months.

26. The formulation of claim 1, wherein the formulation is for administration at a dose of 0.1 mg/kg body weight to 1 g/kg body weight.

* * * * *